US008518678B2

(12) United States Patent
Flint et al.

(10) Patent No.: US 8,518,678 B2
(45) Date of Patent: Aug. 27, 2013

(54) STRAIN COMPRISING INCREASED EXPRESSION OF A CFA CODING REGION FOR BUTANOL PRODUCTION

(75) Inventors: Dennis Flint, Newark, DE (US); Robert A. Larossa, Chadds Ford, PA (US); Vasantha Nagarajan, Wilmington, DE (US); Tina K. Van Dyk, Wilmington, DE (US); Rick W. Ye, Hockessin, DE (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 411 days.

(21) Appl. No.: 12/330,534

(22) Filed: Dec. 9, 2008

(65) Prior Publication Data
US 2009/0203097 A1 Aug. 13, 2009

Related U.S. Application Data

(60) Provisional application No. 61/015,728, filed on Dec. 21, 2007, provisional application No. 61/015,732, filed on Dec. 21, 2007.

(51) Int. Cl.
*C12P 7/16* (2006.01)
*C12N 9/00* (2006.01)
*C12N 1/20* (2006.01)
*C12N 15/00* (2006.01)
*C07H 21/04* (2006.01)

(52) U.S. Cl.
USPC ........ 435/160; 435/183; 435/193; 435/252.3; 435/320.1; 536/23.2

(58) Field of Classification Search
None
See application file for complete search history.

(56) References Cited

U.S. PATENT DOCUMENTS

| 5,192,673 | A | 3/1993 | Jain et al. |
|---|---|---|---|
| 6,358,717 | B1 | 3/2002 | Blaschek et al. |
| 6,960,465 | B1 | 11/2005 | Papoutsakis et al. |
| 8,372,612 | B2 | 2/2013 | LaRossa et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2009/0155870 | A1 | 6/2009 | Donaldson et al. |
| 2009/0162911 | A1 | 6/2009 | LaRossa et al. |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Butanols, Ullmann's Encyclopedia of Industrial Chemistry, Sixth Edition, 2003, vol. 5:716-719.
Carlini et al., Guerbet Condensation of Methanol With N-Propanol to Isobutyl Alcohol Over Heterogeneous Copper Chromite/MG-A1 Mixed Oxides Catalysts, J. Molec. Catal. A: Chem., 2004, vol. 220, 215-220.
Girbal et al., Regulation of Solvent Production in Clostridium Acetobutylicum, Trends in Biotechnology, 1998, vol. 16, 11-16.
Tomas et al., Overexpression of Groesl in Clostridium Acetobutylicum Results in Increased Solvent Production and Tolerance, Prolonged Metabolism, and Change in the Cell's Transcriptional Program, Appl. Environ. Microbiol., 2003, vol. 69, No. 8, 4951-4965.
Quratulain et al., Development and Characterization of Butanol-Resistant Strain of Clostridium Acetobutylicum in Molasses Medium, Folia Microbiologica, 1995, vol. 40, No. 5, 467-471.
Soucaille et al., Butanol Tolerance and Autobacteriocin Production by Clostridium Acetobutylicum, Current Microbiology, 1987, vol. 14:295-299.
Zhao et al., Expression of a Cloned Cyclopropane Fatty Acid Synthase Gene Reduces Solvent Formation in Clostridium Acetobutylicum ATCC 824, Appl. and Environ. Microbiology, 2003, vol. 69, No. 5, 2831-2841.
Desmond et al., Improved Stress Tolerance of Groesl-Overproducing Lactococcus Lactis and Probiotic Lactobacillus Paracasei NFBC 338, Appl. Environ. Microbiol., 2004, vol. 70, No. 10, 5929-5936.
Sardessai et al., Organic Solvent-Tolerant Bacteria in Mangrove Ecosystem, Current Science, 2002, vol. 82, No. 6, 622-623.
Bieszkiewicz et al., Studies on Resistance of Activated Sludge Bacteria to High Concentrations of Methanol. Butanol. Glycol. Cyclohexanone and Cyclohexylamine, Acta Microbiologica Polonica, 1987, vol. 36, No. 3, 259-265.
Kristien Braeken et al., New Horizons for (P) PPGPP in Bacterial and Plant Physiology, Trends in Microbiology, 2006, vol. 14, No. 1, 45-54.
Ying-Ying Chang et al., Membrane Cyclopropane Fatty Acid Conent is a Major Factor in Acid Resistance of *Escherichia coli*, Molecular Microbiology, 1999, vol. 33, No. 2, 249-259.
Johannes Eichel et al., Effect of PPGPP on *Escherichia coli* Cyclopropane Fatty Acid Synthesis Is Mediated Through the RPOS SIGMA Factor, Journal of Bacteriology, 1999, vol. 181:572-576.
Cosette Grandvalet et al., Changes in Membrane Lipid Composition in Ethanol and Acid-Adapted Oenococcus Oeni Cells: Characterization of the CFA Gene by Heterologous Complementation, Microbiology, 2008, vol. 154:2611-2619.
Dennis W. Grogan et al., Cyclopropane Ring Formation in Membrane Lipids of Bacteria, Microbiology and Molecular Biology Reviews, 1997, vol. 61, No. 4, D429-441.
C. Lepage et al., Changes in Membrane Lipid Composition of Clostridium Acetobutylicum During Acetone-Butanol Fermentation: Effects of Solvents, Growth Temperature and Ph, Journal of General Microbiology, 1987, vol. 133:103-110.
Katarzyna Potrykus et al., (p) PPGPP: Still Magical?, Annu. Rev. Microbiol., 2008, vol. 62:35-51.

(Continued)

*Primary Examiner* — Christian Fronda
(74) *Attorney, Agent, or Firm* — Christine M. Lhulier

(57) ABSTRACT

Screening of fatty acid fed bacteria which are not natural butanol producers identified increased membrane cyclopropane fatty acid as providing improved butanol tolerance. Increasing expression of cyclopropane fatty acid synthase in the presence of the enzyme substrate that is either endogenous to the cell or fed to the cell, increased butanol tolerance. Bacterial strains with increased cyclopropane fatty acid synthase and having a butanol biosynthetic pathway are useful for production of butanol.

26 Claims, 3 Drawing Sheets

(56) References Cited

OTHER PUBLICATIONS

Kathryn Vollherbst-Schneck et al., Effect of Butanol on Lipid Composition and Fluidity of Clostridium Acetobutylicum ATCC 824, Applied and Environmental Microbiology, 1984, vol. 47, No. 1, 193-194.
International Search Report and Written Opinion of corresponding PCT/US2008/087646 mailed Mar. 11, 2009.
Couto et al., "Enhancement of apparent resistance to ethanol in *Lactobacillus hilgardii*," Biotechnol. Lett. 19(5):487-90 (1997).
Gentry et al., "Mutational analysis of the *Escherichia coli* spoT gene identifies distinct but overlapping regions involved in ppGpp synthesis and degradation," Mol. Microbiol. 19(6):1373-84 (1996).
Ingram et al., "Effects of alcohols on microorganisms," Adv. Microbial. Physiol. 25:253-300 (1984).
International Search Report and Written Opinion of PCT/US2008/087598 mailed Mar. 11, 2009.
Mitchell et al., "The effect of alcohols on guanosine 5'-diphosphate-3-diphosphate metabolism in stringent and relaxed *Escherichia coli*," JBC 255(13):6307-13 (1980).
Mittenhuber, "Comparative genomics and evolution of genese encoding bacterial (p)ppGpp synthetases/hydrolases (The Rel, RelA and spoT proteins)," J. Mol. Microbiol. Biotechnol. 3(4):585-600 (2001).
Office Action in U.S. Appl. No. 12/330,530 mailed on Feb. 1, 2012.
Paul et al., "DksA potentiates direct activation of amino acid promoters by ppGpp," PNAS 102(22):7823-8 (2005).
Srivatsan et al., "Control of bacterial transcription, translation and replication by (p)ppGpp," Curr. Opin. Microbiol. 11 (2):100-5 (2008).

Baba et al., "Construction of *Escherichia coli* K-12 in-frame, single gene knockout mutants: the Keio collection," Mol. Syst. Biol. 2:2006.0008 (2006).
Battesti and Bouveret, "Acyl carrier protein/SpoT interaction, the switch linking SpoT—dependent stress response to fatty acid metabolism," Molecular Microbiology 62:1048-1063 (2006).
Cashel et al., "The stringent response," Chapter 92, in F. C. Neidhardt (ed.), *Escherichia coli* and Salmonella: Cellular and Molecular Biology, 2nd Ed. ASM Press, Washington, DC (1996).
Chaloner-Larsson and Yamazaki, "Effects of the spoT and relA mutation on the synthesis and accumulation of ppGpp and RNA during glucose starvation," Can. J. Biochem. 56:264-72 (1978).
Datsenko and Wanner, "One-step inactivation of chromosomal genes in Escherichia coli K-12 using PCR products," Proc. Natl. Acad. Sci. USA 97:6640-6645 (2000).
Fujita et al., "Guanosine 5'-diphosphate 3'-diphosphate (ppGpp) synthetic activities on *Escherichia coli* SpoT domains," Biosci. Biotechnol. Biochem. 66:1515-1523 (2002).
Hernandez and Bremer, "*Escherichia coli* ppGpp synthetase II activity requires spoT," J. Biol. Chem. 266:5991-9 (1991).
Mechold et al., "Intramolecular regualtion of the opposing (p)ppGpp catalytic activities of Rel(seq), the Rel/Spo enzyme from *Streptococcus equisimilis*," J. Bacteriol. 184:2878-88 (2002).
Seyfzadeh and Keener, "spoT-dependent accumulation of guanosine tetraphosphate in response to fatty acid starvation in *Escherichia coli*," Proc. Natl. Acad.Sci. U S A 90:11004-8 (1993).

\* cited by examiner

STRAIN COMPRISING INCREASED EXPRESSION OF A CFA CODING REGION FOR BUTANOL PRODUCTION

CROSS REFERENCE TO RELATED APPLICATIONS

This application claims the benefit of U.S. Provisional Applications 61/015,728 and 61/015,732, both filed Dec. 21, 2007.

FIELD OF INVENTION

The invention relates to the fields of microbiology and genetic engineering. More specifically, altered membrane cyclopropane fatty acid composition was found to play a role in butanol tolerance in bacteria which are not natural butanol producers.

BACKGROUND OF INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of butanols are known. For example, 1-butanol may be produced using the Oxo process, the Reppe process, or the hydrogenation of crotonaldehyde (*Ullmann's Encyclopedia of Industrial Chemistry*, 6$^{th}$ edition, 2003, Wiley-VCH Verlag GmbH and Co., Weinheim, Germany, Vol. 5, pp. 716-719). 2-Butanol may be produced using n-butene hydration (*Ullmann's Encyclopedia of Industrial Chemistry*, 6$^{th}$ edition, 2003, Wiley-VCH Verlag GmbH and Co., Weinheim, Germany, Vol. 5, pp. 716-719). Additionally, isobutanol may be produced using Oxo synthesis, catalytic hydrogenation of carbon monoxide (*Ullmann's Encyclopedia of Industrial Chemistry*, 6$^{th}$ edition, 2003, Wiley-VCH Verlag GmbH and Co., Weinheim, Germany, Vol. 5, pp. 716-719) or Guerbet condensation of methanol with n-propanol (Carlini et al., *J. Molec. Catal. A: Chem.* 220:215-220 (2004)). These processes use starting materials derived from petrochemicals, are generally expensive, and are not environmentally friendly.

Methods of producing butanol by fermentation are also known, where the most popular process produces a mixture of acetone, 1-butanol and ethanol and is referred to as the ABE processes (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Additionally, recombinant microbial production hosts expressing a 1-butanol biosynthetic pathway (Donaldson et al., copending and commonly owned U.S. Patent Application Publication No. US20080182308A1), a 2-butanol biosynthetic pathway (Donaldson et al., copending and commonly owned U.S. Patent Application Publication Nos. US20070259410A1 and US 20070292927A1), and an isobutanol biosynthetic pathway (Maggio-Hall et al., copending and commonly owned U.S. Patent Publication No. US 20070092957) have been described. However, biological production of butanols is believed to be limited by butanol toxicity to the host microorganism used in the fermentation.

Bacteria of the genus *Clostridium* naturally produce butanol and have some natural tolerance to butanol. Strains of *Clostridium* that have increased tolerance to 1-butanol have been isolated by chemical mutagenesis (Jain et al. U.S. Pat. No. 5,192,673; and Blaschek et al. U.S. Pat. No. 6,358,717), overexpression of certain classes of genes such as those that express stress response proteins (Papoutsakis et al. U.S. Pat. No. 6,960,465; and Tomas et al., *Appl. Environ. Microbiol.* 69(8):4951-4965 (2003)), and by serial enrichment (Quratulain et al., *Folia Microbiologica* (Prague) 40(5):467-471 (1995); and Soucaille et al., *Current Microbiology* 14(5):295-299 (1987)). Overexpression in *Clostridium* of the endogenous gene encoding cyclopropane fatty acid synthase increased the cyclopropane fatty acid content of early log phase cells and initial butanol resistance (Zhao et al. (2003) Appl. and Environ. Microbiology 69:2831-2841).

Desmond et al. (*Appl. Environ. Microbiol.* 70(10):5929-5936 (2004)) report that overexpression of GroESL, two stress responsive proteins, in *Lactococcus lactis* and *Lactobacillus paracasei* produced strains that were able to grow in the presence of 0.5% volume/volume (v/v) [0.4% weight/volume (w/v)] 1-butanol. Additionally, the isolation of 1-butanol tolerant strains from estuary sediment (Sardessai et al., *Current Science* 82(6):622-623 (2002)) and from activated sludge (Bieszkiewicz et al., *Acta Microbiologica Polonica* 36(3):259-265 (1987)) has been described. However, for most bacteria described in the art, particularly those that do not naturally produce butanol, growth is highly inhibited at low concentrations of 1-butanol.

There is a need, therefore, for bacterial host strains which do not naturally produce butanol but can be engineered to express a butanol biosynthetic pathway, to be more tolerant to these chemicals. In addition there is a need for methods of producing butanols using bacterial host strains engineered for butanol production that are more tolerant to these chemicals.

SUMMARY OF THE INVENTION

The invention provides a recombinant bacterial cell which does not naturally produce butanol, but which is engineered to express a butanol biosynthetic pathway, that comprises a genetic modification that affects an enzyme activity that increases the concentration of cyclopropane fatty acid in the cell membrane fatty acid composition as compared with a wildtype bacterial cell lacking the genetic modification. Such cells have an increased tolerance to butanol as compared with cells that lack the genetic modification. Increased membrane cyclopropane fatty acid composition may be accomplished via increased expression of a gene encoding a cyclopropane fatty acid synthase. The cyclopropane fatty acid synthase substrate is present in the cells either naturally as an endogenous component, or is provided exogenously to the cells.

Accordingly, the invention provides a recombinant bacterial cell which is engineered to produce butanol, and comprises at least one genetic modification affecting an enzyme activity that increases the concentration of cyclopropane fatty acid in the cell membrane fatty acid composition as compared with a wildtype bacterial cell lacking said genetic modification;

wherein the cell contains the substrate for said enzyme; and wherein the cell does not naturally produce butanol.

In one embodiment the invention provides a recombinant host cell comprising a recombinant biosynthetic pathway selected from the group consisting of:

a) a 1-butanol biosynthetic pathway;
b) a 2-butanol biosynthetic pathway; and
c) an isobutanol biosynthetic pathway.

In an alternate embodiment the invention comprises a host cell wherein the at least one genetic modification increases cyclopropane fatty acid synthase activity. In another embodiment the invention provides an additional genetic modification which reduces accumulation of (p)ppGpp as defined here.

In another embodiment the invention provides a process for generating the recombinant cell of the invention comprising:
  a) providing a recombinant bacterial host cell comprising an engineered butanol biosynthetic pathway that is producing butanol; and
  b) creating at least one genetic modification which increases cyclopropane fatty acid in the cell membrane fatty acid composition above natural levels, provided that the bacterial cell does not naturally produce butanol.

In another embodiment the invention provides a process for production of butanol from a recombinant bacterial cell comprising:
  (a) providing a recombinant bacterial host cell that does not naturally produce butanol which
    1) is engineered with a butanol biosynthetic pathway and produces butanol; and
    2) comprises at least one genetic modification which affects an enzyme activity that increases the concentration of cyclopropane fatty acid in the cell membrane fatty acid composition as compared with a wild-type bacterial cell lacking said genetic modification; and
  (b) culturing the strain of (a) under conditions wherein butanol is produced.

BRIEF DESCRIPTION OF THE FIGURES AND SEQUENCE DESCRIPTIONS

The various embodiments of the invention can be more fully understood from the following detailed description, the figures, and the accompanying sequence descriptions, which form a part of this application.

Figure 1A:
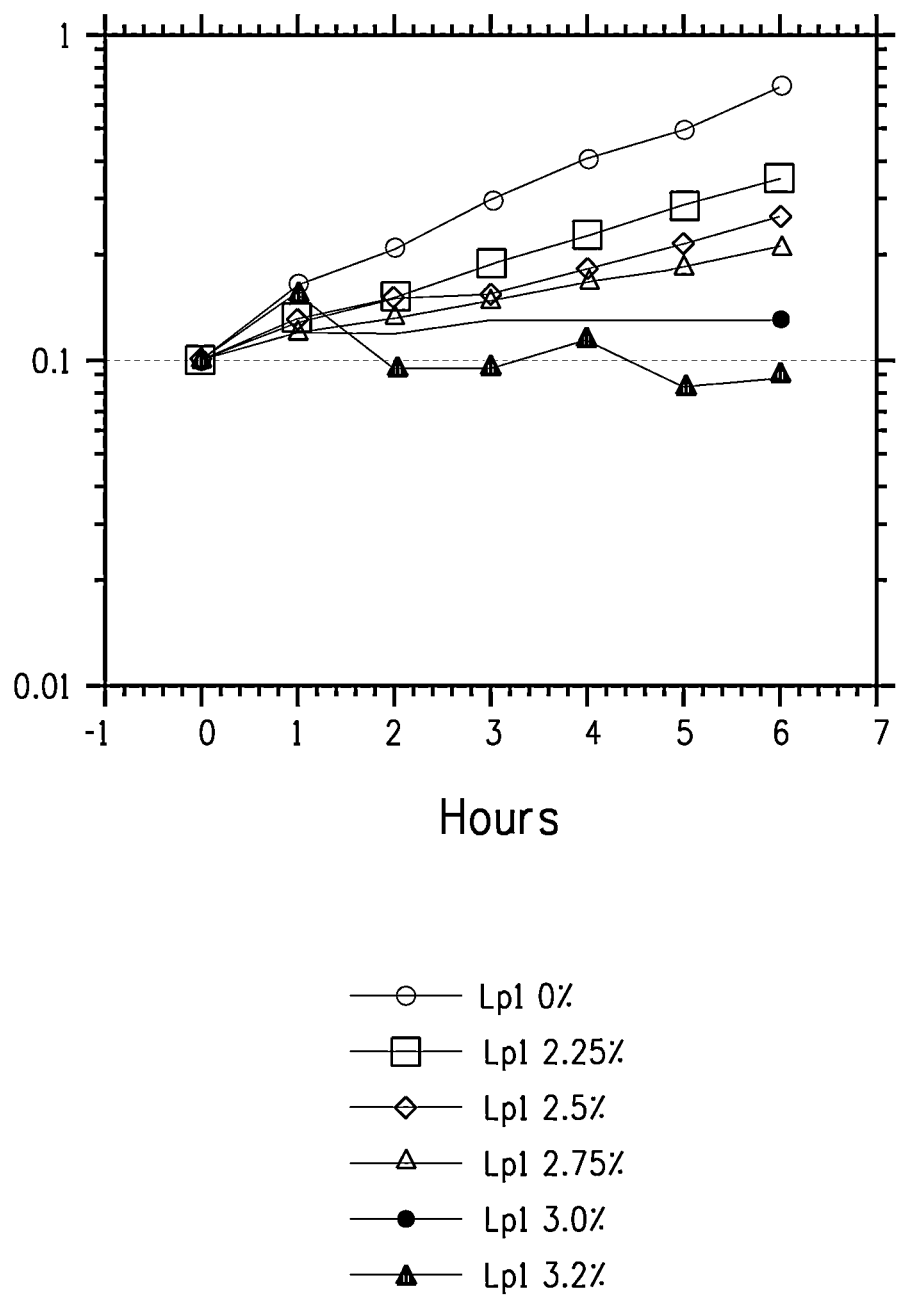
FIG. 1A shows a graph of the growth of *L. plantarum* PN2001, with cfa1 multicopy expression, in the presence of various concentrations of isobutanol.

Table 6 is a table of the Profile HMM for the RelA/SpoT domain. Table 6 is submitted herewith electronically and is incorporated herein by reference.

Table 7 is a table of the Profile HMM for the TGS domain. Table 7 is submitted herewith electronically and is incorporated herein by reference.

Table 8 is a table of the Profile HMM for the HD domain. Table 8 is submitted herewith electronically and is incorporated herein by reference.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers for 1-Butanol Biosynthetic Pathway

| Description | SEQ ID NO: Nucleic aid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| 3-Hydroxybutyryl-CoA dehydrogenase from *Clostridium acetobutylicum* ATCC 82 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| *Euglena gracilis* butyryl-CoA dehydrogenase/trans-2-enoyl-CoA reductase codon optimized | 110 | 114 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATCC 824 | 15 | 16 |

TABLE 2

Summary of Gene and Protein SEQ ID Numbers for 2-Butanol Biosynthetic Pathway

| Description | SEQ ID NO: Nucleic aid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus ruber* 219 | 29 | 30 |

TABLE 3

Summary of Gene and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *E. coli* ilvC (acetohydroxy acid reductoisomerase) | 31 | 32 |
| *B. subtilis* ilvC (acetohydroxy acid reductoisomerase) | 105 | 113 |
| *E. coli* ilvD (acetohydroxy acid dehydratase) | 33 | 34 |
| *Lactococcus lactis* kivD (branched-chain α-keto acid decarboxylase), codon optimize | 35 | 36 |
| *E. coli* yqhD (branched-chain alcohol dehydrogenase) | 37 | 38 |

TABLE 4

Representative spoT and relA modification target genes and encoded proteins

| Organism | Gene name | SEQ ID NO: Nucleic acid | SEQ ID NO: Peptide |
|---|---|---|---|
| E. coli | spoT | 39 | 40 |
| E. coli | relA | 41 | 42 |
| Lactobacillus plantarum WCFS1 | spoT | 43 | 44 |
| Bacillus licheniformis ATCC 14580 | spoT | 45 | 46 |
| Bacillus subtilis subsp. subtilis str. 168 | spoT | 47 | 48 |
| Pseudomonas putida KT2440 | relA | 49 | 50 |
| Pseudomonas putida KT2440 | spoT | 51 | 52 |
| Enterococcus faecium | spoT-1 | 53 | 54 |
| Enterococcus faecium | spoT-2 | 55 | 56 |
| Enterococcus faecalis | spoT | 57 | 58 |
| Rhodococcus erythropolis | spoT | 59 | 60 |

TABLE 5

Representative cfa genes and encoded proteins

| Organism | Gene name | SEQ ID NO: Nucleic acid | SEQ ID NO: Peptide |
|---|---|---|---|
| Lactobacillus plantarum | cfa1 | 61 | 62 |
| Lactobacillus plantarum | cfa2 | 63 | 64 |
| E. coli | cfa | 65 | 66 |
| Pseudomonas putida | cfa | 67 | 68 |
| Enterococcus faecalis | cfa | 69 | 70 |

SEQ ID NO:71 is the nucleotide sequence of pFP996.

SEQ ID NOs:72 and 73 are primers for PCR amplification of the L. Plantarum fba promoter.

SEQ ID NO:74 is the nucleotide sequence of the L. Plantarum atpB promoter.

SEQ ID NOs:75 and 76 are primers for PCR amplification of the L. Plantarum atpB promoter.

SEQ ID NOs:77 and 78 are primers for PCR amplification of the L. Plantarum bdhB coding region.

SEQ ID NO:79 is the nucleotide sequence of a synthetic DNA fragment containing a 5' Shine-Delgarno sequence and bdhB coding region.

SEQ ID NOs:80 and 81 are primers for PCR amplification of the L. Plantarum cfa1 coding region.

SEQ ID NOs:82 and 83 are primers for PCR amplification of the L. Plantarum cfa2 coding region.

SEQ ID NOs:84 and 85 are primers for PCR amplification of the E. coli cfa coding region.

SEQ ID NOs:86 and 87 are primers for PCR amplification of an internal fragment of the L. plantarum spoT coding region.

SEQ ID NOs:88 and 89 are primers for PCR amplification of portion of the Bacillus shuttle vector pMK4.

SEQ ID NOs:90 and 91 are primers for PCR amplification to confirm pMPE69 insertion into the spoT gene.

SEQ ID NOs:92 and 93 are primers for PCR amplification of the region from plasmid pDEW849 with the trc promoter and the E. coli cfa coding region.

SEQ ID NOs:94 and 95 are primers for PCR amplification of a DNA fragment from Lactobacillus plantarum (Genbank NC_004567) with homology to ldhL.

SEQ ID NO:96 is the integration vector pFP988.

SEQ ID NOs:97 and 98 are primers for PCR amplification of the Cm resistance gene with its promoter from pC194 (GenBank NC_002013).

SEQ ID NOs:99 and 100 are oligonucleotides for constructing the P11 promoter.

SEQ ID NOs:101 and 102 are primers for PCR amplification of the L. plantarum ldhL promoter.

SEQ ID NOs:103 and 104 are primers for PCR amplification of the L. plantarum cfa1 coding region.

SEQ ID NO:105 is the Bacillus subtilis ilvC coding region.

SEQ ID NOs:106 and 107 are oligonucleotides for constructing the P11 promoter.

SEQ ID NOs:108 and 109 are primers for PCR amplification of the L. plantarum ldhL promoter.

SEQ ID NO:110 is the sequence of a DNA fragment containing a codon optimized Euglena gracilis butyryl-CoA dehydrogenase lacking the normal mitochondrial presequence.

SEQ ID NOs:111 and 112 are primers for PCR amplification of the atpB promoter and cfa1 gene.

DETAILED DESCRIPTION OF THE INVENTION

The invention provides a recombinant bacterial cell which does not naturally produce butanol, but which is engineered to express a butanol biosynthetic pathway, that comprises a genetic modification that affects an enzyme activity that increases the concentration of cyclopropane fatty acid in the cell membrane fatty acid composition as compared with a wildtype bacterial cell lacking the genetic modification. Such cells have an increased tolerance to butanol as compared with cells that lack the genetic modification. A tolerant bacterial strain of the invention has at least one genetic modification that causes increased concentration of cyclopropane fatty acid in the cell membrane. Increase in membrane cyclopropane fatty acid may be accomplished via increased expression of a cyclopropane fatty acid synthase.

Host cells of the invention are engineered to produce butanol.

Butanol produced using the present strains may be used as an alternative energy source to fossil fuels. Fermentive production of butanol results in less pollutants than typical petrochemical synthesis.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 1-butanol, 2-butanol, isobutanol, or mixtures thereof.

The terms "butanol tolerant bacterial strain" and "tolerant" when used to describe a modified bacterial strain of the invention, refers to a modified bacterium that shows better growth in the presence of butanol than the parent strain from which it is derived.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and H₂O. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase (TER), refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (Enzyme Nomenclature 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence, L04470 NCBI nucleotide sequence), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos:

AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB14789, Z99118).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550, NC_001142), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "dksA" refers to a gene that encodes the DksA protein, which binds directly to RNA polymerase affecting transcript elongation and augmenting the effect of the alarmone ppGpp on transcription initiation.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "(p)ppGpp" refers to either ppGpp or pppGpp, or a combination of both compounds.

The term "relA" refers to a gene that encodes a RelA protein which is a mono-functional enzyme with GTP pyrophosphokinase activity (EC 2.7.6.5), for synthesis of (p)ppGpp. Although in the literature some genes encoding enzymes with (p)ppGpp synthesis and degradation activities are called relA, herein these will be referred to as spoT instead of relA.

The term "spoT" refers to a gene that encodes a SpoT protein, which is a bi-functional enzyme with both GTP pyrophosphokinase, (EC 2.7.6.5) activity for synthesis of (p)ppGpp, and ppGpp pyrophosphohydrolase (EC3.1.7.2) activity for degradation of (p)ppGpp. The related RelA and SpoT proteins and their encoding genes are distinguished by both enzyme activities and domain architectures as described below.

The term "RelA/SpoT" domain will refer to a portion of the SpoT or RelA proteins that may be used to identity SpoT or RelA homologs.

As used herein "TGS domain" will refer to a portion of the SpoT or RelA protein that may be used to identity SpoT and RelA homologs. The TGS domain is named after ThrRS, GTPase, and SpoT and has been detected at the amino terminus of the uridine kinase from the spirochaete *Treponema pallidum*. TGS is a small domain that consists of ~50 amino acid residues and is predicted to possess a predominantly beta-sheet structure. Its presence in two types of regulatory proteins (the GTPases and guanosine polyphosphate phosphohydrolases/synthetases) suggests that it has a nucleotide binding regulatory role. The TGS domain is not unique to the SpoT or RelA protein, however, in combination with the presence of the HD domain and the SpoT/RelA domain it is diagnostic for a protein having SpoT function. In combination with the SpoT/RelA domain, the TGS domain is diagnostic for a protein having RelA function.

The term "HD domain" refers to an amino acid motif that is associated with a superfamily of metal-dependent phosphohydrolases that includes a variety of uncharacterized proteins and domains associated with nucleotidyltransferases and helicases from bacteria, archaea, and eukaryotes (Yakunin et al., *J. Biol. Chem.*, Vol. 279, Issue 35, 36819-36827, Aug. 27, 2004). The HD domain is not unique to the SpoT protein, however in combination with the SpoT/RelA domain and the TGS domain, it may be used to identify SpoT proteins according to the methods described herein.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

As used herein, "substantially similar" enzymes will refer to enzymes belonging to a family of proteins in the art known to share similar structures and function. It is well within the skill of one in the art to identify substantially similar proteins given a known structure. Typical methods to identify substantially similar structures will rely upon known sequence information (nucleotide sequence and/or amino acid sequences) and may include PCR amplification, nucleic acid hybridization, and/or sequence identity/similarity analysis (e.g., sequence alignments between partial and/or complete sequences and/or known functional motifs associated with the desired activity).

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Given the nucleic acid sequences described herein, one of skill in the art can identify substantially similar nucleic acid fragments that may encode proteins having similar activity. Hybridization and washing conditions are well known and exemplified in Sambrook, J., Fritsch, E. F. and Maniatis, T. *Molecular Cloning: A Laboratory Manual*, 3rd ed., Cold Spring Harbor Laboratory Cold Spring Harbor, N.Y. (2001), particularly Chapter 11 and Table 11.1 therein. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS at 65° C. followed by 0.1×SSC, 0.1% SDS at 65° C., for example.

In one aspect, suitable nucleic acid fragments encode polypeptides that are at least about 70% identical to the amino acid sequences reported herein. In another aspect, the nucleic acid fragments encode amino acid sequences that are about 85-90% identical to the amino acid sequences reported herein. In a further aspect, the nucleic acid fragments encode amino acid sequences that are at least about 90-100% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in:

1.) *Computational Molecular Biology* (Lesk, A. M., Ed.) Oxford University: NY (1988); 2.) Biocomputing: Informatics and Genome Projects (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "homology" refers to the relationship among sequences whereby there is some extent of likeness, typically due to descent from a common ancestral sequence. Homologous sequences can share homology based on genic, structural, functional and/or behavioral properties. The term "ortholog" or "orthologous sequences" refers herein to a relationship where sequence divergence follows speciation (i.e., homologous sequences in different species arose from a common ancestral gene during speciation). In contrast, the term "paralogous" refers to homologous sequences within a single species that arose by gene duplication. One skilled in the art will be familiar with techniques required to identify homologous, orthologous and paralogous sequences.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein, "default values" will mean any set of values or parameters (as set by the software manufacturer) which originally load with the software when first initialized.

Standard recombinant DNA and molecular cloning techniques used here are well known in the art and are described by Sambrook, J., Fritsch, E. F. and Maniatis, T. *Molecular Cloning: A Laboratory Manual*, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

Butanol Tolerance in Butanol Non-Producing Bacteria—Membrane Composition

The invention relates to the discovery that events that increase the cyclopropane fatty acid content of the membrane of a bacterial cell that does not naturally produce butanol increases butanol tolerance of the cell. The discovery came from results of studies on feeding butanol non-producing bacterial cells with different fatty acids followed by screening for butanol tolerance. Among the about ten different fatty acids tested, it was found that feeding specifically with the cyclopropane fatty acid dihydrosterculic acid provided increased butanol tolerance.

Increasing Membrane Cyclopropane Fatty Acids

In the bacterial cells of the present invention, at least one genetic modification is made that affects an enzyme activity that increases the concentration of cyclopropane fatty acid in the cell membrane fatty acid composition as compared with a wildtype bacterial cell lacking the genetic modification. The genetic modification may be made in any bacterial cell that does not naturally make butanol. Examples include, but are not limited to, bacterial cells of *Escherichia, Rhodococcus, Pseudomonas, Bacillus, Lactobacillus*, and *Enterococcus*, Specifically, a genetic modification is made that increases cyclopropane fatty acid synthase activity in the bacterial cell. The activity level may be increased by mutation of the coding region to provide an enzyme with higher levels of activity, or by increased expression of a gene encoding the enzyme. The activity level of the enzyme may be increased by mutagenesis and selection or screening using methods well known to one skilled in the art. Methods for increasing expression of a gene in a bacterial cell are common and well known in the art and may be applied to the exercise of increasing cyclopropane fatty acid synthase.

One method is to increase the level of expression of an endogenous gene encoding cyclopropane fatty acid synthase (of a cfa gene). Increased expression of an endogenous gene may be achieved by introducing multiple copies on a plasmid, introducing multiple copies into the genome, and/or expressing the coding region from a stronger promoter than the natural promoter (either from a plasmid or in the genome). For example, the natural promoter may be replaced with a stronger promoter using promoter replacement methods for exchanging the endogenous transcriptional control elements such as described in Yuan et al. (Metab Eng. (2006) 8:79-90). Increased expression of either the endogenous cfa1 gene (coding region SEQ ID NO: 61; encoded protein SEQ ID NO: 62) or cfa2 gene (coding region SEQ ID NO: 63; encoded protein SEQ ID NO: 64) of *Lactobacillus plantarum* is described in Examples 1 and 2 herein. Also described herein in Example 3 is increased expression of the endogenous cfa gene (coding region SEQ ID NO: 65; encoded protein SEQ ID NO: 66) in *E. coli*. Any bacterial cell having at least one endogenous cfa gene may be modified for increased expression of endogenous cyclopropane fatty acid synthase. Some representative cfa genes, including coding region sequences and amino acid sequences of the encoded proteins of various bacteria are given in Table 5 as SEQ ID NOs:61-70. Additional cfa genes may be identified and isolated using methods including bioinformatics, sequence comparison, hybridization, and PCR amplification as described below.

Accordingly the invention provides a recombinant cell wherein the cfa coding region is an isolated nucleic acid molecule selected from the group consisting of:

a) an isolated nucleic acid molecule encoding an amino acid sequence selected from the group consisting of SEQ ID NO:61, 63, 65, 67 and 69;

b) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; and c) an isolated nucleic acid molecule that encodes a polypeptide having 95% identity based on the Clustal method of alignment when compared to a polypeptide having an amino acid sequence selected from the group consisting of SEQ ID NO:61, 63, 65, 67, and 69.

Alternatively a heterologous cfa gene may be expressed in a bacterial cell to produce an increased level of cyclopropane fatty acid synthase activity. A heterologous cfa gene may be expressed from a plasmid, or introduced into the genome. The natural promoter may be used if it is active in the heterologous cell. More typically, a promoter that is not native to the gene and known to be active in the host bacterial cell is operably linked to the heterologous cfa coding region for expression. Examples of promoters and plasmids (vectors) that may be used for transfer and expression of cfa genes in bacteria such as *E. coli, Lactobacillus*, and *Pseudomonas* are the same as those described below for expression of butanol pathway genes.

It may be desirable to codon-optimize a heterologous coding region for optimal expression in a particular bacterial cell. Methods for codon-optimization are well known in the art.

Cfa Genes Used for Increased Cyclopropane Fatty Acid Synthase Expression

Examples of cfa genes that may be used to increase expression of cyclopropane fatty acid synthase in the present invention, in addition to those listed in Table 5, are identified in the literature and in bioinformatics databases well known to the skilled person. Additionally, the sequences described herein or those recited in the art may be used to identify other homologs in nature. For example each of the cfa nucleic acid fragments described herein may be used to isolate genes encoding homologous proteins from the same or other microbial species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the cfa genes described herein could be isolated directly by using all or a portion of the instant nucleic acid fragments as DNA hybridization probes to screen libraries from any desired bacteria using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described cfa sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Bioinformatics approaches include sequence comparisons, either nucleic acid or amino acid, using sequences described herein and sequences in databases available to the public including general sequence databases and specific genome sequence databases. In addition, databases may be used such as Pfam (Pfam: clans, web tools and services: R. D. Finn, J. Mistry, B. Schuster-Böckler, S. Griffiths-Jones, V. Hollich, T. Lassmann, S. Moxon, M. Marshall, A. Khanna, R. Durbin, S. R. Eddy, E. L. L. Sonnhammer and A. Bateman, Nucleic Acids Research (2006) Database Issue 34:D247-D251) which organizes proteins into families of structurally and functionally related members.

Substrate of Cyclopropane Fatty Acid Synthase

In the bacterial cell of the present invention, the substrate for cyclopropane fatty acid synthase is present in the cell such that the genetic modification that increases cyclopropane fatty acid synthase activity leads to increased concentration of cyclopropane fatty acid in the cell membrane. The substrate, which is a cis unsaturated moiety in a fatty acid of a membrane phospholipid, is either endogenous to the cell or is derived from unsaturated fatty acids provided exogenously to the cell. The fatty acid substrates that may be present in the cell or provided to the cell, such as in the growth medium, include but are not limited to oleic acid (C18:1 cis-9), cis-vaccenic acid (C18:1-11) and palmitoleic acid (C16:1). Cyclopropane fatty acid synthase enzymes endogenous to different bacterial cells may prefer different substrates and produce different cyclopropane fatty acids. For example, the cfa encoded enzyme of *L. plantarum* converts the endogenous substrate cis-vaccenic acid to the cyclopropane fatty acid lactobacillic acid (cis-11,12 methylene-octadecanoic acid cis-11,12-methylene-octadecanoic acid). The cfa encoded enzyme of *E. coli* converts endogenous cis-vaccenic acid (C18:1-11) and palmitoleic acid (C16:1-9) substrates to the corresponding 19cyclo and 17cyclopropane fatty acids. The *L. plantarum* cfa2 encoded enzyme does not convert an endogenous (in *L. plantarum*) substrate to cyclopropane fatty acid, but does convert oleic acid to the cyclopropane fatty acid dihydrosterculic acid when this substrate is fed to the cells in the growth medium. One skilled in the art can readily without undue experimentation determine a substrate for a particular cyclopropane fatty acid synthase and assess that it is present in the cell or if not, provide it in the growth medium.

Butanol Tolerance of Increased Cyclopropane Fatty Acid Synthase Strain

A bacterial strain of the present invention genetically modified for increased cyclopropane fatty acid synthase activity has improved tolerance to butanol. The tolerance of increased cyclopropane fatty acid synthase strains may be assessed by assaying their growth in concentrations of butanol that are detrimental to growth of the parental strains (prior to genetic modification for increased cyclopropane fatty acid synthase activity). Improved tolerance is to butanol compounds including 1-butanol, isobutanol, and 2-butanol. The amount of tolerance improvement will vary depending on the inhibiting chemical and its concentration, growth conditions and the specific genetically modified strain. For example, as shown in Example 2 herein, a cfa1 modified strain of *L. plantarum* showed improved growth over the parental strain, being inhibited by 62% in 4.5% 2-butanol while the control strain was inhibited by 79%. Also, in the presence of oleic acid a cfa2 modified strain of *L. plantarum* showed improved growth over the parental strain, being inhibited by 39% in 2.25% isobutanol while control strains were inhibited by 42% and 51%. For example, as shown in Example 3 herein, a cfa modified strain of *E. coli* showed improved growth over the parental strain, being inhibited by 50% in 0.8% isobutanol while the control strain was inhibited by 42%.

Combined Genetic Modifications for Butanol Tolerance

A separate genetic modification conferring butanol tolerance in bacterial cells is disclosed in commonly owned and co-pending U.S. Ser. No. 61/015,689 which is herein incorporated by reference. The additional modification is one that reduces accumulation of (p)ppGpp. Any genetic modification that reduces (p)ppGpp accumulation in a bacterial cell may be combined with a genetic modification that increases cyclopropane fatty acid synthase activity to confer butanol tolerance. Specifically, modifications that reduce expression of spoT and/or relA genes, or increase degradative activity relative to synthetic activity of SpoT, can reduce accumulation of (p)ppGpp. As summarized in Gentry and Cashel (Molec. Micro. 19:1373-1384 (1996)), the protein encoded by the spoT gene of *E. coli* (coding region SEQ ID NO:39; protein SEQ ID NO:40) is an enzyme having both guanosine 3'5'-bis (diphosphate) 3'-pyrophosphohydrolase (ppGppase) and 3',5'-bis(diphosphate synthetase (PSII) activities. In *E. coli* there is a closely related gene called relA (coding region SEQ ID NO:41; protein SEQ ID NO:42), which encodes an enzyme with 3',5'-bis(diphosphate synthetase (PSI) activity. In *E. coli*, the RelA protein is associated with ribosomes and is activated by binding of uncharged tRNAs to the ribosomes. RelA activation and synthesis of (p)ppGpp results in decreased production of ribosomes, and stimulation of amino acid synthesis. The spoT gene product is responsible for synthesis of (p)ppGpp (Hernandez and Bremer, J. Biol. Chem. (1991) 266:5991-9) during carbon source starvation (Chaloner-Larsson and Yamazaki Can. J. Biochem. (1978) 56:264-72; (Seyfzadeh and Keener, Proc. Natl. Acad. Sci. USA (1993) 90:11004-8) in *E. coli*.

Any bacterial gene identified as a spoT or relA gene is a target for modification in the corresponding organism to create a strain of one embodiment of the present invention with combined modifications having reduced (p)ppGpp accumulation and increased cyclopropane fatty acid synthase activity providing increased butanol tolerance. SpoT and/or relA genes and gene products from *E. coli*, *Lactobacillus plantarum*, *Bacillus licheniformis*, *Pseudomonas putida*, *Enterococcus faecium*, *Rhodococcus erythropolis* are specifically described herein (see SEQ ID NOs:39-60, listed in Table 4). Many other examples are identified in the literature and in bioinformatics databases well known the skilled person. Additionally, the sequences described herein or those recited in the art may be used to identify other homologs in nature. For example each of the SpoT/RelA nucleic acid fragments described herein may be used to isolate genes encoding homologous proteins from the same or other microbial species using the same methods described above for isolating cfa genes.

Alternatively, because spoT and relA sequences are so well known and abundant, suitable spoT and relA targets may be identified on the basis of various identifying domains and via Profile Hidden Markov Models (HMM). SpoT and RelA proteins are associated with various identifying domains which can be utilized for the identification of homologs using bioinformatic approaches. One such domain is the TGS domain associated with SpoT and RelA, which senses acylated-Acyl Carrier Protein thereby serving as the switch linking the SpoT-dependent stress response to fatty acid metabolism (Battesti and Bouveret (2006) Molecular Microbiology 62:1048-10630). Another domain is the HD domain which is associated with the SpoT protein and is also associated with a superfamily of metal-dependent phosphohydrolases. In addition to the TGS and HD domains, SpoT and RelA each have a RelA/SpoT domain that is common to both proteins.

It is relevant to note here that within the current art there is some inconsistency with respect to the differentiation between SpoT and RelA proteins. For example, although *E. coli* has both spoT and relA genes, many bacteria have a gene called spoT, but no gene called relA, or vice versa. The genetic nomenclature is not consistent from one species to another with regard to encoded enzyme activity, since in some species the protein called RelA has both synthesis and degradation activities for (p)ppGpp. In *Lactobacillus plantarum* there is no gene called spoT, and there is a gene called relA (coding region SEQ ID NO:43) which encodes a protein (SEQ ID NO:44) with both ppGppase and PSII activities. In the nomenclature herein, the *Lactobacillus plantarum* gene called relA falls under the definition of a spoT gene, and is considered to be a spoT gene encoding a SpoT protein.

For the purposes of this invention it will be understood that a SpoT protein is one that structurally contains all of the RelA/SpoT, TGS and HD domains as described below, encodes a SpoT protein which is a bi-functional enzyme with both guanosine 3'5'-bis(diphosphate) 3'-pyrophosphohydrolase (ppGppase) and 3',5'-bis(diphosphate synthetase (PSII) activities, and whose disruption affects the levels of (p)ppGpp accumulation in the cell. Similarly a RelA protein is one that contains both the RelA/SpoT and TGS domains, encodes a RelA protein which is a mono-functional enzyme with 3',5'-bis(diphosphate synthetase (PSI) activity, and whose disruption affects the levels of (p)ppGpp accumulation in the cell.

Accordingly, proteins with RelA or SpoT activities have been characterized as containing the RelA/SpoT domain and the TGS domain. These domains were identified by Pfam (Pfam: clans, web tools and services: R. D. Finn, J. Mistry, B. Schuster-Böckler, S. Griffiths-Jones, V. Hollich, T. Lassmann, S. Moxon, M. Marshall, A. Khanna, R. Durbin, S. R. Eddy, E. L. L. Sonnhammer and A. Bateman, Nucleic Acids Research (2006) Database Issue 34:D247-D251), and each is characterized by a Profile Hidden Markov Model (HMM). The Profile HMM is prepared using the hmmsearch algorithm of the HMMER software package (Janelia Farm Research Campus, Ashburn, Va.). The theory behind Profile HMMs is described in Durbin et al. ((1998) *Biological sequence analysis: probabilistic models of proteins and nucleic acids*, Cambridge University Press) and Krogh et al. ((1994) J. Mol. Biol. 235:1501-1531), which characterizes a set of proteins based on the probability of each amino acid occurring at each position in the alignment of the proteins of the set. The Profile HMM for the RelA/SpoT domain is in Table 5 and the Profile HMM for the TGS domain is in Table 6. In addition to the RelA/SpoT and TGS domains common to RelA and SpoT proteins, SpoT proteins have an HD domain, also identified by Pfam as above. The Profile HMM for the HD domain is given in Table 7. Tables 5, 6 and 7 are submitted herewith electronically and are incorporated herein by reference. Any protein which has an E-value parameter of 0.01 or less when queried using the Profile HMM for the RelA/SpoT domain and Profile HMM for the TGS domain and that lacks an HD domain can be identified as a RelA protein. Any protein which has an E-value parameter of 0.01 or less when queried using the profiles for these two domains and the Profile HMM for the HD domain can be identified as a SpoT protein. A tree of all known sequences fitting these profiles is shown in FIG. 9. Also marked on the tree are a set of RelA-SpoT related proteins that do not fit the Profile HMMs for RelA and SpoT proteins.

Accordingly in one embodiment the invention provides recombinant bacterial cells wherein an additional genetic modification down regulates a genetic construct encoding, or causes reduced production of, a protein having a) an E-value parameter of 0.01 or less when queried using the Pfam Profile HMM for the RelA/SpoT domain; and b) an E-value parameter of 0.01 or less when queried using the Pfam Profile HMM for the TGS domain; and c) an E-value parameter of 0.01 or less when queried using the Pfam Profile HMM for the HD domain. In another embodiment the invention provides a recombinant bacterial cell wherein the genetic modification down regulates a genetic construct encoding, or causes reduced production of, a protein having; a) an E-value parameter of 0.01 or less when queried using the Pfam Profile HMM for the TGS domain; and an E-value parameter of 0.01 or less when queried using the Pfam Profile HMM for the RelA/SpoT domain. Sequences encoding RelA and SpoT proteins identify relA and spoT genes that may be modified to create bacterial strains of the present invention. In the present bacterial strains, a modification is engineered that results in reduced (p)ppGpp accumulation. This may be accomplished by reduction or elimination of expression of an endogenous spoT and/or relA gene in several ways. Synthesis of ppGpp can be blocked by insuring that the pools of charged tRNA are balanced. The genetic modification may down regulate a genetic construct encoding a SpoT or RelA protein. If the bacterial host has only a relA or a spoT gene, then reduced (p)ppGpp accumulation is obtained by modification of the endogenous relA or spoT gene, causing reduced expression to confer butanol tolerance. If the bacterial host has both genes, then both relA and spoT genes are modified, causing reduced expression of both genes, to confer butanol tolerance. The spoT gene may be modified so that there is no expression, if expression of the relA gene is reduced. Alternatively, with relA unmodified, the expression of spoT may be lowered to provide increased tolerance. In addition, when the bacterial host has both genes, then modification for reduced expression of relA is sufficient to confer butanol tolerance under conditions where an aminoacyl-tRNA species is low and RelA production of (p)ppGpp would be high. Thus effects of the relA mutation in limited aminoacyl-tRNA species conditions better exemplifies the impact on butanol tolerance of RelA-dependent (p)ppGpp synthesis. For example, *E. coli* has both relA and spoT genes as described above. Elimination of spoT expression in a strain where relA expression is reduced, (as demonstrated in Example 3 of commonly owned and co-pending U.S. Ser. No. 61/015,689 which is herein incorporated by reference) confers butanol tolerance. Reduced expression of spoT in a strain where relA expression is unmodified, (as demonstrated in Example 4 of commonly owned and co-pending U.S. Ser. No. 61/015,689 which is herein incorporated by reference) confers butanol tolerance.

*Pseudomonas putida* also has a relA (coding region of SEQ ID NO:49; encoded protein of SEQ ID NO:50) and a spoT gene (coding region of SEQ ID NO:51; encoded protein of SEQ ID NO:52) which can be modified as described for *E. coli* to confer butanol tolerance.

*Lactobacillus plantarum* has only a spoT gene (which is called relA in the literature), and this gene (coding region has SEQ ID NO:43; encoded protein of SEQ ID NO:44) may be modified to reduce expression and confer butanol tolerance. *Bacillus licheniformis Bacillus subtilis, Enterococcus faecalis*, and *Rhodococcus erythropolis* each have a SpoT protein (SEQ ID NOs: 46, 48, 58, and 60, respectively). In each bacterial host the encoding spoT gene (coding regions of SEQ ID NOs:45, 47, 57, and 59, respectively) can be modified to reduce expression, reduce (p)ppGpp synthesis, and increase tolerance. *Enterococcus faecium* has two SpoT proteins (SEQ ID NOs: 54 and 56) encoded by genes with coding regions (SEQ ID NOs: 53 and 55) that may be modified to reduce expression, reduce (p)ppGpp synthesis, and increase tolerance.

Any genetic modification method known by one skilled in the art for reducing the presence of a functional enzyme may be used to alter spoT or relA gene expression to reduce (p)ppGpp accumulation. Methods include, but are not limited to, deletion of the entire gene or a portion of the gene encoding SpoT or RelA, inserting a DNA fragment into the spoT or relA gene (in either the promoter or coding region) so that the protein is not expressed or expressed at lower levels, introducing a mutation into the spoT or relA coding region which adds a stop codon or frame shift such that a functional protein is not expressed, and introducing one or more mutations into the spoT or relA coding region to alter amino acids so that a non-functional or a less enzymatically active protein is expressed. In addition, spoT or relA expression may be blocked by expression of an antisense RNA or an interfering RNA, and constructs may be introduced that result in cosuppression. Moreover, a spoT or relA gene may be synthesized whose expression is low because rare codons are substituted for plentiful ones, and this gene substituted for the endogenous corresponding spoT or relA gene. Such a gene will produce the same polypeptide but at a lower rate. In addition, the synthesis or stability of the transcript may be lessened by mutation. Similarly the efficiency by which a protein is translated from mRNA may be modulated by mutation. All of these methods may be readily practiced by one skilled in the art making use of the known sequences encoding SpoT or RelA enzymes. Hundreds of spoT and relA sequences are publicly available, and representative sequences are listed in Table 4. One skilled in the art may choose specific modification strategies to eliminate or lower the expression of the relA or spoT gene as desired in the situations described above.

Alternatively, to reduce (p)ppGpp accumulation, a genetic modification may be made that increases the (p)ppGpp degradation activity present in a bacterial cell. The endogenous spoT gene may be modified to reduce the (p)ppGpp synthetic function of the encoded protein. Alternatively, a modified spoT gene encoding a protein with only degradative activity may be introduced. Regions of the SpoT protein that are responsible for the synthetic and degradative activities have been mapped (Gentry and Cashel Mol Microbiol. (1996) 19:1373-1384). The RelA/SpoT and TGS domains (described above) function in ppGpp synthesis while the HD domain is responsible for ppGpp hydrolysis. Gentry and Cashel showed that destruction of the HD domain eliminated the hydrolytic activity without loss of biosynthetic capacity while elimination of either of the other 2 domains resulted in loss of the synthetic capacity without loss of the hydrolytic activity. Thus the sequences encoding the RelA/SpoT and/or TGS domains in the endogenous spoT gene may be mutated to reduce (p)ppGpp synthetic activity. For example, in frame deletions eliminating the various dolmans can be readily synthesized in vitro and recombined into the chromosome by standard methods of allelic replacement. Examples of such deletions are readily found in the literature for both RelA (Fujita et al. Biosci. Biotechnol. Biochem. (2002) 66:1515-1523; Mechold et al J. Bacteriol. (2002) 84:2878-88) and SpoT (Battesti and Bouveret (2006) Molecular Microbiology 62:1048-10630). Furthermore, residual degradative capacity can be enhanced by increasing expression of the modified endogenous gene via chromosomal promoter replacements using methods such as described by Yuan et al (Metab. Eng. (2006) 8:79-90), and White et al. (Can. J. Microbiol. (2007) 53:56-62). Alternatively, a mutation affecting the function of either the RelA/SpoT domain or the TGS domain may be made in a spoT gene, and this gene introduced into a bacterial cell to increase (p)ppGpp degradation activity with no increase in synthesis.

DNA sequences surrounding the spoT or relA coding sequence are also useful in some modification procedures and are available for numerous bacteria such as for E. coli in the complete genome sequence of the K12 strain: GenBank Accession #U00096.2. The genome sequences of L. plantarum, L. salivarius, L sakei, L johnsonii, L. acidophilus and L. delbrueckii are known (National Center for Biotechnology Information (NCBI) database), Genbank™ identification as follows:

Lactobacillus plantarum WCFS1, complete genome gi|28376974|ref|NC_004567.1|[28376974]
Lactobacillus salivarius subsp. salivarius UCC118, complete genome gi|90960990|ref|NC_007929.1| [90960990]
Lactobacillus sakei strain 23K complete genome gi|78609255|emb|CR936503.1|[78609255]
Lactobacillus johnsonii NCC 533, complete genome gi|42518084|ref|NC_005362.1|[42518084]
Lactobacillus acidophilus NCFM, complete genome gi|58336354|ref|NC_006814.1|[58336354]
Lactobacillus delbrueckii subsp. bulgaricus ATCC 11842, complete genomegi|104773257|ref|NC_008054.1| [104773257]

Additional bacterial genome sequences are available from the E. coli Genome Project (Madison, Wis.) and other genome sequencing projects. A listing of microbial genome sequences compiled by the National Library of Medicine includes 567 completed efforts (41 archael and the rest bacterial) with another 841 in progress. In all, 1408 genomes have been or are under investigation, and information on relA and spoT genes or surrounding DNA within these sequences may be used in making relA and/or spoT modifications.

In particular, DNA sequences surrounding the spoT or relA coding sequence are useful for modification methods using homologous recombination. An example of this method is using spoT gene flanking sequences bounding a selectable marker gene to mediate homologous recombination whereby the marker gene replaces the spoT gene. Also partial spoT gene sequences and spoT flanking sequences bounding a selectable marker gene may be used to mediate homologous recombination whereby the marker gene replaces a portion of the spoT gene. In addition, the selectable marker may be bounded by site-specific recombination sites, so that following expression of the corresponding site-specific recombinase, the resistance gene is excised from the spoT gene without reactivating the latter. The site-specific recombination leaves behind a recombination site which disrupts expression of the SpoT enzyme. The homologous recombination vector may be constructed to also leave a deletion in the spoT gene following excision of the selectable marker, as is well known to one skilled in the art. Moreover, promoter replacement methods may be used to exchange the endogenous transcriptional control elements allowing another means to modulate expression (Yuan et al. ibid).

The spoT gene of E. coli is within a demonstrated operon while the spoT gene of Lactobacillus plantarum is within a gene cluster whose structure is consistent with it being an operon. When part of an operon, expression of spoT or relA may also be reduced by genetic modification of a coding region that is upstream of the spoT or relA coding region in the operon. For example in the spoT-containing operon in E. coli, upstream of the spoT coding region are coding regions for gmk (guanosine monophosphate kinase) and rpoZ (DNA-directed RNA polymerase subunit omega). A modification of the gmk or rpoZ coding region which produces a polar effect will reduce or eliminate spoT expression. Polar mutations are typically nonsense, frameshift or insertion mutations. With these types of mutations, transcription may be truncated, translational coupling is prevented, and hence both interrupted and downstream genes are not expressed. This type of modification is described in Example 2 of commonly owned and co-pending U.S. Ser. No. 61/015,689 (which is herein incorporated by reference) where a transposon insertion in rpoZ affects spoT expression and butanol tolerance. In addition, in Examples 3 and 4 of commonly owned and co-pending U.S. Ser. No. 61/015,689 (which is herein incorporated by reference) a polar modification in rpoZ was constructed resulting in butanol tolerance. In addition intergenic regions could be modified to prevent translational coupling when it is found.

In the same manner, the yrvE coding region that is upstream of the spoT coding region in an operon in the Lactobacillus plantarum genome (GenBank Accession

AL935263) may be modified to reduce spoT expression. Using gene organization information from genome sequencing of other bacterial strains allows targeted modification of coding regions in operons upstream of spoT or relA coding regions in those strains to reduce (p)ppGpp synthesis and confer butanol tolerance.

Reduced Response to (p)ppGpp

The effect of reducing accumulation of (p)ppGpp may also be obtained in the present strains by reducing responsiveness to (p)ppGpp. Any modification that affects an enzyme activity that increases the concentration of cyclopropane fatty acid in the cell membrane fatty acid composition may be combined with a modification reducing responsiveness to (p)ppGpp. Mutants with reduced response to (p)ppGpp were found in the RNA polymerase core subunit encoding genes and the RNA polymerase binding protein DksA (Potrykus and Cashel (2008) Ann. Rev. Microbiol. 62:35-51). Reduced expression of any of these proteins may be engineered to reduce the response to (p)ppGpp. In particular, reducing expression of DksA may be engineered in the present strains to confer increased tolerance to butanol and 2-butanone. Expression of the endogenous dksA gene in a target bacterial cell may be reduced using any genetic modification method such as described above for spoT or relA. The dksA gene of a target host cell may be readily recognized by one skilled in the art through bioinformatics analysis, or experimental methods as described for spoT.

Butanol Biosynthetic Pathway

In the present invention, a genetic modification conferring increased cyclopropane fatty acid in the membrane is engineered in a bacterial cell that does not naturally produce butanol, but that is engineered to express a butanol biosynthetic pathway. Either genetic modification may take place prior to the other.

The butanol biosynthetic pathway may be a 1-butanol, 2-butanol, or isobutanol biosynthetic pathway. Particularly suitable bacterial hosts for the production of butanol and modification for increased butanol tolerance include, but are not limited to, members of the genera *Escherichia, Rhodococcus, Pseudomonas, Bacillus, Lactobacillus*, and *Enterococcus*. Preferred hosts include: *Escherichia coli Pseudomonas putida, Lactobacillus plantarum, Enterococcus faecium*, and *Enterococcus faecalis*.

1-Butanol Biosynthetic Pathway

A biosynthetic pathway for the production of 1-butanol is described by Donaldson et al. in co-pending and commonly owned U.S. patent application Ser. No. 11/527,995, published as US20080182308A1, which is incorporated herein by reference. This biosynthetic pathway comprises the following substrate to product conversions:
  a) acetyl-CoA to acetoacetyl-CoA, as catalyzed for example by acetyl-CoA acetyltransferase encoded by the genes given as SEQ ID NO:1 or 3;
  b) acetoacetyl-CoA to 3-hydroxybutyryl-CoA, as catalyzed for example by 3-hydroxybutyryl-CoA dehydrogenase encoded by the gene given as SEQ ID NO:5;
  c) 3-hydroxybutyryl-CoA to crotonyl-CoA, as catalyzed for example by crotonase encoded by the gene given as SEQ ID NO:7;
  d) crotonyl-CoA to butyryl-CoA, as catalyzed for example by butyryl-CoA dehydrogenase encoded by the gene given as SEQ ID NO:9;
  e) butyryl-CoA to butyraldehyde, as catalyzed for example by butyraldehyde dehydrogenase encoded by the gene given as SEQ ID NO:11; and
  f) butyraldehyde to 1-butanol, as catalyzed for example by 1-butanol dehydrogenase encoded by the genes given as SEQ ID NO:13 or 15.

The pathway requires no ATP and generates $NAD^+$ and/or $NADP^+$, thus, it balances with the central, metabolic routes that generate acetyl-CoA.

2-Butanol Biosynthetic Pathway

Biosynthetic pathways for the production of 2-butanol are described by Donaldson et al. in co-pending and commonly owned U.S. Patent Application Publication Nos. US20070259410A1 and US 20070292927A1 which are incorporated herein by reference. One 2-butanol biosynthetic pathway comprises the following substrate to product conversions:
  a) pyruvate to alpha-acetolactate, as catalyzed for example by acetolactate synthase encoded by the gene given as SEQ ID NO:19;
  b) alpha-acetolactate to acetoin, as catalyzed for example by acetolactate decarboxylase encoded by the gene given as SEQ ID NO:17;
  c) acetoin to 2,3-butanediol, as catalyzed for example by butanediol dehydrogenase encoded by the gene given as SEQ ID NO:21;
  d) 2,3-butanediol to 2-butanone, catalyzed for example by butanediol dehydratase encoded by genes given as SEQ ID NOs:23, 25, and 27; and
  e) 2-butanone to 2-butanol, as catalyzed for example by 2-butanol dehydrogenase encoded by the gene given as SEQ ID NO:29.

Isobutanol Biosynthetic Pathway

Biosynthetic pathways for the production of isobutanol are described by Maggio-Hall et al. in copending and commonly owned U.S. patent application Ser. No. 11/586,315, published as US20070092957 A1, which is incorporated herein by reference. One isobutanol biosynthetic pathway comprises the following substrate to product conversions:
  a) pyruvate to acetolactate, as catalyzed for example by acetolactate synthase encoded by the gene given as SEQ ID NO:19;
  b) acetolactate to 2,3-dihydroxyisovalerate, as catalyzed for example by acetohydroxy acid isomeroreductase encoded by the gene given as SEQ ID NO:31;
  c) 2,3-dihydroxyisovalerate to α-ketoisovalerate, as catalyzed for example by acetohydroxy acid dehydratase encoded by the gene given as SEQ ID NO:33;
  d) α-ketoisovalerate to isobutyraldehyde, as catalyzed for example by a branched-chain keto acid decarboxylase encoded by the gene given as SEQ ID NO:35; and
  e) isobutyraldehyde to isobutanol, as catalyzed for example by a branched-chain alcohol dehydrogenase encoded by the gene given as SEQ ID NO:37.

Construction of Bacterial Strains for Butanol Production

Any bacterial strain that is genetically modified for butanol tolerance as described herein is additionally genetically modified (before or after modification to tolerance) to incorporate a butanol biosynthetic pathway by methods well known to one skilled in the art. Genes encoding the enzyme activities described above, or homologs that may be identified and obtained by commonly used methods well known to one skilled in the art, are introduced into a bacterial host. Representative coding and amino acid sequences for pathway enzymes that may be used are given in Tables 1, 2, and 3, with SEQ ID NOs:1-38. Methods described in co-pending and commonly owned U.S. Patent Publication Nos. US20080182308A1, US20070259410A1, US 20070292927A1, and US20070092957 A1 may be used.

Vectors or plasmids useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically, the vector or plasmid contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression Gram-positive bacteria, Eichenbaum et al. *Appl. Environ. Microbiol.* 64(8): 2763-2769 (1998)); and the synthetic P11 promoter (useful for expression in *Lactobacillus plantarum*, Rud et al., *Microbiology* 152:1011-1019 (2006)). Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to create gene replacement in a range of Gram-positive bacteria (Maguin et al., *J. Bacteriol.* 174(17):5633-5638 (1992)). Additionally, in vitro transposomes are available to create random mutations in a variety of genomes from commercial sources such as EPICENTRE® (Madison, Wis.).

Expression of a Butanol Biosynthetic Pathway in *E. Coli*

Vectors useful for the transformation of *E. coli* are common and commercially available from the companies listed above. For example, the genes of an isobutanol, 1-butanol, or 2-butanol biosynthetic pathway may be isolated from various sources, as described above, cloned onto a modified pUC19 vector and transformed into *E. coli* host cells, as described in Examples herein. Alternatively, the genes encoding a butanol biosynthetic pathway may be divided into multiple operons, cloned onto expression vectors, and transformed into various *E. coli* strains.

Construction of *Lactobacillus* Strains for Butanol Production

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg R, Golic N, Bongers R, Leer R J, de Vos W M, Siezen R J, Kleerebezem M. *Appl. Environ. Microbiol.* 2005 March; 71(3): 1223-1230), which may be used for transformation.

Initiation control regions or promoters, which are useful to drive expression of the relevant pathway coding regions in the desired *Lactobacillus* host cell, may be obtained from *Lactobacillus* or other lactic acid bacteria, or other Gram-positive organisms. A non-limiting example is the nisA promoter from *Lactococcus*. Termination control regions may also be derived from various genes native to the preferred hosts or related bacteria.

The various genes for a butanol biosynthetic pathway may be assembled into any suitable vector, such as those described above. The codons can be optimized for expression based on the codon index deduced from the genome sequences of the host strain, such as for *Lactobacillus plantarum* or *Lactobacillus arizonensis*. The plasmids may be introduced into the host cell using methods known in the art, such as electroporation, as described in any one of the following references: Cruz-Rodz et al. (*Molecular Genetics and Genomics* 224: 1252-154 (1990)), Bringel and Hubert (*Appl. Microbiol. Biotechnol.* 33: 664-670 (1990)), and Teresa Alegre, Rodriguez and Mesas (*FEMS Microbiology letters* 241:73-77 (2004)). Plasmids can also be introduced to *Lactobacillus plantarum* by conjugation (Shrago, Chassy and Dobrogosz *Appl. Environ. Micro.* 52: 574-576 (1986)). The butanol biosynthetic pathway genes can also be integrated into the chromosome of *Lactobacillus* using integration vectors (Hols et al. *Appl. Environ. Micro.* 60:1401-1403 (1990); Jang et al. *Micro. Lett.* 24:191-195 (2003)).

Fermentation of Butanol Tolerant Bacteria for Butanol Production

The present strains with increased cyclopropane fatty acid synthase activity and having a butanol biosynthesis pathway may be used for fermentation production of butanol.

Fermentation media for the production of butanol must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Sucrose may be obtained from feedstocks such as sugar cane, sugar beets, cassava, and sweet sorghum. Glucose and dextrose may be obtained through saccharification of starch based feedstocks including grains such as corn, wheat, rye, barley, and oats.

In addition, fermentable sugars may be obtained from cellulosic and lignocellulosic biomass through processes of pretreatment and saccharification, as described, for example, in commonly owned and co-pending US patent application publication US20070031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production. Typically cells are grown at a temperature in the range of about 25° C. to about 40° C. in an appropriate medium. Suitable growth media are common commercially prepared media such as Bacto Lactobacilli MRS broth or Agar (Difco), Luria Bertani (LB) broth, Sabouraud Dextrose (SD) broth or Yeast Medium (YM) broth. Other defined or synthetic growth media may also be used, and the appropriate medium for growth of the particular bacterial strain will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

Butanol may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Butanol may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol may be practiced using either batch, fed-batch or continuous processes and that any known mode of fermentation would be suitable. Additionally, it is contemplated that cells may be immobilized on a substrate as whole cell catalysts and subjected to fermentation conditions for butanol production.

Methods for Butanol Isolation from the Fermentation Medium

Bioproduced butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the butanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "KB" means kilobase(s), "min" means minute(s), "h" or "hr" means hour(s), "sec" means second(s), "d" means day(s), "nl" means nanoliter(s), "µl" means microliter(s), "ml" means milliliter(s), "L" means liter(s), "nm" means nanometer(s), "mm" means millimeter(s), "cm" means centimeter(s), "µm" means micrometer(s), "µM" means micromolar, "mM" means millimolar, "M" means molar, "mmol" means millimole(s), "µmole" means micromole(s), "g" means gram(s), "ng" means nanogram(s), "µg" means microgram(s), "mg" means milligram(s), "rpm" means revolutions per minute, "w/v" means weight/volume, "Cm" means chloramphenicol, "OD" means optical density, and "OD600" means optical density measured at a wavelength of 600 nm.

For 1-butanol synthesis the first three genes of the pathway are thl, hbd, and crt, encoding the enzymes acetyl-CoA acetyltransferase, 3-hydroxybutyryl-CoA dehydrogenase, and crotonase, respectively. The last three genes of the pathway are EgTER, ald, and bdhB, encoding the enzymes butyryl-CoA dehydrogenase, butyraldehyde dehydrogenase and butanol dehydrogenase, respectively.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987. Additional methods used in the Examples are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992).

These references include descriptions of the media and buffers used including TE, M9, MacConkey and LB.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Media and Culture Conditions:

Materials and methods suitable for the maintenance and growth of bacterial cultures were found in *Experiments in Molecular Genetics* (Jeffrey H. Miller), Cold Spring Harbor Laboratory Press (1972), *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210-213, American Society for Microbiology, Washington, D.C. or Thomas D. Brock in *Biotechnology: A Textbook of Industrial Microbiology*, Second Edition (1989) Sinauer Associates, Inc., Sunderland Mass. All reagents and materials used for the growth and maintenance of bacterial cells were obtained from Aldrich Chemicals (Milwaukee, Wis.), DIFCO Laboratories (Detroit, Mich.), Gibco/BRL (Gaithersburg, Md.), or Sigma Chemical Company (St. Louis, Mo.) unless otherwise specified.

LB medium contains following per liter of medium: Bacto-tryptone (10 g), Bacto-yeast extract (5 g), and NaCl (10 g). Supplements were added as mentioned in the examples. All additions were pre-sterilized before they were added to the media.

Additional growth media used were MRS medium (Acumedia Manufacturers, Inc. Lansing, Mich. or Difco Laboratories, Detroit, Mich.) or semi-synthetic LAB medium, pH7. The composition of the latter medium was as follows:

0.01M Ammonium Sulfate
0.005M Potassium Phosphate, pH 7.0
0.05M MOPS, pH 7.0
1% S10 Metal Mix
0.01 M Glucose
0.2% Yeast Extract
0.01% Casamino Acids
2.5 µg/ml hematin The composition of S10 Metal Mix is:
200 mM $MgCl_2$
70 mM Ca $Cl_2$
5 mM Mn $Cl_2$
0.1 mM $FeCl_3$
0.1 mM Zn $Cl_2$
0.2 mM Thiamine Hydrochloride
172 µM $CuSO_4$
253 µM $CoCl_2$
242 µM $Na_2MoO_4$ All medium ingredients were purchased from Sigma Chemical Company (St. Louis, Mo.) except yeast extract and casamino acids, which were purchased from Beckton, Dickinson and Co (Sparks, Md.). Isobutanol and 2-butanol were purchased from Sigma Chemical Company (St. Louis, Mo.).

General Molecular Biology Techniques:

Unless otherwise stated, restriction enzyme digestions, ligations, transformations, and methods for agarose gel electrophoresis were performed as described in Sambrook, J., et al., *Molecular Cloning: A Laboratory Manual*, Second Edition, Cold Spring Harbor Laboratory Press (1989). Polymerase Chain Reactions (PCR) techniques were found in White, B., *PCR Protocols: Current Methods and Applications*, Volume 15 (1993) Humana Press Inc.

Genetic Transformation of *Lactobacillus plantarum*

A loop of *Lactobacillus plantarum* cells was inoculated into 5 ml of MRS broth from a fresh MRS plate and incubated overnight. The overnight culture was diluted to an $OD_{600}$ of 0.25 in 25 ml MRS broth and incubated in a shaker for 2-4 hours until the $OD_{600}$ reached between 0.8 and 1.0. The cells were harvested by centrifugation for 5 min at 4° C. at 4000 rpm (Beckman table top centrifuge, with rotor CO650). The cell pellet was washed twice with 50 ml of SM (326 g sucrose (952 mM), 0.7 mg of $MgCl_2.6H_2O$ (3.5 mM) in 1 L of water) by spinning at the same speed for 15 minutes. After two washes, the pellet was re-suspended in 400 µl of SM. An aliquot 100 µl of cells was used for each electroporation. 500 ng of plasmid DNA was added to the cell suspension and the mixture was allowed to incubate on ice for 5 minutes before electroporation. Electroporation was carried out with a Bio-Rad Gene Pulser with a setting of 1.5 kV, 25 µF and 800Ω. Immediately after the electric discharge, 500 µl of MRSSM (MRS with 0.5M sucrose and 0.1M $MgCl_2$) was added and the cell suspension was transferred to a 15 ml culture tube. The cells were allowed to recover by incubating at 37° C. for two hours in a shaker. From each transformation mixture, 50-100 µl of mixture was spread onto selection plates with appropriate antibiotic supplement and the plates were incubated at 30° C. The colonies of transformants are usually visible after 2-5 days.

*L. plantarum* Genomic DNA Purification

*L. plantarum* genomic DNA was prepared using Master-Pure DNA purification kit (Epicentre) as follows. A single colony was grown over night in MRS medium. A culture sample (0.5-1 ml) was centrifuged, the supernatant discarded, and the pellet washed three times with STE [6.7% sucrose, 50 mM Tris-cl, pH8, 1 mM EDTA (filter sterilized with 0.22 µm membrane)]. Add 300 µl of Tissue and cell lysis solution containing Proteinase K, diluted 1 µl of 50 µg/ul Proteinase K into 300 µl of Tissue and cell lysis solution, for each sample and mix thoroughly. The sample was incubated at 65° C. for 5 min, then cooled to 37° C. for 5-10 min. Next 1 µl of RNase (5 µg/µl) was added, the sample mixed thoroughly, incubated at 37° C. for 30 min, and placed on ice for 5 min. 150 µl of MCP protein precipitation reagent (Epicentre, Master pure DNA purification kit) was added to 300 µl of lysed sample. The debris was pelleted by centrifugation in a micro-centrifuge for 3-5 min, and the supernatant transferred to a clean micro-centrifuge tube. 500 µl of iso-propanol was added to the recovered supernatant and the samples inverted 30-40 times. The DNA was pelleted by centrifugation at 4° C. for 10 minutes in a micro-centrifuge, the pellet rinsed twice with 755 ethanol, air-dried, and resuspenced in 35 μl of TE buffer. 5 μl) was run on a gel to assess the concentration.
PCR Amplification High fidelity amplification of DNA fragments was carried out with Pfx enzyme from Invitrogen (Carlsbad, Calif.). The extension time depends on the length of the fragment to be amplified. As a general rule, 1 min was used per kb of DNA. For example, the PCR conditions normally included 3 minutes initial denaturing at 94° C., 25 cycle of amplification (94° C. 30 sec, 54° C. 30 sec, 68° C. 1 min) and a final 3 min of extension at 68° C. for fragments of 1 kb or less.
Plasmid DNA Purification from L. plantarum L. plantarum plasmid-containing strains were grown in 20 ml of MRS medium (with antibiotic if required) without shaking for 16-20 hours at 30° C. The cells were washed one time with sterile deionized water and resuspended in 1 ml of 5 M LiCl. This suspension was incubated for 1 hour at room temperature with shaking. Subsequently, the cells were washed one time with 1 ml of sterile deionized water and resuspended in 1 ml of protoplasting buffer (25 mM sucrose, 50 mM Tris-HCl, pH 8.0, 10 mM EDTA) with 10 mg/ml of lysozyme and 100 μg/ml of RNase, and incubated for 1 hour at 37° C. The protoplasted cells were centrifuged and resuspend in 500 μl of Qiagen buffer P1, then divided in half. Each portion was used separately to extract plasmid DNA according to the Qiagen directions and then combined on one column.
Fatty Acid Methyl Ester (FAME) Analysis For preparation of samples for fatty acid methyl ester analysis (FAME), the cultures were grown to late log phase in semi-synthetic LAB medium, pH7. The cell pellet was harvested by centrifugation and was washed twice with phosphate buffered saline (PBS, Bio-Rad Laboratories, Hercules, Calif.). Cell pellets were stored at −80° C. until analyzed by FAME. For preparation of samples grown in the presence of oleic acid for FAME, the cultures were grown to late-log phase in semi-synthetic LAB medium, pH7, with additional 5 g/l BSA and 50 mg/l oleic acid (Sigma Chemical Company, St. Louis, Mo.). These cultures were washed and stored as above, except that an additional wash with PBS containing 5 g/l BSA was done prior to the two PBS washes.
Lipid Extraction The membrane lipids were extracted by modified Bligh and Dyer protocol (Can. J. Biochem. Physiol. (1959) 37:911-17). The cell pellet prepared as described above was suspended in a mixture of 0.5 ml $CHCl_3$ and 1 ml $CH_3OH$, and transferred to a 13×100 mm tube with a screw top cap. The cap was screwed on about ¾ of the way (i.e., not tight), and the tube was incubated at 40° C. for 30 min. The tube was cooled and an additional 0.5 ml $CHCl_3$ and 1 ml $H_2O$ were added the mixture. This results in the formation of two phases. The two phases were equilibrated by vortexing. The two phases were allowed to separate; then the lower $CHCl_3$ layer was removed and transferred to another 13×100 mm tube with a screw top cap. With the cap removed, the $CHCl_3$ was evaporated under a stream of $N_2$. Methyl esters of the fatty acids in the residue were then formed using one of the following procedures.
Fatty Acid Analysis: Formation of Fatty Acid Methyl Esters by the $H_2SO_4/CH_3OH$ Method This method forms methyl esters of all the fatty acids in the sample. Both free fatty acids and fatty acids present in ester linkages in the lipids in the sample are derivatized to the methyl esters by this procedure.

2 ml 5% $H_2SO_4$ in $CH_3OH$ was added to each of the tubes containing sample. The caps were placed on tubes, screwed on about ¾ of the way (i.e., not tight), then the tubes were heated at 80° C. for 1 hr. The tubes were cooled, and then 1 ml $H_2O$ and 0.5 ml hexane were added to each. The resulting 2 phase mixture was vortexed; then the two phases were allowed to separate. The top hexane layer, which contained the methylated fatty acids was removed and placed in a separate container. 2 μl of this hexane layer was injected into an Agilent GC (model 6890)/MS (model 5973). For routine samples a Supelco Equity-1 column (15 m×0.25 mm×0.25 μm film thickness; catalog #28045-U) was used with an FID detector (GC/FID). For peak identification sample column was used with an Agilent MSD detector was used (GC/MS). When samples requiring difficult separations that were impossible to achieve on a 15 m column were analyzed (e.g., the separation of oleic from elaidic acid), a Supelco S-2380 column (100 m×0.25 mm×0.25 μm film thickness; catalog #24317) was used.
Formation of Fatty Acid Methyl Esters by Transesterification using $CH_3ONa$ in $CH_3OH$ 1 ml freshly made 1.0 M $CH_3ONa$ in $CH_3OH$ was added to the tubes containing lipid samples extracted by the Bligh and Dyer method as described above. The caps were placed on tubes, screwed on about ¾ of the way (i.e., not tight), then the tubes were heated at 60° C. for 30 minutes. The mixture was chilled in ice bath and 1 ml of 1.0 N HCl was added to the solution in the tubes. The pH of the resulting solution was checked with pH paper to make sure a pH of 7 or lower had been reached. 0.5 ml hexane was added into the test tube and mixed well by vortexing. The tubes were allowed to sit for a few minutes until two phases formed. The top hexane layer was removed and placed in a separate tube for storage until analysis, which was done by GC/FID and/or GC/MS as described previously.
Growth Analysis For shake flask experiments, the cultures were grown overnight at 30° C. in semi-synthetic LAB medium, pH7 containing 1 μg/ml erythromycin. The next day, the cultures were diluted to an initial OD600 of 0.1 in the same medium, but without erythromycin, and allowed to grow at 30° C., 80 rpm until doubled. The cultures were then diluted 1:1 into the same medium containing various concentrations of isobutanol or 2-butanol and grown at 30° C., 80 rpm. Samples were taken approximately hourly and OD600 was measured. The growth rates, μ(hr−1) were calculated from an exponential curve fit of the OD600 vs. time data. For growth rates for which the curve fit value was negative, a value of 0.00 was recorded. The % growth rate inhibition was calculated as follows: 100-100[μ(isobutanol)/μ(no isobutanol)]. All solvent concentrations are reported as % (w/v).
Bioscreen-C Growth Analysis For Bioscreen-C (instrument purchased from Growth Curves USA, Piscataway N.J.) growth curves, the cultures were grown overnight in MRS medium containing 1 μg/ml erythromycin at 30° C. The next day, these were diluted to OD600 of 0.1 in the wells of the Bioscreen plate with MRS medium containing 1 μg/ml erythromycin and either 2.25% (w/v) isobutanol or no isobutanol at 30° C. OD was monitored every 15 minutes and growth rates (hr−1) were calculated from an exponential curve fit of the OD600 vs. time data for data in the exponential phase of growth. The % growth rate inhibition was calculated as follows: 100-100[μ(2.25% isobutanol)/μ(no isobutanol)].
Methods for Determining Isobutanol Concentration in Culture Media The concentration of isobutanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Isobutanol had a retention time of 46.6 min under the conditions used. Alternatively, gas chromatography (GC) methods are available. For example, a specific GC method utilized an HP-INNOWax column (30 m×0.53 mm id, 1 μm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of isobutanol was 4.5 min.

Methods for Determining 2-Butanol Concentration in Culture Media

The concentration of 2-butanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Under the conditions used, 2-butanol had a retention time of 44.3 min. Alternatively, gas chromatography (GC) methods are available. For example, a specific GC method utilized an HP-INNOWax column (30 m×0.53 mm id, 1 μm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of 2-butanol was 5.03 min.

Methods for Determining 1-Butanol Concentration in Culture Media

The concentration of 1-butanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. 1-Butanol had a retention time of 52.8 min under the conditions used. Alternatively, gas chromatography (GC) methods are available. For example, a specific GC method utilized an HP-INNOWax column (30 m×0.53 mm id, 1 μm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of 1-butanol was 5.4 min. A similar GC method using a Varian CP-WAX 58(FFAP) CB column (25 m×0.25 mm id×0.2 μm film thickness, Varian, Inc., Palo Alto, Calif.) was also used.

Example 1

Constructions for Overexpresssion of cfa1 and cfa2 Genes in L. plantarum

To express genes in L. plantarum, a series of shuttle vectors derived from pFP996 were constructed. pFP996 (SEQ ID NO: 71) is a shuttle vector for gram-positive bacteria. It can replicate in both E. coli and gram-positive bacteria. It contains the origins of replication from pBR322 (nucleotides #2628 to 5323) and pE194 (nucleotides #43 to 2627). pE194 is a small plasmid isolated originally from a gram positive bacterium, Staphylococcus aureus (Horinouchi and Weisblum J. Bacteriol. (1982) 150(2):804-814). In pFP996, the multiple cloning sites (nucleotides #1 to 50) contain restriction sites for EcoRI, BglII, XhoI, SmaI, ClaI, KpnI, and HindIII. There are two antibiotic resistance markers; one is for resistance to ampicillin and the other for resistance to erythromycin. For selection purposes, ampicillin was used for transformation in E. coli and erythromycin was used for selection in L. plantarum.

First a vector called pFP996-fba was constructed by inserting the fba promoter region of L. plantarum into the multiple cloning site of pFP996. The fba promoter region was amplified with the Pfx enzyme as described in General Methods using L. plantarum PN0512 strain (ATC #PTA-7727) genomic DNA, as a template with the primer set fba-F and fba-R (SEQ ID NOs:72, 73). The genomic DNA was prepared according to the procedure described in General Methods. The resulting fragment was digested with EcoRI and Xho I and cloned into the corresponding sites in pFP996 to create pFP996-fba.

In order to express the cfa1 and cfa2 genes at higher than normal levels, the corresponding coding regions were expressed from the atpB promoter (SEQ ID NO:74). This promoter was originally cloned along with the bdhB coding region in the vector pFP996-fba. The atpB promoter was amplified using the same L. plantarum genomic DNA as a template using the primer set atpB-F and atpB-R (SEQ ID NOs:75, 76). The promoter was obtained by PCR with a high fidelity enzyme Pfx (Invitrogen). The bdhB coding region with attached 5' Shine-Delgarno sequence was amplified from a synthetic construct with primer set bdhB-F and bdhb-R (SEQ ID NOs 77, 78) with Pfx enzyme. The synthetic the bdhB coding region and attached 5' Shine-Delgarno sequence (SEQ ID NO; 79) was obtained from Genscript Corporation (Piscataway, N.J.). The promoter fragment was digested with MluI and Spe I, while the bdhB fragment was digested with SpeI and BamHI. Both PCR products were used in a single ligation reaction with vector pFP996-fba which was linearized with restriction enzymes MluI and BglII. The new vector was designated as pFP996-atpB-bdhB. In this vector the fba promoter was replaced by the atpB promoter and bdhB coding region.

The cfa1 coding region from L. plantarum PNO512 was obtained by amplification of the same genomic DNA with the primer set Cfa1-F and Cfa-1R (SEQ ID NOs:80, 81). The restriction site SpeI and a Shine-Delgarno (SD) sequence for efficient translation was introduced in the forward primer. In the reverse primer, a BglII site was introduced. The DNA fragment obtained by PCR with high fidelity enzyme Pfx was digested with SpeI and Bgl II. The digested product was ligated into the corresponding restriction sites down stream of the atpB promoter in vector pFP996-atpB-bdhB. In the resulting construct, the bdhB coding region was replaced by the cfa1 coding region and this new vector was designated as pFP996-atpB-cfa1. For cloning of the cfa2 gene, its cfa2 coding region was amplified from the same genomic DNA with primer set Cfa2-F and Cfa2-R (SEQ ID NOs:82, 83). The same SD sequence and restriction sites as in the primer set for the cfa1 coding region were used for these two primers. The PCR product from the cfa2 coding region was cloned into the pFP996-atpB-bdhB vector using the same method as described for the cfa1 gene. The vector containing the cfa2 coding region was named pFP996-atpB-cfa2.

To express the cfa1 and cfa2 chimeric genes in *L. plantarum*, the pFP996-atpB-cfa1 and pFP996-atpB-cfa2 plasmids were each introduced into the host by electroporation as described in General Methods. After electroporation, the cells were spread onto MRS plates supplemented with erythromycin (3 μg/L). Plates were incubated at 30° C. Colonies with the plasmid were initially screened with the primer for the atpB promoter, atpB-F (SEQ ID NO:75), and the reverse primers for either the cfa1 and cfa2 coding regions (SEQ ID NOs:81 and 83, respectively). PCR products of the expected sizes were obtained in each case. Furthermore, plasmid DNA was isolated from each transformant and used to transform *E. coli* TOP10 (Invitrogen). Plasmid DNA subsequently isolated from the *E. coli* transformants and digested with restriction enzymes Spe I and Bgl II had the expected restriction digestion patterns, thus further verifying the presence of the cloned genes in the plasmids of the transformed *L. plantarum* PN0512 strains. The following strain names were given to transformants and controls:

| Strain name | Plasmid |
| --- | --- |
| PN2001 | pFP996-atpB-cfa1-8a |
| PN2003 | pFP996-atpB-cfa1-9a |
| PN2005 | pFP996-atpB-cfa2-a |
| PN2010 | pFP996-atpB-cfa2-4 |
| PN2012 | pFP996 |
| PN2014 | pFP996 |

Example 2

Overexpression of cfa1 or cfa2 Overexpression in *L. plantarum* and Effect Butanol Tolerance FAME Analysis of *L. plantarum* PN0512 Transformant Strains

*Lactobacillus plantarum* strains PN2001, PN2003, PN2005, PN2010, PN2012, and PN2014 were grown and prepared for FAME as described in the General Methods section. The results for cultures grown in semi-synthetic medium lacking added fatty acids are shown in Table 10.

TABLE 10

Membrane composition of PN0512 transformant strains grown without added fatty acids.

| | Strain | | | | | |
| --- | --- | --- | --- | --- | --- | --- |
| | PN2001 | PN2003 | PN2005 | PN2010 | PN2012 | PN2014 |
| Gene on plasmid membrane fatty acids | cfa1 | cfa1 | cfa2 | cfa2 | none | none |
| C14:0 | <0.1 | 0.5 | <0.1 | <0.1 | 0.3 | 0.4 |
| C16:0 | 34.6 | 31.9 | 34.9 | 33.2 | 30.8 | 33.4 |
| C16:1 | 6.0 | 4.5 | 6.2 | 4.9 | 5.3 | 5.1 |

TABLE 10-continued

Membrane composition of PN0512 transformant strains grown without added fatty acids.

| | Strain | | | | | |
| --- | --- | --- | --- | --- | --- | --- |
| | PN2001 | PN2003 | PN2005 | PN2010 | PN2012 | PN2014 |
| C18:0 | 13.8 | 11.6 | 9.3 | 9.7 | 8.6 | 7.6 |
| C18:1 | 5.8 | 7.1 | 40.8 | 42.9 | 47.2 | 45.9 |
| cyc-C19:0 | 28.0 | 32.2 | 6.4 | 6.4 | 5.0 | 5.6 |

It is clear from this data that the strains with the cloned cfa1 gene converted a much higher percentage of the C18:1 fatty acid, cis-vaccenic acid, to the cyclopropane fatty acid (cyc-C19:0) derived from it, lactobacillic acid. Thus, strains PN2001 and PN2003 represent strains that have been genetically modified to have increased levels of cyclopropane fatty acids in the membrane lipids.

The same six strains were grown in semi-synthetic medium with added 50 μg/ml oleic acid and 5 g/l BSA as a carrier. FAME was performed with transesterification using $CH_3ONa$ in $CH_3OH$ as described in General Methods, and results are shown in Table 11. For this analysis a longer 100 meter column was used so that the isomers of monounsaturated 18 carbon fatty acids and the cyclopropane fatty acids derived from them could be distinguished. The only C18:1 fatty acid that *L. plantarum* synthesized was cis-vaccenic (C18:1 11-cis). This was converted to lactobacillic acid (cyc-C19:0 11-). Oleic acid (C18:1 9-cis) was taken up from the medium and incorporated into the membrane lipids and converted to dihydrosterculic acid (cyc-C19:0 9-).

TABLE 11

Membrane composition of PN0512 transformant strains grown with added oleic acid.

| | Strain | | | | | |
| --- | --- | --- | --- | --- | --- | --- |
| | PN2001 | PN2003 | PN2005 | PN2010 | PN2012 | PN2014 |
| Gene on plasmid membrane fatty acids | cfa1 | cfa1 | cfa2 | cfa2 | none | none |
| C16:0 | 17.3 | 18.6 | 19.9 | 20.0 | 17.6 | 16.0 |
| C16:1 | 4.7 | Trace | 2.8 | 4.5 | 5.2 | 4.9 |
| C18:0 | 1.4 | trace | trace | 1.4 | 1.3 | 1.2 |
| C18:1, 9-cis | 22.7 | 10.6 | 27.1 | 24.4 | 40.7 | 44.8 |
| C18:1, 11-cis | 1.6 | trace | 17.9 | 19.1 | 17.7 | 12.5 |
| cyc-C19:0, 9- | 24.5 | 43.4 | 21.9 | 20.4 | 9.5 | 9.8 |
| cyc-C19:0, 11- | 27.9 | 27.4 | 10.3 | 10.2 | 9.4 | 9.1 |

The strains with either cfa1 or cfa2 on the multicopy plasmid had increased levels of dihydrosterculic acid (cyc-C19:0 9-) in the membrane lipids as compared with the control strains. Thus, strains PN2001, PN2003, PN2005, and PN2010 represent strains that have been genetically modified to have increased levels of cyclopropane fatty acids in the membrane lipids when oleic acid is present in the growth medium.

Improved Tolerance of the Strains with cfa1 Overexpression to Isobutanol

Figure 1B:
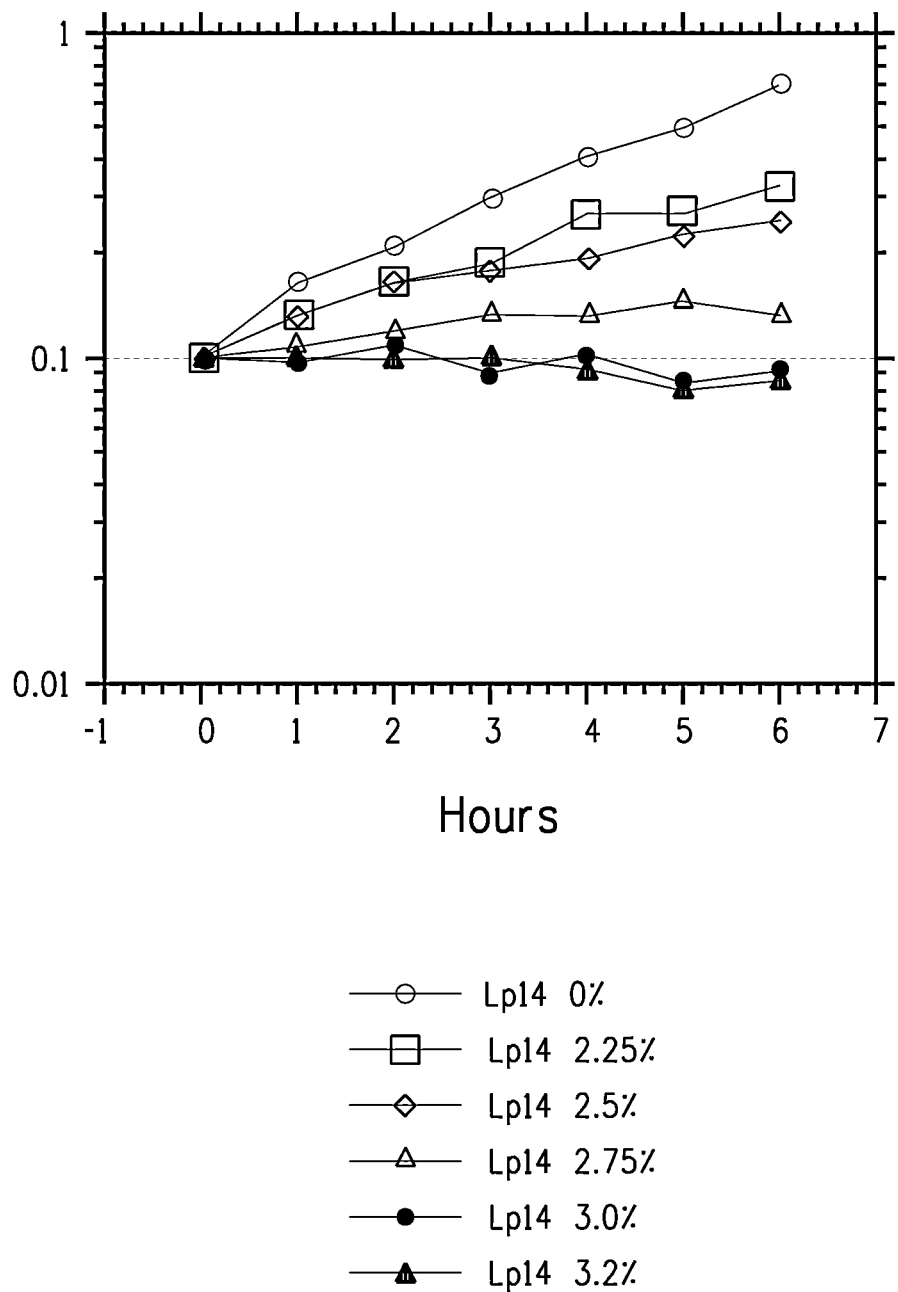
FIG. 1B shows a graph of the growth of *L. plantarum* PN2014, with control plasmid pFP996, in the presence of various concentrations of isobutanol.

*Lactobacillus plantarum* strains PN2001, which overexpresses cfa1, and PN2014, a control strain with the vector alone, were grown in shake flasks in semi-synthetic LAB medium, pH7 with various concentrations of isobutanol as described in General Methods. The growth vs. time for each strain is plotted in FIG. 1 (A:PN2001; B:PN2014). It is clear that the strain PN2001 grew in the presence of 3% isobutanol, while strain PN2014 did not grow in the presence of 3% isobutanol. Furthermore, the growth in 2.75% isobutanol was faster for PN2001 than for PN2014. Growth rates and % growth inhibition were calculated from these growth curves above and are shown in Table 12.

TABLE 12

PN2001 and PN2014 growth rates and % growth inhibition in the presence of isobutanol

| [Isobutanol] % w/v | PN2001 (cfa1 plasmid) μ, hr$^{-1}$ | PN2014 (control plasmid) μ, hr$^{-1}$ | PN2001, % Growth inhibition | PN2014, % Growth inhibition |
|---|---|---|---|---|
| 0 | 0.347 | 0.343 | 0 | 0 |
| 2.25 | 0.187 | 0.170 | 46 | 50 |
| 2.5 | 0.119 | 0.118 | 66 | 66 |
| 2.75 | 0.104 | 0.037 | 70 | 89 |
| 3.0 | 0.029 | 0.00 | 92 | 100 |
| 3.2 | 0.00 | 0.00 | 100 | 100 |

At 2.75% and 3% isobutanol, the growth of PN2001 overexpressing cfa1 was less inhibited than was the growth of the control strain PN2014. Thus, elevated expression of cfa1 and the resultant increase in membrane cyclopropane fatty acid levels produced improved tolerance to isobutanol.

Improved Tolerance of the Strains with cfa1 Overexpression to 2-butanol

*Lactobacillus plantarum* strains PN2001, which overexpresses cfa1, and PN2014, a control strain with the vector alone, were grown in shake flasks in semi-synthetic LAB medium, pH7 with various concentrations of 2-butanol as described in General Methods. Growth rates and % growth inhibition calculated from the growth curves are shown in Table 13.

TABLE 13

PN2001 and PN2014 growth rates and % growth inhibition in the presence of 2-butanol

| [2-Butanol] % w/v | PN2001 (cfa1 plasmid) μ, hr$^{-1}$ | PN2014 (control plasmid) μ, hr$^{-1}$ | PN2001, % Growth inhibition | PN2014, % Growth inhibition |
|---|---|---|---|---|
| 0 | 0.284 | 0.297 | 0 | 0 |
| 3.5 | 0.132 | 0.153 | 54 | 48 |
| 4.0 | 0.125 | 0.123 | 56 | 59 |
| 4.25 | 0.111 | 0.158 | 61 | 47 |
| 4.5 | 0.108 | 0.061 | 62 | 79 |
| 4.75 | 0.068 | 0.034 | 76 | 89 |
| 5.0 | 0.078 | 0.00 | 73 | 100 |

At 4.5, 4.75 and 5.0% 2-butanol, the growth of PN2001 overexpressing cfa1 was less inhibited than was the growth of the control strain PN2014. Thus, elevated expression of cfa1 and the resultant increase in membrane cyclopropane fatty acid levels yielded improved tolerance to 2-butanol.

Improved Tolerance of the Strains with cfa1 or cfa2 Overexpression to Isobutanol when Grown in Medium Containing a Source of Oleic Acid

*L. plantarum* strains PN2001, PN2003, PN2005, PN2010, PN2012, and PN2014 were tested for growth in a Bioscreen-C growth curve machine in the presence of isobutanol as described in General Methods. These growth assays were conducted in MRS medium, which contains 1 g/L polysorbate 80 (commercially also known as Tween® 80) that serves as a source of oleic acid. Erythromycin at 1 μg/ml was added to the medium to maintain the plasmids. It is well known that *L. plantarum* grown in MRS medium incorporates oleic acid into membrane lipids (Johnsson et al. (1995) Appl. Environ. Microbiol. 61:4497-4499). Table 14 shows the growth rates in the presence or absence of 2.25% isobutanol and the % growth inhibition.

TABLE 14

PN2001, PN2003, PN2005, PN2010, PN2012 and PN2014 growth rates in MRS medium and % growth inhibition in the presence of isobutanol

| Strain | Gene on plasmid | μ (no isobutanol), hr$^{-1}$ | μ (2.25% isobutanol), hr$^{-1}$ | % Growth inhibition |
|---|---|---|---|---|
| PN2001 | cfa1 | 0.47 | 0.32 | 32 |
| PN2003 | cfa1 | 0.50 | 0.33 | 34 |
| PN2005 | cfa2 | 0.51 | 0.31 | 39 |
| PN2010 | cfa2 | 0.54 | 0.33 | 39 |
| PN2012 | none | 0.41 | 0.20 | 51 |
| PN2014 | none | 0.38 | 0.22 | 42 |

The growth of strains PN2001 and PN2003 with the cfa1 overexpression plasmid was less inhibited by 2.25% isobutanol than was the growth of the control strains, PN2012 and PN2014. Likewise, the growth of PN2005 and PN2010 with the cfa2 overexpression plasmid was less inhibited by 2.25% isobutanol than was the growth of the control strains, PN2012 and PN2014, According, in medium containing a source of oleic acid, elevated expression of either cfa1 or cfa2 and the resultant increase in membrane cyclopropane fatty acid levels resulted in improved tolerance to isobutanol.

Example 3

Overexpression of cfa in *E. coli* and Effect on Butanol Tolerance

Plasmid pDEW849 contains the *E. coli* cfa coding region under control of the trc promoter in a multicopy plasmid. To construct this plasmid, the cfa coding region was obtained by PCR amplification using chromosomal DNA from *E. coli* strain MG1655 as template and the primers cfa_sense and cfa_antisense (SEQ ID NOs:84, 85). The cfa_sense primer was designed so that when the amplified DNA is cloned into the pTrcHis2TOPO® vector (Invitrogen, Carlsbad, Calif.), an N-terminal fusion protein would not be formed and thus the native Cfa protein is expressed. The cfa_sense primer also has an EcoRI site that was used to determine orientation of the inserted DNA. The cfa_antisense primer was designed to contain the termination codon of cfa and thus the native Cfa protein is expressed, rather than a C-terminal fusion protein.

A 1165 bp PCR product was obtained from amplification reactions using ExTaq™ (TaKaRa) and the following conditions: 94° C. for 5 minutes, 35 cycles of (94° C. for 1 minute, 60° C. for 2 minutes, 72° C. for 3 minutes), and 72° C. for 15 minutes. The product of the PCR reaction was purified using a Qiaquick PCR clean-up kit (Qiagen) following the manufacturer's instructions and was then ligated into pTrcHis2TOPO® (Invitrogen) following the protocol supplied by the vendor. After transformation of *E. coli* strain TOP10 (Invitrogen) and selection for ampicillin resistance, plasmid DNA from individual transformants was digested with EcoRI. One plasmid, for which two fragments of sizes 4.4 KB (vector) and 1.2 KB (insert) resulted, was named pDEW849. The presence of the cfa coding region in the correct orientation was confirmed by DNA sequence analysis. Plasmid pDEW849 and a control plasmid, pTrcHis2TOPO®/lacZ (Invitrogen), were moved by transformation to E. coli strain BW25113 (Datsenko and Wanner (2000) Proc. Nat. Acad. Sci. USA 97:6640-6645) selecting for ampicillin resistance, to generate strains DPD4655 and DPD4658, respectively.

E. coli strains DPD4655 and DPD4658 were grown overnight in LB medium containing 100 µg/ml ampicillin at 37° C. The next day, these were diluted to OD600 of 0.1 in the wells of a Bioscreen-C plate (instrument and plates purchased from Growth Curves USA, Piscataway N.J.) with LB medium and either 0.4%, 0.8% (w/v) isobutanol or no isobutanol at 37° C. in triplicate. OD was monitored and the OD at the 3 hour and 15 minute time point was used to calculate the % of growth in the presence of isobutanol as compared with its absence, given in Table 15.

TABLE 15

% of growth vs control in cfa overexpressing E. coli strains

| [Isobutanol] % (w/v) | DPD4655 (cfa overexpression) | | DPD4658 (control lacZ overexpression) | |
|---|---|---|---|---|
| | OD600 (+/− st dev) | % OD +isobutanol/ −isobutanol | OD600 (+/− st dev) | % OD +isobutanol/ −isobutanol |
| 0 | 0.442 +/− 0.006 | 100 | 0.413 +/− 0.016 | 100 |
| 0.4 | 0.318 +/− 0.005 | 72 | 0.259 +/− 0.004 | 63 |
| 0.8 | 0.220 +/− 0.006 | 50 | 0.174 +/− 0.011 | 42 |

At both 0.4% and 0.8% isobutanol, there was an increased amount of growth for the DPD4655 cultures overexpressing cfa as compared with the control DPD4658 cultures. Thus, overexpression of cfa in E. coli confers tolerance to isobutanol.

Example 4

Construction of Insertional Mutants in Lactobacillus spoT

Figure 2A:
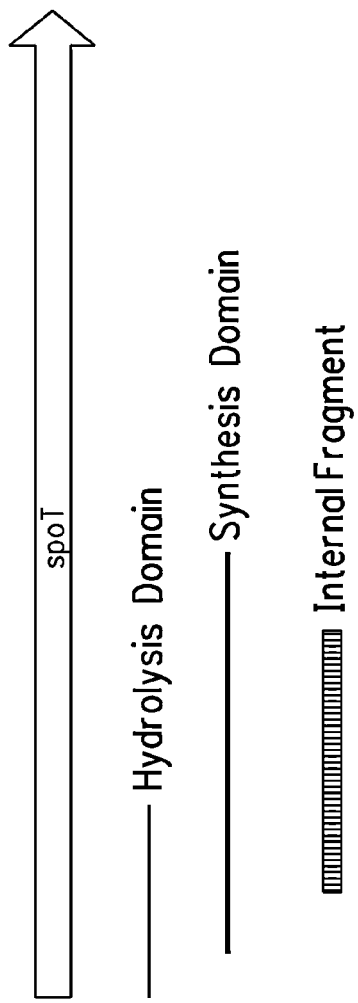
FIG. 2 shows a diagram of domains of the SpoT protein, and the internal fragment used in the insertional disruption plasmid pMPE69 (in A), and a diagram of the structure of the chromosomal spoT locus after insertion of plasmid pMPE69, with positions of the primers used for confirmation (in B).
Figure 2B:
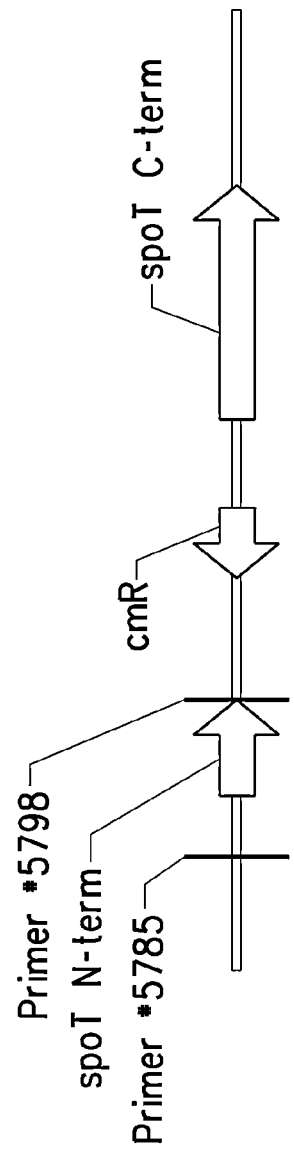

An internal fragment amplified from the L. plantarum (ATCC #BAA-793; also called NCIMB 8826 and WCFS1) spoT gene (SEQ ID NO:43) was chosen to disrupt both the ppGpp synthase and hydrolase domains. The 601 bp internal fragment, from nucleotide position 235 to 835, counting from the A of the initiator ATG, was chosen as it is predicted to disrupt the function of both domains, removing the first 234 bp of the hydrolase domain, and the last 191 bp of the synthesis domain as shown in FIG. 2, A. The internal fragment was PCR amplified using the primers #5807 and #5808 (SEQ ID NOs:86 and 87). These primers bound a portion of the spoT gene at nucleotide positions 235-259 and 816-835, respectively. Lactobacillus plantarum BAA-793 genomic DNA was used as the template in a PCR reaction using HI-FI Taq polymerase. An annealing temperature of 60° C. and an elongation time of 1 minute were used for 30 rounds of amplification. The amplified PCR product was inserted into the TOPO cloning vector pCR2.1-TOPO as per the manufacturer's (Invitrogen) instructions. The insertion of the PCR product was confirmed by restriction digestion. This construct was designated pTOPO-relAint.

A plasmid pMPE3 was constructed by amplifying a 2.45 kb fragment of the Bacillus shuttle vector pMK4 (purchased from Bacillus Genetics Stock center) using the primers pUCCMNotIR (SEQ ID NO:88) and pUCCMNotIF (SEQ ID NO:89). The amplified fragment contained the multiple cloning site, lacZ-alpha, pMB1 origin of replication and chloramphenicol resistance gene from pMK4. The amplified fragment was digested with NotI and then circularized by ligation, generating pMPE3 which can replicate in E. coli but not in Lactobacillus plantarum.

The spot fragment was excised from the pTOPO-relAint plasmid using BamHI and PstI sites that flank the inserted PCR product. The resulting ~650 bp band was gel purified and ligated into similarly digested plasmid pMPE3. The resulting plasmid was again confirmed by restriction digestion and designated pMPE69.

pMPE69 was transformed into L. plantarum PNO512 (ATCC #PTA-7727), using 5 µg of DNA and 60 µl of competent cells prepared using standard procedures. Aliquots of the transformation were plated on MRS with 10 ug/ml chloramphenicol and incubated at 30° C. overnight. 10 putative single crossover integrants were transferred into MRS with 10 ug/ml of chloramphenicol and again grown up overnight at 30° C. Aliquots of the 10 integrant cultures were used for Instagene [Bio-Rad Laboratories, Hercules, Calif.] preparations of genomic DNA. PCR confirmation of pMPE69 insertion into the spoT gene was performed using primers #5785 and #5798 (SEQ ID NOs:90 and 91). Primer #5785 binds upstream of the spoT gene, while #5798 binds within the pMPE3 backbone. The PCR reactions were predicted to produce a ~1400 bp product. This product was observed in 8 of the 10 putative integrants. The first two integrants were saved and designated MS0280 and MS0281. The structure of the chromosomal spoT locus after insertion of plasmid pMPE69, and positions of the primers used for confirmation, are shown in FIG. 2, B.

Example 5

Improved Tolerance with Combination cfa1 Overexpression and spoT Mutation

The purpose of this Example was to test the effect of a combination of cfa1 overexpression and spoT mutation on the isobutanol tolerance of Lactobacillus plantarum. To create a strain with both gene modifications, pFP996-atpB-cfa1 (described in Example 1; also called pFP996-1)) was transformed into the MS0280 strain (described in Example 4; also called PN1300) creating strain PN1312. For a control strain, pFP996 (described in Example 1) was transformed into MS0280 creating PN1310. Strain PN1312, which contained a multicopy expression plasmid with cfa1, was compared to strain PN1310, which contained the vector control.

The growth of the strains over time was followed, and tolerance compared as follows. The strains were cultured in S36 medium (contains 10 mM ammonium sulfate, 5 mM potassium phosphate buffer, pH 6.0, 50 mM MES, pH 6.0, 2 mM $MgCl_2$, 0.7 mM $CaCl_2$, 50 µM $MnCl_2$, 1 µM $FeCl_3$, 1 µM $ZnCl_2$, 1.72 µM $CuCl_2$, 2.53 µM $CoCl_2$, 2.42 µM $Na_2MoO_4$, 2 µM thiamine hydrochloride, 0.01 M glucose, 0.2% yeast extract and 0.01% casamino acids) overnight at 30° C. under anaerobic conditions. The next day, cultures were started from the overnight cultures in fresh medium, with initial OD600 values of 0.18. These cultures were incubated at 30° C. under anaerobic conditions for 4 hours. During this time, PN1310 reached an OD600 of 0.83, and PN1312 reach an OD600 of 0.61. This incubation period allowed the cyclopropane fatty acid to increase in the membrane. Following the 4 hour incubation period, 6 ml of the PN1310 culture was dispensed into 4 tubes, while 5 ml of the PN1312 culture was dispensed into 4 tubes. The cells were collected by centrifugation and resuspended as follows: 2 tubes each of 5 ml S36 medium and 2 tubes each of 5 ml S36 medium+3% isobutanol. After obtaining Initial OD600 values, the tubes were incubated at 30° C. under anaerobic conditions. OD600 values were obtained at 2 hours. Duplicate samples were averaged to calculate the change in OD600 values. The results are summarized in Table 16.

TABLE 16

The change in OD600 for both strains in the presence and absence of isobutanol.

|  | PN1310 (vector) | | PN1312 (cfa1) | |
| --- | --- | --- | --- | --- |
|  | 0% | 3% | 0% | 3% |
| 2 h Δ OD | 1.2 | 0.3 | 1.2 | 0.5 |

The vector alone was inhibited 75% for growth at 3% isobutanol and the strain with cfa1 overexpression was inhibited 59% for growth at 3% isobutanol. Thus, improvements in tolerance for strain PN1312 (spoT) were obtained at a high concentration of isobutanol.

Example 6

Prophetic

Producing Isobutanol Using E. coli Strain with Increased Expression of cfa

E. coli strains engineered to express an isobutanol biosynthetic pathway are described in commonly owned and co-pending US patent application publication #US20070092957A1, Examples 9-15, which are herein incorporated by reference. Strain BL21 (DE) 1.5GI yqhD/pTrc99a::budB-ilvC-ilvD-kivD was derived from BL21 (DE3) (Invitrogen) and was engineered to contain an operon expressed from the trc promoter that includes the *Klebsiella pneumoniae* budB coding region for acetolactate synthase, the *E. coli* ilvC coding region for acetohydroxy acid reductoisomerase, the *E. coli* ilvD coding region for acetohydroxy acid dehydratase and the *Lactococcus lactis* kivD coding region for branched chain α-keto acid decarboxylase. In addition, in this strain the native promoter of the yqhD gene (encoding 1,3-propanediol dehydrogenase) was replaced with the 1.5GI promoter (WO 2003/089621). The same promoter replacement was made in *E. coli* strain MG1655 to create MG1655 1.5GI-yqhD::Cm, and the same plasmid was introduced resulting in strain MG655 1.5/GI yqhD/pTrc99A::budB-ilvC-ilvD-kivD.

These isobutanol pathway containing strains are engineered for butanol tolerance by introducing a compatible plasmid for overexpression of the cfa gene. This plasmid is constructed by amplifying the region from plasmid pDEW849 (described in Example 3) with the trc promoter and the *E. coli* cfa gene. Both of the primers for amplification (SEQ ID NOs:92 and 93) also have a BsrD I restriction site. The PCR product is digested with BsrD I and ligated into BsrD I digested vector pACYC184 (New England Biolabs, Beverly, Mass.). Transformants of *E. coli* TOP10 are selected for tetracycline resistance and screened for sensitivity to chloramphenicol. Plasmid DNA is isolated from tetracycline resistant and chloramphenicol sensitive transformants. The presence of the trc promoter and the *E. coli* cfa gene are verified by DNA sequence analysis. This cfa plasmid is used to transform strains BL21 (DE) 1.5GI yqhD/pTrc99a::budB-ilvC-ilvD-kivD and MG655 1.5/GI yqhD/pTrc99A::budB-ilvC-ilvD-kivD selecting for ampicillin resistance and tetracycline resistance.

These strains are analyzed for butanol production.

The cells from cultures of each strain are used to inoculate shake flasks (approximately 175 mL total volume) containing 50 or 170 mL of TM3a/glucose medium (with appropriate antibiotics) to represent high and low oxygen conditions, respectively. TM3a/glucose medium contains (per liter): glucose (10 g), $KH_2PO_4$ (13.6 g), citric acid monohydrate (2.0 g), $(NH_4)_2SO_4$ (3.0 g), $MgSO_4.7H_2O$ (2.0 g), $CaCl_2.2H_2O$ (0.2 g), ferric ammonium citrate (0.33 g), thiamine HCl (1.0 mg), yeast extract (0.50 g), and 10 mL of trace elements solution. The pH was adjusted to 6.8 with $NH_4OH$. The trace elements solution contains: citric acid $H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L).

The flasks are inoculated at a starting $OD_{600}$ of $\leq 0.01$ units and incubated at 34° C. with shaking at 300 rpm. The flasks containing 50 mL of medium are closed with 0.2 μm filter caps; the flasks containing 150 mL of medium are closed with sealed caps. IPTG is added to a final concentration of 0.04 mM when the cells reach an $OD_{600}$ of $\geq 0.4$ units. Approximately 18 h after induction, an aliquot of the broth is analyzed by HPLC (Shodex Sugar SH1011 column (Showa Denko America, Inc. NY) with refractive index (RI) detection) and GC (Varian CP-WAX 58(FFAP) CB, 0.25 mm×0.2 μm×25 m (Varian, Inc., Palo Alto, Calif.) with flame ionization detection (FID)) for isobutanol content, as described in the General Methods section. No isobutanol is detected in control strains. Molar selectivities and titers of isobutanol produced by strains carrying pTrc99A::budB-ilvC-ilvD-kivD are obtained. Significantly higher titers of isobutanol are obtained in the cultures of the strains with the cfa plasmid than in the parental strains.

Example 7

Prophetic

Producing 2-Butanol Using E. coli Strain with Increased Expression of cfa

The engineering of *E. coli* for expression of a 2-butanol biosynthetic pathway is described in commonly owned and co-pending US Patent Application Publication US20070259410A1, Examples 6 and 7, which are herein incorporated by reference. Construction is described of two plasmids for upper and lower pathway expression. In pBen-budABC, an NPR promoter (*Bacillus amyloliquefaciens* neutral protease promoter) directs expression of *Klebsiella pneumoniae* budABC coding regions for acetolactate decarboxylase, acetolactate synthase, and butanediol dehydrogenase. In pBen-pdd-sadh an NPR promoter directs expression of *Klebsiella oxytoca* pddABC coding regions for butanediol dehydratase alpha subunit, butanediol dehydratase beta subunit, and butanediol dehydratase gamma subunit, and the *Rhodococcus ruber* sadh coding region for butanol dehydrogenase. Plasmid p2BOH is described containing both operons, and strain NM522/p2BOH containing this plasmid for 2-butanol pathway expression is described.

The NM522/p2BOH strain is engineered for butanol tolerance by introducing the cfa overexpression plasmid (described in Example 6). *E. coli* NM522/p2BOH with and without the cfa plasmid are inoculated into a 250 mL shake flask containing 50 mL of medium and shaken at 250 rpm and 35°

C. The medium is composed of: dextrose, 5 g/L; MOPS, 0.05 M; ammonium sulfate, 0.01 M; potassium phosphate, monobasic, 0.005 M; S10 metal mix, 1% (v/v); yeast extract, 0.1% (w/v); casamino acids, 0.1% (w/v); thiamine, 0.1 mg/L; proline, 0.05 mg/L; and biotin 0.002 mg/L, and is titrated to pH 7.0 with KOH. S10 metal mix contains: $MgCl_2$, 200 mM; $CaCl_2$, 70 mM; $MnCl_2$, 5 mM; $FeCl_3$, 0.1 mM; $ZnCl_2$, 0.1 mM; thiamine hydrochloride, 0.2 mM; $CuSO_4$, 172 µM; $CoCl_2$, 253 µM; and $Na_2MoO_4$, 242 µM. After 18 h, 2-butanol is detected by HPLC or GC analysis using methods that are well known in the art, for example, as described in the General Methods section above. Higher titers are obtained from the strain with the cfa plasmid.

Example 8

Prophetic

Producing 1-Butanol Using E. coli Strain with Increased Expression of cfa

E. coli strains engineered to express a 1-butanol biosynthetic pathway are described in commonly owned and co-pending US Patent Application Publication US20080182308A1, Example 13, which is herein incorporated by reference. Two plasmids were constructed that carry genes encoding the 1-butanol pathway. Plasmid PBHR T7-ald contains a gene for expression of butyraldehyde dehydrogenase (ald). Plasmid pTrc99a-E-C-H-T contains a four gene operon comprising the upper pathway, for expression of acetyl-CoA acetyltransferase (thlA), 3-hydroxybutyryl-CoA dehydrogenase (hbd), crotonase (crt), and butyryl-CoA dehydrogenase (trans-2-enoyl-CoA reductase, EgTER(opt)) (EgTER(opt), crt, hbd and thlA). In addition, in this strain the native promoter of the yqhD gene (encoding 1,3-propanediol dehydrogenase) was replaced with the 1.5GI promoter (WO 2003/089621).

The 1-butanol producing strain is engineered for butanol tolerance by introducing the cfa overexpression plasmid (described in Example 6).

The parental strain and the transformant with the cfa overexpression plasmid are used to inoculate shake flasks (approximately 175 mL total volume) containing 15, 50 and 150 mL of TM3a/glucose medium (with appropriate antibiotics) to represent high, medium and low oxygen conditions, respectively. TM3a/glucose medium contains (per liter): 10 g glucose, 13.6 g $KH_2PO_4$, 2.0 g citric acid monohydrate, 3.0 g $(NH_4)_2SO_4$, 2.0 g $MgSO_4.7H_2O$, 0.2 g $CaCl_2.2H_2O$, 0.33 g ferric ammonium citrate, 1.0 mg thiamine HCl, 0.50 g yeast extract, and 10 mL trace elements solution, adjusted to pH 6.8 with $NH_4OH$. The solution of trace elements contains: citric acid $H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L). The flasks are inoculated at a starting $OD_{600}$ of $\leqq 0.01$ units and incubated at 34° C. with shaking at 300 rpm. The flasks containing 15 and 50 mL of medium are capped with vented caps; the flasks containing 150 mL, are capped with non-vented caps to minimize air exchange. IPTG is added to a final concentration of 0.04 mM; the $OD_{600}$ of the flasks at the time of addition is $\geqq 0.4$ units. Approximately 15 h after induction, an aliquot of the broth is analyzed by HPLC (Shodex Sugar SH1011 column) with refractive index (RI) detection and GC (Varian CP-WAX 58(FFAP) CB column, 25 m×0.25 mm id×0.2 µm film thickness) with flame ionization detection (FID) for 1-butanol content, as described in the General Methods section. Titers of 1-butanol are found to be higher in the strain harboring the cfa expression plasmid.

Example 9

Prophetic

Expression of an Isobutanol Biosynthetic Pathway in Lactobacillus plantarum with Increased Expression of cfa1

The purpose of this prophetic Example is to describe how to express an isobutanol biosynthetic pathway in a Lactobacillus plantarum strain that overexpresses cfa1. The five genes of the isobutanol pathway, encoding five enzyme activities, are divided into two operons for expression. The budB, ilvD and kivD genes, encoding the enzymes acetolactate synthase, acetohydroxy acid dehydratase, and branched-chain α-keto acid decarboxylase, respectively, are integrated into the chromosome of Lactobacillus plantarum by homologous recombination using the method described by Hols et al. (Appl. Environ. Microbiol. 60:1401-1413 (1994)). The remaining two genes of the isobutanol biosynthetic pathway (ilvC and bdhB, encoding the enzymes acetohydroxy acid reductoisomerase and butanol dehydrogenase, respectively) and the cfa1 gene are cloned into an expression plasmid and transformed into the Lactobacillus strain carrying the integrated isobutanol genes. Lactobacillus plantarum is grown in MRS medium (Difco Laboratories, Detroit, Mich.) at 37° C., and chromosomal DNA is isolated as described by Moreira et al. (BMC Microbiol. 5:15 (2005)).

Integration

The budB-ilvD-kivD cassette under the control of the synthetic P11 promoter (Rud et al., Microbiology 152:1011-1019 (2006)) is integrated into the chromosome of Lactobacillus plantarum ATCC BAA-793 (NCIMB 8826) at the ldhL1 locus by homologous recombination. To build the ldhL integration targeting vector, a DNA fragment from Lactobacillus plantarum (Genbank NC_004567) with homology to ldhL is PCR amplified with primers LDH EcoRV F (SEQ ID NO:94) and LDH AatIIR (SEQ ID NO:95). The 1986 bp PCR fragment is cloned into pCR4Blunt-TOPO and sequenced. The pCR4Blunt-TOPO-ldhL1 clone is digested with EcoRV and AatII releasing a 1982 bp ldhL1 fragment that is gel-purified. The integration vector pFP988 (a Bacillus integration vector that contains an E. coli replicon from pBR322, an ampicillin antibiotic marker for selection in E. coli and two sections of homology to the sacB gene in the Bacillus chromosome that directs integration of the vector and intervening sequence by homologous recombination; given as SEQ ID NO:96) is digested with HindIII and treated with Klenow DNA polymerase to blunt the ends. The linearized plasmid is then digested with AatII and the 2931 bp vector fragment is gel purified. The EcoRV/AatII ldhL1 fragment is ligated with the pFP988 vector fragment and transformed into E. coli Top10 cells. Transformants are selected on LB agar plates containing ampicillin (100 µg/mL) and are screened by colony PCR to confirm construction of pFP988-ldhL.

To add a selectable marker to the integrating DNA, the Cm resistance gene with its promoter is PCR amplified from pC194 (GenBank NC_002013) with primers Cm F (SEQ ID NO:97) and Cm R (SEQ ID NO:98), amplifying a 836 bp PCR product. This PCR product is cloned into pCR4Blunt-TOPO and transformed into E. coli Top10 cells, creating pCR4Blunt-TOPO-Cm. After sequencing to confirm that no errors are introduced by PCR, the Cm cassette is digested from pCR4Blunt-TOPO-Cm as an 828 bp MluI/SwaI fragment and is gel purified. The ldhL-homology containing integration vector pFP988-ldhL is digested with MluI and SwaI and the 4740 bp vector fragment is gel purified. The Cm cassette fragment is ligated with the pFP988-ldhL vector creating pFP988-DldhL::Cm.

Finally the budB-ilvD-kivD cassette which includes the *Klebsiella pneumoniae* budB coding region (SEQ ID NO:19), the *E. coli* ilvD coding region (SEQ ID NO:33), and the codon optimized *Lactococcus lactis* kivD coding region (SEQ ID NO:35) from pFP988DssPspac-budB-ilvD-kivD (described in Examples 1, 4, 9, 10, 11, 12, 14, and 20 of US 2007-0092957 A1) is modified to replace the amylase promoter with the synthetic P11 promoter. Then, the whole operon is moved into pFP988-DldhL::Cm. The P11 promoter is built by oligonucleotide annealing with primers P11 F-StuI (SEQ ID NO:99) and P11 R-SpeI (SEQ ID NO:100). The annealed oligonucleotide is gel-purified on a 6% Ultra PAGE gel (Embi Tec, San Diego, Calif.). The plasmid pFP988DssPspac-budB-ilvD-kivD, containing the amylase promoter, is digested with StuI and SpeI and the resulting 10.9 kbp vector fragment is gel-purified. The isolated P11 fragment is ligated with the digested pFP988DssPspac-budB-ilvD-kivD to create pFP988-P11-budB-ilvD-kivD. Plasmid pFP988-P11-budB-ilvD-kivD is then digested with StuI and BamHI and the resulting 5.4 kbp P11-budB-ilvD-kivD fragment is gel-purified. pFP988-DldhL::Cm is digested with HpaI and BamHI and the 5.5 kbp vector fragment isolated. The budB-ilvD-kivD operon is ligated with the integration vector pFP988-DldhL::Cm to create pFP988-DldhL-P11-budB-ilvD-kivD::Cm.

Integration of pFP988-DldhL-P11-budB-ilvD-kivD::Cm into *L. plantarum* BAA-793 to Form *L. plantarum* ΔldhL1:: budB-ilvD-kivD::Cm Comprising Exogenous budB, ilvD, and kivD Genes.

Electrocompetent cells of *L. plantarum* are prepared as described by Aukrust, T. W., et al. (In: *Electroporation Protocols for Microorganisms*; Nickoloff, J. A., Ed.; *Methods in Molecular Biology*, Vol. 47; Humana Press, Inc., Totowa, N.J., 1995, pp 201-208). After electroporation, cells are outgrown in MRSSM medium (MRS medium supplemented with 0.5 M sucrose and 0.1 M MgCl$_2$) as described by Aukrust et al. supra for 2 h at 37° C. without shaking. Electroporated cells are plated for selection on MRS plates containing chloramphenicol (10 µg/mL) and incubated at 37° C. Transformants are initially screened by colony PCR amplification to confirm integration, and initial positive clones are then more rigorously screened by PCR amplification with a battery of primers.

Plasmid Expression of ilvC, bdhB and cfa1 Genes.

The remaining two isobutanol genes and cfa1 under the control of the *L. plantarum* ldhL promoter (Ferain et al., *J. Bacteriol.* 176:596-601 (1994)) are expressed from plasmid pTRKH3 (O'Sullivan D J and Klaenhammer T R, *Gene* 137: 227-231 (1993)). The ldhL promoter is PCR amplified from the genome of *L. plantarum* ATCC BAA-793 using primers PldhL F-HindIII (SEQ ID NO:101) and PldhL R-BamHI (SEQ ID NO:102). The 411 bp PCR product is cloned into pCR4Blunt-TOPO and sequenced. The resulting plasmid, pCR4Blunt-TOPO-PldhL is digested with HindIII and BamHI releasing the PldhL fragment. The cfa1 coding region is PCR amplified from *L. plantarum* PN0512 genomic DNA using primers F-SphI-cfa1 and R-SphI-cfa1 (SEQ ID NOs: 103 and 104). The 1182 bp PCR product is cloned into pCR4Blunt-TOPO and sequenced. The resulting plasmid, pCR4Blunt-TOPO-cfa1, is digested with SphI releasing the fragment with the cfa1 coding region.

Plasmid pTRKH3 is digested with SphI and partially digested with HindIII. The gel-purified approximately 7 Kb vector fragment is ligated with the PldhL fragment and the gel-purified 2.4 kbp BamHI/SphI fragment containing ilvC (B.s.)-bdhB, which includes the *Bacillus subtilis* ilvC coding region (SEQ ID NO:105) and the *Clostridium acetobutylicum* bdhB coding region (SEQ ID NO:13) from a *Bacillus* expression plasmid pBDPgroE-ilvC(B.s.)-bdhB (described in Example 20 of US 2007-0092957 A1) in a three-way ligation. The ligation mixture is transformed into *E. coli* Top 10 cells and transformants are grown on Brain Heart Infusion (BHI, Difco Laboratories, Detroit, Mich.) plates containing erythromycin (150 mg/L). Transformants are screened by PCR to confirm construction. The resulting plasmid, pTRKH3-ilvC (B.s.)-bdhB, is digested with SphI, treated with calf intestinal alkaline phosphatase, and ligated with the cfa1 coding region fragment. The ligation mixture is transformed into *E. coli* Top 10 cells and transformants are grown on Brain Heart Infusion (BHI, Difco Laboratories, Detroit, Mich.) plates containing erythromycin (150 mg/L). The transformants are screened by PCR and one with the cfa1 gene in the same orientation as ilvC and bdhB is retained and named pTRKH3-ilvC(B.s.)-bdhB-cfa1. This plasmid and plasmid pTRKH3-ilvC(B.s.)-bdhB are transformed into *L. plantarum* ΔldhL1::budB-ilvD-kivD::Cm by electroporation, as described above.

*L. plantarum* ΔldhL1::budB-ilvD-kivD::Cm containing pTRKH3-ilvC(B.s.)-bdhB-cfa1 or containing pTRKH3-ilvC (B.s.)-bdhB are inoculated into a 250 mL shake flask containing 50 mL of MRS medium plus erythromycin (10 µg/mL) and grown at 37° C. for 18 to 24 h without shaking, after which isobutanol is detected by HPLC or GC analysis. Higher titers of isobutanol are obtained from the strain with the cfa1 gene on the plasmid.

Example 10

Prophetic

Expression of the 1-Butanol Biosynthetic Pathway in *Lactobacillus plantarum* with Increased Expression of cfa1

The purpose of this prophetic Example is to describe how to express the 1-butanol biosynthetic pathway in a *Lactobacillus plantarum* strain that overexpresses cfa1. The six genes of the 1-butanol pathway, encoding six enzyme activities, are divided into two operons for expression. The first three genes of the pathway (thl, hbd, and crt, encoding the enzymes acetyl-CoA acetyltransferase, 3-hydroxybutyryl-CoA dehydrogenase, and crotonase, respectively) are integrated into the chromosome of *Lactobacillus plantarum* by homologous recombination using the method described by Hols et al. (*Appl. Environ. Microbiol.* 60:1401-1413 (1994)). The last three genes of the 1-butanol pathway (EgTER, ald, and bdhB, encoding the enzymes butyryl-CoA dehydrogenase, butyraldehyde dehydrogenase and butanol dehydrogenase, respectively) and cfa1 are cloned into an expression plasmid and transformed into the *Lactobacillus* strain carrying the integrated upper pathway 1-butanol genes. *Lactobacillus* is grown in MRS medium (Difco Laboratories, Detroit, Mich.) at 37° C. Chromosomal DNA is isolated from *Lactobacillus plantarum* as described by Moreira et al. (*BMC Microbiol.* 5:15 (2005)).

Integration

The thl-hbd-crt cassette under the control of the synthetic P11 promoter (Rud et al., *Microbiology* 152:1011-1019 (2006)) is integrated into the chromosome of *Lactobacillus*

*plantarum* ATCC BAA-793 (NCIMB 8826) at the ldhL1 locus by homologous recombination. To build the ldhL integration targeting vector, a DNA fragment from *Lactobacillus plantarum* (Genbank NC_004567) with homology to ldhL is PCR amplified with primers LDH EcoRV F (SEQ ID NO:94) and LDH AatIIR (SEQ ID NO:95). The 1986 bp PCR fragment is cloned into pCR4Blunt-TOPO and sequenced. The pCR4Blunt-TOPO-ldhL1 clone is digested with EcoRV and AatII releasing a 1982 bp ldhL1 fragment that is gel-purified. The integration vector pFP988, described in Example 9, is digested with HindIII and treated with Klenow DNA polymerase to blunt the ends. The linearized plasmid is then digested with AatII and the 2931 bp vector fragment is gel-purified. The EcoRV/AatII ldhL1 fragment is ligated with the pFP988 vector fragment and transformed into *E. coli* Top10 cells. Transformants are selected on LB agar plates containing ampicillin (100 μg/mL) and are screened by colony PCR to confirm construction of pFP988-ldhL.

To add a selectable marker to the integrating DNA, the Cm gene with its promoter is PCR amplified from pC194 (Genbank NC_002013) with primers Cm F (SEQ ID NO:97) and Cm R (SEQ ID NO:98), amplifying a 836 bp PCR product. The amplicon is cloned into pCR4Blunt-TOPO and transformed into *E. coli* Top10 cells, creating pCR4Blunt-TOPO-Cm. After sequencing to confirm that no errors are introduced by PCR, the Cm cassette is digested from pCR4Blunt-TOPO-Cm as an 828 bp MluI/SwaI fragment and is gel-purified. The ldhL-homology containing integration vector pFP988-ldhL is digested with MluI and SwaI and the 4740 bp vector fragment is gel-purified. The Cm cassette fragment is ligated with the pFP988-ldhL vector creating pFP988-DldhL::Cm.

Finally the thl-hbd-crt cassette from pFP988Dss-T-H-C (described in WO2007041269 Examples 13 and 14, which are herein incorporated by reference) including the *Clostridium acetobutylicum* thlA, hbd, and crt coding regions (SEQ ID NOs:1, 5, and 7 respectively) is modified to replace the amylase promoter with the synthetic P11 promoter. Then, the whole operon is moved into pFP988-DldhL::Cm. The P11 promoter is built by oligonucleotide annealing with primer P11 F (SEQ ID NO:106) and P11 R (SEQ ID NO:107). The annealed oligonucleotide is gel-purified on a 6% Ultra PAGE gel (Embi Tec, San Diego, Calif.). The plasmid pFP988Dss-T-H-C is digested with XhoI and SmaI and the 9 kbp vector fragment is gel-purified. The isolated P11 fragment is ligated with the digested pFP988Dss-T-H-C to create pFP988-P11-T-H-C. Plasmid pFP988-P11-T-H-C is digested with XhoI and BamHI and the 3034 bp P11-T-H-C fragment is gel-purified. pFP988-DldhL::Cm is digested with XhoI and BamHI and the 5558 bp vector fragment isolated. The upper pathway operon is ligated with the integration vector to create pFP988-DldhL-P11-THC::Cm.

Integration of pFP988-DldhL-P11-THC::Cm into *L. plantarum* BAA-793 to Form *L. plantarum* ΔldhL1::T-H-C::Cm Comprising Exogenous thl, hbd, and crt Genes Electrocompetent cells of *L. plantarum* are prepared as described by Aukrust, T. W., et al. (In: *Electroporation Protocols for Microorganisms*; Nickoloff, J. A., Ed.; *Methods in Molecular Biology*, Vol. 47; Humana Press, Inc., Totowa, N.J., 1995, pp 201-208). After electroporation, cells are outgrown in MRSSM medium (MRS medium supplemented with 0.5 M sucrose and 0.1 M MgCl$_2$) as described by Aukrust et al. supra for 2 h at 37° C. without shaking. Electroporated cells are plated for selection on MRS plates containing chloramphenicol (10 μg/mL) and incubated at 37° C. Transformants are initially screened by colony PCR amplification to confirm integration, and initial positive clones are then more rigorously screened by PCR amplification with a battery of primers.

Plasmid Expression of EgTER, ald, and bdhB Genes.

The three remaining 1-butanol genes under the control of the *L. plantarum* ldhL promoter (Ferain et al., *J. Bacteriol.* 176:596-601 (1994)). and cfa1 under control of the atpB promoter are expressed from plasmid pTRKH3 (O'Sullivan D J and Klaenhammer T R, *Gene* 137:227-231 (1993)). The ldhL promoter is PCR amplified from the genome of *L. plantarum* ATCC BAA-793 with primers PldhL F (SEQ ID NO:108) and PldhL R (SEQ ID NO:109). The 369 bp PCR product is cloned into pCR4Blunt-TOPO and sequenced. The resulting plasmid, pCR4Blunt-TOPO-PldhL is digested with SacI and BamHI releasing the 359 bp PldhL fragment.

pHT01-ald-EB (described in WO2007041269 Examples 9, 13 and 14) including the *Clostridium beijerinckii* ald coding region, the *Clostridium acetobutylicum* bdhB and a codon optimized *Euglena gracilis* TER fragment (SEQ ID NOs:11, 13, and 110 respectively) is digested with SacI and BamHI and the 10503 bp vector fragment is recovered by gel purification. The PldhL fragment and vector are ligated creating pHT01-Pldhl-ald-EB.

To subclone the ldhL promoter-ald-EgTER-bdh cassette, pHT01-Pldhl-ald-EB is digested with MluI and the ends are treated with Klenow DNA polymerase. The linearized vector is digested with SalI and the 4270 bp fragment containing the PldhL-AEB fragment is gel-purified. Plasmid pTRKH3 is digested with SalI and EcoRV and the gel-purified vector fragment is ligated with the PldhL-AEB fragment. The ligation mixture is transformed into *E. coli* Top 10 cells and transformants are plated on Brain Heart Infusion (BHI, Difco Laboratories, Detroit, Mich.) plates containing erythromycin (150 mg/L). Transformants are screened by PCR to confirm construction of pTRKH3-ald-E-B.

The atpB promoter and cfa1 gene are amplified using plasmid pFP996-atpB-cfa1 (described in Example 1) as a template and the primers F-NruI-atpB and R-XhoI-cfa1 SEQ ID NOs: 111 and 112). The 1496 bp PCR product is cloned into pCR4Blunt-TOPO and sequenced. The resulting plasmid, pCR4Blunt-TOPO-PatpB-cfa1, is digested with NruI and XhoI releasing the fragment with the atpB promoter and cfa1 coding region.

The plasmid pTRKH3-ald-E-B is digested with NruI and XhoI and the large fragment is gel purified and ligated with the PatpB-cfa1 fragment. The ligation mixture is transformed into *E. coli* Top 10 cells and transformants are grown on Brain Heart Infusion (BHI, Difco Laboratories, Detroit, Mich.) plates containing erythromycin (150 mg/L). Transformants are screened by PCR to confirm construction of plasmid pTRKH3-ald-E-B-PatpB-cfa1.

Plasmids pTRKH3-ald-E-B and pTRKH3-ald-E-B-PatpB-cfa1 are transformed into *L. plantarum* ΔldhL1::T-H-C::Cm by electroporation, as described above.

*L. plantarum* ΔldhL1::T-H-C::Cm containing pTRKH3-ald-E-B or containing pTRKH3-ald-E-B-PatpB-cfa1 are inoculated into a 250 mL shake flask containing 50 mL of MRS medium plus erythromycin (10 μg/mL) and grown at 37° C. for 18 to 24 h without shaking. After 18 h to 24, 1-butanol is detected by HPLC or GC analysis. Higher titers of 1-butanol are obtained from the strain with the cfa1 gene on the plasmid.

TABLE 6

```
HMMER2.0 [2.3.2]                                      Program name and version
NAME RelA_SpoT                                        Name of input sequence alighment file
DESC Region found in RelA/SpoT proteins               Domain description
LENG 131                                              Length of alignment
ALPH Amino                                            Type of residues
MAP yes                                               Map of the match states to the columns of the alignment
COM hmmbuild -F --wme HMM_Is.ann SEED.ann             Commands used to generate the file: this one means that hmmbuild (default parameters) was
                                                      applied to the alignment file
COM hmmcalibrate --seed 0 HMM_Is.ann                  Commands used to generate the file: this one means that hmmcalibrate (default parameters) was
                                                      applied to the hmm profile
NSEQ 105                                              Number of sequences in the alignment file
DATE Sun Apr 29 16:27:35 2007                         When file was generated
XT -8455 -4 -1000 -1000 -8455 -4 -8455 -4
NULT -4 -8455                                         The transition probability distribution for the null model (single G state).
NULE 595 -1558 85 338 -294 453 -1158 197 249          The symbol emission probability distribution for the null model (G state)
902 -1085 -142 -21 -313 45 531 201 384 -1998 -644
EVD -69.960602 0.225039                               The extreme value distribution parameters μ and lambda respectively
The highest probability is highlighted for each position
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -36 | * | -5356 | | | | | | | | | | | | | | | | | | |
| 1(S) | -269 | -3394 | -3033 | -1314 | -3476 | 1305 | 1299 | 179 | -2367 | -3304 | -21 | -2699 | -3943 | -2287 | -134 | 2447 | 587 | -2807 | -600 | -3142 | 1 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | -36 | * | | | | | | | | | | | | |
| 2(R) | -8636 | -7266 | -8174 | -8366 | -8675 | -7221 | -7550 | -9684 | -7568 | -9015 | -8918 | -8342 | -7640 | -8024 | 4273 | -9078 | -8724 | -9380 | -7386 | -8557 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 3(I) | 346 | -2709 | -5178 | -1171 | -2663 | -4419 | -3247 | 2104 | -4149 | 475 | -1911 | -2635 | 754 | -2873 | -3589 | -3342 | 180 | 1910 | -3166 | 782 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 4(K) | 379 | -5857 | -6629 | -4816 | -6997 | -5784 | -3655 | -6203 | 3759 | -5791 | -5155 | -4564 | -5740 | -3239 | 546 | -5247 | -5012 | -5975 | -5575 | -5575 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 5(S) | -2636 | -4111 | 545 | 897 | -4431 | -1109 | 2025 | -4183 | 95 | -4127 | -3200 | 1523 | -1245 | -1807 | -966 | 2270 | -291 | -3733 | -4294 | -3610 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 6(P) | 24 | -2715 | -5120 | -2766 | 701 | -4410 | -1823 | 1032 | -4108 | 586 | -470 | -1629 | 2144 | 1120 | 218 | -2515 | -2814 | 607 | 1680 | -1014 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 7(Y) | -523 | -3971 | 1548 | -166 | -774 | 99 | -921 | -2261 | -7 | -3964 | 807 | -1289 | -3233 | -1852 | -1705 | 475 | -824 | -54 | -29 | 2960 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 8(S) | -2932 | -4786 | -3950 | -3310 | -5645 | -1484 | 2163 | -5264 | 832 | -5129 | -4299 | -3445 | -4731 | -2796 | -515 | 3051 | 689 | -4806 | -5167 | -4744 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 9(L) | -836 | -3136 | -5739 | 568 | -3139 | -5005 | -3930 | 1925 | -4759 | 2017 | 453 | -4650 | -5023 | -4394 | -4581 | -4110 | 748 | 760 | -3763 | -3421 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 10(H) | -743 | -2709 | -5175 | -4542 | -975 | -3798 | 2757 | 1631 | 1480 | 567 | 1236 | -4049 | -4469 | -3336 | -1344 | -3501 | -239 | -1729 | 1427 | 1587 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 11(E) | 812 | -2296 | 359 | 2322 | -4413 | -120 | -2251 | -4164 | 1065 | -2680 | -1059 | 753 | -3686 | -234 | 851 | -1728 | -2361 | -3714 | -4275 | -1555 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

TABLE 6-continued

| | | | | | | | | | | | | | | | | | | | |
|---|---|---|---|---|---|---|---|---|---|---|---|---|---|---|---|---|---|---|---|
| 12(K) | -6000 | -6172 | -6992 | -6261 | -7382 | -6247 | -5316 | -6761 | 3952 | -6949 | -6478 | -5972 | -6585 | -5040 | -4055 | -6134 | -6056 | 28 | -6575 | -6738 | 12 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -152 | -10485 | -3328 | -894 | -1115 | -701 | -1378 | * | * | | | | | | | | | | | |

| | | | | | | | | | | | | | | | | | | | |
|---|---|---|---|---|---|---|---|---|---|---|---|---|---|---|---|---|---|---|---|
| 13(M) | 137 | 813 | -5304 | -4679 | -2722 | -4525 | -3418 | 1984 | -4284 | 1963 | 2332 | -4173 | -4564 | -3911 | -4091 | -6 | -2738 | -53 | -3271 | -2929 | 13 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |

| | | | | | | | | | | | | | | | | | | | |
|---|---|---|---|---|---|---|---|---|---|---|---|---|---|---|---|---|---|---|---|
| 14(R) | -239 | -3927 | -2354 | 695 | -4232 | -3472 | -543 | 1665 | 63 | -1374 | -3020 | 56 | -3565 | 931 | 2320 | -532 | -715 | -1005 | -4120 | -1420 | 14 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |

| | | | | | | | | | | | | | | | | | | | |
|---|---|---|---|---|---|---|---|---|---|---|---|---|---|---|---|---|---|---|---|
| 15(R) | -2550 | -4002 | -1611 | -873 | -4325 | -3228 | -2166 | -3858 | 1929 | -2335 | -3093 | -1941 | -3612 | -592 | 3410 | -1607 | -1881 | -1789 | -4177 | -796 | 15 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |

| | | | | | | | | | | | | | | | | | | | |
|---|---|---|---|---|---|---|---|---|---|---|---|---|---|---|---|---|---|---|---|
| 16(K) | -2592 | -4054 | 441 | -1541 | -2782 | -1228 | 1146 | -4128 | 2757 | -4065 | -3145 | 345 | -3645 | 62 | 2325 | -2471 | -2528 | -3682 | -4223 | -2987 | 16 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -10 | -10334 | -7388 | -894 | -1115 | -2589 | -262 | * | * | | | | | | | | | | | |

| | | | | | | | | | | | | | | | | | | | |
|---|---|---|---|---|---|---|---|---|---|---|---|---|---|---|---|---|---|---|---|
| 17(G) | -439 | -3947 | -910 | -411 | -4264 | 2055 | 412 | -1602 | -540 | -932 | -3037 | 1223 | 1400 | 456 | -2125 | -1475 | 285 | -1173 | -4132 | -1559 | 17 |
| - | -148 | -503 | 230 | 43 | -384 | 397 | 103 | -624 | 210 | -463 | -723 | 279 | 395 | 42 | 93 | 356 | 120 | -372 | -297 | -225 |
| - | -2030 | -764 | -2589 | -9 | -7320 | -2351 | -315 | * | * | | | | | | | | | | | |

| | | | | | | | | | | | | | | | | | | | |
|---|---|---|---|---|---|---|---|---|---|---|---|---|---|---|---|---|---|---|---|
| 18(R) | -2270 | -3720 | 1435 | 161 | -4031 | -3248 | -1632 | -709 | 1079 | 1110 | -2811 | -1818 | 486 | -137 | 1515 | -1074 | -1407 | -113 | -3909 | -3232 | 19 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -933 | -10074 | -1073 | -894 | -1115 | -2322 | -322 | * | * | | | | | | | | | | | |

| | | | | | | | | | | | | | | | | | | | |
|---|---|---|---|---|---|---|---|---|---|---|---|---|---|---|---|---|---|---|---|
| 19(Y) | -1704 | -2350 | -2063 | 357 | -2425 | 330 | -1574 | 766 | -1385 | 638 | -1511 | 847 | -1019 | 176 | 354 | -1814 | -1643 | -225 | -2702 | 2577 | 20 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -59 | -9265 | -4693 | -894 | -1115 | -4748 | -55 | * | * | | | | | | | | | | | |

| | | | | | | | | | | | | | | | | | | | |
|---|---|---|---|---|---|---|---|---|---|---|---|---|---|---|---|---|---|---|---|
| 20(A) | 1291 | -3051 | -1441 | -892 | -3368 | -1078 | 1251 | -3115 | 1274 | -1686 | -2141 | -1202 | 1189 | 807 | 949 | -657 | 1066 | -2671 | -3236 | -2557 | 21 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -4 | -9209 | -10252 | -894 | -1115 | -4786 | -53 | * | * | | | | | | | | | | | |

| | | | | | | | | | | | | | | | | | | | |
|---|---|---|---|---|---|---|---|---|---|---|---|---|---|---|---|---|---|---|---|
| 21(E) | 1183 | -1955 | -1696 | 2066 | -496 | -3023 | -1792 | -1306 | -1882 | 442 | 1796 | -2114 | -2398 | -1737 | -929 | -1208 | 532 | -69 | -2366 | -1289 | 22 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -142 | -9209 | -3439 | -894 | -1115 | -4786 | -53 | * | * | | | | | | | | | | | |

| | | | | | | | | | | | | | | | | | | | |
|---|---|---|---|---|---|---|---|---|---|---|---|---|---|---|---|---|---|---|---|
| 22(K) | -1206 | -2955 | 636 | 1415 | -3275 | -2459 | -187 | -1129 | 2085 | 592 | -2044 | 110 | -2552 | 332 | 491 | -1366 | -1424 | -2047 | -3139 | -2457 | 23 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -243 | -9071 | -2706 | -894 | -1115 | -4871 | -50 | * | * | | | | | | | | | | | |

| | | | | | | | | | | | | | | | | | | | |
|---|---|---|---|---|---|---|---|---|---|---|---|---|---|---|---|---|---|---|---|
| 23(Y) | -190 | -2753 | -1190 | 199 | -3056 | -2310 | -976 | -2792 | -566 | -2763 | -1852 | 2167 | 1110 | -524 | 188 | 740 | -377 | -2366 | -2952 | 2331 | 24 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -220 | -8833 | -2844 | -894 | -1115 | -317 | -2340 | * | * | | | | | | | | | | | |

| | | | | | | | | | | | | | | | | | | | |
|---|---|---|---|---|---|---|---|---|---|---|---|---|---|---|---|---|---|---|---|
| 24(Y) | 589 | -3857 | -323 | 1165 | -4178 | -774 | 528 | -82 | 564 | -1707 | -2947 | 655 | 624 | 1450 | -1620 | -304 | -2324 | -2385 | -4041 | 1578 | 25 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -25 | -10213 | -5947 | -894 | -1115 | -3206 | -165 | * | * | | | | | | | | | | | |

| | | | | | | | | | | | | | | | | | | | |
|---|---|---|---|---|---|---|---|---|---|---|---|---|---|---|---|---|---|---|---|
| 25(L) | -2433 | -2599 | 287 | -592 | 1393 | -3986 | -2798 | 632 | -992 | 1726 | -491 | -3290 | 1216 | -2592 | -1706 | -963 | -2509 | -1387 | -3035 | 1676 | 26 |
| - | -160 | -511 | 238 | 56 | -357 | 388 | 95 | -626 | 218 | -467 | -713 | 280 | 390 | 34 | 89 | 357 | 110 | -373 | -305 | -198 |
| - | -570 | -1618 | -11232 | -2833 | -218 | -644 | -1475 | * | * | | | | | | | | | | | |

| | | | | | | | | | | | | | | | | | | | |
|---|---|---|---|---|---|---|---|---|---|---|---|---|---|---|---|---|---|---|---|
| 26(E) | -1873 | -4007 | 501 | 1640 | -4329 | -1258 | -627 | -4079 | 1047 | -3289 | -3097 | 1574 | -3601 | -1555 | 1328 | 578 | 837 | -3630 | -4191 | -406 | 37 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10387 | -11429 | -894 | -1115 | -214 | -2856 | * | * | | | | | | | | | | | |

TABLE 6-continued

| | | | | | | | | | | | | | | | | | | | | |
|---|---|---|---|---|---|---|---|---|---|---|---|---|---|---|---|---|---|---|---|---|
| 27(E) | -2620 | -4093 | 1181 | 2198 | -4414 | -2323 | 35 | -832 | 14 | -4109 | -3182 | 1504 | -3686 | -362 | 1046 | -370 | 824 | -3715 | -4276 | -2893 | 38 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -152 | -10485 | -3328 | -894 | -1115 | -701 | -1378 | * | * | | | | | | | | | | | |
| 28(I) | -4696 | -4224 | -7270 | -6828 | -3963 | 34 | -6270 | 2763 | -6665 | 1361 | 2414 | -6604 | -6610 | -6204 | -6563 | -6223 | -4653 | 1300 | -5515 | -5324 | 39 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 29(H) | 11 | -3932 | -2351 | -1019 | -808 | -3470 | 2074 | -3981 | -380 | -1097 | -1102 | 464 | -3563 | 1970 | -775 | 724 | 1837 | -3547 | -4124 | 1088 | 40 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 30(D) | -8244 | -7150 | 4231 | -7134 | -8528 | -6919 | -7294 | -9565 | -8093 | -8923 | -8858 | -7383 | -7382 | -7716 | -7899 | -8437 | -8388 | -9207 | -7288 | -8394 | 41 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 31(I) | -1871 | -3171 | -5759 | -5138 | 836 | -5012 | -3897 | 2342 | -4756 | 2340 | 1079 | -4661 | -4994 | -4328 | -4547 | -1960 | -3024 | -515 | -3655 | -3362 | 42 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 32(I) | 1206 | -1286 | -5086 | -4450 | 899 | 7 | -1562 | 2311 | -4045 | 495 | -485 | -3935 | -4339 | -3668 | -3090 | -466 | -2682 | 431 | -3026 | 909 | 43 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 33(G) | 1730 | -4170 | -6390 | -6633 | -6820 | 3263 | -5895 | -6670 | -6002 | -6872 | -5939 | -5150 | -5219 | -5907 | 507 | -3823 | -4041 | -5382 | -6876 | -6914 | 44 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 34(V) | -4715 | 495 | -7356 | -6983 | 48 | -7148 | -6799 | 2376 | -6900 | 1439 | -3040 | -6807 | -6806 | -6588 | -6917 | -6494 | -4688 | 2503 | -5991 | -5708 | 45 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 35(R) | -6891 | -6578 | -7555 | -6772 | -6828 | -6642 | -5674 | -7049 | -4555 | -322 | -6244 | -6542 | -6904 | -5501 | 4149 | -7034 | -6798 | -7202 | -6476 | -6615 | 46 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 36(I) | -809 | -2626 | -7283 | -6968 | -4807 | -7135 | -7181 | 3148 | -6942 | -2135 | -927 | -6787 | -6871 | -6918 | -7124 | -6513 | -4581 | 2629 | -6565 | -6024 | 47 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 37(I) | -2877 | -2705 | 842 | 558 | -2684 | -4440 | -3321 | 2114 | -4135 | 1302 | 724 | -4051 | -4484 | -3782 | -3978 | -3035 | 756 | 1139 | -3212 | -2865 | 48 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 38(C) | 463 | 3678 | -5102 | -4467 | -678 | -4306 | 1997 | -2059 | -4063 | 1068 | -1474 | -3953 | -4356 | -3686 | -3864 | -3392 | 779 | 1688 | -3045 | -2703 | 49 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 39(Y) | -1716 | -3961 | 1444 | 370 | -4281 | -1092 | -467 | -529 | -137 | 594 | -2157 | 189 | -2473 | 1437 | 1009 | -1138 | -593 | -3582 | -4144 | 1770 | 50 |
| - | -150 | -493 | 237 | 46 | -385 | 397 | 101 | -624 | 207 | -466 | -713 | 272 | 399 | 41 | 94 | 362 | 114 | -366 | -286 | -254 |
| - | -157 | -3284 | -11376 | -3067 | -183 | -2589 | -262 | * | * | | | | | | | | | | | |
| 40(F) | -2498 | -3888 | -170 | 776 | 2736 | -236 | 2134 | -3902 | -1588 | 495 | -2986 | -85 | -3577 | -1699 | -941 | -445 | -818 | -3492 | -4092 | 1033 | 62 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 41(K) | -1410 | -3932 | 462 | 917 | -4239 | -3470 | -2130 | 895 | 1496 | 403 | -2749 | -2111 | -532 | 616 | -1216 | 406 | -125 | 345 | -4123 | -3449 | 63 |
| - | -149 | -500 | 234 | 43 | -381 | 398 | 105 | -627 | 210 | -459 | -721 | 275 | 393 | 45 | 95 | 359 | 117 | -370 | -295 | -250 |
| - | -188 | -3034 | -11376 | -42 | -5124 | -2589 | -262 | * | * | | | | | | | | | | | |

TABLE 6-continued

| 42(D) | 339 | -3961 | 2081 | 1022 | -1210 | 477 | -609 | -1360 | 72 | -2393 | -1457 | -76 | 123 | -844 | -562 | -674 | -120 | -3582 | -4144 | 744 | 65 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -158 | -3266 | * | * | | | | | | | | | | | | |

| 43(D) | -101 | -4094 | 2856 | 1495 | -4414 | -3181 | -1173 | 648 | -1257 | -1565 | -3184 | -450 | -3691 | 1371 | -1233 | -2505 | -2017 | -3716 | -4278 | -3596 | 66 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 44(C) | -909 | 4411 | -5205 | 415 | 203 | -4444 | -3315 | 1101 | -4178 | -2572 | -1931 | -4077 | -4493 | 1120 | -3992 | -3528 | -2838 | 1245 | 2022 | -2847 | 67 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 45(Y) | -281 | -4059 | -1394 | 965 | -1715 | -3602 | 150 | -434 | -384 | -4069 | -3152 | 216 | -260 | -63 | -2353 | -2510 | 722 | -3673 | 1528 | 3505 | 68 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 46(H) | 891 | -4091 | -206 | -506 | -4411 | -3440 | 2694 | -2567 | 467 | -641 | -1587 | 1059 | -605 | 216 | 1753 | -1642 | -892 | -362 | -4274 | -3592 | 69 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 47(I) | 1027 | -3968 | -6946 | -6495 | -4336 | -6512 | -5844 | 2389 | -6289 | 916 | -10 | -6163 | -6380 | -6047 | -6253 | -5739 | -525 | 2177 | -5501 | -5107 | 70 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 48(H) | 333 | 1113 | -760 | -2481 | 81 | -4388 | 2787 | -1134 | -2869 | 1860 | -1935 | -3954 | -4441 | -3668 | -809 | -722 | -2809 | 118 | -3187 | 1374 | 71 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 49(G) | 372 | -4099 | 266 | 1262 | -4420 | 1836 | 293 | -4171 | 1088 | -4115 | -3188 | 697 | -3691 | -1797 | 1238 | -793 | -2564 | -2805 | -4282 | -3599 | 72 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -134 | -10485 | -3508 | -894 | -1115 | -701 | -1378 | * | * | | | | | | | | | | | | |

| 50(E) | -721 | -2620 | -4816 | 1550 | 1391 | -4263 | -3119 | 1195 | -177 | 1133 | 68 | -3815 | -4316 | -1938 | -2286 | -522 | -1502 | 258 | -3073 | 934 | 73 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10353 | -11395 | -894 | -1115 | -2459 | -290 | * | * | | | | | | | | | | | | |

| 51(I) | -4963 | -4419 | -7610 | -7245 | -4166 | -7488 | -7164 | 2857 | -7197 | 1545 | -951 | -7156 | -6997 | -6719 | -7162 | -6890 | -4927 | 2143 | -6022 | -5889 | 74 |
|---|---|---|---|---|---|---|---|---|---|---|---|---|---|---|---|---|---|---|---|---|---|
| - | -152 | -503 | 238 | 40 | -384 | 395 | 102 | -617 | 211 | -462 | -724 | 278 | 390 | 42 | 99 | 356 | 119 | -369 | -249 | -253 | |
| - | -5517 | -3374 | -182 | -2761 | -230 | -883 | -1127 | * | * | | | | | | | | | | | | |

| 52(E) | -3896 | -4207 | -2040 | 3880 | -5087 | -3451 | -3239 | -5508 | -3501 | -5270 | -4921 | -2730 | -3971 | -3131 | -3885 | -3752 | -4038 | -5087 | -4437 | -4574 | 82 |
|---|---|---|---|---|---|---|---|---|---|---|---|---|---|---|---|---|---|---|---|---|---|
| - | -149 | -500 | 232 | 42 | -373 | 398 | 105 | -623 | 212 | -467 | -721 | 275 | 393 | 45 | 95 | 359 | 119 | -370 | -295 | -250 | |
| - | -2941 | -205 | -8819 | -35 | -5382 | -5289 | -37 | * | * | | | | | | | | | | | | |

| 53(C) | -883 | 3248 | -2990 | -2490 | -1202 | -2158 | -1617 | -655 | -2161 | 1453 | -406 | -2017 | 1405 | -1885 | -2120 | -1338 | 1496 | -540 | -1720 | -1379 | 84 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -309 | -7777 | -2410 | -894 | -1115 | -2972 | -197 | * | * | | | | | | | | | | | | |

| 54(K) | -2617 | -3525 | -2979 | -1922 | -4255 | -3281 | -1323 | -3669 | 2824 | -3376 | -2649 | -1937 | -3250 | 1605 | 1993 | -2492 | 1260 | -3386 | -3274 | -3067 | 85 |
|---|---|---|---|---|---|---|---|---|---|---|---|---|---|---|---|---|---|---|---|---|---|
| - | -156 | -488 | 239 | 40 | -372 | 395 | 120 | -619 | 218 | -474 | -728 | 289 | 386 | 42 | 97 | 351 | 121 | -374 | -277 | -243 | |
| - | -3429 | -143 | -9307 | -2786 | -226 | -5185 | -40 | * | * | | | | | | | | | | | | |

| 55(Y) | -1491 | -2411 | -1434 | 1638 | -2300 | -2442 | -1017 | -2203 | 1581 | 848 | -1536 | -1170 | -2539 | -682 | -778 | -1473 | -1410 | -1966 | -2445 | 2677 | 93 |
|---|---|---|---|---|---|---|---|---|---|---|---|---|---|---|---|---|---|---|---|---|---|
| - | -150 | -501 | 240 | 42 | -381 | 398 | 105 | -627 | 210 | -467 | -721 | 277 | 393 | 44 | 95 | 358 | 116 | -365 | -295 | -250 | |
| - | -3429 | -409 | -2697 | -29 | -5653 | -4128 | -85 | * | * | | | | | | | | | | | | |

| 56(G) | -2187 | -3222 | -986 | 2351 | -3705 | 2526 | -1945 | -3430 | -1890 | 353 | -2862 | -1468 | -3052 | -1643 | -2389 | -2104 | -2290 | -3086 | -3841 | -3203 | 95 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -203 | -8207 | -2965 | -894 | -1115 | -2841 | -217 | * | * | | | | | | | | | | | | |

TABLE 6-continued

| 57(Y) | 2024 | -1844 | -3412 | -2976 | 1771 | 284 | -2011 | -1674 | -2755 | -1961 | -1326 | -2601 | 1523 | -2465 | -2791 | -2091 | -1787 | -1525 | -1974 | 2354 | 96 |
|---|---|---|---|---|---|---|---|---|---|---|---|---|---|---|---|---|---|---|---|---|---|
| - | -152 | -479 | 239 | 40 | -383 | 396 | 125 | -629 | 211 | -469 | -723 | 273 | 395 | 42 | 93 | 359 | 114 | -372 | -297 | -223 | |
| - | -3779 | -111 | -9656 | -998 | -1002 | -27 | -5755 | * | * | | | | | | | | | | | | |

| 58(H) | 578 | -4067 | -2480 | -738 | 1104 | -3600 | 3545 | -4119 | 887 | -1353 | -3159 | 217 | -3693 | 84 | -590 | 660 | -582 | -622 | -4257 | -3582 | 99 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 59(S) | -556 | -4088 | -468 | 837 | -4407 | 461 | -1081 | -1740 | 905 | 154 | -1263 | 339 | -3687 | 398 | -1962 | 1191 | 588 | -1311 | -4272 | 383 | 100 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 60(Q) | 362 | 1839 | -1029 | -2484 | -244 | -4092 | 718 | 1745 | -2940 | 89 | 855 | 132 | -4162 | 1893 | 587 | -1372 | -78 | -1629 | -3446 | -3034 | 101 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 61(W) | -2409 | -4076 | 1458 | 6 | 614 | -3598 | -1974 | -4135 | 176 | -3634 | 1345 | 985 | 1026 | -1544 | -560 | -1556 | -2560 | -3694 | 4075 | 1228 | 102 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 62(K) | -1621 | -4092 | 1605 | 1195 | -4414 | -1552 | -2069 | -4164 | 1733 | -3177 | -3181 | 292 | -141 | 1444 | -183 | -454 | 633 | -3714 | -4276 | -568 | 103 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 63(P) | -2065 | -954 | -4981 | -273 | 1718 | -1238 | 653 | -756 | -4006 | -1387 | -168 | 1092 | 2910 | -3672 | -2681 | -2968 | -854 | -531 | 1505 | -263 | 104 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 64(I) | 311 | -4053 | 864 | 14 | -4356 | -3604 | -825 | 2348 | 694 | -1463 | -307 | -273 | -3696 | -481 | -495 | -844 | -867 | 644 | -4247 | -3575 | 105 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 65(P) | -2751 | 372 | -713 | -3859 | 63 | -4294 | -3120 | 1670 | 455 | -2163 | -2015 | -454 | 2400 | -3019 | -3649 | 353 | -2784 | 1484 | -3261 | -2896 | 106 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 66(H) | -557 | -4087 | 605 | -193 | -4406 | -6 | 2487 | -947 | -871 | 315 | -1927 | 190 | -3687 | 751 | 1403 | 644 | -2559 | -1098 | -4272 | -836 | 107 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 67(D) | -2027 | -4091 | 1587 | 1501 | -4412 | -3593 | -2189 | -1142 | 1262 | -2253 | -3180 | -1100 | -3686 | -1105 | 1509 | 289 | 1031 | -2573 | -4275 | -32 | 108 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 68(F) | -2821 | -1798 | -5155 | 77 | 2369 | -4416 | -3283 | -75 | -4133 | 1275 | -574 | -781 | -4466 | -2448 | -2434 | 918 | -170 | 1306 | -3168 | -2803 | 109 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 69(K) | -3209 | 551 | -141 | -2811 | 1280 | -4232 | -2803 | -3863 | 2906 | -3993 | -3223 | -3007 | -4306 | -2443 | 2119 | -3227 | -153 | -555 | -4300 | -3826 | 110 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 70(D) | -4918 | -6975 | 3727 | 529 | -7088 | -432 | -4115 | -7070 | -360 | -6902 | 33 | 594 | -5267 | -3802 | -5471 | -4528 | -5011 | -6513 | -7104 | -5985 | 111 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

| 71(Y) | -584 | -3368 | -3100 | -212 | 1352 | -3890 | 2686 | -3039 | 579 | -3272 | -2529 | -501 | -3971 | -2336 | -2820 | -2845 | -435 | -1020 | 1448 | 3474 | 112 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

TABLE 6-continued

| | | | | | | | | | | | | | | | | | | | | |
|---|---|---|---|---|---|---|---|---|---|---|---|---|---|---|---|---|---|---|---|---|
| 72(I) | -611 | -3580 | -873 | -289 | -3712 | -3773 | -2465 | 2848 | -501 | -15 | -2724 | -2536 | 797 | 1139 | -2628 | -704 | -2625 | -178 | -3890 | -3347 | 113 |
| - | -149 | -500 | 233 | 43 | -381 | 398 | 105 | -626 | 214 | -466 | -721 | 275 | 394 | 45 | 96 | 359 | 117 | -369 | -295 | -250 | |
| - | -453 | -4367 | -2179 | -90 | -4041 | -701 | -1378 | * | * | | | | | | | | | | | | |
| 73(A) | 1788 | 147 | 422 | 37 | -4104 | -834 | -1444 | -3855 | 420 | -748 | -2873 | 134 | 1049 | -461 | -429 | 498 | -272 | -3405 | -3967 | -875 | 115 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10125 | -11167 | -894 | -1115 | -3509 | -133 | * | * | | | | | | | | | | | | |
| 74(N) | -743 | -3484 | -2342 | 149 | -3684 | -3375 | 619 | 1364 | -1438 | -577 | -2606 | 1367 | -3465 | 725 | 868 | -706 | 1250 | 365 | -3745 | 482 | 116 |
| - | -148 | -502 | 230 | 50 | -383 | 396 | 103 | -618 | 208 | -469 | -723 | 277 | 391 | 48 | 98 | 357 | 123 | -369 | -297 | -252 | |
| - | -319 | -2335 | -11167 | -1571 | -592 | -780 | -1260 | * | * | | | | | | | | | | | | |
| 75(P) | -1131 | -3355 | -2856 | -2299 | -3456 | -3718 | -1331 | -3068 | 115 | -821 | -2163 | -2526 | 3269 | 689 | -2218 | 150 | -1574 | 1034 | -3687 | -3176 | 120 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| 76(K) | -3329 | -4732 | 530 | -348 | -5126 | -535 | 705 | -4822 | 3267 | -4704 | -3839 | -2744 | -4250 | 1304 | 514 | -3185 | -3247 | -4401 | -4800 | -4211 | 121 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -166 | -3202 | * | * | | | | | | | | | | | | |
| 77(H) | -288 | -4090 | -2172 | 1044 | 709 | -671 | 1942 | -2762 | 1192 | -2271 | -3180 | -926 | 1802 | 434 | 580 | -33 | -2558 | -2113 | -671 | -3592 | 122 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 78(N) | 381 | -4094 | -5118 | -5061 | 2133 | -2547 | 229 | -5663 | -5171 | -5890 | -5049 | 3573 | -5038 | -4885 | -5347 | 622 | -1690 | -4867 | -6147 | -5793 | 123 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -9 | -10485 | -7539 | -894 | -1115 | -701 | -1378 | * | * | | | | | | | | | | | | |
| 79(G) | -3141 | 1351 | -3469 | -4628 | -2952 | 3386 | 968 | -2874 | -4181 | 306 | -2569 | -3106 | -4705 | -4107 | -4335 | -3625 | -3192 | -1881 | -3769 | -3387 | 124 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10477 | -11520 | -894 | -1115 | -596 | -1563 | * | * | | | | | | | | | | | | |
| 80(Y) | -7124 | -6061 | -7507 | -7869 | 1269 | -7364 | -3601 | -6055 | -7436 | -5357 | -5454 | -6019 | -171 | -6163 | -6799 | -6643 | -6989 | -6208 | -2848 | 4723 | 125 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 81(Q) | -3629 | -4894 | -3611 | 793 | -5374 | -678 | -2881 | -4996 | 667 | -4836 | 37 | -3129 | -4534 | 3181 | 2436 | -3505 | -300 | -4611 | -4874 | -4407 | 126 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 82(S) | 614 | -3589 | -5585 | -5196 | -4321 | -1350 | -4438 | -157 | -4853 | -1079 | -3526 | -4524 | -4882 | -4605 | -223 | 3232 | -1918 | -3607 | -4752 | -4430 | 127 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 83(L) | -4083 | -3821 | -6195 | -5712 | 426 | -5522 | 1811 | -107 | -5307 | 2301 | -2844 | -4974 | -5518 | -4767 | -5041 | -4633 | -4015 | 1438 | 1385 | 1880 | 128 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 84(H) | -5529 | -6097 | -5071 | -4692 | -6225 | -5755 | 5216 | -6683 | -2887 | -6282 | -5697 | -8 | -5949 | -3804 | 889 | -5418 | -5367 | -6386 | -5724 | -5336 | 129 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 85(T) | -2884 | -2710 | -5229 | -2438 | -4 | -4432 | -3304 | 961 | -4188 | 541 | 1053 | -1020 | -4482 | -3811 | -3989 | -3517 | 2237 | 1405 | -3169 | 2193 | 130 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -138 | -10485 | -3468 | -894 | -1115 | -701 | -1378 | * | * | | | | | | | | | | | | |
| 86(W) | 799 | -2601 | -5102 | -656 | -2558 | -4322 | -3195 | 1547 | -4068 | 171 | -1804 | -3962 | -4371 | -3695 | -3876 | -2350 | 2103 | 1266 | 2902 | -2722 | 131 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -168 | -10349 | -3192 | -894 | -1115 | -2488 | -283 | * | * | | | | | | | | | | | | |

TABLE 6-continued

| 87(V) | -4376 | -2356 | -6906 | -6422 | -3681 | -6476 | -5665 | 1833 | -6203 | 1429 | 1919 | -6134 | -6222 | -5750 | -6070 | -5707 | -4329 | 2685 | -5062 | -1119 | 132 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -246 | -10182 | -2683 | -894 | -1115 | -3322 | -152 | * | * | | | | | | | | | | | | |

| 88(R) | 541 | -3631 | 569 | 1591 | -3952 | -709 | -1791 | -3702 | -986 | -1505 | -2720 | -1767 | -3225 | 84 | 2620 | 59 | -815 | -3253 | -3814 | -3132 | 133 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9939 | -10981 | -894 | -1115 | -1244 | -791 | * | * | | | | | | | | | | | | |

| 89(V) | -493 | -2433 | -4949 | -4313 | 76 | -4153 | -3024 | 798 | -3908 | 1075 | 1324 | -3798 | 668 | -3532 | 552 | -733 | -480 | 1737 | -2891 | 1016 | 134 |
|---|---|---|---|---|---|---|---|---|---|---|---|---|---|---|---|---|---|---|---|---|---|
| - | -149 | -502 | 237 | 42 | -379 | 396 | 105 | -622 | 208 | -464 | -723 | 273 | 397 | 47 | 94 | 360 | 118 | -371 | -297 | -250 | |
| - | -3109 | -3075 | -386 | -1969 | -425 | -3322 | -152 | * | * | | | | | | | | | | | | |

| 90(P) | -1522 | -2968 | -714 | 570 | -3327 | -2199 | -993 | -3060 | 1810 | -2978 | -2121 | 798 | 2922 | -570 | -942 | -1364 | -916 | -2626 | -3120 | -2459 | 139 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -8 | -8093 | -9135 | -894 | -1115 | -3809 | -107 | * | * | | | | | | | | | | | | |

| 91(Q) | -1021 | -2350 | 932 | 858 | -2615 | -2015 | -681 | 150 | 1342 | -427 | -1455 | -675 | -2108 | 1923 | -780 | -929 | -960 | 797 | -2568 | -1922 | 140 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -7 | -8354 | -9396 | -894 | -1115 | -2844 | -216 | * | * | | | | | | | | | | | | |

| 92(D) | -1408 | 1541 | 2699 | -284 | 1533 | -666 | -1311 | 1066 | -1167 | -1874 | -1142 | -1220 | -2666 | -357 | -1553 | -1088 | -1348 | -1451 | -2341 | -1213 | 141 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8833 | -9875 | -894 | -1115 | -3458 | -138 | * | * | | | | | | | | | | | | |

| 93(M) | 15 | -2122 | 1765 | -1428 | -2178 | 1522 | 731 | -1784 | -1318 | 400 | 2313 | -1615 | -2810 | -1222 | -1704 | -1692 | 539 | -1607 | -2498 | -2024 | 142 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9015 | -10057 | -894 | -1115 | -4902 | -49 | * | * | | | | | | | | | | | | |

| 94(F) | 434 | -1932 | -2214 | 782 | 2754 | -51 | -1539 | -254 | 915 | -302 | -1109 | -1779 | -2868 | -1387 | -1833 | -488 | -1233 | -678 | -2324 | -1887 | 143 |
|---|---|---|---|---|---|---|---|---|---|---|---|---|---|---|---|---|---|---|---|---|---|
| - | -144 | -502 | 234 | 45 | -383 | 396 | 103 | -623 | 208 | -461 | -723 | 277 | 391 | 43 | 93 | 357 | 122 | -372 | -297 | -242 | |
| - | -1576 | -591 | -10057 | -998 | -1002 | -4902 | -49 | * | * | | | | | | | | | | | | |

| 95(D) | -1461 | -2878 | 1725 | 1319 | -333 | -2438 | -696 | 726 | -695 | -2884 | -1974 | 1469 | -2533 | 817 | -1199 | -241 | -1329 | -2487 | -3075 | 1698 | 146 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9015 | -10057 | -894 | -1115 | -1013 | -987 | * | * | | | | | | | | | | | | |

| 96(G) | 754 | -3611 | 878 | 1003 | -3932 | 2097 | -1758 | -3683 | -891 | -1399 | -2700 | 91 | -3037 | -320 | -881 | 689 | -1098 | -3233 | -3794 | -3112 | 147 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1277 | -9914 | -770 | -894 | -1115 | -2715 | -238 | * | * | | | | | | | | | | | | |

| 97(E) | -1416 | -1618 | -1727 | 1935 | 970 | -2744 | 1535 | 592 | -1651 | 514 | -803 | -1867 | -2812 | 1175 | -1895 | -1749 | -1356 | 875 | -2033 | -1629 | 148 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8803 | -9845 | -894 | -1115 | -3428 | -141 | * | * | | | | | | | | | | | | |

| 98(T) | 302 | -2867 | -1385 | -829 | -3162 | -2476 | -1124 | -2881 | 1103 | -66 | -1968 | -1127 | 1085 | 1473 | 655 | -1144 | 1941 | -2476 | -3062 | -2414 | 149 |
|---|---|---|---|---|---|---|---|---|---|---|---|---|---|---|---|---|---|---|---|---|---|
| - | -147 | -502 | 238 | 41 | -382 | 400 | 114 | -622 | 211 | -468 | -722 | 273 | 392 | 47 | 94 | 357 | 118 | -371 | -296 | -251 | |
| - | -4160 | -84 | -10038 | -14 | -6680 | -670 | -1428 | * | * | | | | | | | | | | | | |

| 99(E) | -1276 | -3754 | 216 | 2239 | -1832 | -2976 | 630 | -3824 | 623 | -1468 | -2552 | -1352 | 1581 | -180 | -193 | -1987 | -485 | -2182 | -3938 | 1629 | 151 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10091 | -11133 | -894 | -1115 | -765 | -1281 | * | * | | | | | | | | | | | | |

| 100(D) | -609 | -3961 | 1121 | 583 | -2379 | -309 | -136 | -3270 | 616 | -1599 | 81 | 43 | 921 | 132 | 638 | 872 | -593 | -445 | -4144 | -691 | 152 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -10334 | -9944 | -894 | -1115 | -2589 | -262 | * | * | | | | | | | | | | | | |

| 101(D) | 474 | -1087 | 1676 | -1803 | -1820 | 1628 | -1200 | -1690 | 1435 | -3899 | -2959 | 307 | -3557 | -1691 | 387 | -1741 | 28 | -580 | -4097 | -1180 | 153 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -10333 | -8824 | -894 | -1115 | -2559 | -268 | * | * | | | | | | | | | | | | |

TABLE 6-continued

| | | | | | | | | | | | | | | | | | | | | |
|---|---|---|---|---|---|---|---|---|---|---|---|---|---|---|---|---|---|---|---|---|
| 102(F) | -2707 | -33 | -4343 | -1698 | 1250 | 493 | 687 | 38 | -1868 | 623 | -593 | -2876 | 200 | 961 | -187 | -1810 | 1158 | 727 | -3117 | 359 | 154 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10331 | -11373 | -894 | -1115 | -2505 | -280 | * | * | | | | | | | | | | | |
| 103(W) | -2739 | 1251 | -5025 | -3597 | -583 | -4280 | -3149 | 1173 | -1928 | 525 | -1777 | 1247 | 708 | -3636 | 1450 | -1131 | -793 | 1408 | 1631 | -1440 | 155 |
| - | -149 | -500 | 240 | 42 | -381 | 398 | 105 | -627 | 210 | -467 | -721 | 275 | 393 | 45 | 95 | 359 | 121 | -370 | -295 | -250 |
| - | -74 | -4333 | -11376 | -1540 | -608 | -2589 | -262 | * | * | | | | | | | | | | | |
| 104(V) | 438 | 2329 | -5197 | -4566 | 2047 | -4409 | -3288 | 456 | -4166 | -942 | 1371 | -4055 | -4453 | -3790 | -3968 | -3497 | -2786 | 2467 | -3147 | 773 | 159 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 105(E) | -8291 | -7147 | -6862 | 3979 | -8533 | -6942 | -7335 | -9573 | -8101 | -8925 | -8867 | -7489 | -7401 | -7786 | -7871 | -8517 | -8434 | -9223 | -7285 | -8412 | 160 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 106(I) | -4994 | -4450 | -7620 | -7234 | -829 | -7477 | -7024 | 3212 | -7166 | 748 | -1833 | -7148 | -6959 | -6609 | -7080 | -6867 | -4950 | 2064 | -5866 | -5777 | 161 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -2589 | -262 | * | * | | | | | | | | | | | |
| 107(Q) | -6886 | -6510 | -6906 | -7042 | -5962 | -6671 | -6416 | -6343 | -6317 | -302 | -5628 | -6950 | -7071 | 4507 | -6207 | -7179 | -7041 | -6814 | -6361 | -6170 | 162 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10334 | -11376 | -894 | -1115 | -158 | -3266 | * | * | | | | | | | | | | | |
| 108(I) | -2795 | -4275 | -7484 | -7164 | -781 | -7345 | -7344 | 3562 | -7137 | -974 | -3511 | -6999 | -7043 | -7038 | -7288 | -6730 | -4783 | 1828 | -6609 | -6149 | 163 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |
| 109(R) | -5786 | -6172 | -6929 | -5121 | -7234 | -6077 | -3950 | -6516 | 737 | -6082 | -5466 | -4887 | -6018 | -3544 | 4095 | -5670 | -5392 | -6324 | -5792 | -5852 | 164 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |
| 110(T) | -3873 | -4640 | -1889 | -4266 | -6955 | -4496 | -5137 | -6843 | -5651 | -6971 | -6127 | -1319 | -5246 | -4951 | -6113 | 1214 | 3761 | -5675 | -7120 | -6627 | 165 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |
| 111(I) | -1052 | -2860 | -4257 | 914 | -1869 | -4250 | 1817 | 2158 | -419 | 810 | 920 | -3557 | -3817 | -1892 | 526 | -1069 | -1857 | 282 | -3034 | -1253 | 166 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |
| 112(F) | 536 | -4010 | 209 | 1431 | 1527 | -2480 | -2279 | -4020 | -876 | 981 | 600 | -1359 | -3708 | 885 | -212 | -1276 | -2567 | 364 | -4216 | -3556 | 167 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |
| 113(M) | -4643 | -6360 | -2587 | 1113 | -6714 | -4642 | -3955 | -6594 | -4007 | -6463 | 4367 | 1023 | -5159 | 2379 | -4662 | -643 | -4711 | -6073 | -6627 | -5707 | 168 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |
| 114(H) | -4743 | -6697 | 2419 | 1515 | -6849 | -4633 | 3499 | -242 | -4274 | -6645 | -5988 | 1402 | -5175 | -3668 | -5164 | 382 | -4813 | -6252 | -6842 | -5796 | 169 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |
| 115(F) | 747 | -3929 | -1018 | -780 | 1668 | 543 | -612 | 250 | 930 | 1056 | -957 | -1686 | -3732 | 2 | -797 | -1003 | -2576 | -3513 | -4156 | 227 | 170 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |
| 116(W) | -2877 | -2705 | -4202 | -3546 | -225 | -3381 | -3295 | 1434 | -4176 | -1157 | -790 | -428 | -4474 | -2237 | -3870 | -2288 | -1345 | 592 | 5179 | 1395 | 171 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10485 | -11527 | -894 | -1115 | -701 | -1378 | * | * | | | | | | | | | | | |

TABLE 6-continued

| | | | | | | | | | | | | | | | | | | | | | |
|---|---|---|---|---|---|---|---|---|---|---|---|---|---|---|---|---|---|---|---|---|---|
| 117(A) | 3188 | -4152 | -6000 | -6359 | -6833 | 1270 | 972 | -6670 | -6580 | -6914 | -5952 | -3398 | -5204 | -6011 | -6351 | 240 | -4003 | -5355 | -7046 | -6966 | 172 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1206 | -10485 | -822 | -894 | -1115 | -701 | -1378 | * | * | | | | | | | | | | | | |
| 118(E) | -107 | -4101 | -1399 | 3347 | -4390 | -3132 | -2087 | -4161 | -1100 | -4111 | -3264 | 1172 | -3425 | -1224 | -2415 | -2394 | -2556 | -347 | -4300 | -3551 | 173 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9282 | -10324 | -894 | -1115 | -4736 | -55 | * | * | | | | | | | | | | | | |
| 119(R) | 1014 | -2925 | -1588 | -175 | 1466 | 556 | -1330 | -2865 | -105 | -794 | -1165 | -437 | -2753 | -411 | 2180 | -832 | -1593 | -2504 | -3157 | 478 | 174 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9282 | -10324 | -894 | -1115 | -283 | -2487 | * | * | | | | | | | | | | | | |
| 120(G) | -3803 | -4611 | -3535 | 2686 | -6829 | 2723 | -4860 | -6715 | -5328 | -6816 | -5994 | -3974 | -5107 | -4649 | -5860 | -218 | -48 | -5591 | -6972 | -6414 | 175 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| 121(I) | -2762 | -2590 | -2282 | -1294 | 929 | -4310 | -3181 | 2665 | -4054 | 513 | -1620 | -2444 | -4359 | -3681 | -3862 | -1349 | -532 | 2026 | -3052 | -2709 | 176 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| 122(E) | 2282 | -3689 | 1469 | 2373 | -5606 | -4253 | -3712 | -4203 | -3698 | -5393 | -4622 | -3233 | -4724 | -3377 | -4276 | -2893 | -3823 | 776 | -5719 | -5046 | 177 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| 123(H) | 1750 | -3963 | -6384 | -6675 | -6408 | -4257 | 4524 | -6183 | -6431 | -6516 | -5608 | -5019 | -5061 | -5949 | -6125 | 498 | -3833 | 756 | -6683 | -6541 | 178 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| 124(H) | -1628 | -3951 | 1518 | -1647 | -4263 | -3477 | 3429 | -1015 | 1109 | -451 | -3042 | -2115 | -3570 | 788 | -438 | 142 | -1534 | -3568 | -4139 | 1603 | 179 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -110 | -10343 | -3781 | -894 | -1115 | -2524 | -275 | * | * | | | | | | | | | | | | |
| 125(W) | -761 | -2492 | -5011 | -4375 | -1936 | -4214 | -3085 | 1010 | -3971 | 1570 | 1433 | -3860 | -4263 | -3592 | -3770 | 45 | -2606 | 393 | 3828 | 1786 | 180 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10235 | -11277 | -894 | -1115 | -755 | -1295 | * | * | | | | | | | | | | | | |
| 126(N) | -1247 | -3072 | -3373 | -2806 | -2817 | -1310 | -2682 | 1261 | 797 | -15 | -1145 | 2612 | -4014 | -2532 | 2219 | -2923 | -2062 | -2529 | -3462 | -1900 | 181 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10387 | -11429 | -894 | -1115 | -2179 | -360 | * | * | | | | | | | | | | | | |
| 127(Y) | -6975 | -5957 | -7400 | -7762 | 1411 | 621 | -3521 | -5974 | -7341 | -5279 | -5374 | -5926 | -7131 | -6076 | -6708 | -6522 | -6864 | -6119 | -2769 | 4593 | 182 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10387 | -11429 | -894 | -1115 | -2179 | -360 | * | * | | | | | | | | | | | | |
| 128(K) | -4600 | -5225 | -5076 | -4581 | -5453 | -5168 | -3874 | -6204 | 3604 | -5897 | -5269 | -4398 | 1148 | -3590 | -2693 | -957 | -4658 | -5728 | -5293 | 1623 | 183 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -53 | -10387 | -4835 | -894 | -1115 | -2179 | -360 | * | * | | | | | | | | | | | | |
| 129(N) | -2151 | 1342 | -1005 | 1531 | -4024 | -215 | 1376 | -4033 | -1437 | -2124 | -3051 | 1878 | -3557 | -257 | 10 | 1397 | -1140 | -2713 | -4146 | 1288 | 184 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10336 | -11378 | -894 | -1115 | -1699 | -531 | * | * | | | | | | | | | | | | |
| 130(N) | -1259 | -3989 | 801 | -622 | -4310 | 679 | -757 | -4061 | 137 | 995 | -3078 | 1476 | -97 | 890 | -553 | 515 | -1592 | -3611 | -4172 | 357 | 185 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10301 | -11343 | -894 | -1115 | -188 | -3035 | * | * | | | | | | | | | | | | |
| 131(W) | -2442 | -3920 | -1325 | 934 | -4187 | 1231 | -686 | -39 | -522 | 301 | 821 | 1033 | -3200 | -108 | -2341 | 604 | -183 | 69 | 1481 | -3486 | 186 |
| - | * | * | * | * | * | * | * | * | * | * | * | * | * | * | * | * | * | * | * | * | |
| - | * | * | * | * | * | * | * | * | 0 | | | | | | | | | | | | |

TABLE 7

| | |
|---|---|
| HMMER2.0 [2.3.2] | Program name and version |
| NAME TGS | Name of input sequence alighment file |
| DESC TGS domain | Domain description |
| LENG 75 | Length of alignment |
| ALPH Amino | Type of residues |
| MAP yes | Map of the match states to the columns of the alignment |
| COM hmmbuild -F HMM_Is.ann SEED.ann | Commands used to generate the file: this one means that hmmbuild (default patrameters) was applied to the alignment file |
| COM hmmcalibrate --seed 0 HMM_Is.ann | Commands used to generate the file: this one means that hmmcalibrate (default parametrs) was applied to the hmm profile |
| NSEQ 62 | Number of sequences in the alignment file |
| DATE Fri Apr 27 19:07:53 2007 | When file was generated |
| XT -8455 -4 -1000 -1000 -8455 -4 -8455 -4 | |
| NULT -4 -8455 | The transition probability distribution for the null model (single G state). |
| NULE 595 -1558 85 338 -294 453 -1158 197 249 902 -1085 -142 -21 -313 45 531 201 384 -1998 -644 | The symbol emission probability distribution for the null model (G state) |
| EVD -50.809875 0.221806 | The extreme value distribution parameters μ and lambda respectively |

The highest probability is highlighted for each position

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -41 | * | -5168 | | | | | | | | | | | | | | | | | | |
| 1(I) | -2697 | -2550 | -4876 | -1956 | -1064 | -4226 | -3089 | 2627 | -854 | -1421 | 1812 | -1442 | -568 | -578 | -3742 | -1595 | -788 | 2091 | -3005 | -717 | 1 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | -41 | * | | | | | | | | | | | | |
| 2(R) | -2518 | -402 | -1171 | -2139 | 1158 | 282 | 864 | 58 | 991 | -3310 | -2527 | -733 | -3699 | -690 | 2236 | -2551 | -365 | -628 | 191 | 1875 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 3(V) | -1740 | 55 | -4917 | -4289 | -2561 | -4268 | -9 | 2381 | -3865 | -2445 | -1802 | 634 | -4321 | -799 | -1609 | -3350 | -3350 | 2818 | -3061 | -2715 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 4(Y) | -2706 | -2538 | -5008 | -4375 | 2592 | -4248 | -4248 | -1084 | -1374 | -1493 | -1741 | -3880 | -4299 | -842 | -3794 | -1456 | 1353 | 1106 | -2992 | 3188 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -701 | * | * | | | | | | | | | | | | |
| 5(T) | -3121 | -2956 | -5433 | -4809 | 163 | -4649 | -3559 | -2267 | -4377 | 1935 | -9 | -4316 | -4691 | -4003 | -1351 | -998 | 2997 | -2314 | -3376 | -3054 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1646 | -10291 | -557 | -894 | -1115 | -701 | -1378 | * | * | | | | | | | | | | | | |
| 6(K) | -3330 | -4170 | 143 | -2361 | -4986 | -3733 | -1863 | -4361 | 3565 | -4013 | -3341 | -2393 | -3790 | -1450 | 1494 | -3165 | -3068 | -4098 | -3862 | -3698 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -33 | -5480 | * | * | | | | | | | | | | | | |
| 7(P) | -4636 | 1330 | -5058 | -4057 | -6367 | -5214 | -3346 | -5730 | 861 | -5415 | -4723 | -944 | 3908 | -1087 | -877 | -2109 | -4428 | -5432 | -5285 | -5145 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1376 | * | * | | | | | | | | | | | | |
| 8(D) | -1627 | -3947 | 2648 | -467 | -4269 | -3441 | 662 | -4020 | 2108 | -3963 | -3037 | -30 | 708 | 535 | 71 | -2353 | -1314 | -3570 | -4130 | -3447 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 9(G) | 447 | -3988 | -5373 | -5656 | -6525 | 3468 | -5550 | -6332 | -5983 | -6564 | -5633 | -1523 | -4996 | 594 | -5917 | -2551 | -3812 | -1128 | -6730 | -6576 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 10(K) | 193 | -3921 | 1189 | 741 | -659 | -365 | -2085 | -374 | 1704 | -1416 | 215 | -231 | -3520 | 1440 | -13 | -217 | -2391 | -1600 | -4105 | -3424 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 11(V) | -371 | -3806 | -1114 | 276 | -4075 | -1625 | -2124 | 783 | -124 | 450 | -473 | -131 | -586 | 1346 | -437 | -2370 | -335 | 1841 | -4022 | -3372 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -137 | -10291 | -3475 | -894 | -1115 | -701 | -1378 | * | * | | | | | | | | | | | | |
| 12(P) | -1500 | -2480 | -4414 | -3808 | 501 | -4051 | -211 | 634 | 1008 | -75 | -1679 | -3523 | 2182 | -46 | 371 | -3112 | -2504 | 1656 | -2928 | 568 | 12 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10156 | -11198 | -894 | -1115 | -2348 | -316 | * | * | | | | | | | | | | | | |
| 13(D) | -528 | -3817 | 2558 | 2089 | -4138 | -1482 | 576 | -3889 | -697 | -3833 | -2906 | -316 | -3409 | 312 | -2064 | -375 | -24 | -898 | -4000 | -3317 | 13 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1576 | -10156 | -591 | -894 | -1115 | -2348 | -316 | * | * | | | | | | | | | | | | |
| 14(F) | -4824 | -3963 | -5533 | -5724 | 3604 | -5356 | -1737 | -3748 | -5200 | -747 | -3198 | -4073 | -5231 | -4149 | 205 | -4582 | -4697 | -3893 | -999 | 3427 | 14 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -149 | -4305 | -4391 | -976 | -1024 | -4198 | -81 | * | * | | | | | | | | | | | | |

TABLE 7-continued

| | | | | | | | | | | | | | | | | | | | | |
|---|---|---|---|---|---|---|---|---|---|---|---|---|---|---|---|---|---|---|---|---|
| 15(D) | -1299 | -2788 | 2047 | 903 | -3104 | -2204 | -912 | -2860 | 297 | -2802 | -1884 | 232 | -2331 | 941 | -1041 | 1453 | 985 | -2408 | -2970 | -2275 | 17 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -6 | -8585 | -9627 | -894 | -1115 | -4198 | -81 | * | * | | | | | | | | | | | |
| 16(D) | -1813 | -3374 | 2529 | 2243 | -3667 | -2480 | -1355 | -3448 | 437 | -3378 | -2493 | -1097 | -231 | 431 | -1646 | 215 | -1779 | -2985 | -3550 | -2802 | 18 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -5 | -8650 | -9693 | -894 | -1115 | -4803 | -53 | * | * | | | | | | | | | | | |
| 17(P) | 539 | -2421 | -4342 | -4676 | -5052 | 467 | -4229 | -4886 | -4786 | -5130 | -4188 | -3352 | 3894 | -4270 | -4553 | -2056 | -2281 | -3610 | -5224 | -5180 | 19 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -5 | -8650 | -9693 | -894 | -1115 | -4803 | -53 | * | * | | | | | | | | | | | |
| 18(L) | -3461 | -3003 | -5904 | -5350 | 127 | -5473 | -4387 | 1691 | -5100 | 2175 | 1175 | -5148 | -4991 | -4302 | -4791 | -4710 | -3369 | 1996 | -3447 | -3447 | 20 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -5 | -8650 | -9693 | -894 | -1115 | -4089 | -87 | * | * | | | | | | | | | | | |
| 19(I) | 229 | -2576 | -5746 | -5431 | -3299 | -5463 | -5513 | 3129 | -5379 | -2095 | -2004 | -5191 | -5289 | -5326 | -5526 | -4825 | -3059 | 2438 | -4975 | -4452 | 21 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -5 | -8723 | -9765 | -894 | -1115 | -33 | -5446 | * | * | | | | | | | | | | | |
| 20(L) | -198 | -2604 | -5128 | -4493 | 585 | -444 | -3205 | -397 | -4090 | 2435 | 442 | -3981 | -4377 | -3706 | -3888 | -3420 | -2722 | 1114 | -3059 | 877 | 22 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 21(P) | -254 | -3925 | 144 | -1093 | -4247 | -3426 | 330 | -3997 | 1039 | -1905 | -3015 | -1007 | 2633 | -398 | 1765 | -612 | 213 | -3547 | -4109 | -3426 | 23 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 22(R) | 107 | -3925 | -972 | 729 | -347 | -1852 | -164 | -3996 | 1688 | -3941 | -673 | -273 | -1178 | -357 | 1860 | 654 | -219 | -1006 | -4108 | -385 | 24 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 23(G) | -1601 | -4537 | 157 | -705 | -4839 | 3160 | -2581 | -4609 | -1248 | -4546 | -3648 | 248 | -1400 | -743 | -2809 | -1763 | -2966 | -4152 | 2813 | -3992 | 25 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 24(S) | 1616 | -3800 | -2376 | 536 | -4066 | -3466 | -100 | 53 | -543 | -3792 | -2905 | -2126 | -3558 | -1691 | 1048 | 1860 | 465 | -478 | -4018 | -3372 | 26 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 25(T) | -2556 | -217 | -2821 | -2266 | -3440 | -805 | -2389 | -1163 | -1227 | -3256 | -2490 | -944 | -3764 | -746 | -4791 | 671 | 3424 | -1065 | -3668 | -3155 | 27 |
| - | -149 | -490 | 233 | 43 | -381 | 400 | 105 | -626 | 210 | -466 | -721 | 275 | 394 | 45 | 96 | 359 | 117 | -369 | -295 | -250 |
| - | -2283 | -5310 | -378 | -984 | -1016 | -701 | -1378 | * | * | | | | | | | | | | | |
| 26(T) | -1308 | -1921 | -3835 | -4072 | -4376 | -2182 | -3609 | -4171 | -4005 | -4450 | -3548 | -2822 | -2972 | -3622 | -3843 | 1755 | 3504 | -3023 | -4598 | -4452 | 30 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -7 | -8178 | -9220 | -894 | -1115 | -59 | -4632 | * | * | | | | | | | | | | | |
| 27(P) | 1187 | 243 | -5824 | -5395 | -3614 | -4409 | -4202 | 841 | -5014 | -3400 | -2805 | -4563 | 2828 | -4623 | -4802 | -1660 | -1104 | 2066 | -4160 | -3832 | 31 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10267 | -11309 | -894 | -1115 | -466 | -1857 | * | * | | | | | | | | | | | |
| 28(M) | -579 | -2747 | -1398 | 1451 | -26 | -1034 | -2815 | 846 | 691 | 208 | 1870 | -3238 | -4084 | -2882 | 838 | -3041 | -2583 | 1018 | -3175 | -242 | 32 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |

TABLE 7-continued

| 29(D) | -4832 | -6961 | 3746 | 1464 | -7043 | -4527 | 869 | -7059 | -4458 | -6875 | -6344 | -3104 | -5129 | -370 | -5514 | -1809 | -4940 | -6485 | -7083 | -5908 | 33 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 30(F) | 110 | -106 | -5395 | -4776 | 2935 | -4631 | -3528 | 1512 | -4387 | 937 | -1975 | -4277 | -4659 | -4012 | -4196 | -3727 | -2970 | 1534 | -3367 | -752 | 34 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 31(C) | 3159 | 3870 | -6715 | -7056 | -6591 | -4197 | -5976 | -6255 | -6660 | -6645 | -5699 | -5044 | -5013 | -6085 | -6250 | -1955 | -3780 | -650 | -6834 | -6815 | 35 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 32(Y) | -2556 | -495 | -2342 | -149 | -613 | -1473 | 1320 | -1844 | 776 | -2137 | -774 | 1573 | -3540 | 471 | 443 | -2357 | -1347 | -3448 | -4050 | 3178 | 36 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 33(K) | 1595 | -3924 | -399 | -767 | -4245 | -179 | 1508 | -1607 | 1774 | -1396 | -149 | -768 | -3519 | 571 | 1104 | -122 | -2391 | -3546 | -4108 | -3425 | 37 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 34(I) | -4958 | -4437 | -7532 | -7093 | -3800 | -7295 | -6594 | 3471 | -6960 | 805 | 89 | -6968 | -6790 | -1108 | -6792 | -6630 | -4900 | 1148 | -5532 | -5480 | 38 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 35(H) | -4087 | -5292 | -2951 | -3009 | -5657 | 729 | 4722 | -5740 | -250 | -5608 | -4865 | -838 | -4875 | -3152 | -3209 | 1141 | -4118 | -5273 | -5515 | -729 | 39 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -10291 | -5518 | -894 | -1115 | -701 | -1378 | * | * | | | | | | | | | | | | |
| 36(T) | -1378 | -3899 | -2274 | -775 | -4220 | -802 | -2058 | -3970 | 1487 | -3915 | -121 | -582 | 186 | 441 | 1571 | 966 | 2014 | -3521 | -4082 | -3400 | 40 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10260 | -11302 | -894 | -1115 | -1296 | -755 | * | * | | | | | | | | | | | | |
| 37(D) | -2974 | -4506 | 2224 | 1617 | -4809 | 1101 | -2547 | -4580 | -2227 | -4515 | -3615 | -1156 | -3933 | -837 | -350 | 1601 | 124 | -4121 | -4685 | -3959 | 41 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10260 | -11302 | -894 | -1115 | -1296 | -755 | * | * | | | | | | | | | | | | |
| 38(L) | -2822 | -2641 | -1487 | -4533 | 635 | -4377 | 935 | 1674 | -4130 | 2209 | 753 | -4023 | -4413 | -3739 | -3926 | -3464 | -2761 | 1162 | 693 | -2750 | 42 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10260 | -11302 | -894 | -1115 | -424 | -1973 | * | * | | | | | | | | | | | | |
| 39(G) | 1745 | 296 | -1147 | -1011 | -3419 | 2149 | -2349 | -53 | 124 | -2081 | -2466 | -2446 | -3731 | 563 | 563 | -2590 | -2470 | 687 | -3644 | -3126 | 36 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 40(K) | -1012 | -3928 | 1593 | 1007 | -32 | -3428 | 2070 | -4000 | 2071 | -3944 | -3018 | 1281 | -3521 | -399 | 345 | -812 | -2394 | -3550 | -4112 | -3429 | 44 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -67 | -10291 | -4492 | -894 | -1115 | -701 | -1378 | * | * | | | | | | | | | | | | |
| 41(K) | 520 | -3870 | 527 | -598 | -4191 | -1082 | 1272 | -3942 | 1772 | -3886 | -2959 | 660 | -3464 | 1433 | 1467 | 155 | -191 | -3492 | -4053 | -3370 | 45 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10226 | -11268 | -894 | -1115 | -1735 | -515 | * | * | | | | | | | | | | | | |
| 42(F) | 1552 | 2563 | -4990 | -4354 | 2952 | -4194 | -3065 | -1965 | -3949 | -517 | 1339 | -3839 | -4244 | -3573 | -3750 | -1391 | 847 | -521 | -2931 | -905 | 46 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10226 | -11268 | -894 | -1115 | -300 | -2412 | * | * | | | | | | | | | | | | |

TABLE 7-continued

| | | | | | | | | | | | | | | | | | | | | |
|---|---|---|---|---|---|---|---|---|---|---|---|---|---|---|---|---|---|---|---|---|
| 43(I) | -292 | 242 | -4934 | -4306 | -2509 | -4243 | -3108 | 2033 | 1510 | 600 | -1755 | -3849 | -4294 | -3572 | 1179 | -1964 | -381 | 1226 | -3010 | -2666 | 47 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 44(Y) | 339 | -173 | -1340 | -4224 | -780 | 2159 | 1092 | 560 | -3862 | -2406 | -1758 | -1461 | -4275 | -3521 | -3731 | -3299 | -2639 | 339 | -3009 | 3122 | 48 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 45(A) | 3337 | 47 | -6711 | -7050 | -6592 | 232 | -5967 | -6387 | -6655 | -6669 | -5704 | -5038 | -5007 | -6077 | -6245 | 386 | -3775 | 117 | -6825 | -6808 | 49 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 46(K) | -1434 | -2999 | -3271 | -1147 | -3029 | -3851 | -2590 | 971 | 2046 | 1085 | -2175 | -2833 | -3925 | -57 | 1665 | -2833 | -525 | -143 | -3388 | 290 | 50 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 47(V) | -1559 | -3260 | 127 | -5233 | -3460 | -5213 | -4288 | 1561 | -4982 | -1561 | -2558 | -697 | -5247 | -4666 | -4882 | -2241 | -3472 | 3302 | -4163 | -3793 | 51 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 48(W) | 37 | -3847 | 57 | -1124 | -4103 | -1905 | -2220 | -3809 | -1845 | -3840 | -2965 | 3319 | -3634 | -1789 | -2343 | -1184 | -1126 | -1772 | 4072 | -1019 | 52 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -137 | -10291 | -3475 | -894 | -1115 | -701 | -1378 | * | * | | | | | | | | | | | | |
| 49(G) | -4588 | -6618 | 27 | -885 | -6758 | 3574 | -454 | -6734 | -4157 | -6568 | -5979 | -1229 | -4945 | -3479 | -1668 | -1436 | -4681 | -6177 | -6767 | -5659 | 53 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1511 | -10156 | -625 | -894 | -1115 | -2348 | -316 | * | * | | | | | | | | | | | | |
| 50(K) | -313 | -2214 | -1363 | -812 | -2394 | -2309 | -1017 | -522 | 2024 | -988 | -1378 | -1069 | -14 | -646 | -1154 | 1381 | 1577 | -1764 | -2534 | -1975 | 54 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4803 | -53 | * | * | | | | | | | | | | | | |
| 51(S) | -1853 | -2504 | -3099 | -3260 | -4321 | -2675 | -3378 | -4270 | -3456 | -4467 | 685 | 630 | -3394 | -3261 | -3581 | 3458 | -2254 | -3380 | -4582 | -4145 | 55 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4803 | -53 | * | * | | | | | | | | | | | | |
| 52(V) | 2066 | -1956 | -3760 | -3341 | -2659 | -2763 | -2703 | -1843 | -2900 | -2472 | -1826 | -2807 | -3247 | -2788 | 345 | -2007 | 1475 | 2359 | -3110 | -2775 | 56 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4803 | -53 | * | * | | | | | | | | | | | | |
| 53(K) | -3429 | -4109 | -4119 | -2717 | -5012 | -3935 | -1792 | -4286 | 3425 | -3910 | -3244 | -2596 | 1211 | 738 | 1057 | -3296 | -3089 | -4062 | -3736 | -3656 | 57 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -2644 | -251 | * | * | | | | | | | | | | | | |
| 54(H) | -2743 | -2902 | -3619 | -2956 | 1756 | -3870 | 3947 | -39 | 858 | -2676 | -2104 | -2832 | -3890 | -2277 | 1101 | -2947 | -2644 | -2450 | -1985 | 2132 | 58 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9006 | -10048 | -894 | -1115 | -4612 | -60 | * | * | | | | | | | | | | | | |
| 55(P) | -1438 | -2910 | 962 | -736 | -3231 | -447 | -1070 | -2982 | 975 | -2926 | -1999 | 963 | 1212 | 872 | -68 | 1142 | 746 | -2532 | -3094 | -236 | 59 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9006 | -10048 | -894 | -1115 | -4612 | -60 | * | * | | | | | | | | | | | | |
| 56(P) | -3076 | -4867 | 308 | 192 | -5104 | 1841 | -2406 | -4978 | 1515 | -4858 | -4121 | -1758 | 2926 | -2052 | -3197 | -2778 | -3115 | -4470 | -5037 | -4110 | 60 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9006 | -10048 | -894 | -1115 | -37 | -5289 | * | * | | | | | | | | | | | | |

TABLE 7-continued

| | | | | | | | | | | | | | | | | | | | | |
|---|---|---|---|---|---|---|---|---|---|---|---|---|---|---|---|---|---|---|---|---|
| 57(Q) | -1419 | -3917 | -2305 | 1207 | -4234 | -3430 | 84 | -1890 | 1496 | -2165 | 1330 | -858 | -3523 | 2924 | 1094 | -1395 | -2393 | -1044 | -4102 | -3423 | 61 |
| - | -149 | -500 | 233 | 43 | -381 | 399 | 106 | -626 | 210 | -466 | -720 | 275 | 394 | 45 | 96 | 359 | 117 | -368 | -294 | -249 |
| - | -25 | -5885 | -11333 | -246 | -2675 | -701 | -1378 | * | * | | | | | | | | | | | |
| 58(R) | -2654 | -2705 | -4009 | -504 | -170 | -4059 | -689 | 796 | 372 | 1198 | 359 | -1565 | 346 | -901 | 2253 | -3090 | -2594 | 29 | 214 | -842 | 63 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 59(W) | -663 | 1284 | -4998 | -4365 | -2490 | -4244 | -3113 | -781 | -480 | -1587 | -1738 | -3874 | -4294 | -3603 | -412 | -442 | -1067 | 2923 | 3099 | 588 | 64 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 60(D) | -382 | -4141 | 2495 | -4417 | -6327 | 2416 | -4862 | -6130 | -5070 | -2073 | -5398 | -4179 | 1894 | -4652 | -5380 | -865 | -1802 | -5093 | -6478 | -6094 | 65 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 61(L) | -465 | -2655 | -1752 | -534 | -1084 | -4109 | -2931 | 914 | -1022 | 2498 | 731 | -3469 | -206 | -3140 | -629 | -1595 | -2607 | -1192 | -3096 | -2729 | 66 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 62(D) | -1602 | 848 | 2184 | 705 | -4244 | -1863 | -326 | -3995 | -679 | -1987 | -208 | 1111 | -3519 | -1625 | -322 | 1608 | 664 | -3545 | -4107 | -3425 | 67 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 63(H) | -1539 | -3911 | -1064 | -1771 | -987 | -3440 | 3665 | -3965 | 89 | -3922 | -3003 | -2079 | -3533 | 414 | 1231 | -980 | 1434 | -3528 | -4099 | 2266 | 68 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 64(P) | -1562 | -3849 | -2347 | 984 | -4135 | -3452 | 625 | -1059 | 923 | -2137 | -2948 | -2102 | 1978 | 275 | 621 | -2362 | 58 | 1752 | -4053 | -3394 | 69 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 65(L) | -5917 | -5267 | -8304 | -7710 | -63 | -8160 | -6754 | 1091 | -7532 | 2986 | 881 | -7898 | -7049 | -6185 | -6958 | -7579 | -5742 | -426 | -5154 | -5423 | 70 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 66(E) | -1601 | -3925 | -159 | 2553 | -4246 | -3426 | -2084 | -1908 | 1231 | -2098 | -140 | 654 | -1178 | 1570 | 384 | -1182 | -1332 | -3547 | -4108 | -3425 | 71 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 67(D) | -1385 | -3930 | 2537 | 650 | -1544 | -112 | 865 | -4001 | -1671 | -3946 | -643 | 2111 | -3524 | 169 | -2179 | 326 | -357 | -3552 | -4113 | -3431 | 72 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 68(G) | -2002 | -6836 | 1569 | 2060 | -6992 | 2666 | -3980 | -6995 | -4423 | -6821 | -6267 | 986 | -5111 | -3675 | -5457 | -1804 | -4888 | -6416 | -7028 | -5876 | 73 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 69(D) | 807 | 2570 | 3588 | -859 | -6772 | -1507 | -3941 | -6718 | -4285 | -6595 | -5957 | -3121 | -5040 | 237 | -5198 | -4231 | -4665 | -6110 | -6796 | -5756 | 74 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 70(V) | -2546 | -3222 | -2878 | 27 | -3303 | -3694 | -2405 | 1532 | 420 | -2296 | -396 | -882 | -3776 | -137 | -1587 | -1301 | 1582 | 2337 | -3570 | -3074 | 75 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 71(V) | -4634 | -4116 | -7310 | -1746 | -4535 | -7163 | -7086 | 1617 | -6943 | 1384 | -3239 | -6818 | -6846 | -6787 | -7061 | -6542 | -4619 | 3066 | -6314 | -5911 | 76 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 72(E) | -2453 | -3926 | -1058 | 2334 | -4247 | -3427 | -2085 | -3998 | 937 | -1905 | -3015 | -996 | -3520 | 1808 | 865 | 122 | 979 | -1417 | -4109 | -3426 | 77 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 73(I) | -5032 | -4481 | -7644 | -7246 | 140 | -7505 | -6959 | 3445 | -7172 | 999 | -2645 | -7178 | -6937 | -6532 | -7041 | -6899 | -4980 | 1004 | -5737 | -5682 | 78 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 74(V) | -2707 | 144 | -5051 | -4415 | 1002 | -4254 | 321 | 1953 | -714 | 1197 | -1735 | -3900 | -4304 | -3633 | -1785 | -3339 | -2647 | 2263 | -2990 | -854 | 79 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10291 | -11333 | -894 | -1115 | -701 | -1378 | * | * | | | | | | | | | | | |
| 75(T) | 135 | 109 | -1468 | -3349 | -2712 | -4040 | -2842 | -623 | 1838 | -1521 | -33 | -3288 | -4104 | -2937 | -3291 | 119 | 2847 | -764 | -3160 | -2777 | 80 |
| - | * | * | * | * | * | * | * | * | * | * | * | * | * | * | * | * | * | * | * | * |
| - | * | * | * | * | * | * | * | * | 0 | | | | | | | | | | | |

TABLE 8

| | |
|---|---|
| HMMER2.0 [2.3.2] | Program name and version |
| NAME HD | Name of input sequence alighment file |
| DESC HD domain | Domain description |
| LENG 154 | Length of alignment |
| ALPH Amino | Type of residues |
| MAP yes | Map of the match states to the columns of the alignment |
| COM hmmbuild -F HMM_Is.ann SEED.ann | Commands used to generate the file: this one means that hmmbuild (default patrameters) was applied to the alignment file |
| COM hmmcalibrate-seed 0 HMM_Is.ann | Commands used to generate the file: this one means that hmmcalibrate (default parametrs) was applied to the hmm profile |
| NSEQ 160 | Number of sequences in the alignment file |
| DATE Sun Apr 29 14:25:51 2007 | When file was generated |
| XT -8455 -4 -1000 -1000 -8455 -4 -8455 -4 | |
| NULT -4 -8455 | The transition probability distribution for the null model (single G state). |
| NULE 595 -1558 85 338 -294 453 -1158 197 249 902 -1085 -142 -21 -313 45 531 201 384 -1998 -644 | The symbol emission probability distribution for the null model (G state) |
| EVD -43.966183 0.276183 | The extreme value distribution parameters µ and lambda respectively |

The highest probability is highlighted for each position

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -10 | * | -7160 | | | | | | | | | | | | | | | | | | |
| 1(R) | -2416 | -4435 | -683 | -6310 | -327 | -400 | -5025 | 136 | -5907 | -100 | -519 | -1035 | -6205 | -5531 | 1904 | -2161 | 1210 | 1787 | -729 | 1644 | 1 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | -10 | * | | | | | | | | | | | | |
| 2(F) | 532 | -4556 | 252 | -1153 | 1895 | -146 | -1075 | 1016 | -2256 | 744 | -1710 | -5362 | -6064 | -2250 | -1047 | -635 | -2746 | -183 | 613 | 1850 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 3(E) | -527 | -1390 | 691 | 1854 | -2832 | -231 | -155 | 372 | -548 | -3070 | -2239 | 762 | -5380 | 326 | -420 | 256 | 753 | -1860 | -5966 | 444 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -35 | -12317 | -5392 | -894 | -1115 | -701 | -1378 | * | * | | | | | | | | | | | | |
| 4(H) | -3183 | -6629 | -6277 | -6376 | -8583 | -6562 | 5396 | -8426 | -5521 | -8325 | -7574 | -1447 | -2678 | -6100 | -1632 | -6048 | -6240 | -7528 | -8205 | -7923 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -21 | -12282 | -6125 | -894 | -1115 | -2423 | -298 | * | * | | | | | | | | | | | | |
| 5(S) | -612 | 1679 | -6898 | -6262 | -1366 | -6102 | -4973 | -692 | -5857 | -505 | -834 | -5747 | 1116 | -2235 | -2476 | 2429 | 1404 | -10 | -4839 | -4497 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12262 | -13304 | -894 | -1115 | -2917 | -205 | * | * | | | | | | | | | | | | |
| 6(L) | -1733 | 7 | -3085 | -894 | 439 | -2985 | -4966 | 930 | -571 | 2172 | 520 | -5732 | -6147 | -2530 | 270 | -3052 | -4494 | 612 | 1224 | 329 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12262 | -13304 | -894 | -1115 | -1176 | -843 | * | * | | | | | | | | | | | | |
| 7(R) | 308 | -5752 | -1620 | 1313 | -2660 | 1137 | -1344 | -2220 | -820 | -1011 | 449 | 478 | -5348 | 101 | 2251 | -664 | -1116 | -5373 | -1053 | -1846 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12284 | -13326 | -894 | -1115 | -1284 | -763 | * | * | | | | | | | | | | | | |
| 8(V) | -536 | -160 | -6955 | -6321 | -2167 | -2340 | -5033 | -2309 | -5917 | -1649 | 1176 | -5805 | -6208 | -5540 | -5717 | -1330 | 1399 | 3265 | -4898 | -4555 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12294 | -13336 | -894 | -1115 | -2025 | -407 | * | * | | | | | | | | | | | | |
| 9(A) | 2327 | -4455 | -6573 | -493 | -102 | 86 | -4930 | -860 | -2705 | 369 | 1206 | -2785 | -6131 | -681 | -3038 | -468 | 35 | -556 | 850 | -50 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12294 | -13336 | -894 | -1115 | -2025 | -407 | * | * | | | | | | | | | | | | |
| 10(K) | 106 | 143 | -540 | 565 | 685 | -1207 | 519 | -254 | 759 | 301 | -153 | -86 | -5386 | 680 | 325 | -947 | -74 | -957 | -1277 | 752 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12294 | -13336 | -894 | -1115 | -2025 | -407 | * | * | | | | | | | | | | | | |
| 11(I) | -1672 | -4431 | -1705 | -6136 | 563 | -2139 | 579 | 2041 | -1029 | 1666 | -61 | -643 | -6160 | -996 | -1360 | -3179 | -672 | 229 | 120 | 931 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12294 | -13336 | -894 | -1115 | -873 | -1139 | * | * | | | | | | | | | | | | |
| 12(A) | 2331 | 708 | -6943 | -6307 | -942 | 70 | -1636 | -90 | -5901 | 969 | -53 | -5791 | -2589 | -5524 | -5701 | 529 | 266 | -557 | -4881 | -4539 | 12 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -38 | -12306 | -5292 | -894 | -1115 | -1510 | -624 | * | * | | | | | | | | | | | | |
| 13(R) | 1024 | -294 | -2416 | 793 | -1452 | 217 | 143 | -1928 | 44 | -225 | 380 | -921 | -5348 | 62 | 1539 | -450 | -606 | 101 | -5884 | -139 | 13 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12268 | -13311 | -894 | -1115 | -1705 | -528 | * | * | | | | | | | | | | | | |
| 14(E) | -61 | -460 | -736 | 1184 | -2769 | -906 | -428 | 232 | 796 | 76 | 823 | -980 | -2857 | 322 | 1100 | -471 | -263 | -1162 | 173 | 171 | 14 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12279 | -13321 | -894 | -1115 | -825 | -1199 | * | * | | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 15(I) | -802 | -1524 | -6937 | -2206 | 7 | -6139 | -522 | 2283 | -2763 | 2037 | 1603 | -5785 | -6189 | -1341 | -5695 | -3146 | -4532 | -870 | 995 | 545 | 15 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12300 | -13342 | -894 | -1115 | -1806 | -486 | * | * | | | | | | | | | | | |
| 16(A) | 2333 | 1375 | -1364 | -1583 | -868 | 1228 | -980 | -1889 | -783 | -1301 | -1420 | -97 | -5429 | -497 | -1394 | -148 | -451 | -1153 | -901 | -2014 | 16 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -15 | -12300 | -6586 | -894 | -1115 | -1085 | -920 | * | * | | | | | | | | | | | |
| 17(E) | -508 | -1353 | 1150 | 1704 | -6074 | -715 | -1372 | -581 | -54 | 185 | 626 | -191 | -131 | -580 | 1156 | -1161 | -2738 | -522 | 139 | -5259 | 17 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -41 | -12291 | -5172 | -894 | -1115 | -2155 | -367 | * | * | | | | | | | | | | | |
| 18(D) | -229 | -5721 | 1297 | 1157 | -2426 | -361 | 1053 | -249 | 920 | -1935 | -197 | -289 | -2682 | -150 | 1188 | 61 | -816 | -1579 | -5904 | -517 | 18 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -30 | -12250 | -5594 | -894 | -1115 | -1947 | -433 | * | * | | | | | | | | | | | |
| 19(L) | -683 | -5040 | -1357 | 560 | -260 | -2605 | 306 | 884 | -1771 | 1549 | 883 | -640 | 113 | -2005 | -1223 | -1317 | -466 | 286 | 168 | 551 | 19 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -13 | -12233 | -6827 | -894 | -1115 | -3401 | -143 | * | * | | | | | | | | | | | |
| 20(G) | -33 | -5693 | 618 | 205 | -400 | 2100 | -1605 | -5764 | 598 | -789 | -4782 | 945 | 61 | -455 | -244 | -1169 | -745 | -5315 | -747 | -2247 | 20 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1376 | -12220 | -702 | -894 | -1115 | -3568 | -127 | * | * | | | | | | | | | | | |
| 21(L) | -967 | -330 | -404 | 1355 | 819 | -3938 | 883 | -4321 | 715 | 1566 | 1186 | -1136 | -4030 | -2156 | 11 | -1333 | -546 | -3918 | -4527 | 330 | 21 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10845 | -11887 | -894 | -1115 | -6678 | -14 | * | * | | | | | | | | | | | |
| 22(S) | -2938 | -4411 | 833 | 1016 | -4732 | 1037 | -558 | -1768 | 17 | -4427 | -3500 | -2547 | 438 | 554 | 813 | 1452 | -469 | -639 | -4594 | -635 | 22 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2135 | -10845 | -374 | -894 | -1115 | -5759 | -27 | * | * | | | | | | | | | | | |
| 23(K) | 653 | -2755 | -1181 | 1147 | -3063 | -2297 | -952 | 316 | 1700 | 199 | -1848 | 579 | -2389 | 1127 | 344 | -1206 | -1257 | -2370 | -2943 | -2273 | 23 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -5 | -8811 | -9853 | -894 | -1115 | -7183 | -10 | * | * | | | | | | | | | | | |
| 24(H) | -1361 | -2811 | 694 | -648 | -3121 | -2319 | 3483 | -2868 | -566 | -2822 | -1905 | -957 | 493 | 1015 | 711 | 302 | -1300 | -2430 | -2995 | 1919 | 24 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -121 | -8811 | -3679 | -894 | -1115 | -4003 | -93 | * | * | | | | | | | | | | | |
| 25(P) | 561 | 1575 | -2251 | 763 | 315 | -2987 | -1765 | -2207 | -1584 | -2440 | -1695 | 429 | 2670 | -1496 | -1983 | 593 | -1800 | -76 | -2886 | -2401 | 25 |
| - | -142 | -502 | 230 | 45 | -378 | 396 | 103 | -623 | 212 | -460 | -723 | 273 | 391 | 43 | 98 | 357 | 115 | -369 | -297 | -252 |
| - | -4564 | -63 | -10442 | -11 | -7098 | -7112 | -10 | * | * | | | | | | | | | | | |
| 26(W) | 662 | 1121 | -3977 | -3360 | 201 | 1100 | -2296 | -1303 | -3018 | 361 | 1280 | 219 | -3495 | 1823 | -2923 | -2513 | -384 | -1220 | 2650 | 871 | 27 |
| - | -148 | -493 | 231 | 43 | -378 | 396 | 108 | -624 | 213 | -464 | -723 | 275 | 394 | 46 | 94 | 363 | 115 | -372 | -297 | -252 |
| - | -4564 | -147 | -4190 | -11 | -7015 | -7112 | -10 | * | * | | | | | | | | | | | |
| 27(E) | -124 | -3120 | -1534 | 1849 | 332 | -2653 | -1311 | -3173 | 1563 | -3131 | 474 | 464 | -2746 | -855 | 869 | -1561 | 1470 | -2737 | -3309 | -2635 | 29 |
| - | -149 | -500 | 233 | 43 | -381 | 398 | 105 | -627 | 210 | -464 | -721 | 278 | 393 | 45 | 96 | 359 | 119 | -370 | -295 | -250 |
| - | -4484 | -2472 | -368 | -57 | -4701 | -7124 | -10 | * | * | | | | | | | | | | | |
| 28(F) | -665 | -1391 | -929 | -444 | 1996 | -1685 | -451 | -1255 | 1745 | -1418 | -695 | -613 | -1850 | -202 | -447 | 1413 | -646 | -1024 | -1560 | -911 | 31 |
| - | -149 | -500 | 233 | 43 | -376 | 398 | 105 | -626 | 210 | -464 | -721 | 275 | 394 | 45 | 96 | 359 | 117 | -370 | -295 | -250 |
| - | -2336 | -899 | -1912 | -82 | -4179 | -6161 | -20 | * | * | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 29(F) | -2165 | -1761 | -4457 | -3893 | 2442 | -3991 | -2646 | 2145 | -3596 | 1858 | 559 | -3601 | -3602 | -2842 | -3298 | -3183 | -2068 | -224 | -1854 | -1590 | 33 |
| - | -150 | -501 | 234 | 44 | -382 | 398 | 105 | -623 | 212 | -465 | -721 | 274 | 393 | 48 | 98 | 358 | 116 | -370 | -295 | -250 |
| - | -2334 | -325 | -8212 | -1212 | -815 | -5655 | -29 | * | * | | | | | | | | | | | |
| 30(H) | 921 | -2125 | -640 | -137 | -2481 | 816 | 2372 | -2198 | 17 | -2183 | -1295 | 1292 | -1861 | 2 | 1445 | -699 | -744 | -1787 | -2375 | -1739 | 37 |
| - | -149 | -500 | 232 | 43 | -381 | 400 | 105 | -627 | 212 | -466 | -721 | 275 | 394 | 48 | 95 | 359 | 117 | -370 | -295 | -244 |
| - | -1869 | -466 | -8764 | -43 | -5082 | -5244 | -39 | * | * | | | | | | | | | | | |
| 31(V) | -1106 | -1168 | -2422 | -1835 | -1153 | 445 | -1301 | 700 | 774 | 1026 | -357 | -1761 | -2564 | 1168 | -1704 | -1535 | -1045 | 1667 | -1608 | -1229 | 39 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -7 | -8272 | -9314 | -894 | -1115 | -3590 | -125 | * | * | | | | | | | | | | | |
| 32(L) | -2525 | -2329 | -4759 | -4141 | 1398 | -4064 | -2752 | 809 | -3685 | 2288 | -1194 | -3648 | -4062 | 372 | 1504 | -3158 | -2458 | -1664 | -2487 | 502 | 40 |
| - | -147 | -502 | 233 | 41 | -379 | 398 | 110 | -628 | 211 | -466 | -709 | 276 | 396 | 43 | 94 | 358 | 115 | -368 | -286 | -251 |
| - | -1940 | -437 | -10450 | -11 | -6738 | -4999 | -46 | * | * | | | | | | | | | | | |
| 33(Q) | -1949 | -2946 | -17 | 1465 | 877 | -3010 | -1696 | 1014 | -1381 | -75 | -2081 | -241 | 1422 | 1926 | -1844 | -1941 | -1889 | -2478 | -3235 | 432 | 42 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -3 | -9620 | -10662 | -894 | -1115 | -3911 | -99 | * | * | | | | | | | | | | | |
| 34(W) | -2450 | -2411 | -4111 | 22 | -25 | 2176 | -2734 | 1018 | 662 | 51 | -1608 | -3306 | -3964 | -2979 | 171 | -2958 | -2390 | -613 | 3120 | -2491 | 43 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -188 | -10029 | -3047 | -894 | -1115 | -5179 | -40 | * | * | | | | | | | | | | | |
| 35(Y) | -660 | -3617 | 1283 | -234 | -3923 | 89 | 382 | -3662 | 1266 | -349 | -2710 | -1802 | -407 | -1366 | -1912 | -29 | 757 | 606 | -3810 | 1513 | 44 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -9966 | -11008 | -894 | -1115 | -1630 | -563 | * | * | | | | | | | | | | | |
| 36(E) | -1718 | -4708 | 1063 | 1951 | 101 | -1877 | -452 | -325 | -533 | -830 | -3797 | 183 | 866 | 828 | -280 | 229 | -1678 | -1022 | -4891 | -1535 | 45 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11173 | -12216 | -894 | -1115 | -644 | -1474 | * | * | | | | | | | | | | | |
| 37(E) | 500 | 125 | -65 | 1207 | 81 | -342 | -1412 | 55 | -227 | 865 | 276 | -2309 | -155 | -1226 | -938 | -1391 | -658 | 626 | -5547 | -4911 | 46 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -12001 | -13043 | -894 | -1115 | -2448 | -292 | * | * | | | | | | | | | | | |
| 38(D) | -452 | -5536 | 2804 | 412 | 378 | -5037 | -652 | -5608 | 322 | -3511 | -510 | 1811 | -1670 | -1101 | -147 | -239 | -2517 | -3012 | -5719 | -5037 | 47 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -12056 | -13099 | -894 | -1115 | -4789 | -53 | * | * | | | | | | | | | | | |
| 39(P) | -55 | -5488 | -681 | 428 | -5786 | -1574 | -3712 | -49 | 758 | 2288 | -202 | -3695 | 1630 | -1018 | 1236 | -2 | -4008 | 980 | -5684 | -5016 | 48 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -12056 | -13099 | -894 | -1115 | -4789 | -53 | * | * | | | | | | | | | | | |
| 40(E) | -269 | -870 | 1503 | 2205 | -1301 | -1321 | -516 | -294 | -323 | -422 | -4622 | 404 | -5131 | -770 | -65 | -159 | -944 | -1046 | -5717 | -5035 | 49 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -12056 | -13099 | -894 | -1115 | -4789 | -53 | * | * | | | | | | | | | | | |
| 41(L) | -764 | 664 | -606 | -965 | -5070 | -5259 | -1163 | 370 | 1275 | 1778 | -4109 | -2284 | -5343 | -997 | 645 | -4199 | 86 | 600 | -474 | -380 | 50 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -12056 | -13099 | -894 | -1115 | -33 | -5466 | * | * | | | | | | | | | | | |
| 42(L) | 1140 | 1390 | -6954 | -1564 | -2054 | -6156 | -5027 | 1258 | -5913 | 1579 | -1826 | -5802 | -6206 | -5535 | -5712 | -1218 | 556 | 1302 | 1563 | -1075 | 51 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -43 | -12317 | -5098 | -894 | -1115 | -701 | -1378 | * | * | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 43(R) | 31 | -4876 | -3076 | 154 | -520 | -2185 | -1420 | 163 | 292 | 929 | -270 | -4587 | -5719 | 397 | 1713 | -2015 | -1806 | 376 | 728 | 1566 | 52 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12274 | -13316 | -894 | -1115 | -153 | -3312 | * | * | | | | | | | | | | | | |
| 44(W) | 573 | 677 | -4914 | -1803 | 201 | -6150 | -5019 | 803 | 555 | 1139 | 921 | -2881 | -6200 | -2416 | 133 | -3346 | 678 | 1111 | 1796 | -4553 | 53 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 45(A) | 2913 | 326 | -6953 | -6317 | -4389 | 975 | -1402 | 188 | -5913 | -851 | 278 | -5802 | -6206 | -5536 | -5713 | -627 | -679 | -2661 | -4893 | -658 | 54 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 46(A) | 2785 | 1854 | -7201 | -6621 | -4736 | 1960 | -5343 | -1888 | -6218 | -3077 | -3983 | -6003 | -2518 | -5833 | -6010 | -1199 | -667 | -1348 | -5236 | -1073 | 55 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 47(L) | -1113 | -4435 | -6954 | -3337 | -45 | -6156 | -1733 | 1240 | -5913 | 2747 | -619 | -5802 | -895 | -5535 | -1997 | -5240 | -1821 | -1446 | -4892 | 579 | 56 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 48(L) | -810 | 364 | -7041 | -6405 | 941 | -6247 | -5117 | -619 | -6002 | 2713 | 733 | -5893 | -6289 | -5618 | -5800 | -2221 | -4634 | -216 | -4971 | 1438 | 57 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 49(H) | -10904 | -9193 | -10099 | -10486 | -10487 | -9143 | 5479 | -11804 | -10682 | -11065 | -11093 | -10541 | -9573 | -10579 | -10094 | -11509 | -11021 | -11538 | -9266 | -10430 | 58 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 50(D) | -6916 | -8991 | 4191 | -1873 | -9117 | -6590 | -6077 | -9156 | -6563 | -8965 | -8450 | 2365 | -7196 | -5780 | -7634 | -6502 | -7029 | -8579 | -9124 | -7992 | 59 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 51(I) | -869 | 410 | -7191 | -6566 | -1443 | -6415 | -5307 | 2973 | -6172 | 1082 | -79 | -6061 | -6453 | -5800 | -5980 | -5507 | 69 | 1364 | -5159 | -1099 | 60 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 52(G) | 810 | -1204 | -1331 | -6312 | -2257 | 3101 | -1437 | -246 | -5908 | -1368 | -1385 | -5799 | -1547 | -5532 | -5713 | -1667 | -2487 | 386 | -4893 | -4551 | 61 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 53(K) | -4313 | -5786 | -1770 | 1872 | -6107 | -2886 | 2495 | -5858 | 2750 | -2037 | -663 | -496 | -5380 | -1206 | 216 | -2114 | -1256 | -5408 | -5969 | -591 | 62 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 54(D) | 520 | 295 | 1427 | -1551 | -145 | 896 | -4933 | 776 | -5587 | -1516 | -355 | -5587 | 1181 | -1085 | -2646 | 130 | -507 | 602 | -4938 | 14 | 63 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 55(P) | -600 | -5636 | -1245 | -1015 | -630 | -398 | 235 | -40 | -177 | 545 | -1847 | -1526 | 1440 | -370 | 792 | -1748 | 883 | 481 | -1142 | 529 | 64 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -341 | -12317 | -2251 | -894 | -1115 | -701 | -1378 | * | * | | | | | | | | | | | | |
| 56(F) | -2461 | -5343 | -2308 | -195 | 1966 | -359 | 871 | 925 | -1423 | -1913 | -4446 | -836 | 1131 | -111 | -973 | -285 | 1184 | 631 | -399 | -1383 | 65 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11977 | -13019 | -894 | -1115 | -3241 | -161 | * | * | | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 57(P) | -4017 | -5489 | -1601 | -369 | -738 | 1622 | 56 | -5560 | -669 | -2674 | -406 | 174 | 1938 | -256 | 456 | 953 | -162 | -2251 | -5672 | 635 | 66 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -111 | -12007 | -3765 | -894 | -1115 | -1895 | -452 | * | * | | | | | | | | | | | |
| 58(H) | -456 | -5470 | 2679 | 197 | -5790 | -707 | 3012 | -2004 | -2203 | -3345 | -356 | -1859 | -2388 | 6 | 244 | -468 | -690 | -1410 | -5653 | -827 | 67 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -711 | -11988 | -1362 | -894 | -1115 | -2047 | -400 | * | * | | | | | | | | | | | |
| 59(W) | 186 | -4915 | -759 | 511 | 523 | 282 | 1063 | 206 | 485 | -2786 | -4005 | -1065 | -1111 | 109 | -852 | 509 | -200 | 235 | 1111 | 1045 | 68 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11406 | -12448 | -894 | -1115 | -6236 | -19 | * | * | | | | | | | | | | | |
| 60(F) | -3516 | -4446 | 12 | -1005 | 2098 | 694 | -3285 | 1423 | -915 | -138 | 722 | -1439 | 233 | 412 | -1483 | -877 | 106 | -390 | -4749 | -1295 | 69 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11406 | -12448 | -894 | -1115 | -6236 | -19 | * | * | | | | | | | | | | | |
| 61(E) | -1185 | -4871 | 302 | 2034 | -5168 | -4440 | -3101 | -1407 | -782 | 1593 | -3967 | -3085 | 98 | -430 | -798 | -388 | -506 | 64 | -5069 | -1222 | 70 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -143 | -11406 | -3411 | -894 | -1115 | -5306 | -37 | * | * | | | | | | | | | | | |
| 62(E) | -95 | -4805 | -125 | 1652 | -5124 | 4310 | -2969 | -1517 | 1183 | -244 | -3894 | 1074 | -4403 | 734 | 1560 | -1202 | -3275 | -1052 | 250 | 248 | 71 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -40 | -11281 | -5212 | -894 | -1115 | -6363 | -18 | * | * | | | | | | | | | | | |
| 63(K) | 611 | -3809 | 348 | -3620 | -3831 | -1134 | -3474 | 1558 | 1790 | -360 | 406 | 810 | -4796 | -3344 | -141 | -3708 | 251 | -179 | -4206 | 19 | 72 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11242 | -12284 | -894 | -1115 | -6399 | -17 | * | * | | | | | | | | | | | |
| 64(Q) | 201 | -4524 | -1401 | -596 | 212 | -1050 | -3024 | 427 | -563 | 1134 | -3642 | -3038 | 1037 | 1176 | -340 | 164 | -412 | -1058 | -4773 | 616 | 73 |
| - | -150 | -501 | 232 | 42 | -382 | 397 | 104 | -628 | 209 | -465 | -722 | 277 | 397 | 44 | 97 | 358 | 118 | -367 | -265 | -251 |
| - | -174 | -3704 | -4757 | -853 | -1164 | -5302 | -37 | * | * | | | | | | | | | | | |
| 65(E) | 592 | -4743 | -969 | 1615 | -5065 | 988 | 890 | -2042 | 663 | -4759 | 1097 | 595 | -4337 | -952 | 501 | -329 | 753 | -4365 | -4927 | -4244 | 76 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -876 | -11211 | -1137 | -894 | -1115 | -4296 | -75 | * | * | | | | | | | | | | | |
| 66(K) | -505 | 1389 | -998 | 1059 | -698 | 314 | -2233 | 565 | 2527 | -1590 | -3131 | 139 | -3666 | -1777 | 17 | -1183 | -2534 | -3654 | -4229 | -3554 | 77 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -2 | -10453 | -11496 | -894 | -1115 | -4566 | -62 | * | * | | | | | | | | | | | |
| 67(L) | -701 | 271 | 661 | -4531 | -543 | -150 | 1056 | 1380 | -4158 | 1637 | -2007 | 788 | -4539 | -638 | -4009 | -3566 | -2897 | -529 | -3261 | 1517 | 78 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -196 | -10578 | -2988 | -894 | -1115 | -6807 | -13 | * | * | | | | | | | | | | | |
| 68(M) | 718 | -3961 | 340 | -1853 | 44 | 491 | 362 | 795 | 23 | -3969 | 2259 | 190 | 1143 | 494 | -2270 | 425 | -2475 | -3572 | -4156 | -3486 | 79 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -107 | -10384 | -3826 | -894 | -1115 | -4481 | -66 | * | * | | | | | | | | | | | |
| 69(R) | -714 | -4046 | 448 | -791 | 709 | -658 | 448 | -4117 | 558 | 644 | -3135 | 1169 | -3640 | 1135 | 1755 | -1026 | -156 | -3667 | -4229 | -3546 | 80 |
| - | -144 | -505 | 228 | 47 | -370 | 396 | 105 | -632 | 217 | -467 | -726 | 273 | 398 | 46 | 96 | 358 | 112 | -371 | -300 | -249 |
| - | -5596 | -31 | -11474 | -5 | -8151 | -4464 | -67 | * | * | | | | | | | | | | | |
| 70(H) | -2694 | -4157 | -124 | 783 | -1390 | -195 | 2538 | -412 | 438 | -157 | -3247 | 30 | -852 | -354 | 1140 | -2576 | 361 | -1269 | -4343 | 1362 | 82 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10569 | -11612 | -894 | -1115 | -6811 | -13 | * | * | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 71(H) | -2701 | -4173 | 1863 | 1171 | -4493 | 434 | 2194 | 635 | 476 | -4189 | -338 | -2308 | 432 | -317 | -2422 | 794 | -2640 | -3795 | -4356 | -3674 | 83 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -656 | -10569 | -1455 | -894 | -1115 | -5895 | -24 | * | * | | | | | | | | | | | | |
| 72(Q) | -2173 | -3634 | -574 | 1547 | -3949 | 1717 | -1808 | -578 | 821 | -3647 | 186 | -1786 | -509 | 1747 | -1897 | -95 | -2112 | 51 | -3820 | -3141 | 84 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1487 | -9958 | -639 | -894 | -1115 | -5197 | -40 | * | * | | | | | | | | | | | | |
| 73(L) | -1532 | -1473 | -3246 | 981 | -1395 | -3003 | -1831 | 1418 | -2332 | 1799 | 1683 | -2421 | -3050 | -2087 | 323 | -2059 | 566 | -849 | -1914 | -1563 | 85 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8772 | -9814 | -894 | -1115 | -3661 | -119 | * | * | | | | | | | | | | | | |
| 74(P) | -3187 | -2946 | -5461 | -4875 | 1864 | -4784 | -3540 | 1543 | -4505 | 1882 | -1394 | 795 | 1970 | -3998 | -4274 | -3903 | -3120 | -2025 | -3149 | -2759 | 86 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9603 | -10645 | -894 | -1115 | -4951 | -47 | * | * | | | | | | | | | | | | |
| 75(T) | -591 | -3110 | 1410 | -1587 | -3278 | -3133 | -1816 | -127 | -319 | 794 | -2243 | -183 | -196 | -1432 | -1956 | 977 | 1815 | -2648 | -3394 | 62 | 87 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9792 | -10835 | -894 | -1115 | -3098 | -179 | * | * | | | | | | | | | | | | |
| 76(P) | -2757 | -2940 | 410 | -3206 | -2941 | -4086 | 1890 | -976 | -3006 | -836 | -2130 | -3229 | 2783 | -2861 | -736 | -3102 | 2340 | -798 | -3361 | -2962 | 88 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10402 | -11444 | -894 | -1115 | -3561 | -128 | * | * | | | | | | | | | | | | |
| 77(E) | 600 | -4259 | 289 | 1784 | -4577 | -3768 | 54 | -1398 | -238 | -650 | -3349 | -2405 | 530 | 547 | 374 | -854 | 4 | 22 | -4444 | 1095 | 89 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10682 | -11724 | -894 | -1115 | -3432 | -140 | * | * | | | | | | | | | | | | |
| 78(E) | -1711 | -4456 | -527 | 2330 | -1854 | -1549 | -2644 | -4510 | 57 | 390 | -3547 | -1128 | -4078 | -2188 | -1311 | 180 | 1487 | 552 | -4645 | -3969 | 90 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10919 | -11961 | -894 | -1115 | -2001 | -415 | * | * | | | | | | | | | | | | |
| 79(D) | -1425 | -566 | 2163 | 1620 | -5237 | -166 | -3081 | -4986 | -1343 | -287 | -104 | -1367 | -849 | 71 | -259 | -430 | -193 | -774 | -5102 | 1076 | 91 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11403 | -12445 | -894 | -1115 | -6240 | -19 | * | * | | | | | | | | | | | | |
| 80(F) | -36 | -414 | -1889 | -32 | 2365 | -438 | 769 | -4836 | 558 | -593 | -1232 | -537 | -1175 | -244 | 519 | -3358 | 73 | -289 | 1859 | 641 | 92 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11403 | -12445 | -894 | -1115 | -6240 | -19 | * | * | | | | | | | | | | | | |
| 81(E) | -1293 | -4920 | 143 | 1492 | -53 | 1150 | 276 | -2131 | -425 | -1715 | -4009 | 1198 | -317 | -1278 | 60 | -75 | -263 | 533 | -5103 | -4421 | 93 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -165 | -11403 | -3214 | -894 | -1115 | -3270 | -158 | * | * | | | | | | | | | | | | |
| 82(I) | -2079 | 653 | -1027 | 818 | -5117 | -1066 | -3066 | 1629 | 539 | -484 | -56 | -882 | 1048 | -605 | 102 | 448 | -503 | -149 | 716 | -4359 | 94 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11365 | -12407 | -894 | -1115 | -2529 | -274 | * | * | | | | | | | | | | | | |
| 83(M) | -2298 | -543 | -1544 | 1357 | 1983 | -267 | 705 | 754 | -258 | 274 | 2610 | -3731 | -4956 | -195 | -1656 | -1286 | -2027 | -1000 | -4707 | -4220 | 95 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11570 | -12613 | -894 | -1115 | -2225 | -347 | * | * | | | | | | | | | | | | |
| 84(H) | -688 | -5080 | -1979 | -160 | -1216 | -677 | 1920 | 450 | 1278 | 385 | 1004 | -1979 | -1090 | 90 | 1125 | -3721 | -2370 | 443 | -5310 | 649 | 96 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -42 | -11757 | -5146 | -894 | -1115 | -2091 | -386 | * | * | | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 85(S) | 542 | -5350 | 897 | -223 | -2003 | 941 | -322 | -348 | 81 | 371 | -4440 | -43 | -2010 | -923 | -622 | 1108 | -383 | -2981 | -452 | -731 | 97 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11865 | -12907 | -894 | -1115 | -719 | -1349 | * | * | | | | | | | | | | | |
| 86(H) | -4276 | -5484 | -844 | -3668 | 535 | -5274 | 5023 | -2699 | -3580 | -5457 | -2130 | -19 | -831 | -1759 | -837 | -1604 | -2488 | -5054 | -5727 | -5111 | 98 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12156 | -13198 | -894 | -1115 | -417 | -1993 | * | * | | | | | | | | | | | |
| 87(E) | 833 | -5727 | -447 | 982 | -943 | 110 | -450 | 437 | -522 | -819 | -462 | -370 | -61 | -1826 | -2362 | 784 | 284 | 641 | -5917 | -5241 | 99 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12280 | -13322 | -894 | -1115 | -171 | -3160 | * | * | | | | | | | | | | | |
| 88(E) | -1407 | -5763 | 205 | 1018 | 93 | -3222 | -1465 | 988 | 982 | -1212 | -138 | -1574 | -854 | 181 | 400 | -940 | 249 | 985 | -5953 | 285 | 100 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 89(V) | 436 | -5272 | 839 | 450 | 330 | -5478 | -55 | 697 | -713 | 610 | -954 | -1425 | -458 | -910 | -1770 | -2199 | -889 | 1170 | 687 | 777 | 101 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 90(G) | 508 | -4444 | -6956 | -6321 | -339 | 2933 | -5037 | -1598 | -5918 | -2910 | -1739 | -5807 | -6211 | -5542 | -1761 | 1057 | 286 | -228 | -4905 | -4562 | 102 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 91(A) | 2127 | -362 | -1357 | 39 | -1134 | -1758 | -4787 | -774 | -1294 | -1394 | -1759 | -2472 | -6035 | -4941 | 1287 | -1488 | -3029 | 1353 | -753 | 1467 | 103 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -112 | -12317 | -3747 | -894 | -1115 | -701 | -1378 | * | * | | | | | | | | | | | |
| 92(E) | -570 | -1209 | -47 | 2128 | -820 | -1232 | -1274 | -1185 | 886 | -1150 | -1569 | -474 | -2676 | -115 | 381 | -537 | 641 | -1255 | -5858 | 808 | 104 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12205 | -13247 | -894 | -1115 | -1639 | -559 | * | * | | | | | | | | | | | |
| 93(I) | -2106 | -4474 | -211 | -93 | 136 | -5934 | -4758 | 2176 | 796 | 1062 | 1994 | -5302 | -2601 | -318 | -1115 | -4980 | -1873 | 139 | -4915 | -470 | 105 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12237 | -13280 | -894 | -1115 | -2468 | -288 | * | * | | | | | | | | | | | |
| 94(L) | 1572 | -1591 | -6886 | -6250 | -1338 | -1408 | -4959 | 1159 | -5845 | 1676 | -3570 | -1557 | -2589 | -5467 | -5645 | -914 | -310 | 1496 | -4825 | -4483 | 106 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12245 | -13287 | -894 | -1115 | -3208 | -165 | * | * | | | | | | | | | | | |
| 95(R) | 210 | 275 | -441 | 308 | -1383 | -1685 | 374 | -3081 | 1590 | -961 | -1548 | -3859 | -1641 | 115 | 1927 | 678 | -595 | -920 | -5891 | -663 | 107 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12245 | -13287 | -894 | -1115 | -2112 | -379 | * | * | | | | | | | | | | | |
| 96(K) | -246 | -5727 | 1122 | 1400 | -6049 | -545 | 534 | -2023 | 1443 | -1689 | -4816 | -315 | -801 | 1384 | 995 | -815 | -1332 | -5349 | -5911 | -96 | 108 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12256 | -13298 | -894 | -1115 | -3019 | -190 | * | * | | | | | | | | | | | |
| 97(F) | -424 | -1406 | -1791 | 877 | 1060 | -3307 | 377 | 355 | -769 | 641 | -193 | -441 | -5546 | -694 | 280 | 144 | -1229 | 694 | 567 | 904 | 109 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -49 | -12256 | -4905 | -894 | -1115 | -3019 | 190 | * | * | | | | | | | | | | | |
| 98(F) | -33 | 1324 | -269 | 906 | 1374 | 774 | -696 | -1059 | 641 | 537 | -237 | 72 | -176 | -916 | -1791 | -1274 | -614 | -5291 | -5857 | -1406 | 110 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12207 | -13250 | -894 | -1115 | -2592 | -262 | * | * | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 99(K) | -1012 | -5687 | -641 | 1017 | 633 | 322 | -56 | 414 | 1495 | 103 | -4776 | -63 | -3046 | -207 | -280 | -832 | -1329 | -493 | -5871 | 590 | 111 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12219 | -13261 | -894 | -1115 | -3580 | -126 | * | * | | | | | | | | | | | |
| 100(R) | 120 | -985 | 491 | 130 | -73 | -2013 | -827 | -1509 | -581 | 238 | -2070 | -234 | 1573 | -1282 | 1646 | -572 | -2814 | 310 | 100 | -2091 | 112 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12219 | -13261 | -894 | -1115 | -3580 | -126 | * | * | | | | | | | | | | | |
| 101(E) | -1479 | -798 | 617 | 1007 | 100 | -1433 | 740 | -88 | -569 | 604 | 212 | 598 | 329 | -432 | 353 | -194 | -557 | -2483 | -59 | 40 | 113 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -792 | -12219 | -1244 | -894 | -1115 | -2716 | -238 | * | * | | | | | | | | | | | |
| 102(G) | 9 | -4952 | 691 | -45 | -53 | 1668 | -1223 | -233 | 912 | -1118 | 190 | -92 | -422 | 127 | 860 | -2158 | -3423 | -4572 | 909 | -1101 | 114 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11441 | -12484 | -894 | -1115 | -6196 | -20 | * | * | | | | | | | | | | | |
| 103(W) | -2238 | -3702 | -915 | 1453 | 1039 | -5181 | -4008 | -590 | -448 | 1347 | -861 | -4565 | -440 | -4240 | -1163 | -93 | -522 | 683 | 1535 | 646 | 115 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1984 | -11441 | -421 | -894 | -1115 | -5297 | -37 | * | * | | | | | | | | | | | |
| 104(N) | 422 | -3217 | 635 | -1157 | -3505 | -2813 | -1475 | 457 | 1974 | -3219 | -2315 | 2098 | -2905 | -1026 | 157 | -1723 | 32 | -2821 | 1417 | 209 | 116 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -3 | -9517 | -10559 | -894 | -1115 | -4757 | -54 | * | * | | | | | | | | | | | |
| 105(Q) | -2007 | -3478 | -1855 | 657 | 333 | 703 | 976 | -3549 | 967 | -372 | -2567 | 701 | -3074 | 1391 | 452 | 1301 | -1946 | -3100 | -3661 | -2980 | 117 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -241 | -9754 | -2714 | -894 | -1115 | -5545 | -31 | * | * | | | | | | | | | | | |
| 106(E) | -1911 | -3381 | 582 | 1799 | -3701 | 635 | -1543 | -3450 | 1113 | 335 | -2471 | -1519 | 561 | -1084 | 598 | -362 | -1850 | -3002 | -3565 | 286 | 118 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1784 | -9629 | -497 | -894 | -1115 | -7074 | -11 | * | * | | | | | | | | | | | |
| 107(K) | -2457 | -3808 | 1635 | -910 | -4290 | -2543 | -1665 | -4144 | 3475 | -3974 | -3296 | -1242 | -2974 | -1319 | -1603 | -2208 | -2467 | -3700 | -3918 | -3329 | 119 |
| - | -150 | -501 | 232 | 42 | -378 | 399 | 105 | -627 | 209 | -467 | -721 | 274 | 395 | 47 | 97 | 360 | 118 | -368 | -295 | -250 |
| - | -3019 | -1262 | -1121 | -1407 | -683 | -4773 | -54 | * | * | | | | | | | | | | | |
| 108(Y) | -4177 | -3479 | -4751 | -4713 | 2821 | -4740 | 2600 | -3362 | -4026 | -2860 | -2810 | -3448 | -4641 | -3414 | 2053 | -3942 | -4051 | -3443 | -553 | 3186 | 124 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -8 | -8094 | -9136 | -894 | -1115 | -1593 | -581 | * | * | | | | | | | | | | | |
| 109(D) | -260 | -4425 | 1518 | 244 | -1148 | 928 | -259 | -4496 | -601 | -626 | -3514 | 676 | 1492 | -724 | -2672 | 1054 | -606 | -4047 | -4608 | -3925 | 125 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10860 | -11902 | -894 | -1115 | -4294 | -75 | * | * | | | | | | | | | | | |
| 110(P) | 450 | -422 | 92 | 1043 | -4837 | -44 | -282 | -4588 | 776 | -614 | -3605 | -1077 | 1766 | 1079 | -622 | -1724 | -1269 | -1096 | -4699 | 900 | 126 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -10962 | -12004 | -894 | -1115 | -5125 | -42 | * | * | | | | | | | | | | | |
| 111(E) | 244 | -4554 | 780 | 1863 | -1065 | 312 | -121 | -611 | 885 | -4570 | 455 | 800 | -165 | 751 | -14 | -1504 | -3020 | -4176 | -4737 | -4054 | 127 |
| - | -149 | -508 | 242 | 58 | -381 | 393 | 98 | -634 | 213 | -458 | -717 | 272 | 386 | 53 | 91 | 354 | 114 | -369 | -302 | -242 |
| - | -6167 | -21 | -12045 | -3 | -8730 | -5734 | -27 | * | * | | | | | | | | | | | |
| 112(I) | 753 | -3228 | -1508 | -1620 | -39 | -4880 | -3737 | 1659 | -792 | 366 | 1174 | -4441 | -4932 | -4154 | -156 | -1830 | 1468 | 1324 | -3682 | -3333 | 129 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11021 | -12063 | -894 | -1115 | -3670 | -118 | * | * | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 113(E) | -677 | -4695 | 1529 | 2164 | -5015 | -4198 | -2856 | -225 | 497 | -729 | 1322 | -1416 | -1210 | 984 | -179 | -722 | -1351 | -4317 | 981 | -4196 | 130 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11160 | -12202 | -894 | -1115 | -472 | -1840 | * | * | | | | | | | | | | | |
| 114(D) | 699 | -5480 | 1676 | 1262 | -2163 | -5080 | -3742 | 341 | -784 | -74 | -183 | -758 | -884 | -1899 | 497 | -580 | 345 | -151 | -5685 | -1838 | 131 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12077 | -13119 | -894 | -1115 | -428 | -1963 | * | * | | | | | | | | | | | |
| 115(V) | 390 | -1260 | 1425 | -6246 | 364 | -2143 | -4969 | 1880 | -3164 | 311 | -1567 | -2699 | -6149 | -924 | -1444 | -3260 | 1069 | 2493 | -4840 | -1327 | 132 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12261 | -13303 | -894 | -1115 | -124 | -3603 | * | * | | | | | | | | | | | |
| 116(C) | 1423 | 1712 | -1842 | -516 | -285 | -842 | -4557 | 612 | -127 | 1024 | -3956 | -4858 | -5865 | 313 | -603 | 257 | -1781 | -27 | -728 | -1020 | 133 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 117(H) | -249 | -5785 | 504 | 1156 | -2836 | -1623 | 1825 | -2077 | 1110 | -1422 | -4874 | 1283 | -829 | 479 | 495 | -224 | -630 | -1531 | 1265 | -930 | 134 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 118(I) | 1580 | -4439 | -6912 | -2094 | -2401 | -781 | -1712 | 1731 | -2202 | 1505 | 213 | -5783 | -6200 | -617 | -5697 | -866 | -172 | -460 | 1669 | -4553 | 135 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 119(I) | 859 | -1314 | -6951 | -2110 | -2383 | -6155 | -5026 | 2570 | -1556 | -1064 | -75 | -5801 | -6205 | -1809 | -2661 | -5240 | -899 | 2271 | -4892 | 121 | 136 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 120(R) | 999 | 312 | -1005 | 1277 | -1115 | -949 | -1769 | -871 | 245 | 687 | -1562 | -360 | -2037 | -1361 | 1554 | -587 | -1748 | -1881 | -1158 | -397 | 137 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 121(H) | 590 | -237 | -1178 | 1134 | -1253 | -690 | 2085 | -1410 | -281 | -768 | -1633 | 583 | -956 | -591 | 837 | 440 | -1943 | -3014 | 212 | 1219 | 138 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 122(H) | -4352 | -1143 | -2593 | -335 | -626 | -5385 | 4714 | -5363 | -448 | -567 | 899 | 222 | -5474 | -2303 | -1125 | -1879 | -4291 | -523 | -5753 | -2090 | 139 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 123(H) | -1398 | -1263 | -4501 | -1896 | 818 | -1726 | 3542 | -1112 | -2766 | 167 | -187 | 715 | -1059 | 337 | 517 | 86 | 1094 | -3153 | -5620 | -5067 | 140 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 124(E) | -1593 | -1311 | 1122 | 1374 | 887 | 827 | -28 | -791 | 425 | -390 | -4856 | 161 | -1647 | -3495 | 943 | -1292 | -521 | -1734 | -5954 | -274 | 141 |
| - | -154 | -520 | 239 | 42 | -377 | 393 | 107 | -637 | 216 | -461 | -669 | 265 | 401 | 39 | 112 | 364 | 103 | -376 | -290 | -259 |
| - | -5929 | -24 | -13359 | -1 | -10036 | -701 | -1378 | * | * | | | | | | | | | | | |
| 125(W) | -457 | -1303 | -1230 | 334 | 194 | 214 | 1284 | 401 | 563 | -466 | 558 | -1868 | -226 | -2353 | -626 | 309 | -914 | -1137 | 3031 | 378 | 143 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -107 | -12317 | -3808 | -894 | -1115 | -701 | -1378 | * | * | | | | | | | | | | | |
| 126(M) | -1473 | -5660 | 1013 | 997 | -1403 | -915 | -454 | 230 | -506 | -489 | 1585 | 406 | 659 | -354 | 114 | -113 | -884 | 417 | -916 | -2004 | 144 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -590 | -12210 | -1575 | -894 | -1115 | -2171 | -362 | * | * | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 127(G) | -136 | -5044 | -1271 | -1230 | -5318 | 1876 | -147 | 1143 | -998 | -625 | 734 | -948 | -664 | -1593 | 344 | -1585 | 1164 | -967 | 877 | -1604 | 145 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -54 | -11648 | -4792 | -894 | -1115 | -4037 | -91 | * | * | | | | | | | | | | | |
| 128(A) | 1341 | -5135 | -546 | 843 | -1797 | -328 | -3297 | -1713 | 974 | -888 | 391 | -1249 | 372 | -386 | -478 | 10 | 886 | -4757 | -5319 | 394 | 146 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -439 | -11635 | -1931 | -894 | -1115 | -5931 | -24 | * | * | | | | | | | | | | | |
| 129(G) | -1169 | -4730 | -137 | 634 | -1781 | 1868 | -2890 | -1311 | 1251 | -1143 | -3819 | -1326 | -1765 | 1230 | -646 | -538 | 276 | -4351 | -4913 | 988 | 147 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11196 | -12238 | -894 | -1115 | -5415 | -34 | * | * | | | | | | | | | | | |
| 130(Y) | -14 | -4708 | -3146 | 735 | 158 | -2123 | -324 | -257 | 401 | -1122 | -3802 | -1351 | -661 | -353 | 1455 | -958 | -1478 | -4319 | 1092 | 2987 | 148 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -47 | -11217 | -4987 | -894 | -1115 | -6421 | -17 | * | * | | | | | | | | | | | |
| 131(P) | 353 | -3950 | -3751 | 291 | -438 | -396 | 507 | -833 | -849 | -590 | -482 | -3390 | 2641 | -1102 | 535 | -2004 | -1438 | -194 | -4310 | 932 | 149 |
| - | -142 | -522 | 270 | 102 | -358 | 364 | 63 | -614 | 213 | -450 | -719 | 245 | 382 | 18 | 123 | 322 | 89 | -345 | -216 | -232 |
| - | -1805 | -487 | -12213 | -3622 | -122 | -5037 | -45 | * | * | | | | | | | | | | | |
| 132(W) | -673 | -4707 | 1234 | -162 | 1947 | -1172 | 947 | -2153 | -183 | -1123 | -3800 | -2888 | -489 | 1320 | 572 | -1129 | -799 | -540 | 2391 | 136 | 193 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11204 | -12247 | -894 | -1115 | -3149 | -173 | * | * | | | | | | | | | | | |
| 133(G) | 291 | -4549 | -3486 | 327 | -655 | 1468 | 344 | -1997 | -372 | 6 | 603 | -1207 | 920 | -493 | 808 | -1145 | -3398 | -751 | 137 | 1061 | 194 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11368 | -12410 | -894 | -1115 | -4191 | -81 | * | * | | | | | | | | | | | |
| 134(L) | -696 | -4583 | -3553 | 1392 | -762 | -1044 | -689 | -1234 | 371 | 1690 | -1136 | -1421 | 135 | -1269 | 185 | -583 | -1014 | -1051 | 710 | -499 | 195 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11424 | -12466 | -894 | -1115 | -2615 | -257 | * | * | | | | | | | | | | | |
| 135(Y) | -296 | -5099 | 719 | -669 | -288 | 153 | -1088 | -2442 | 819 | -308 | -4189 | 331 | 378 | -172 | 801 | -1468 | -899 | -82 | 262 | 1890 | 196 |
| - | -140 | -499 | 228 | 58 | -393 | 409 | 93 | -619 | 208 | -465 | -708 | 267 | 391 | 39 | 94 | 348 | 118 | -366 | -307 | -243 |
| - | -6766 | -14 | -12644 | -2 | -9333 | -2780 | -227 | * | * | | | | | | | | | | | |
| 136(E) | 202 | -5216 | -329 | 1544 | -2025 | -727 | -963 | -1675 | 47 | -258 | 1363 | -435 | -448 | -290 | 1449 | -227 | 420 | -1591 | -5400 | -4717 | 198 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -1 | -11720 | -12762 | -894 | -1115 | -523 | -1717 | * | * | | | | | | | | | | | |
| 137(P) | 392 | -59 | 530 | 1108 | -2297 | -878 | -1550 | -769 | -376 | -1289 | 1213 | -266 | 1589 | 1046 | -204 | -752 | -1285 | -542 | -934 | -1132 | 199 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12161 | -13203 | -894 | -1115 | -4149 | -84 | * | * | | | | | | | | | | | |
| 138(I) | -745 | -1453 | -106 | -465 | -416 | -5244 | -3921 | 1662 | 107 | 531 | 1115 | -521 | 265 | 1193 | -26 | -479 | -203 | -793 | -5586 | -1049 | 200 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12161 | -13203 | -894 | -1115 | -906 | -1101 | * | * | | | | | | | | | | | |
| 139(T) | -748 | 763 | 1156 | -732 | 2748 | -1127 | 9 | 75 | -819 | 35 | -4704 | -163 | 1040 | -3476 | -2236 | 1170 | 1492 | -1311 | -5816 | -1377 | 201 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12245 | -13287 | -894 | -1115 | -3213 | -165 | * | * | | | | | | | | | | | |
| 140(L) | -832 | -1308 | -317 | 82 | -2724 | -5229 | -15 | 1022 | -201 | 1323 | -4772 | 12 | 1221 | -507 | 30 | -815 | 34 | 14 | -5872 | -5200 | 202 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12245 | -13287 | -894 | -1115 | -1419 | -676 | * | * | | | | | | | | | | | |

TABLE 8-continued

| | | | | | | | | | | | | | | | | | | | | |
|---|---|---|---|---|---|---|---|---|---|---|---|---|---|---|---|---|---|---|---|---|
| 141(E) | -1092 | -315 | -1199 | 2220 | -1396 | -629 | -1348 | -620 | -1607 | 515 | -4688 | -267 | -308 | -3523 | 1050 | -529 | -2466 | -120 | -5807 | 1019 | 203 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12269 | -13311 | -894 | -1115 | -139 | -3443 | * | * | | | | | | | | | | | |
| 142(A) | 2031 | 290 | 443 | 217 | -6077 | -133 | -3952 | -765 | -420 | 301 | -4857 | -1446 | -2575 | -693 | -2326 | -323 | -1348 | 939 | -5954 | -5277 | 204 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 143(R) | -696 | 345 | -4871 | -868 | -1482 | -624 | -315 | 974 | 1002 | 55 | 304 | -1404 | -2714 | 1422 | 1873 | -2030 | -655 | 130 | -1180 | -1972 | 205 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 144(I) | -1176 | 1332 | 651 | -2001 | 59 | -2368 | -4902 | 2481 | -1474 | 946 | -3706 | -5518 | -2672 | -1515 | -1719 | -2054 | -877 | 909 | -4955 | 139 | 206 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 145(V) | 495 | -1326 | -6954 | -6318 | -229 | -6156 | -5027 | 1660 | -1955 | 1249 | 361 | -5802 | -6206 | -1434 | -2649 | -3143 | -1078 | 2352 | -4892 | -2253 | 207 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 146(K) | 683 | 613 | 1226 | -2295 | 47 | -2915 | -72 | -2826 | 1887 | -5799 | 611 | -902 | -5380 | 800 | 251 | 546 | 217 | -2887 | -5967 | 312 | 208 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 147(I) | 49 | -4924 | 756 | -355 | -887 | -5679 | 253 | 1333 | -771 | 1272 | -4096 | -2538 | -5756 | -1111 | 903 | -4650 | -2576 | 1255 | -427 | -373 | 209 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 148(A) | 2971 | 187 | -6953 | -2933 | -481 | -3509 | -5027 | 515 | -5912 | -283 | 1273 | -5801 | -6206 | -2324 | -5712 | -816 | -1291 | -1528 | 114 | -990 | 210 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 149(D) | -6833 | -325 | 4153 | -2133 | -9067 | -6527 | -6012 | -9088 | -2921 | -8904 | -8381 | -2633 | -7135 | -5713 | -7558 | -3022 | -6950 | -8501 | -9112 | -7932 | 211 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 150(R) | 915 | -1446 | -1186 | -599 | -6094 | -2043 | 86 | -965 | 1293 | -2019 | -4867 | 486 | -5382 | -1891 | 1803 | 312 | -1938 | 220 | 229 | 1580 | 212 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12317 | -13359 | -894 | -1115 | -701 | -1378 | * | * | | | | | | | | | | | |
| 151(L) | -2885 | 763 | -1829 | -1559 | 1009 | -6155 | -1446 | 645 | -2196 | 2171 | -1373 | -5798 | -6205 | -5532 | -1716 | -2128 | 246 | 727 | -759 | 1371 | 213 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12266 | -13308 | -894 | -1115 | -701 | -1378 | * | * | | | | | | | | | | | |
| 152(H) | 688 | -1052 | 2063 | 1405 | -2415 | -2888 | 2292 | -1528 | -3618 | -1042 | -4614 | -4000 | -5405 | 227 | -2454 | 1018 | -315 | -1590 | -5745 | -1912 | 214 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12254 | -13296 | -894 | -1115 | -701 | -1378 | * | * | | | | | | | | | | | |
| 153(A) | 2073 | -4641 | -5485 | -1843 | -940 | -1167 | -4575 | -2330 | -1825 | -1511 | 1417 | 1641 | -54 | -4567 | 1351 | -1062 | 229 | -1377 | -598 | -157 | 215 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | 0 | -12254 | -13296 | -894 | -1115 | -701 | -1378 | * | * | | | | | | | | | | | |
| 154(M) | 596 | -1117 | 976 | -607 | -5529 | 291 | -4035 | 234 | -1252 | 783 | 2669 | 185 | -5442 | -1909 | -599 | -962 | -356 | -1614 | 516 | -385 | 216 |
| - | * | * | * | * | * | * | * | * | * | * | * | * | * | * | * | * | * | * | * | * |
| - | * | * | * | * | * | * | * | * | 0 | | | | | | | | | | | |

What is claimed is:

1. A recombinant bacterial cell which is engineered to produce butanol, and comprises at least one genetic modification affecting an enzyme activity that increases the concentration of cyclopropane fatty acid in the cell membrane fatty acid composition as compared with a wildtype bacterial cell lacking said genetic modification;
wherein the cell contains the substrate for said enzyme; and
wherein the cell does not naturally produce butanol; and
wherein the at least one genetic modification increases expression of a cfa coding region wherein the cfa coding region is selected from the group consisting of:
a) a nucleic acid molecule encoding an amino acid sequence selected from the group consisting of SEQ ID NO:61, 63, 65, 67 and 69;
b) a nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; and
c) a nucleic acid molecule that encodes a polypeptide having 95% identity based on the Clustal method of alignment when compared to a polypeptide having an amino acid sequence selected from the group consisting of SEQ ID NO:61, 63, 65, 67, and 69; and
wherein the cell is a member of the genera selected from the group consisting of *Escherichia* and *Lactobacillus*.

2. The recombinant cell of claim 1 wherein the enzyme substrate is endogenous to said cell.

3. The recombinant cell of claim 1 wherein the enzyme substrate is provided exogenously to said cell.

4. The recombinant cell of claim 1 comprising a recombinant biosynthetic pathway selected from the group consisting of:
a) a 1-butanol biosynthetic pathway;
b) a 2-butanol biosynthetic pathway; and
c) an isobutanol biosynthetic pathway.

5. The recombinant cell of claim 1, additionally comprising at least one genetic modification which reduces accumulation of (p)ppGpp.

6. The recombinant cell of claim 5, wherein the at least one genetic modification which reduces accumulation of (p)ppGpp reduces production of SpoT or RelA.

7. The recombinant cell of claim 6, wherein the at least one genetic modification which reduces accumulation of (p)ppGpp is a disruption in an endogenous gene selected from the group consisting of spoT and relA or in an operon comprising an open reading frame encoding SpoT or RelA.

8. The recombinant cell of claim 5, wherein the genetic modification reduces (p)ppGpp synthetic activity of encoded endogenous SpoT protein.

9. The recombinant cell of claim 5, wherein the genetic modification increases (p)ppGpp degradative activity by increasing expression of a SpoT with reduced (p)ppGpp synthetic activity.

10. The bacterial cell of claim 1 wherein the cell is of the genus *Lactobacillus* and the genetic modification is overexpression of the *Lactobacillus* cfa1 coding region of SEQ ID NO:61.

11. The recombinant bacterial cell of claim 4 wherein the 1-butanol biosynthetic pathway comprises:
a) at least one genetic construct encoding an acetyl-CoA acetyltransferase;
b) at least one genetic construct encoding 3-hydroxybutyryl-CoA dehydrogenase;
c) at least one genetic construct encoding crotonase;
d) at least one genetic construct encoding butyryl-CoA dehydrogenase;
e) at least one genetic construct encoding butyraldehyde dehydrogenase; and
f) at least one genetic construct encoding 1-butanol dehydrogenase.

12. The recombinant bacterial cell of claim 4 wherein the 2-butanol biosynthetic pathway comprises:
a) at least one genetic construct encoding an acetolactate synthase;
b) at least one genetic construct encoding acetolactate decarboxylase;
c) at least one genetic construct encoding butanediol dehydrogenase;
d) at least one genetic construct encoding butanediol dehydratase; and
e) at least one genetic construct encoding 2-butanol dehydrogenase.

13. The recombinant bacterial cell of claim 4 wherein the isobutanol biosynthetic pathway comprises:
a) at least one genetic construct encoding an acetolactate synthase;
b) at least one genetic construct encoding acetohydroxy acid isomeroreductase;
c) at least one genetic construct encoding acetohydroxy acid dehydratase;
d) at least one genetic construct encoding branched-chain keto acid decarboxylase; and
e) at least one genetic construct encoding branched-chain alcohol dehydrogenase.

14. A process for generating the recombinant cell of claim 1 comprising:
a) providing a recombinant bacterial host cell comprising an engineered butanol biosynthetic pathway that is producing butanol; and
b) creating at least one genetic modification which increases cyclopropane fatty acid in the cell membrane fatty acid composition above natural levels, provided that the bacterial cell does not naturally produce butanol.

15. A process for production of butanol from a recombinant bacterial cell comprising:
(a) providing the recombinant bacterial host cell of claim 1; and
(b) culturing the host cell of (a) under conditions wherein butanol is produced.

16. The process of claim 15, wherein the bacterial host cell is a member of a genus selected from the group consisting of *Escherichia* and *Lactobacillus*.

17. The process of claim 15 wherein the recombinant bacterial host comprises a recombinant biosynthetic pathway selected from the group consisting of:
   a) a 1-butanol biosynthetic pathway;
   b) a 2-butanol biosynthetic pathway; and
   c) an isobutanol biosynthetic pathway.

18. The process of claim 17 wherein the 1-butanol biosynthetic pathway comprises:
   a) at least one genetic construct encoding an acetyl-CoA acetyltransferase;
   b) at least one genetic construct encoding 3-hydroxybutyryl-CoA dehydrogenase;
   c) at least one genetic construct encoding crotonase;
   d) at least one genetic construct encoding butyryl-CoA dehydrogenase;
   e) at least one genetic construct encoding butyraldehyde dehydrogenase; and
   f) at least one genetic construct encoding 1-butanol dehydrogenase.

19. The process of claim 17 wherein the 2-butanol biosynthetic pathway comprises:
   a) at least one genetic construct encoding an acetolactate synthase;
   b) at least one genetic construct encoding acetolactate decarboxylase;
   c) at least one genetic construct encoding butanediol dehydrogenase;
   d) at least one genetic construct encoding butanediol dehydratase; and
   e) at least one genetic construct encoding 2-butanol dehydrogenase.

20. The process of claim 17 wherein the isobutanol biosynthetic pathway comprises:
   a) at least one genetic construct encoding an acetolactate synthase;
   b) at least one genetic construct encoding acetohydroxy acid isomeroreductase;
   c) at least one genetic construct encoding acetohydroxy acid dehydratase;
   d) at least one genetic construct encoding branched-chain keto acid decarboxylase; and
   e) at least one genetic construct encoding branched-chain alcohol dehydrogenase.

21. The process of claim 15 wherein the enzyme substrate is endogenous to the cell or provided exogenously to said cell.

22. The process of claim 15 wherein the cell is of the genus *Lactobacillus* and the genetic modification is overexpression of the *Lactobacillus* cfa1 coding region of SEQ ID NO:61.

23. The process of claim 15 additionally comprising an additional genetic modification which reduces accumulation of (p)ppGpp reduces production of SpoT or RelA.

24. The process of claim 23, wherein the at least one genetic modification which reduces accumulation of (p)ppGpp is a disruption in an endogenous gene selected from the group consisting of spoT and relA or in an operon comprising an open reading frame encoding SpoT or RelA.

25. The recombinant host cell of claim 1 wherein the host cell is *Escherichia coli* or *Lactobacillus plantarum*.

26. The recombinant host cell of claim 4 wherein the host cell is *Escherichia coli* or *Lactobacillus plantarum*.

* * * * *

SEQUENCE LISTING

<160> NUMBER OF SEQ ID NOS: 114

<210> SEQ ID NO 1
<211> LENGTH: 1179
<212> TYPE: DNA
<213> ORGANISM: Clostridium acetobutylicum

<400> SEQUENCE: 1
atgaaagaag ttgtaatagc tagtgcagta agaacagcga ttggatctta tggaaagtct     60
cttaaggatg taccagcagt agatttagga gctacagcta taaggaagc agttaaaaaa    120 gcaggaataa aaccagagga tgttaatgaa gtcattttag gaaatgttct tcaagcaggt   180
ttaggacaga atccagcaag acaggcatct tttaaagcag gattaccagt tgaaattcca    240
gctatgacta ttaataaggt ttgtggttca ggacttagaa cagttagctt agcagcacaa   300

-continued

```
attataaaag caggagatgc tgacgtaata atagcaggtg gtatggaaaa tatgtctaga    360
gctccttact tagcgaataa cgctagatgg ggatatagaa tgggaaacgc taaatttgtt    420
gatgaaatga tcactgacgg attgtgggat gcatttaatg attaccacat gggaataaca    480
gcagaaaaca tagctgagag atggaacatt tcaagagaag aacaagatga gtttgctctt    540
gcatcacaaa aaaagctga agaagctata aaatcaggtc aatttaaaga tgaaatagtt    600
cctgtagtaa ttaaaggcag aaagggagaa actgtagttg atacagatga gcaccctaga    660
tttggatcaa ctatagaagg acttgcaaaa ttaaaacctg ccttcaaaaa agatggaaca    720
gttacagctg gtaatgcatc aggattaaat gactgtgcag cagtacttgt aatcatgagt    780
gcagaaaaag ctaaagagct tggagtaaaa ccacttgcta agatagtttc ttatggttca    840
gcaggagttg acccagcaat aatgggatat ggaccttcct atgcaacaaa agcagctatt    900
gaaaaagcag gttggacagt tgatgaatta gatttaatag aatcaaatga agcttttgca    960
gctcaaagtt tagcagtagc aaaagattta aaatttgata tgaataaagt aaatgtaaat   1020
ggaggagcta ttgccctttgg tcatccaatt ggagcatcag gtgcaagaat actcgttact   1080
cttgtacacg caatgcaaaa aagagatgca aaaaaggct tagcaacttt atgtataggt   1140
ggcggacaag gaacagcaat attgctagaa aagtgctag                          1179
```

<210> SEQ ID NO 2
<211> LENGTH: 392
<212> TYPE: PRT
<213> ORGANISM: Clostridium acetobutylicum

<400> SEQUENCE: 2

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220
```

```
Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
            245                 250                 255

Val Ile Met Ser Ala Glu Lys Ala Lys Glu Leu Gly Val Lys Pro Leu
        260                 265                 270

Ala Lys Ile Val Ser Tyr Gly Ser Ala Gly Val Asp Pro Ala Ile Met
    275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390

<210> SEQ ID NO 3
<211> LENGTH: 1179
<212> TYPE: DNA
<213> ORGANISM: Clostridium acetobutylicum

<400> SEQUENCE: 3
atgagagatg tagtaatagt aagtgctgta agaactgcaa taggagcata tggaaaaaca      60
ttaaaggatg tacctgcaac agagttagga gctatagtaa taaggaagc tgtaagaaga     120 gctaatataa atccaaatga gattaatgaa gttattttg gaaatgtact tcaagctgga     180
ttaggccaaa acccagcaag acaagcagca gtaaaagcag gattaccttt agaaacacct    240
gcgtttacaa tcaataaggt ttgtggttca ggtttaagat ctataagttt agcagctcaa    300
attataaaag ctggagatgc tgataccatt gtagtaggtg gtatggaaaa tatgtctaga    360
tcaccatatt tgattaacaa tcagagatgg ggtcaaagaa tgggagatag tgaattagtt    420
gatgaaatga taaaggatgg tttgtgggat gcatttaatg atatcatat gggagtaact    480 gcagaaaata ttgcagaaca atggaatata caagagaag agcaagatga atttcactt     540 atgtcacaac aaaaagctga aaaagccatt aaaaatggag aatttaagga tgaaatagtt    600
cctgtattaa taaagactaa aaaaggtgaa atagtctttg atcaagatga atttcctaga    660
ttcggaaaca ctattgaagc attaagaaaa cttaaaccta ttttcaagga aaatggtact    720
gttacagcag gtaatgcatc cggattaaat gatggagctg cagcactagt aataatgagc    780
gctgataaag ctaacgctct cggaataaaa ccacttgcta agattacttc ttacggatca    840 tatgggtag atccatcaat aatgggatat ggagctttt atgcaactaa agctgcctta     900
gataaaatta tttaaaaacc tgaagactta gatttaattg aagctaacga ggcatatgct    960
tctcaaagta tagcagtaac tagagattta aatttagata tgagtaaagt taatgttaat   1020
ggtggagcta tagcacttgg acatccaata ggtgcatctg gtgcacgtat tttagtaaca   1080
ttactatacg ctatgcaaaa aagagattca aaaaaaggtc ttgctactct atgtattggt   1140
```

```
ggaggtcagg gaacagctct cgtagttgaa agagactaa                              1179
```

<210> SEQ ID NO 4
<211> LENGTH: 392
<212> TYPE: PRT
<213> ORGANISM: Clostridium acetobutylicum

<400> SEQUENCE: 4

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
```

```
                 370           375              380
Thr Ala Leu Val Val Glu Arg Asp
385              390

<210> SEQ ID NO 5
<211> LENGTH: 849
<212> TYPE: DNA
<213> ORGANISM: Clostridium acetobutylicum

<400> SEQUENCE: 5
atgaaaaagg tatgtgttat aggtgcaggt actatgggtt caggaattgc tcaggcattt      60
gcagctaaag gatttgaagt agtattaaga gatattaaag atgaatttgt tgatagagga     120
ttagatttta tcaataaaaa tctttctaaa ttagttaaaa aaggaaagat agaagaagct     180
actaaagttg aaatcttaac tagaatttcc ggaacagttg accttaatat ggcagctgat     240
tgcgatttag ttatagaagc agctgttgaa agaatggata ttaaaaagca gattttttgct     300 gacttagaca atatatgcaa gccagaaaca attcttgcat caaatacatc atcactttca     360
ataacagaag tggcatcagc aactaaaaga cctgataagg ttataggtat gcatttcttt     420
aatccagctc ctgttatgaa gcttgtagag gtaataagag aatagctac atcacaagaa     480 acttttgatg cagttaaaga gacatctata gcaataggaa aagatcctgt agaagtagca     540
gaagcaccag gatttgttgt aaatagaata ttaataccaa tgattaatga gcagttggt     600 atattagcag aaggaatagc ttcagtagaa gacatagata aagctatgaa acttggagct     660
aatcacccaa tgggaccatt agaattaggt gattttatag gtcttgatat atgtcttgct     720
ataatggatg tttatactc agaaactgga gattctaagt atagaccaca tacattactt     780
aagaagtatg taagagcagg atggcttgga agaaaatcag gaaaaggttt ctacgattat     840
tcaaaataa                                                              849

<210> SEQ ID NO 6
<211> LENGTH: 282
<212> TYPE: PRT
<213> ORGANISM: Clostridium acetobutylicum

<400> SEQUENCE: 6

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
                20                  25                  30

Lys Asp Glu Phe Val Asp Arg Gly Leu Asp Phe Ile Asn Lys Asn Leu
            35                  40                  45

Ser Lys Leu Val Lys Lys Gly Lys Ile Glu Glu Ala Thr Lys Val Glu
        50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160
```

```
Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
                195                 200                 205

Val Glu Asp Ile Asp Lys Ala Met Lys Leu Gly Ala Asn His Pro Met
            210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
                260                 265                 270

Ser Gly Lys Gly Phe Tyr Asp Tyr Ser Lys
                275                 280

<210> SEQ ID NO 7
<211> LENGTH: 786
<212> TYPE: DNA
<213> ORGANISM: Clostridium acetobutylicum

<400> SEQUENCE: 7
atggaactaa acaatgtcat ccttgaaaag gaaggtaaag ttgctgtagt taccattaac      60
agacctaaag cattaaatgc gttaaatagt gatacactaa agaaatggga ttatgttata     120
ggtgaaattg aaaatgatag cgaagtactt gcagtaattt taactggagc aggagaaaaa     180
tcatttgtag caggagcaga tatttctgag atgaaggaaa tgaataccat gaaggtagaa     240
aaattcggga tacttggaaa taagtgtttt agaagattag aacttcttga aaagcctgta     300
atagcagctg ttaatggttt tgctttagga ggcggatgcg aaatagctat gtcttgtgat     360
ataagaatag cttcaagcaa cgcaagattt ggtcaaccag aagtaggtct cggaataaca     420
cctggttttg gtggtacaca aagactttca agattagttg gaatgggcat ggcaaagcag     480
cttatattta ctgcacaaaa tataaaggca gatgaagcat taagaatcgg acttgtaaat     540
aaggtagtag aacctagtga attaatgaat acagcaaaag aaattgcaaa caaaattgtg     600
agcaatgctc cagtagctgt taagttaagc aaacaggcta ttaatagagg aatgcagtgt     660
gatattgata ctgctttagc atttgaatca gaagcatttg gagaatgctt ttcaacagag     720
gatcaaaagg atgcaatgac agctttcata gagaaaagaa aaattgaagg cttcaaaaat     780
agatag                                                                786

<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60
```

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Leu Glu Leu Leu
            85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
            115                 120                 125

Arg Phe Gly Gln Pro Glu Val Gly Leu Gly Ile Thr Pro Gly Phe Gly
            130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
            165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
            195                 200                 205

Leu Ser Lys Gln Ala Ile Asn Arg Gly Met Gln Cys Asp Ile Asp Thr
210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
            245                 250                 255

Gly Phe Lys Asn Arg
            260

<210> SEQ ID NO 9
<211> LENGTH: 1197
<212> TYPE: DNA
<213> ORGANISM: Clostridium acetobutylicum

<400> SEQUENCE: 9
atgatagtaa aagcaaagtt tgtaaaagga tttatcagag atgtacatcc ttatggttgc    60
agaagggaag tactaaatca aatagattat tgtaagaagg ctattgggtt taggggacca   120
aagaaggttt taattgttgg agcctcatct gggtttggtc ttgctactag aatttcagtt   180
gcatttggag gtccagaagc tcacacaatt ggagtatcct atgaaacagg agctacagat   240
agaagaatag gaacagcggg atggtataat aacatatttt ttaaagaatt tgctaaaaaa   300
aaaggattag ttgcaaaaaa cttcattgag gatgcctttt ctaatgaaac caaagataaa   360
gttattaagt atataaagga tgaatttggt aaaatagatt tatttgttta gtttagct    420 gcgcctagga gaaaggacta taaaactgga aatgtttata cttcaagaat aaaaacaatt   480
ttaggagatt ttgagggacc gactattgat gttgaaagag acgagattac tttaaaaaag   540
gttagtagtg ctagcattga agaaattgaa gaaactagaa aggtaatggg tggagaggat   600
tggcaagagt ggtgtgaaga gctgctttat gaagattgtt tttcggataa agcaactacc   660
atagcatact cgtatatagg atccccaaga acctacaaga tatatagaga aggtactata   720
ggaatagcta aaaggatct tgaagataag gctaagctta taaatgaaaa acttaacaga   780
gttataggtg gtagagcctt tgtgtctgtg aataaagcat tagttacaaa agcaagtgca   840
tatattccaa cttttcctct ttatgcagct atttttatata aggtcatgaa agaaaaaaat   900
attcatgaaa attgtattat gcaaattgag agaatgtttt ctgaaaaaat atattcaaat   960

-continued

```
gaaaaaatac aatttgatga caagggaaga ttaaggatgg acgatttaga gcttagaaaa    1020
gacgttcaag acgaagttga tagaatatgg agtaatatta ctcctgaaaa ttttaaggaa    1080
ttatctgatt ataagggata caaaaagaa ttcatgaact taaacggttt tgatctagat     1140
ggggttgatt atagtaaaga cctggatata gaattattaa gaaaattaga accttaa       1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
```

```
              340             345             350
Ile Thr Pro Glu Asn Phe Lys Glu Leu Ser Asp Tyr Lys Gly Tyr Lys
            355                 360                 365

Lys Glu Phe Met Asn Leu Asn Gly Phe Asp Leu Asp Gly Val Asp Tyr
            370                 375                 380

Ser Lys Asp Leu Asp Ile Glu Leu Leu Arg Lys Leu Glu Pro
385                 390                 395
```

<210> SEQ ID NO 11
<211> LENGTH: 1407
<212> TYPE: DNA
<213> ORGANISM: Clostridium beijerinckii

<400> SEQUENCE: 11

```
atgaataaag acacactaat acctacaact aaagatttaa agtaaaaac  aaatggtgaa      60
aacattaatt taaagaacta caaggataat tcttcatgtt tcggagtatt cgaaaatgtt     120
gaaaatgcta aagcagcgc  tgtacacgca caaaagatat tatcccttca ttatacaaaa     180
gagcaaagag aaaaaatcat aactgagata agaaaggccg cattacaaaa taagagggtc     240
ttggctacaa tgattctaga agaaacacat atgggaagat atgaggataa atattaaaa     300
catgaattgg tagctaaata tactcctggt acagaagatt taactactac tgcttggtca     360
ggtgataatg tcttacagt  tgtagaaatg tctccatatg gtgttatagg tgcaataact     420
ccttctacga atccaactga aactgtaata tgtaatagca taggcatgat agctgctgga     480
aatgctgtag tatttaacgg acacccatgc gctaaaaaat gtgttgcctt tgctgttgaa     540
atgataaata aggcaattat ttcatgtggc ggtcctgaaa atcagtaac  aactataaaa     600
aatccaacta tggagtctct agatgcaatt attaagcatc cttcaataaa acttctttgc     660
ggaactgggg gtccaggaat ggtaaaaacc ctcttaaatt ctggtaagaa agctataggt     720
gctggtgctg gaaatccacc agttattgta gatgatactg ctgatataga aaaggctggt     780
aggagcatca ttgaaggctg ttctttttgat aataatttac cttgtattgc agaaaaagaa     840
gtatttgttt ttgagaatgt tgcagatgat ttaatatcta acatgctaaa aaataatgct     900
gtaattataa atgaagatca agtatcaaaa ttaatagatt tagtattaca aaaaaataat     960
gaaactcaag aatactttat aaacaaaaaa tgggtaggaa agatgcaaa  attattctta    1020
gatgaaatag atgttgagtc tccttcaaat gttaaatgca taatctgcga agtaaatgca    1080
aatcatccat ttgttatgac agaactcatg atgccaatat tgccaattgt aagagttaaa    1140
gatatagatg aagctattaa atatgcaaag atagcagaac aaaatagaaa acatagtgcc    1200
tatatttatt ctaaaaatat agacaaccta aatagatttg aaagagaaat agatactact    1260
attttttgtaa agaatgctaa atcttttgct ggtgttggtt atgaagcaga aggatttaca    1320
actttcacta ttgctggatc tactggtgag ggaataaccct ctgcaaggaa ttttacaaga    1380
caaagaagat gtgtacttgc cggctaa                                        1407
```

<210> SEQ ID NO 12
<211> LENGTH: 468
<212> TYPE: PRT
<213> ORGANISM: Clostridium beijerinckii

<400> SEQUENCE: 12

```
Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30
```

Cys Phe Gly Val Phe Glu Asn Val Glu Asn Ala Ile Ser Ser Ala Val
            35                  40                  45

His Ala Gln Lys Ile Leu Ser Leu His Tyr Thr Lys Glu Gln Arg Glu
 50                  55                  60

Lys Ile Ile Thr Glu Ile Arg Lys Ala Ala Leu Gln Asn Lys Glu Val
 65                  70                  75                  80

Leu Ala Thr Met Ile Leu Glu Glu Thr His Met Gly Arg Tyr Glu Asp
                     85                  90                  95

Lys Ile Leu Lys His Glu Leu Val Ala Lys Tyr Thr Pro Gly Thr Glu
                    100                 105                 110

Asp Leu Thr Thr Thr Ala Trp Ser Gly Asp Asn Gly Leu Thr Val Val
                    115                 120                 125

Glu Met Ser Pro Tyr Gly Val Ile Gly Ala Ile Thr Pro Ser Thr Asn
                130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                    165                 170                 175

Phe Ala Val Glu Met Ile Asn Lys Ala Ile Ile Ser Cys Gly Gly Pro
                180                 185                 190

Glu Asn Leu Val Thr Thr Ile Lys Asn Pro Thr Met Glu Ser Leu Asp
            195                 200                 205

Ala Ile Ile Lys His Pro Ser Ile Lys Leu Leu Cys Gly Thr Gly Gly
        210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                    245                 250                 255

Glu Lys Ala Gly Arg Ser Ile Ile Glu Gly Cys Ser Phe Asp Asn Asn
                260                 265                 270

Leu Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
                340                 345                 350

Cys Ile Ile Cys Glu Val Asn Ala Asn His Pro Phe Val Met Thr Glu
            355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys

```
                450              455            460
Val Leu Ala Gly
465

<210> SEQ ID NO 13
<211> LENGTH: 1215
<212> TYPE: DNA
<213> ORGANISM: Clostridium acetobutylicum

<400> SEQUENCE: 13
atggttgatt tcgaatattc aataccaact agaattttt tcggtaaaga taagataaat     60
gtacttggaa gagagcttaa aaatatggt tctaaagtgc ttatagttta tggtggagga    120
agtataaaga gaaatggaat atatgataaa gctgtaagta tacttgaaaa aacagtatt    180 aaattttatg aacttgcagg agtagagcca atccaagag taactacagt tgaaaaagga    240
gttaaaatat gtagagaaaa tggagttgaa gtagtactag ctataggtgg aggaagtgca    300
atagattgcg caaaggttat agcagcagca tgtgaatatg atggaaatcc atgggatatt    360
gtgttagatg gctcaaaaat aaaaggggtg cttcctatag ctagtatatt aaccattgct    420
gcaacaggat cagaaatgga tacgtgggca gtaataaata tatggatac aaacgaaaaa    480 ctaattgcgg cacatccaga tatggctcct aagttttcta tattagatcc aacgtatacg    540
tataccgtac taccaatca aacagcagca ggaacagctg atattatgag tcatatattt    600
gaggtgtatt ttagtaatac aaaaacagca tatttgcagg atagaatggc agaagcgtta    660
ttaagaactt gtattaaata tggaggaata gctcttgaga agccggatga ttatgaggca    720
agagccaatc taatgtgggc ttcaagtctt gcgataaatg gacttttaac atatggtaaa    780
gacactaatt ggagtgtaca cttaatgaa catgaattaa gtgcttatta cgacataaca    840
cacggcgtag gcttgcaat tttaacacct aattggatgg agtatatttt aaataatgat    900
acagtgtaca gtttgttga atatggtgta aatgtttggg aatagacaa agaaaaaaat    960 cactatgaca tagcacatca agcaatacaa aaacaagag attactttgt aaatgtacta   1020
ggtttaccat ctagactgag agatgttgga attgaagaag aaaaattgga cataatggca   1080
aaggaatcag taaagcttac aggaggaacc ataggaaacc taagaccagt aaacgcctcc   1140
gaagtcctac aaatattcaa aaatctgtg taaaacgcct ccgaagtcct acaaatattc   1200
aaaaaatctg tgtaa                                                   1215

<210> SEQ ID NO 14
<211> LENGTH: 390
<212> TYPE: PRT
<213> ORGANISM: Clostridium acetobutylicum

<400> SEQUENCE: 14

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95
```

Gly Gly Ser Ala Ile Asp Cys Ala Lys Val Ile Ala Ala Cys Glu
            100                 105                 110

Tyr Asp Gly Asn Pro Trp Asp Ile Val Leu Asp Gly Ser Lys Ile Lys
            115                 120                 125

Arg Val Leu Pro Ile Ala Ser Ile Leu Thr Ile Ala Ala Thr Gly Ser
        130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 15
<211> LENGTH: 1170
<212> TYPE: DNA
<213> ORGANISM: Clostridium acetobutylicum

<400> SEQUENCE: 15
atgctaagtt ttgattattc aataccaact aaagtttttt ttggaaaagg aaaaatagac      60
gtaattggag aagaaattaa gaaatatggc tcaagagtgc ttatagttta tggcggagga     120
agtataaaaa ggaacggtat atatgataga gcaacagcta tattaaaaga aaacaatata     180
gctttctatg aactttcagg agtagagcca atcctagga taacaacagt aaaaaaaggc     240
atagaaatat gtagagaaaa taatgtggat ttagtattag caataggggg aggaagtgca     300
atagactgtt ctaaggtaat tgcagctgga gtttattatg atggcgatac atgggacatg     360
gttaaagatc catctaaaat aactaaagtt cttccaattg caagtatact tactctttca     420

-continued

```
gcaacagggt ctgaaatgga tcaaattgca gtaatttcaa atatggagac taatgaaaag    480
cttggagtag acatgatga tatgagacct aaatttcag tgttagatcc tacatatact    540
tttacagtac ctaaaaatca aacagcagcg ggaacagctg acattatgag tcacaccttt    600
gaatcttact ttagtggtgt tgaaggtgct tatgtgcagg acggtatagc agaagcaatc    660
ttaagaacat gtataaagta tggaaaaata gcaatggaga agactgatga ttacgaggct    720
agagctaatt tgatgtgggc ttcaagttta gctataaatg gtctattatc acttggtaag    780
gatagaaaat ggagttgtca tcctatggaa cacgagttaa gtgcatatta tgatataaca    840
catggtgtag gacttgcaat tttaacacct aattggatgg aatatattct aaatgacgat    900
acacttcata aatttgtttc ttatggaata aatgtttggg aatagacaa gaacaaagat    960
aactatgaaa tagcacgaga ggctattaaa aatacgagag aatactttaa ttcattgggt   1020
attccttcaa agcttagaga agttggaata ggaaaagata actagaact aatggcaaag   1080
caagctgtta gaaattctgg aggaacaata ggaagtttaa gaccaataaa tgcagaggat   1140
gttcttgaga tatttaaaaa atcttattaa                                   1170
```

<210> SEQ ID NO 16
<211> LENGTH: 389
<212> TYPE: PRT
<213> ORGANISM: Clostridium acetobutylicum

<400> SEQUENCE: 16

```
Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
```

Ser Leu Gly Lys Asp Arg Lys Trp Ser Cys His Pro Met Glu His Glu
    245                 250                 255
                260                 265                 270

Leu Ser Ala Tyr Tyr Asp Ile Thr His Gly Val Gly Leu Ala Ile Leu
                275                 280                 285

Thr Pro Asn Trp Met Glu Tyr Ile Leu Asn Asp Asp Thr Leu His Lys
            290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                    325                 330                 335

Asn Ser Leu Gly Ile Pro Ser Lys Leu Arg Glu Val Gly Ile Gly Lys
                340                 345                 350

Asp Lys Leu Glu Leu Met Ala Lys Gln Ala Val Arg Asn Ser Gly Gly
                355                 360                 365

Thr Ile Gly Ser Leu Arg Pro Ile Asn Ala Glu Asp Val Leu Glu Ile
            370                 375                 380

Phe Lys Lys Ser Tyr
385

<210> SEQ ID NO 17
<211> LENGTH: 780
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc      180 ggcacctttta tgagctgga cggggagctg atcgccttca gcagtcaggt ctatcagctg     240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca atcccctct gacaacctgt tctgcgccct gcgcatcgac      420
ggccatttcc gccatgccca tacccgcacc gtgccgcgcc agacgccgcc gtaccgggcg     480
atgaccgacg tcctcgacga tcagccggtg ttccgcttta accagcgcga aggggtgctg     540
gtcggcttcc ggaccccgca gcatatgcag gggatcaacg tcgccgggta tcacgagcac     600
tttattaccg atgaccgcaa aggcggcggt cacctgctgg attaccagct cgaccatggg     660
gtgctgacct tcggcgaaat tcacaagctg atgatcgacc tgcccgccga cagcgcgttc     720
ctgcaggcta atctgcatcc cgataatctc gatgccgcca tccgttccgt agaaagttaa     780

<210> SEQ ID NO 18
<211> LENGTH: 259
<212> TYPE: PRT
<213> ORGANISM: Klebsiella pneumoniae

<400> SEQUENCE: 18

Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

```
Ile Ala Asp Leu Leu Lys His Gly Asp Phe Gly Leu Gly Thr Phe Asn
 50                  55                  60
Glu Leu Asp Gly Glu Leu Ile Ala Phe Ser Ser Gln Val Tyr Gln Leu
 65                  70                  75                  80
Arg Ala Asp Gly Ser Ala Arg Lys Ala Gln Pro Glu Gln Lys Thr Pro
                 85                  90                  95
Phe Ala Val Met Thr Trp Phe Gln Pro Gln Tyr Arg Lys Thr Phe Asp
            100                 105                 110
His Pro Val Ser Arg Gln Gln Leu His Glu Val Ile Asp Gln Gln Ile
            115                 120                 125
Pro Ser Asp Asn Leu Phe Cys Ala Leu Arg Ile Asp Gly His Phe Arg
130                 135                 140
His Ala His Thr Arg Thr Val Pro Arg Gln Thr Pro Pro Tyr Arg Ala
145                 150                 155                 160
Met Thr Asp Val Leu Asp Asp Gln Pro Val Phe Arg Phe Asn Gln Arg
                165                 170                 175
Glu Gly Val Leu Val Gly Phe Arg Thr Pro Gln His Met Gln Gly Ile
            180                 185                 190
Asn Val Ala Gly Tyr His Glu His Phe Ile Thr Asp Asp Arg Lys Gly
            195                 200                 205
Gly Gly His Leu Leu Asp Tyr Gln Leu Asp His Gly Val Leu Thr Phe
        210                 215                 220
Gly Glu Ile His Lys Leu Met Ile Asp Leu Pro Ala Asp Ser Ala Phe
225                 230                 235                 240
Leu Gln Ala Asn Leu His Pro Asp Asn Leu Asp Ala Ala Ile Arg Ser
                245                 250                 255
Val Glu Ser

<210> SEQ ID NO 19
<211> LENGTH: 1680
<212> TYPE: DNA
<213> ORGANISM: Klebsiella pneumoniae

<400> SEQUENCE: 19
atggacaaac agtatccggt acgccagtgg gcgcacggcg ccgatctcgt cgtcagtcag      60
ctggaagctc agggagtacg ccaggtgttc ggcatcccg gcgccaaaat tgacaaggtc     120
ttcgactcac tgctggattc ctcgattcgc attattccgg tacgccacga agccaacgcc     180
gcgtttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata agcgaagca ggtccaccag     360 agtatggata cggtggcgat gttcagcccg gtcaccaaat acgccgtcga ggtgacggcg     420
ccggatgcgc tggcggaagt ggtctccaac gccttccgcg ccgccgagca gggccggccg     480
ggcagcgcgt tcgttagcct gccgcaggat gtggtcgatg gccggtcag cggcaaagtg     540 ctgccggcca gcggggcccc gcagatgggc gccgcgccgg atgatgccat cgaccaggtg     600
gcgaagctta tcgcccaggc gaagaacccg atcttcctgc tcggcctgat ggccagccag     660
ccggaaaaca gcaaggcgct gcgccgtttg ctggagacca gccatattcc agtcaccagc     720
acctatcagg ccgccggagc ggtgaatcag ataacttct ctcgcttcgc cggccgggtt     780
gggctgttta acaaccaggc cggggaccgt ctgctgcagc tcgccgacct ggtgatctgc     840
atcggctaca gcccggtgga atacgaaccg gcgatgtgga cagcggcaa cgcgacgctg     900 gtgcacatcg acgtgctgcc cgcctatgaa gagcgcaact acaccccgga tgtcgagctg     960
```

-continued

```
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctgaa ccagtttgcc ctgcatccgc tgcgcatcgt tcgcgccatg   1140
caggacatcg tcaacagcga cgtcacgttg accgtggaca tgggcagctt ccatatctgg   1200
attgcccgct acctgtacag cttccgcgcc cgtcaggtga tgatctccaa cggccagcag   1260
accatgggcg tcgccctgcc ctgggctatc ggcgcctggc tggtcaatcc tgagcgaaaa   1320
gtggtctccg tctccggcga cggcggcttc ctgcagtcga gcatggagct ggagaccgcc   1380
gtccgcctga aagccaacgt actgcacctg atctgggtcg ataacggcta caacatggtg   1440
gccattcagg aagagaaaaa ataccagcgc ctgtccggcg tcgagttcgg gccgatggat   1500
tttaaagcct atgccgaatc cttcggcgcg aaagggtttg ccgtggaaag cgccgaggcg   1560
ctggagccga ccctgcacgc ggcgatggac gtcgacggcc cggcggtggt ggccattccg   1620
gtggattatc gcgataaccc gctgctgatg ggccagctgc atctgagtca gattctgtaa   1680
```

<210> SEQ ID NO 20
<211> LENGTH: 559
<212> TYPE: PRT
<213> ORGANISM: Klebsiella pneumoniae

<400> SEQUENCE: 20

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255
```

```
Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555

<210> SEQ ID NO 21
<211> LENGTH: 771
<212> TYPE: DNA
<213> ORGANISM: Klebsiella pneumoniae

<400> SEQUENCE: 21
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt gaacaggcgc gcaaaacgct gggcggcttc     240
gacgtcatcg tcaataacgc cggtgtggca ccgtctacgc cgatcgagtc cattaccccg     300
gagattgtcg acaaagtcta caacatcaac gtcaaagggg tgatctgggg tattcaggcg     360
gcggtcgagg cctttaagaa agaggggcac ggcgggaaaa tcatcaacgc ctgttcccag     420
```

```
gccggccacg tcggcaaccc ggagctggcg gtgtatagct ccagtaaatt cgcggtacgc      480
ggcttaaccc agaccgccgc tcgcgacctc gcgccgctgg gcatcacggt caacggctac      540
tgcccgggga ttgtcaaaac gccaatgtgg gccgaaattg accgccaggt gtccgaagcc      600
gccggtaaac cgctgggcta cggtaccgcc gagttcgcca aacgcatcac tctcggtcgt      660
ctgtccgagc cggaagatgt cgccgcctgc gtctcctatc ttgccagccc ggattctgat      720
tacatgaccg tcagtcgtt gctgatcgac ggcgggatgg tatttaacta a               771
```

<210> SEQ ID NO 22
<211> LENGTH: 256
<212> TYPE: PRT
<213> ORGANISM: Klebsiella pneumoniae

<400> SEQUENCE: 22

```
Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255
```

<210> SEQ ID NO 23
<211> LENGTH: 1665
<212> TYPE: DNA
<213> ORGANISM: Klebsiella oxytoca

<400> SEQUENCE: 23

```
atgagatcga aaagatttga agcactggcg aaacgccctg tgaatcagga cggcttcgtt      60
aaggagtgga tcgaagaagg ctttatcgcg atggaaagcc cgaacgaccc aaaaccgtcg     120
```

-continued

```
attaaaatcg ttaacggcgc ggtgaccgag ctggacggga aaccggtaag cgattttgac      180
ctgatcgacc actttatcgc ccgctacggt atcaacctga accgcgccga agaagtgatg      240
gcgatggatt cggtcaagct ggccaacatg ctgtgcgatc cgaacgttaa acgcagcgaa      300
atcgtcccgc tgaccaccgc gatgacgccg gcgaaaattg tcgaagtggt ttcgcatatg      360
aacgtcgtcg agatgatgat ggcgatgcag aaaatgcgcg cccgccgcac cccgtcccag      420
caggcgcacg tcaccaacgt caaagataac ccggtacaga ttgccgccga cgccgccgaa      480
ggggcatggc gcggatttga cgaacaggaa accaccgttg cggtagcgcg ctatgcgccg      540
ttcaacgcca tcgcgctgct ggtgggctcg caggtaggcc gtccgggcgt gctgacgcag      600
tgctcgctgg aagaagccac cgagctgaag ctcggcatgc tgggccacac ctgctacgcc      660
gaaaccatct ccgtctacgg caccgagccg gtctttaccg acggcgacga cacgccgtgg      720
tcgaagggct tcctcgcctc gtcctacgcc tctcgcgggc tgaaaatgcg ctttacctcc      780
ggctccggct cggaagtgca gatgggctac gccgaaggca aatccatgct ttatctggaa      840
gcgcgctgca tctacatcac caaagccgcg ggcgtacagg tctgcaaaa cggttccgta      900
agctgcatcg gcgtgccgtc tgcggtgcct ccggcattc gcgcggtgct ggcggaaaac      960
ctgatctgtt cgtcgctgga tctggagtgc gcctccagca acgaccagac cttcacccac     1020
tccgatatgc gtcgtaccgc gcgcctgctg atgcagttcc tgccgggcac cgactttatc     1080
tcctccggtt attccgcggt gccgaactac gacaacatgt tcgccggctc caacgaagat     1140
gccgaagact ttgacgacta caacgtcatc cagcgcgacc tgaaggtgga cggcggtttg     1200
cgtccggttc gcgaagagga cgtcatcgcc atccgtaaca aagccgcccg cgcgctgcag     1260
gccgtgtttg ccggaatggg gctgccgccg attaccgatg aagaagttga agccgcgacc     1320
tacgcccacg gttcgaaaga tatgccggag cgcaacatcg tcgaagacat caagttcgcc     1380
caggaaatca tcaataaaaa ccgcaacggt ctggaagtgg tgaaagcgct ggcgcagggc     1440
ggattcaccg acgtggccca ggacatgctc aacatccaga aagctaagct gaccggggac     1500
tacctgcata cctccgcgat tatcgtcggc gacgggcagg tgctgtcagc cgtcaacgac     1560
gtcaacgact atgccggtcc ggcaacgggc tatcgcctgc agggcgaacg ctgggaagag     1620
attaaaaaca tccctggcgc tcttgatccc aacgagattg attaa                     1665
```

<210> SEQ ID NO 24
<211> LENGTH: 554
<212> TYPE: PRT
<213> ORGANISM: Klebsiella oxytoca

<400> SEQUENCE: 24

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110
```

```
Ile Val Glu Val Val Ser His Met Asn Val Glu Met Met Met Ala
            115                 120                 125
Met Gln Lys Met Arg Ala Arg Arg Thr Pro Ser Gln Gln Ala His Val
    130                 135                 140
Thr Asn Val Lys Asp Asn Pro Val Gln Ile Ala Ala Asp Ala Ala Glu
145                 150                 155                 160
Gly Ala Trp Arg Gly Phe Asp Glu Gln Glu Thr Thr Val Ala Val Ala
                165                 170                 175
Arg Tyr Ala Pro Phe Asn Ala Ile Ala Leu Leu Val Gly Ser Gln Val
            180                 185                 190
Gly Arg Pro Gly Val Leu Thr Gln Cys Ser Leu Glu Glu Ala Thr Glu
        195                 200                 205
Leu Lys Leu Gly Met Leu Gly His Thr Cys Tyr Ala Glu Thr Ile Ser
    210                 215                 220
Val Tyr Gly Thr Glu Pro Val Phe Thr Asp Gly Asp Asp Thr Pro Trp
225                 230                 235                 240
Ser Lys Gly Phe Leu Ala Ser Ser Tyr Ala Ser Arg Gly Leu Lys Met
                245                 250                 255
Arg Phe Thr Ser Gly Ser Gly Ser Glu Val Gln Met Gly Tyr Ala Glu
            260                 265                 270
Gly Lys Ser Met Leu Tyr Leu Glu Ala Arg Cys Ile Tyr Ile Thr Lys
        275                 280                 285
Ala Ala Gly Val Gln Gly Leu Gln Asn Gly Ser Val Ser Cys Ile Gly
    290                 295                 300
Val Pro Ser Ala Val Pro Ser Gly Ile Arg Ala Val Leu Ala Glu Asn
305                 310                 315                 320
Leu Ile Cys Ser Ser Leu Asp Leu Glu Cys Ala Ser Ser Asn Asp Gln
                325                 330                 335
Thr Phe Thr His Ser Asp Met Arg Arg Thr Ala Arg Leu Leu Met Gln
            340                 345                 350
Phe Leu Pro Gly Thr Asp Phe Ile Ser Ser Gly Tyr Ser Ala Val Pro
        355                 360                 365
Asn Tyr Asp Asn Met Phe Ala Gly Ser Asn Glu Asp Ala Glu Asp Phe
    370                 375                 380
Asp Asp Tyr Asn Val Ile Gln Arg Asp Leu Lys Val Asp Gly Gly Leu
385                 390                 395                 400
Arg Pro Val Arg Glu Glu Asp Val Ile Ala Ile Arg Asn Lys Ala Ala
                405                 410                 415
Arg Ala Leu Gln Ala Val Phe Ala Gly Met Gly Leu Pro Pro Ile Thr
            420                 425                 430
Asp Glu Val Glu Ala Ala Thr Tyr Ala His Gly Ser Lys Asp Met
        435                 440                 445
Pro Glu Arg Asn Ile Val Glu Asp Ile Lys Phe Ala Gln Glu Ile Ile
    450                 455                 460
Asn Lys Asn Arg Asn Gly Leu Glu Val Val Lys Ala Leu Ala Gln Gly
465                 470                 475                 480
Gly Phe Thr Asp Val Ala Gln Asp Met Leu Asn Ile Gln Lys Ala Lys
                485                 490                 495
Leu Thr Gly Asp Tyr Leu His Thr Ser Ala Ile Ile Val Gly Asp Gly
            500                 505                 510
Gln Val Leu Ser Ala Val Asn Asp Val Asn Asp Tyr Ala Gly Pro Ala
        515                 520                 525
Thr Gly Tyr Arg Leu Gln Gly Glu Arg Trp Glu Glu Ile Lys Asn Ile
```

```
                    530            535            540
Pro Gly Ala Leu Asp Pro Asn Glu Ile Asp
545                 550
```

<210> SEQ ID NO 25
<211> LENGTH: 675
<212> TYPE: DNA
<213> ORGANISM: Klebsiella oxytoca

<400> SEQUENCE: 25

```
atggaaatta atgaaaaatt gctgcgccag ataattgaag acgtgctcag cgagatgaag    60
ggcagcgata aaccggtctc gtttaatgcg ccggcggcct ccgcggcgcc ccaggccacg   120
ccgcccgccg cgacggctt cctgacggaa gtgggcgaag cgcgtcaggg aacccagcag   180
gacgaagtga ttatcgccgt cggcccggct ttcggcctgg cgcagaccgt caatatcgtc   240
ggcatcccgc ataagagcat tttgcgcgaa gtcattgccg gtattgaaga agaaggcatt   300
aaggcgcgcg tgattcgctg ctttaaatcc tccgacgtgg ccttcgtcgc cgttgaaggt   360
aatcgcctga gcggctccgg catctctatc ggcatccagt cgaaaggcac cacggtgatc   420
caccagcagg gctgccgcc gctctctaac ctggagctgt tcccgcaggc gccgctgctg   480
accctggaaa cctatcgcca gatcggcaaa aacgccgccc gctatgcgaa acgcgaatcg   540
ccgcagccgg tcccgacgct gaatgaccag atggcgcggc cgaagtacca ggcgaaatcg   600
gccattttgc acattaaaga gaccaagtac gtggtgacgg caaaaaccc gcaggaactg    660
cgcgtggcgc tttga                                                    675
```

<210> SEQ ID NO 26
<211> LENGTH: 224
<212> TYPE: PRT
<213> ORGANISM: Klebsiella oxytoca

<400> SEQUENCE: 26

```
Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190
```

Arg Pro Lys Tyr Gln Ala Lys Ser Ala Ile Leu His Ile Lys Glu Thr
                195                 200                 205

Lys Tyr Val Val Thr Gly Lys Asn Pro Gln Glu Leu Arg Val Ala Leu
    210                 215                 220

<210> SEQ ID NO 27
<211> LENGTH: 522
<212> TYPE: DNA
<213> ORGANISM: Klebsiella oxytoca

<400> SEQUENCE: 27
atgaataccg acgcaattga atcgatggta cgcgacgtat tgagccgcat gaacagcctg      60
cagggcgagg cgcctgcggc ggctccggcg gctggcggcg cgtcccgtag cgccagggtc     120
agcgactacc cgctggcgaa caagcacccg gaatgggtga aaaccgccac caataaaacg     180
ctggacgact ttacgctgga aaacgtgctg agcaataaag tcaccgccca ggatatgcgt     240
attaccccgg aaaccctgcg cttacaggct tctattgcca agacgcgggg ccgcgaccgg     300
ctggcgatga acttcgagcg cgccgccgag ctgaccgcgg taccggacga tcgcattctt     360
gaaatctaca cgccctccg ccctatcgc tcgacgaaag aggagctgct ggcgatcgcc     420
gacgatctcg aaagccgcta tcaggcgaag atttgcgccg ctttcgttcg cgaagcggcc     480
acgctgtacg tcgagcgtaa aaaactcaaa ggcgacgatt aa                        522

<210> SEQ ID NO 28
<211> LENGTH: 173
<212> TYPE: PRT
<213> ORGANISM: Klebsiella oxytoca

<400> SEQUENCE: 28

Met Asn Thr Asp Ala Ile Glu Ser Met Val Arg Asp Val Leu Ser Arg
1               5                   10                  15

Met Asn Ser Leu Gln Gly Glu Ala Pro Ala Ala Pro Ala Ala Gly
                20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170

<210> SEQ ID NO 29
<211> LENGTH: 1041
<212> TYPE: DNA
<213> ORGANISM: Rhodococcus ruber

<400> SEQUENCE: 29

```
atgaaagccc tccagtacac cgagatcggc tccgagccgg tcgtcgtcga cgtccccacc      60
ccggcgcccg ggccgggtga gatcctgctg aaggtcaccg cggccggctt gtgccactcg     120
gacatcttcg tgatggacat gccggcagag cagtacatct acggtcttcc cctcacccct    180
ggccacgagg gcgtcggcac cgtcgccgaa ctcggcgccg gcgtcaccgg attcgagacg     240
ggggacgccg tcgccgtgta cgggccgtgg ggtgcggtg cgtgccacgc gtgcgcgcgc     300
ggccgggaga actactgcac ccgcgccgcc gagctgggca tcaccccgcc cggtctcggc     360
tcgcccgggt cgatggccga gtacatgatc gtcgactcgg cgcgccacct cgtcccgatc     420
ggggacctcg accccgtcgc ggcggttccg ctcaccgacg cgggcctgac gccgtaccac     480
gcgatctcgc gggtcctgcc cctgctggga cccggctcga ccgcggtcgt catcggggtc    540
ggcggactcg ggcacgtcgg catccagatc ctgcgcgccg tcagcgcggc ccgcgtgatc     600
gccgtcgatc tcgacgacga ccgactcgcg ctcgcccgcg aggtcggcgc cgacgcggcg     660
gtgaagtcgg cgccggggc ggcggacgcg atccgggagc tgaccggcgg tgagggcgcg     720
acggcggtgt cgacttcgt cggcgcccag tcgacgatcg acacggcgca gcaggtggtc     780
gcgatcgacg ggcacatctc ggtggtcggc atccatgccg gcgcccacgc caaggtcggc     840
ttcttcatga tcccgttcgg cgcgtccgtc gtgacgccgt actggggcac gcggtccgag     900
ctgatggacg tcgtggacct ggcccgtgcc ggccggctcg acatccacac cgagacgttc     960
acccctcgacg agggacccac ggcctaccgg cggctacgcg agggcagcat ccgcggccgc    1020
ggggtggtcg tcccgggctg a                                               1041
```

<210> SEQ ID NO 30
<211> LENGTH: 346
<212> TYPE: PRT
<213> ORGANISM: Rhodococcus ruber

<400> SEQUENCE: 30

```
Met Lys Ala Leu Gln Tyr Thr Glu Ile Gly Ser Glu Pro Val Val
1               5                   10                  15

Asp Val Pro Thr Pro Ala Pro Gly Pro Gly Glu Ile Leu Leu Lys Val
                20                  25                  30

Thr Ala Ala Gly Leu Cys His Ser Asp Ile Phe Val Met Asp Met Pro
            35                  40                  45

Ala Glu Gln Tyr Ile Tyr Gly Leu Pro Leu Thr Leu Gly His Glu Gly
        50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
```

```
                       180                 185                 190
Ala Val Ser Ala Ala Arg Val Ile Ala Val Asp Leu Asp Asp Arg
        195                 200                 205
Leu Ala Leu Ala Arg Glu Val Gly Ala Asp Ala Val Lys Ser Gly
    210                 215                 220
Ala Gly Ala Ala Asp Ala Ile Arg Glu Leu Thr Gly Gly Glu Gly Ala
225                 230                 235                 240
Thr Ala Val Phe Asp Phe Val Gly Ala Gln Ser Thr Ile Asp Thr Ala
                245                 250                 255
Gln Gln Val Val Ala Ile Asp Gly His Ile Ser Val Gly Ile His
            260                 265                 270
Ala Gly Ala His Ala Lys Val Gly Phe Phe Met Ile Pro Phe Gly Ala
        275                 280                 285
Ser Val Val Thr Pro Tyr Trp Gly Thr Arg Ser Glu Leu Met Asp Val
    290                 295                 300
Val Asp Leu Ala Arg Ala Gly Arg Leu Asp Ile His Thr Glu Thr Phe
305                 310                 315                 320
Thr Leu Asp Glu Gly Pro Thr Ala Tyr Arg Arg Leu Arg Glu Gly Ser
                325                 330                 335
Ile Arg Gly Arg Gly Val Val Val Pro Gly
            340                 345

<210> SEQ ID NO 31
<211> LENGTH: 1476
<212> TYPE: DNA
<213> ORGANISM: Escherichia coli

<400> SEQUENCE: 31
atggctaact acttcaatac actgaatctg cgccagcagc tggcacagct gggcaaatgt        60
cgctttatgg ccgcgatga attcgccgat ggcgcgagct accttcaggg taaaaaagta       120
gtcatcgtcg gctgtggcgc acagggtctg aaccagggcc tgaacatgcg tgattctggt       180
ctcgatatct cctacgctct gcgtaaagaa gcgattgccg agaagcgcgc gtcctggcgt       240
aaagcgaccg aaaatggttt taagtgggt acttacgaag aactgatccc acaggcggat       300
ctggtgatta acctgacgcc ggacaagcag cactctgatg tagtgcgcac cgtacagcca       360
ctgatgaaag acgcgcggc gctgggctac tcgcacggtt tcaacatcgt cgaagtgggc       420
gagcagatcc gtaaagatat caccgtagtg atggttgcgc cgaaatgccc aggcaccgaa       480
gtgcgtgaag agtacaaacg tgggttcggc gtaccgacgc tgattgccgt tcacccggaa       540
aacgatccga aggcgaagg catggcgatt gccaaagcct gggcggctgc aaccggtggt       600
caccgtgcgg gtgtgctgga atcgtccttc gttgcggaag tgaaatctga cctgatgggc       660
gagcaaacca tcctgtgcgg tatgttgcag gctggctctc tgctgtgctt cgacaagctg       720
gtggaagaag gtaccgatcc agcatacgca gaaaaactga ttcagttcgg ttgggaaacc       780
atcaccgaag cactgaaaca gggcggcatc accctgatga tggaccgtct ctctaacccg       840
gcgaaactgc gtgcttatgc gctttctgaa cagctgaaag atcatggc accccctgttc       900 cagaaacata tggacgacat catctccggc gaattctctt ccggtatgat ggcggactgg       960
gccaacgatg ataagaaact gctgacctgg cgtgaagaga ccggcaaaac cgcgtttgaa      1020
accgcgccgc agtatgaagg caaaatcggc gagcaggagt acttcgataa aggcgtactg      1080
atgattgcga tggtgaaagc gggcgttgaa ctggcgttcg aaaccatggt cgattccggc      1140
atcattgaag agtctgcata ttatgaatca ctgcacgagc tgccgctgat tgccaacacc      1200
```

-continued

```
atcgcccgta agcgtctgta cgaaatgaac gtggttatct ctgataccgc tgagtacggt   1260
aactatctgt tctcttacgc ttgtgtgccg ttgctgaaac cgtttatggc agagctgcaa   1320
ccgggcgacc tgggtaaagc tattccggaa ggcgcggtag ataacgggca actgcgtgat   1380
gtgaacgaag cgattcgcag ccatgcgatt gagcaggtag gtaagaaact gcgcggctat   1440
atgacagata tgaaacgtat tgctgttgcg ggttaa                             1476
```

```
<210> SEQ ID NO 32
<211> LENGTH: 491
<212> TYPE: PRT
<213> ORGANISM: Escherichia coli

<400> SEQUENCE: 32
```

| | | | | | | | | | | | | | | |
|---|---|---|---|---|---|---|---|---|---|---|---|---|---|---|
| Met | Ala | Asn | Tyr | Phe | Asn | Thr | Leu | Asn | Leu | Arg | Gln | Gln | Leu | Ala | Gln |
| 1 | | | | 5 | | | | | 10 | | | | | 15 | |
| Leu | Gly | Lys | Cys | Arg | Phe | Met | Gly | Arg | Asp | Glu | Phe | Ala | Asp | Gly | Ala |
| | | | 20 | | | | | 25 | | | | | 30 | | |
| Ser | Tyr | Leu | Gln | Gly | Lys | Lys | Val | Ile | Val | Gly | Cys | Gly | Ala | Gln | |
| | | 35 | | | | | 40 | | | | | 45 | | | |
| Gly | Leu | Asn | Gln | Gly | Leu | Asn | Met | Arg | Asp | Ser | Gly | Leu | Asp | Ile | Ser |
| | 50 | | | | | 55 | | | | | 60 | | | | |
| Tyr | Ala | Leu | Arg | Lys | Glu | Ala | Ile | Ala | Glu | Lys | Arg | Ala | Ser | Trp | Arg |
| 65 | | | | | 70 | | | | | 75 | | | | | 80 |
| Lys | Ala | Thr | Glu | Asn | Gly | Phe | Lys | Val | Gly | Thr | Tyr | Glu | Glu | Leu | Ile |
| | | | | 85 | | | | | 90 | | | | | 95 | |
| Pro | Gln | Ala | Asp | Leu | Val | Ile | Asn | Leu | Thr | Pro | Asp | Lys | Gln | His | Ser |
| | | | 100 | | | | | 105 | | | | | 110 | | |
| Asp | Val | Val | Arg | Thr | Val | Gln | Pro | Leu | Met | Lys | Asp | Gly | Ala | Ala | Leu |
| | | | 115 | | | | | 120 | | | | | 125 | | |
| Gly | Tyr | Ser | His | Gly | Phe | Asn | Ile | Val | Glu | Val | Gly | Glu | Gln | Ile | Arg |
| | 130 | | | | | 135 | | | | | 140 | | | | |
| Lys | Asp | Ile | Thr | Val | Val | Met | Val | Ala | Pro | Lys | Cys | Pro | Gly | Thr | Glu |
| 145 | | | | | 150 | | | | | 155 | | | | | 160 |
| Val | Arg | Glu | Glu | Tyr | Lys | Arg | Gly | Phe | Gly | Val | Pro | Thr | Leu | Ile | Ala |
| | | | | 165 | | | | | 170 | | | | | 175 | |
| Val | His | Pro | Glu | Asn | Asp | Pro | Lys | Gly | Glu | Gly | Met | Ala | Ile | Ala | Lys |
| | | | 180 | | | | | 185 | | | | | 190 | | |
| Ala | Trp | Ala | Ala | Ala | Thr | Gly | Gly | His | Arg | Ala | Gly | Val | Leu | Glu | Ser |
| | | 195 | | | | | 200 | | | | | 205 | | | |
| Ser | Phe | Val | Ala | Glu | Val | Lys | Ser | Asp | Leu | Met | Gly | Glu | Gln | Thr | Ile |
| | 210 | | | | | 215 | | | | | 220 | | | | |
| Leu | Cys | Gly | Met | Leu | Gln | Ala | Gly | Ser | Leu | Leu | Cys | Phe | Asp | Lys | Leu |
| 225 | | | | | 230 | | | | | 235 | | | | | 240 |
| Val | Glu | Glu | Gly | Thr | Asp | Pro | Ala | Tyr | Ala | Glu | Lys | Leu | Ile | Gln | Phe |
| | | | | 245 | | | | | 250 | | | | | 255 | |
| Gly | Trp | Glu | Thr | Ile | Thr | Glu | Ala | Leu | Lys | Gln | Gly | Gly | Ile | Thr | Leu |
| | | | 260 | | | | | 265 | | | | | 270 | | |
| Met | Met | Asp | Arg | Leu | Ser | Asn | Pro | Ala | Lys | Leu | Arg | Ala | Tyr | Ala | Leu |
| | | 275 | | | | | 280 | | | | | 285 | | | |
| Ser | Glu | Gln | Leu | Lys | Glu | Ile | Met | Ala | Pro | Leu | Phe | Gln | Lys | His | Met |
| | 290 | | | | | 295 | | | | | 300 | | | | |
| Asp | Asp | Ile | Ile | Ser | Gly | Glu | Phe | Ser | Ser | Gly | Met | Met | Ala | Asp | Trp |
| 305 | | | | | 310 | | | | | 315 | | | | | 320 |
| Ala | Asn | Asp | Asp | Lys | Lys | Leu | Leu | Thr | Trp | Arg | Glu | Glu | Thr | Gly | Lys |
| | | | | 325 | | | | | 330 | | | | | 335 | |

```
Thr Ala Phe Glu Thr Ala Pro Gln Tyr Glu Gly Lys Ile Gly Glu Gln
            340                 345                 350
Glu Tyr Phe Asp Lys Gly Val Leu Met Ile Ala Met Val Lys Ala Gly
        355                 360                 365
Val Glu Leu Ala Phe Glu Thr Met Val Asp Ser Gly Ile Ile Glu Glu
    370                 375                 380
Ser Ala Tyr Tyr Glu Ser Leu His Glu Leu Pro Leu Ile Ala Asn Thr
385                 390                 395                 400
Ile Ala Arg Lys Arg Leu Tyr Glu Met Asn Val Val Ile Ser Asp Thr
                405                 410                 415
Ala Glu Tyr Gly Asn Tyr Leu Phe Ser Tyr Ala Cys Val Pro Leu Leu
            420                 425                 430
Lys Pro Phe Met Ala Glu Leu Gln Pro Gly Asp Leu Gly Lys Ala Ile
        435                 440                 445
Pro Glu Gly Ala Val Asp Asn Gly Gln Leu Arg Asp Val Asn Glu Ala
    450                 455                 460
Ile Arg Ser His Ala Ile Glu Gln Val Gly Lys Lys Leu Arg Gly Tyr
465                 470                 475                 480
Met Thr Asp Met Lys Arg Ile Ala Val Ala Gly
                485                 490
```

<210> SEQ ID NO 33
<211> LENGTH: 1851
<212> TYPE: DNA
<213> ORGANISM: Escherichia coli

<400> SEQUENCE: 33

| | | | | | |
|---|---|---|---|---|---|
| atgcctaagt | accgttccgc | caccaccact | catggtcgta | atatggcggg | tgctcgtgcg | 60 |
| ctgtggcgcg | ccaccggaat | gaccgacgcc | gatttcggta | agccgattat | cgcggttgtg | 120 |
| aactcgttca | cccaatttgt | accgggtcac | gtccatctgc | gcgatctcgg | taaactggtc | 180 |
| gccgaacaaa | ttgaagcggc | tggcggcgtt | gccaaagagt | tcaacaccat | tgcggtggat | 240 |
| gatgggattg | ccatgggcca | cgggggggatg | ctttattcac | tgccatctcg | cgaactgatc | 300 |
| gctgattccg | ttgagtatat | ggtcaacgcc | cactgcgccg | acgccatggt | ctgcatctct | 360 |
| aactgcgaca | aaatcacccc | gggggatgctg | atggcttccc | tgcgcctgaa | tattccggtg | 420 |
| atctttgttt | ccggcggccc | cgatggaggcc | gggaaaacca | aactttccga | tcagatcatc | 480 |
| aagctcgatc | tggttgatgc | gatgatccag | ggcgcagacc | cgaaagtatc | tgactcccag | 540 |
| agcgatcagg | ttgaacgttc | cgcgtgtccg | aactgcggtt | cctgctccgg | gatgtttacc | 600 |
| gctaactcaa | tgaactgcct | gaccgaagcg | ctgggcctgt | cgcagccggg | caacggctcg | 660 |
| ctgctggcaa | cccacgccga | ccgtaagcag | ctgttcctta | tgctggtaa | acgcattgtt | 720 |
| gaattgacca | aacgttatta | cgagcaaaac | gacgaaagtg | cactgccgcg | taatatcgcc | 780 |
| agtaaggcgg | cgtttgaaaa | cgccatgacg | ctggatatcg | cgatgggtgg | atcgactaac | 840 |
| accgtacttc | acctgctggc | ggcggcgcag | gaagcggaaa | tcgacttcac | catgagtgat | 900 |
| atcgataagc | tttcccgcaa | ggttccacag | ctgtgtaaag | ttgcgccgag | cacccagaaa | 960 |
| taccatatgg | aagatgttca | ccgtgctggt | ggtgttatcg | gtattctcgg | cgaactggat | 1020 |
| cgcgcggggt | tactgaaccg | tgatgtgaaa | aacgtacttg | gcctgacgtt | gccgcaaacg | 1080 |
| ctggaacaat | acgacgttat | gctgacccag | gatgacgcgg | taaaaaatat | gttccgcgca | 1140 |
| ggtcctgcag | gcattcgtac | cacacaggca | ttctcgcaag | attgccgttg | ggatacgctg | 1200 |
| gacgacgatc | gcgccaatgg | ctgtatccgc | tcgctggaac | acgcctacag | caaagacggc | 1260 |

```
ggcctggcgg tgctctacgg taactttgcg gaaaacggct gcatcgtgaa acggcaggc    1320 gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aaggcggtcc ggggatgcag gaaatgctct acccaaccag cttcctgaaa    1500
tcaatgggtc tcggcaaagc ctgtgcgctg atcaccgacg tcgtttctc ggtggcacc     1560 tctggtcttt ccatcggcca cgtctcaccg gaagcggcaa gcggcggcag cattggcctg    1620
attgaagatg gtgacctgat cgctatcgac atcccgaacc gtggcattca gttacaggta    1680
agcgatgccg aactggcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tggggggtta a            1851
```

<210> SEQ ID NO 34
<211> LENGTH: 616
<212> TYPE: PRT
<213> ORGANISM: Escherichia coli

<400> SEQUENCE: 34

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270
```

```
Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Val Ile Gly Ile Leu
                325                 330                 335

Gly Glu Leu Asp Arg Ala Gly Leu Leu Asn Arg Asp Val Lys Asn Val
                340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
                420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
                500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
                580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
610                 615
```

<210> SEQ ID NO 35
<211> LENGTH: 1662
<212> TYPE: DNA
<213> ORGANISM: Lactococcus lactis

<400> SEQUENCE: 35

```
tctagacata tgtatactgt gggggattac ctgctggatc gcctgcacga actggggatt     60
gaagaaattt cggtgtgcc aggcgattat aacctgcagt tcctggacca gattatctcg    120
cacaaagata tgaagtgggt cggtaacgcc aacgaactga acgcgagcta tatggcagat    180
```

```
ggttatgccc gtaccaaaaa agctgctgcg tttctgacga cctttggcgt tggcgaactg      240
agcgccgtca acggactggc aggaagctac gccgagaacc tgccagttgt cgaaattgtt      300
gggtcgccta cttctaaggt tcagaatgaa ggcaaatttg tgcaccatac tctggctgat      360
ggggatttta acattttat gaaaatgcat gaaccggtta ctgcggcccg cacgctgctg       420
acagcagaga atgctacggt tgagatcgac cgcgtcctgt ctgcgctgct gaaagagcgc      480
aagccggtat atatcaatct gcctgtcgat gttgccgcag cgaaagccga aaagccgtcg      540
ctgccactga aaaagaaaa cagcacctcc aatacatcgg accaggaaat tctgaataaa       600
atccaggaat cactgaagaa tgcgaagaaa ccgatcgtca tcaccggaca tgagatcatc      660
tcttttggcc tggaaaaaac ggtcacgcag ttcatttcta agaccaaact gcctatcacc      720
accctgaact tcggcaaatc tagcgtcgat gaagcgctgc cgagttttct gggtatctat      780
aatggtaccc tgtccgaacc gaacctgaaa gaattcgtcg aaagcgcgga ctttatcctg      840
atgctgggcg tgaaactgac ggatagctcc acaggcgcat ttacccacca tctgaacgag      900
aataaaatga tttccctgaa atcgacgaa ggcaaaatct ttaacgagcg catccagaac       960
ttcgattttg aatctctgat tagttcgctg ctggatctgt ccgaaattga gtataaaggt     1020
aaatatattg ataaaaaaca ggaggatttt gtgccgtcta atgcgctgct gagtcaggat     1080
cgtctgtggc aagccgtaga aaacctgaca cagtctaatg aaacgattgt tgcggaacag     1140
ggaacttcat ttttcggcgc ctcatccatt tttctgaaat ccaaaagcca tttcattggc     1200
caaccgctgt gggggagtat tggttatacc tttccggcgg cgctgggttc acagattgca     1260
gataaggaat cacgccatct gctgtttatt ggtgacggca gcctgcagct gactgtccag     1320
gaactggggc tggcgatccg tgaaaaaatc aatccgattt gctttatcat caataacgac     1380
ggctacaccg tcgaacgcga aattcatgga ccgaatcaaa gttacaatga catcccgatg     1440
tggaactata gcaaactgcc ggaatccttt ggcgcgacag aggatcgcgt ggtgagtaaa     1500
attgtgcgta cggaaaacga atttgtgtcg gttatgaaag aagcgcaggc tgacccgaat     1560
cgcatgtatt ggattgaact gatcctggca aaagaaggcg caccgaaagt tctgaaaaag     1620
atggggaaac tgtttgcgga gcaaaataaa agctaaggat cc                       1662
```

<210> SEQ ID NO 36
<211> LENGTH: 548
<212> TYPE: PRT
<213> ORGANISM: Lactococcus lactis

<400> SEQUENCE: 36

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
```

-continued

```
                115                 120                   125
    Pro Val Thr Ala Ala Arg Thr Leu Leu Thr Ala Glu Asn Ala Thr Val
    130                 135                 140
    Glu Ile Asp Arg Val Leu Ser Ala Leu Leu Lys Glu Arg Lys Pro Val
    145                 150                 155                 160
    Tyr Ile Asn Leu Pro Val Asp Val Ala Ala Lys Ala Glu Lys Pro
                    165                 170                 175
    Ser Leu Pro Leu Lys Lys Glu Asn Ser Thr Ser Asn Thr Ser Asp Gln
                180                 185                 190
    Glu Ile Leu Asn Lys Ile Gln Glu Ser Leu Lys Asn Ala Lys Lys Pro
                195                 200                 205
    Ile Val Ile Thr Gly His Glu Ile Ile Ser Phe Gly Leu Glu Lys Thr
    210                 215                 220
    Val Thr Gln Phe Ile Ser Lys Thr Lys Leu Pro Ile Thr Thr Leu Asn
    225                 230                 235                 240
    Phe Gly Lys Ser Ser Val Asp Glu Ala Leu Pro Ser Phe Leu Gly Ile
                    245                 250                 255
    Tyr Asn Gly Thr Leu Ser Glu Pro Asn Leu Lys Glu Phe Val Glu Ser
                260                 265                 270
    Ala Asp Phe Ile Leu Met Leu Gly Val Lys Leu Thr Asp Ser Ser Thr
                275                 280                 285
    Gly Ala Phe Thr His His Leu Asn Glu Asn Lys Met Ile Ser Leu Asn
                290                 295                 300
    Ile Asp Glu Gly Lys Ile Phe Asn Glu Arg Ile Gln Asn Phe Asp Phe
    305                 310                 315                 320
    Glu Ser Leu Ile Ser Ser Leu Leu Asp Leu Ser Glu Ile Glu Tyr Lys
                    325                 330                 335
    Gly Lys Tyr Ile Asp Lys Lys Gln Glu Asp Phe Val Pro Ser Asn Ala
                340                 345                 350
    Leu Leu Ser Gln Asp Arg Leu Trp Gln Ala Val Glu Asn Leu Thr Gln
                355                 360                 365
    Ser Asn Glu Thr Ile Val Ala Glu Gln Gly Thr Ser Phe Phe Gly Ala
    370                 375                 380
    Ser Ser Ile Phe Leu Lys Ser Lys Ser His Phe Ile Gly Gln Pro Leu
    385                 390                 395                 400
    Trp Gly Ser Ile Gly Tyr Thr Phe Pro Ala Ala Leu Gly Ser Gln Ile
                    405                 410                 415
    Ala Asp Lys Glu Ser Arg His Leu Leu Phe Ile Gly Asp Gly Ser Leu
                420                 425                 430
    Gln Leu Thr Val Gln Glu Leu Gly Leu Ala Ile Arg Glu Lys Ile Asn
                435                 440                 445
    Pro Ile Cys Phe Ile Ile Asn Asn Asp Gly Tyr Thr Val Glu Arg Glu
    450                 455                 460
    Ile His Gly Pro Asn Gln Ser Tyr Asn Asp Ile Pro Met Trp Asn Tyr
    465                 470                 475                 480
    Ser Lys Leu Pro Glu Ser Phe Gly Ala Thr Glu Asp Arg Val Val Ser
                    485                 490                 495
    Lys Ile Val Arg Thr Glu Asn Glu Phe Val Ser Val Met Lys Glu Ala
                500                 505                 510
    Gln Ala Asp Pro Asn Arg Met Tyr Trp Ile Glu Leu Ile Leu Ala Lys
                515                 520                 525
    Glu Gly Ala Pro Lys Val Leu Lys Lys Met Gly Lys Leu Phe Ala Glu
    530                 535                 540
```

Gln Asn Lys Ser
545

<210> SEQ ID NO 37
<211> LENGTH: 1164
<212> TYPE: DNA
<213> ORGANISM: Escherichia coli

<400> SEQUENCE: 37

```
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta cgccgcagc ggctaactat ccggaaaata tcgatccgtg cacattctg      360
caaacgggcg taaagagat aaaagcgcc atcccgatgg gctgtgtgct gacgctgcca      420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacaccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660
ttgctgacgc taatcgaaga tggtccgaaa gccctgaaag agccagaaaa ctacgatgtg     720
cgcgccaacg tcatgtgggc ggcgactcag gcgctgaacg gtttgattgg cgctggcgta     780
ccgcaggact gggcaacgca tatgctgggc cacgaactga ctgcgatgca cggtctggat     840
cacgcgcaaa cactggctat cgtcctgcct gcactgtgga tgaaaaacg cgataccaag     900
cgcgctaagc tgctgcaata tgctgaacgc gtctggaaca tcactgaagg ttccgatgat     960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa aatcatgaca ttacgttgga tgtcagccgc    1140
cgtatatacg aagccgcccg ctaa                                           1164
```

<210> SEQ ID NO 38
<211> LENGTH: 387
<212> TYPE: PRT
<213> ORGANISM: Escherichia coli

<400> SEQUENCE: 38

```
Met Asn Asn Phe Asn Leu His Thr Pro Thr Arg Ile Leu Phe Gly Lys
1               5                  10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110
```

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 39
<211> LENGTH: 2109
<212> TYPE: DNA
<213> ORGANISM: Escherichia coli

<400> SEQUENCE: 39
ttgtatctgt tgaaagcct gaatcaactg attcaaacct acctgccgga agaccaaatc      60
aagcgtctgc ggcaggcgta tctcgttgca cgtgatgctc acgagggca acacgttca     120 agcggtgaac cctatatcac gcacccggta gcggttgcct gcattctggc cgagatgaaa    180
ctcgactatg aaacgctgat ggcggcgctg ctgcatgacg tgattgaaga tactcccgcc    240
acctaccagg atatggaaca gcttttggt aaaagcgtcg ccgagctggt agaggggtg     300 tcgaaacttg ataaactcaa gttccgcgat aagaaagagg cgcaggccga aaactttcgc    360
aagatgatta tggcgatggt gcaggatatc cgcgtcatcc tcatcaaact tgccgaccgt    420
acccacaaca tgcgcacgct gggctcactt cgcccggaca aacgtcgccg catcgcccgt    480
gaaactctcg aaatttatag cccgctggcg caccgtttag gtatccacca cattaaaacc    540

```
gaactcgaag agctgggttt tgaggcgctg tatcccaacc gttatcgcgt aatcaaagaa    600
gtggtgaaag ccgcgcgcgg caaccgtaaa gagatgatcc agaagattct ttctgaaatc    660
gaagggcgtt tgcaggaagc gggaataccg tgccgcgtca gtggtcgcga agcatcttt    720
tattcgattt actgcaaaat ggtgctcaaa gagcagcgtt ttcactcgat catggacatc    780
tacgctttcc gcgtgatcgt caatgattct gacacctgtt atcgcgtgct gggccagatg    840
cacagcctgt acaagccgcg tccgggccgc gtgaaagact atatcgccat tccaaaagcg    900
aacggctatc agtctttgca cacctcgatg atcggcccgc acggtgtgcc ggttgaggtc    960
cagatccgta ccgaagatat ggaccagatg gcggagatgg tgttgccgc gcactgggct   1020
tataaagagc acggcgaaac cagtactacc gcacaaatcc gcgcccagcg ctggatgcaa   1080
agcctgctgg agctgcaaca gagcgccggt agttcgtttg aatttatcga gagcgttaaa   1140
tccgatctct ccccggatga gatttacgtt ttcacaccgg aagggcgcat tgtcgagctg   1200
cctgccggtg caacgcccgt cgacttcgct tatgcagtgc ataccgatat cggtcatgcc   1260
tgcgtgggcg cacgcgttga ccgccagcct tacccgctgt cgcagccgct taccagcggt   1320
caaaccgttg aaatcattac cgctccgggc gctcgcccga atgccgcttg gctgaacttt   1380
gtcgttagct cgaaagcgcg cgccaaaatt cgtcagttgc tgaaaaacct caagcgtgat   1440
gattctgtaa gcctgggccg tcgtctgctc aaccatgctt gggtggtag ccgtaagctg   1500
aatgaaatcc gcaggaaaa tattcagcgc gagctggatc gcatgaagct ggcaacgctt   1560
gacgatctgc tggcagaaat cggacttggt aacgcaatga cgtggtggt cgcgaaaaat   1620
ctgcaacatg gggacgcctc cattccaccg gcaacccaaa gccacggaca tctgcccatt   1680
aaaggtgccg atggcgtgct gatcaccttt gcgaaatgct gccgcctat tcctggcgac   1740
ccgattatcg cccacgtcag ccccggtaaa ggtctggtga tccaccatga atcctgccgt   1800
aatatccgtg ctaccagaa agagccagag aagtttatgg ctgtggaatg ggataaagag   1860
acggcgcagg agttcatcac cgaaatcaag gtggagatgt caatcatca gggtgcgctg   1920
gcaaacctga cggcggcaat taacaccacg acttcgaata ttcaaagttt gaatacggaa   1980
gagaaagatg gtcgcgtcta cagcgccttt attcgtctga ccgctcgtga ccgtgtgcat   2040
ctggcgaata tcatgcgcaa aatccgcgtg atgccagacg tgattaaagt cacccgaaac   2100
cgaaattaa                                                           2109
```

<210> SEQ ID NO 40
<211> LENGTH: 702
<212> TYPE: PRT
<213> ORGANISM: Escherichia coli

<400> SEQUENCE: 40

Met Tyr Leu Phe Glu Ser Leu Asn Gln Leu Ile Gln Thr Tyr Leu Pro
1               5                   10                  15

Glu Asp Gln Ile Lys Arg Leu Arg Gln Ala Tyr Leu Val Ala Arg Asp
            20                  25                  30

Ala His Glu Gly Gln Thr Arg Ser Ser Gly Glu Pro Tyr Ile Thr His
        35                  40                  45

Pro Val Ala Val Ala Cys Ile Leu Ala Glu Met Lys Leu Asp Tyr Glu
    50                  55                  60

Thr Leu Met Ala Ala Leu Leu His Asp Val Ile Glu Asp Thr Pro Ala
65                  70                  75                  80

Thr Tyr Gln Asp Met Glu Gln Leu Phe Gly Lys Ser Val Ala Glu Leu
                85                  90                  95

-continued

Val Glu Gly Val Ser Lys Leu Asp Lys Leu Lys Phe Arg Asp Lys Lys
          100                 105                 110

Glu Ala Gln Ala Glu Asn Phe Arg Lys Met Ile Met Ala Met Val Gln
          115                 120                 125

Asp Ile Arg Val Ile Leu Ile Lys Leu Ala Asp Arg Thr His Asn Met
      130                 135                 140

Arg Thr Leu Gly Ser Leu Arg Pro Asp Lys Arg Arg Ile Ala Arg
145                 150                 155                 160

Glu Thr Leu Glu Ile Tyr Ser Pro Leu Ala His Arg Leu Gly Ile His
                  165                 170                 175

His Ile Lys Thr Glu Leu Glu Glu Leu Gly Phe Glu Ala Leu Tyr Pro
          180                 185                 190

Asn Arg Tyr Arg Val Ile Lys Glu Val Val Lys Ala Ala Arg Gly Asn
      195                 200                 205

Arg Lys Glu Met Ile Gln Lys Ile Leu Ser Glu Ile Glu Gly Arg Leu
      210                 215                 220

Gln Glu Ala Gly Ile Pro Cys Arg Val Ser Gly Arg Glu Lys His Leu
225                 230                 235                 240

Tyr Ser Ile Tyr Cys Lys Met Val Leu Lys Glu Gln Arg Phe His Ser
                  245                 250                 255

Ile Met Asp Ile Tyr Ala Phe Arg Val Ile Val Asn Asp Ser Asp Thr
              260                 265                 270

Cys Tyr Arg Val Leu Gly Gln Met His Ser Leu Tyr Lys Pro Arg Pro
          275                 280                 285

Gly Arg Val Lys Asp Tyr Ile Ala Ile Pro Lys Ala Asn Gly Tyr Gln
      290                 295                 300

Ser Leu His Thr Ser Met Ile Gly Pro His Gly Val Pro Val Glu Val
305                 310                 315                 320

Gln Ile Arg Thr Glu Asp Met Asp Gln Met Ala Glu Met Gly Val Ala
                  325                 330                 335

Ala His Trp Ala Tyr Lys Glu His Gly Glu Thr Ser Thr Thr Ala Gln
              340                 345                 350

Ile Arg Ala Gln Arg Trp Met Gln Ser Leu Leu Glu Leu Gln Gln Ser
          355                 360                 365

Ala Gly Ser Ser Phe Glu Phe Ile Glu Ser Val Lys Ser Asp Leu Phe
      370                 375                 380

Pro Asp Glu Ile Tyr Val Phe Thr Pro Glu Gly Arg Ile Val Glu Leu
385                 390                 395                 400

Pro Ala Gly Ala Thr Pro Val Asp Phe Ala Tyr Ala Val His Thr Asp
                  405                 410                 415

Ile Gly His Ala Cys Val Gly Ala Arg Val Asp Arg Gln Pro Tyr Pro
              420                 425                 430

Leu Ser Gln Pro Leu Thr Ser Gly Gln Thr Val Glu Ile Ile Thr Ala
          435                 440                 445

Pro Gly Ala Arg Pro Asn Ala Ala Trp Leu Asn Phe Val Val Ser Ser
      450                 455                 460

Lys Ala Arg Ala Lys Ile Arg Gln Leu Leu Lys Asn Leu Lys Arg Asp
465                 470                 475                 480

Asp Ser Val Ser Leu Gly Arg Arg Leu Leu Asn His Ala Leu Gly Gly
                  485                 490                 495

Ser Arg Lys Leu Asn Glu Ile Pro Gln Glu Asn Ile Gln Arg Glu Leu
              500                 505                 510

Asp Arg Met Lys Leu Ala Thr Leu Asp Asp Leu Leu Ala Glu Ile Gly
          515                 520                 525

```
Leu Gly Asn Ala Met Ser Val Val Ala Lys Asn Leu Gln His Gly
    530                 535                 540

Asp Ala Ser Ile Pro Pro Ala Thr Gln Ser His Gly His Leu Pro Ile
545                 550                 555                 560

Lys Gly Ala Asp Gly Val Leu Ile Thr Phe Ala Lys Cys Cys Arg Pro
                565                 570                 575

Ile Pro Gly Asp Pro Ile Ile Ala His Val Ser Pro Gly Lys Gly Leu
                580                 585                 590

Val Ile His His Glu Ser Cys Arg Asn Ile Arg Gly Tyr Gln Lys Glu
                595                 600                 605

Pro Glu Lys Phe Met Ala Val Glu Trp Asp Lys Glu Thr Ala Gln Glu
610                 615                 620

Phe Ile Thr Glu Ile Lys Val Glu Met Phe Asn His Gln Gly Ala Leu
625                 630                 635                 640

Ala Asn Leu Thr Ala Ala Ile Asn Thr Thr Ser Asn Ile Gln Ser
                645                 650                 655

Leu Asn Thr Glu Glu Lys Asp Gly Arg Val Tyr Ser Ala Phe Ile Arg
                660                 665                 670

Leu Thr Ala Arg Asp Arg Val His Leu Ala Asn Ile Met Arg Lys Ile
                675                 680                 685

Arg Val Met Pro Asp Val Ile Lys Val Thr Arg Asn Arg Asn
690                 695                 700

<210> SEQ ID NO 41
<211> LENGTH: 2235
<212> TYPE: DNA
<213> ORGANISM: Escherichia coli

<400> SEQUENCE: 41
```

| | | | | | |
|---|---|---|---|---|---|
| atggttgcgg | taagaagtgc | acatatcaat | aaggctggtg | aatttgatcc | ggaaaaatgg | 60 |
| atcgcaagtc | tgggtattac | cagccagaag | tcgtgtgagt | gcttagccga | aacctgggcg | 120 |
| tattgtctgc | aacagacgca | ggggcatccg | gatgccagtc | tgttattgtg | gcgtggtgtt | 180 |
| gagatggtgg | agatcctctc | gacattaagt | atggacattg | acacgctgcg | ggcggcgctg | 240 |
| cttttccctc | tggcggatgc | caacgtagtc | agcgaagatg | tgctgcgtga | gagcgtcggt | 300 |
| aagtcggtcg | ttaaccttat | tcacggcgtg | cgtgatatgg | cggcgatccg | ccagctgaaa | 360 |
| gcgacgcaca | ctgattctgt | ttcctccgaa | caggtcgata | acgttcgccg | gatgttattg | 420 |
| gcgatggtcg | atgattttcg | ctgcgtagtc | atcaaactgg | cggagcgtat | tgctcatctg | 480 |
| cgcgaagtaa | aagatgcgcc | ggaagatgaa | cgtgtactgg | cggcaaaaga | gtgtaccaac | 540 |
| atctacgcac | cgctggctaa | ccgtctcgga | tcggacaac | tgaaatggga | actggaagat | 600 |
| tactgcttcc | gttacctcca | tccaaccgaa | tacaaacgaa | ttgccaaact | gctgcatgaa | 660 |
| cggcgtctcg | accgcgaaca | ctacatcgaa | gagttcgttg | gtcatctgcg | cgctgagatg | 720 |
| aaagctgaag | gcgttaaagc | ggaagtgtat | ggtcgtccga | acacatctca | cagcatctgg | 780 |
| cgtaaaatgc | agaaaaagaa | cctcgccttt | gatgagctgt | tgatgtgcg | tgcggtacgt | 840 |
| attgtcgccg | agcgtttaca | ggattgctat | gccgcactgg | ggatagtgca | cactcactat | 900 |
| cgccacctgc | cggatgagtt | tgacgattac | gtcgctaacc | cgaaaccaaa | cggttatcag | 960 |
| tctattcata | ccgtggttct | ggggccgggt | ggaaaaaccg | ttgagatcca | aatccgcacc | 1020 |
| aaacagatgc | atgaagatgc | agagttgggt | gttgctgcgc | actggaaata | taagagggc | 1080 |
| gcggctgctg | gcggcgcacg | ttcgggacat | gaagaccgga | ttgcctggct | gcgtaaactg | 1140 |

-continued

```
attgcgtggc aggaagagat ggctgattcc ggcgaaatgc tcgacgaagt acgtagtcag    1200
gtctttgacg accgggtgta cgtctttacg ccgaaaggtg atgtcgttga tttgcctgcg    1260
ggatcaacgc cgctggactt cgcttaccac atccacagtg atgtcggaca ccgctgcatc    1320
ggggcaaaaa ttggcgggcg cattgtgccg ttcacctacc agctgcagat gggcgaccag    1380
attgaaatta tcacccagaa acagccgaac cccagccgtg actggttaaa cccaaacctc    1440
ggttacgtca caaccagccg tgggcgttcg aaaattcacg cctggttccg taaacaggac    1500
cgtgacaaaa acattctggc tgggcggcaa atccttgacg acgagctgga acatctgggg    1560
atcagcctga agaagcaga aaacatctg ctgccgcgtt acaacttcaa tgatgtcgac    1620
gagttgctgg cggcgattgg tggcggggat atccgtctca atcagatggt gaacttcctg    1680
caatcgcaat ttaataagcc gagtgccgaa gagcaggacg ccgccgcgct gaagcaactt    1740
cagcaaaaaa gctacacgcc gcaaaaccgc agtaaagata acggtcgcgt ggtagtcgaa    1800
ggtgttggca acctgatgca ccacatcgcg cgctgctgcc agccgattcc tggagatgag    1860
attgtcggct tcattaccca ggggcgcggt atttcagtac accgcgccga ttgcgaacaa    1920
ctggcggaac tgcgctccca tgcgccagaa cgcattgttg acgcggtatg gggtgagagc    1980
tactccgccg gatattcgct ggtggtccgc gtggtagcta atgatcgtag tgggttgtta    2040
cgtgatatca cgaccattct cgccaacgag aaggtgaacg tgcttggcgt tgccagccgt    2100
agcgacacca aacagcaact ggcgaccatc gacatgacca ttgagattta caacctgcaa    2160
gtgctggggc gcgtgctggg taaactcaac caggtgccgg atgttatcga cgcgcgtcgg    2220
ttgcacggga gttag                                                    2235
```

<210> SEQ ID NO 42
<211> LENGTH: 744
<212> TYPE: PRT
<213> ORGANISM: Echerichia coli

<400> SEQUENCE: 42

```
Met Val Ala Val Arg Ser Ala His Ile Asn Lys Ala Gly Glu Phe Asp
1               5                   10                  15

Pro Glu Lys Trp Ile Ala Ser Leu Gly Ile Thr Ser Gln Lys Ser Cys
                20                  25                  30

Glu Cys Leu Ala Glu Thr Trp Ala Tyr Cys Leu Gln Gln Thr Gln Gly
            35                  40                  45

His Pro Asp Ala Ser Leu Leu Leu Trp Arg Gly Val Glu Met Val Glu
        50                  55                  60

Ile Leu Ser Thr Leu Ser Met Asp Ile Asp Thr Leu Arg Ala Ala Leu
65                  70                  75                  80

Leu Phe Pro Leu Ala Asp Ala Asn Val Val Ser Glu Asp Val Leu Arg
                85                  90                  95

Glu Ser Val Gly Lys Ser Val Val Asn Leu Ile His Gly Val Arg Asp
            100                 105                 110

Met Ala Ala Ile Arg Gln Leu Lys Ala Thr His Thr Asp Ser Val Ser
        115                 120                 125

Ser Glu Gln Val Asp Asn Val Arg Arg Met Leu Leu Ala Met Val Asp
    130                 135                 140

Asp Phe Arg Cys Val Val Ile Lys Leu Ala Glu Arg Ile Ala His Leu
145                 150                 155                 160

Arg Glu Val Lys Asp Ala Pro Glu Asp Glu Arg Val Leu Ala Ala Lys
                165                 170                 175

Glu Cys Thr Asn Ile Tyr Ala Pro Leu Ala Asn Arg Leu Gly Ile Gly
```

-continued

```
                180                 185                 190
Gln Leu Lys Trp Glu Leu Glu Asp Tyr Cys Phe Arg Tyr Leu His Pro
            195                 200                 205
Thr Glu Tyr Lys Arg Ile Ala Lys Leu Leu His Glu Arg Arg Leu Asp
            210                 215                 220
Arg Glu His Tyr Ile Glu Glu Phe Val Gly His Leu Arg Ala Glu Met
225                 230                 235                 240
Lys Ala Glu Gly Val Lys Ala Glu Val Tyr Gly Arg Pro Lys His Ile
            245                 250                 255
Tyr Ser Ile Trp Arg Lys Met Gln Lys Lys Asn Leu Ala Phe Asp Glu
            260                 265                 270
Leu Phe Asp Val Arg Ala Val Arg Ile Val Ala Glu Arg Leu Gln Asp
            275                 280                 285
Cys Tyr Ala Ala Leu Gly Ile Val His Thr His Tyr Arg His Leu Pro
290                 295                 300
Asp Glu Phe Asp Asp Tyr Val Ala Asn Pro Lys Pro Asn Gly Tyr Gln
305                 310                 315                 320
Ser Ile His Thr Val Val Leu Gly Pro Gly Gly Lys Thr Val Glu Ile
            325                 330                 335
Gln Ile Arg Thr Lys Gln Met His Glu Asp Ala Glu Leu Gly Val Ala
            340                 345                 350
Ala His Trp Lys Tyr Lys Glu Gly Ala Ala Gly Gly Ala Arg Ser
            355                 360                 365
Gly His Glu Asp Arg Ile Ala Trp Leu Arg Lys Leu Ile Ala Trp Gln
            370                 375                 380
Glu Glu Met Ala Asp Ser Gly Glu Met Leu Asp Glu Val Arg Ser Gln
385                 390                 395                 400
Val Phe Asp Asp Arg Val Tyr Val Phe Thr Pro Lys Gly Asp Val Val
                405                 410                 415
Asp Leu Pro Ala Gly Ser Thr Pro Leu Asp Phe Ala Tyr His Ile His
            420                 425                 430
Ser Asp Val Gly His Arg Cys Ile Gly Ala Lys Ile Gly Gly Arg Ile
            435                 440                 445
Val Pro Phe Thr Tyr Gln Leu Gln Met Gly Asp Gln Ile Glu Ile Ile
            450                 455                 460
Thr Gln Lys Gln Pro Asn Pro Ser Arg Asp Trp Leu Asn Pro Asn Leu
465                 470                 475                 480
Gly Tyr Val Thr Thr Ser Arg Gly Arg Ser Lys Ile His Ala Trp Phe
            485                 490                 495
Arg Lys Gln Asp Arg Asp Lys Asn Ile Leu Ala Gly Arg Gln Ile Leu
            500                 505                 510
Asp Asp Glu Leu Glu His Leu Gly Ile Ser Leu Lys Glu Ala Glu Lys
            515                 520                 525
His Leu Leu Pro Arg Tyr Asn Phe Asn Asp Val Asp Glu Leu Leu Ala
            530                 535                 540
Ala Ile Gly Gly Gly Asp Ile Arg Leu Asn Gln Met Val Asn Phe Leu
545                 550                 555                 560
Gln Ser Gln Phe Asn Lys Pro Ser Ala Glu Glu Gln Asp Ala Ala Ala
            565                 570                 575
Leu Lys Gln Leu Gln Lys Ser Tyr Thr Pro Gln Asn Arg Ser Lys
            580                 585                 590
Asp Asn Gly Arg Val Val Glu Gly Val Gly Asn Leu Met His His
            595                 600                 605
```

-continued

```
            Ile Ala Arg Cys Cys Gln Pro Ile Pro Gly Asp Glu Ile Val Gly Phe
            610                 615                 620
            Ile Thr Gln Gly Arg Gly Ile Ser Val His Arg Ala Asp Cys Glu Gln
            625                 630                 635                 640
            Leu Ala Glu Leu Arg Ser His Ala Pro Glu Arg Ile Val Asp Ala Val
                            645                 650                 655
            Trp Gly Glu Ser Tyr Ser Ala Gly Tyr Ser Leu Val Arg Val Val
                            660                 665                 670
            Ala Asn Asp Arg Ser Gly Leu Leu Arg Asp Ile Thr Thr Ile Leu Ala
                        675                 680                 685
            Asn Glu Lys Val Asn Val Leu Gly Val Ala Ser Arg Ser Asp Thr Lys
            690                 695                 700
            Gln Gln Leu Ala Thr Ile Asp Met Thr Ile Glu Ile Tyr Asn Leu Gln
            705                 710                 715                 720
            Val Leu Gly Arg Val Leu Gly Lys Leu Asn Gln Val Pro Asp Val Ile
                            725                 730                 735
            Asp Ala Arg Arg Leu His Gly Ser
                        740
```

<210> SEQ ID NO 43
<211> LENGTH: 2268
<212> TYPE: DNA
<213> ORGANISM: Lactobacillus plantarum

<400> SEQUENCE: 43

```
atgcccaaac aacctacctg gactgcccag gatgtcctgg acatggttca aaagtatatg      60
aatagtgatc acgtcgcgtt agttaaacgg gcgtgtgatt ttgcaactta tgtgcataag     120
gatcagtatc gccaatctgg tgagccgtat attatgcatc cgattcaagt tgctggtatc     180
ttagctgaat tgaagatgga ccctgaaacc gtcgcttcgg gtttcttaca cgacgttgtg     240
gaagatactg tgttactttt aggagacgtt gaagaactgt ttggtcatga cgtggccgtt     300
attgttgacg gggtcaccaa gctgggtaag attcggtaca agtccaacaa agaacagctt     360
gctgaaaatc accgtaaatt actgttggcg atgtctaaag atattcgagt catgattgtc     420
aaattagctg atcgcttgca taatatgcgg acattgcagc atctgcggcc cgataaacag     480
cggcgaattg caaatgaaac gttggaaatt tacgccccca ttgccgatcg attagggatc     540
agcacgatta atgggaact agaagatatt tcactacgtt atttgaatcc tcaacagtat     600
tatcgcattg tccacttgat gaattcgcgg cgtgaggacc gtgaaaagta catcgagatt     660
gccattcaag acattcaaaa ggcgctccat gatctggaac taccagaagc tgaaatttat     720
ggtcgtccga agcatatcta ttcaatttat aagaagatgc gggacaaaca caaacagttt     780
agccaacttt acgatctgct ggcaattcgg gtggtcgtgg attcaatcaa ggactgttat     840
gcagttttag gtgcgattca cacacaatgg aagcccatgc cggggcgttt aaagattat     900
attgcgatgc ccaaggccaa tatgtatcaa tctttgcata ccacggtggt cggtcctgaa     960
ggtaagcccc tcgaaataca gatccggacg tttgaaatgc accgggtcgc tgaatacggg    1020
gtcgcagcac actgggcgta taggaaggt aaacgcgacg aggtccaaga gactcagtcg    1080
ggcaacaagt tgaacttagt caaagaaatc attgagctac aggatgaaag taaggacgct    1140
gccgacttta tggaggcgt caaggcgac ctcttagtg accgggtcta tgcttttacg    1200
cccaagggtg acgtgacaga attaccaaag ggcgctggac cactggatat ggcatattcg    1260
atccatacgg aagtgggtaa ccatacgact ggtgcgaaag tcaatggcaa gatcgttcca    1320
ttggattacc aaatcaaaaa tggtgatatc gtggatattt aacgtccac tagttcaact    1380
```

```
ggtcctagcc gtgattggca gaaattagtc tatacgcggc gggcccgtaa taaaatcaaa    1440
cagttcttcc gcaatgctga ccgtgaggaa aacatcatta cgggtcgtga tttgcttgag    1500
aagcagctac gtgatttaga gtttaatcca aaagaaatca tgactaagga caaggtgacg    1560
gcggtcgctc aaaagatgca ctacggtagt gaggatgatt tgttcgcggc cttgggtttt    1620
ggtgacgtcc aaccggtagg gattgctaac cggttaacga gtgatgttcg taaacagcgc    1680
gaggctaatc ggcagcgtga acgtgaggag gccattttgg cagactctac ggaagcgcca    1740
gcgaagaaga aatcgaaaga tcatcataat gaggatcagg agaagcagga tcggaagcgg    1800
caaaaggtct catcttctgg tggggtgatt attcaaggcg tcgacaactt actcgtacgt    1860
ctaagtcatt gctgttctcc aattccgggt gatgagattg ttggttatat tacgaagggg    1920
cgcggtgttt cggttcaccg tgttgattgt ccgaacgtta agagcgcaga agcaaatggt    1980
gaacggttga ttgatgttca gtgggagaat cccgagggtg accgaacgaa ctacaattct    2040
gatttggaaa ttcaaggtta taaccgtaat ggcatgctca acgatgtgtt gaaagttatc    2100
aataatcaca cgaaattttt gaccaatgtc aacggtaagg tcgatcacaa caagatggtc    2160
attattagtg tttcgttggg ggttcgcaac ttgaacatc tccaacgaat cattgacagt    2220
ctgaaaaatg ttcaggatct ttacgttgtc gaacggaaaa tgttttag                 2268
```

<210> SEQ ID NO 44
<211> LENGTH: 755
<212> TYPE: PRT
<213> ORGANISM: Lactobacillus plantarum

<400> SEQUENCE: 44

```
Met Pro Lys Gln Pro Thr Trp Thr Ala Gln Asp Val Leu Asp Met Val
1               5                   10                  15

Gln Lys Tyr Met Asn Ser Asp His Val Ala Leu Val Lys Arg Ala Cys
            20                  25                  30

Asp Phe Ala Thr Tyr Val His Lys Asp Gln Tyr Arg Gln Ser Gly Glu
        35                  40                  45

Pro Tyr Ile Met His Pro Ile Gln Val Ala Gly Ile Leu Ala Glu Leu
    50                  55                  60

Lys Met Asp Pro Glu Thr Val Ala Ser Gly Phe Leu His Asp Val Val
65                  70                  75                  80

Glu Asp Thr Gly Val Thr Leu Gly Asp Val Glu Glu Leu Phe Gly His
                85                  90                  95

Asp Val Ala Val Ile Val Asp Gly Val Thr Lys Leu Gly Lys Ile Arg
            100                 105                 110

Tyr Lys Ser Asn Lys Glu Gln Leu Ala Glu Asn His Arg Lys Leu Leu
        115                 120                 125

Leu Ala Met Ser Lys Asp Ile Arg Val Met Ile Val Lys Leu Ala Asp
    130                 135                 140

Arg Leu His Asn Met Arg Thr Leu Gln His Leu Arg Pro Asp Lys Gln
145                 150                 155                 160

Arg Arg Ile Ala Asn Glu Thr Leu Glu Ile Tyr Ala Pro Ile Ala Asp
                165                 170                 175

Arg Leu Gly Ile Ser Thr Ile Lys Trp Glu Leu Glu Asp Ile Ser Leu
            180                 185                 190

Arg Tyr Leu Asn Pro Gln Gln Tyr Tyr Arg Ile Val His Leu Met Asn
        195                 200                 205

Ser Arg Arg Glu Asp Arg Glu Lys Tyr Ile Glu Ile Ala Ile Gln Asp
    210                 215                 220
```

```
Ile Gln Lys Ala Leu His Asp Leu Glu Leu Pro Glu Ala Glu Ile Tyr
225                 230                 235                 240

Gly Arg Pro Lys His Ile Tyr Ser Ile Tyr Lys Lys Met Arg Asp Lys
            245                 250                 255

His Lys Gln Phe Ser Gln Leu Tyr Asp Leu Leu Ala Ile Arg Val Val
        260                 265                 270

Val Asp Ser Ile Lys Asp Cys Tyr Ala Val Leu Gly Ala Ile His Thr
    275                 280                 285

Gln Trp Lys Pro Met Pro Gly Arg Phe Lys Asp Tyr Ile Ala Met Pro
290                 295                 300

Lys Ala Asn Met Tyr Gln Ser Leu His Thr Thr Val Val Gly Pro Glu
305                 310                 315                 320

Gly Lys Pro Leu Glu Ile Gln Ile Arg Thr Phe Glu Met His Arg Val
            325                 330                 335

Ala Glu Tyr Gly Val Ala Ala His Trp Ala Tyr Lys Glu Gly Lys Arg
        340                 345                 350

Asp Glu Val Gln Glu Thr Gln Ser Gly Asn Lys Leu Asn Leu Val Lys
    355                 360                 365

Glu Ile Ile Glu Leu Gln Asp Glu Ser Lys Asp Ala Ala Asp Phe Met
370                 375                 380

Glu Gly Val Lys Gly Asp Leu Phe Ser Asp Arg Val Tyr Ala Phe Thr
385                 390                 395                 400

Pro Lys Gly Asp Val Thr Glu Leu Pro Lys Gly Ala Gly Pro Leu Asp
            405                 410                 415

Met Ala Tyr Ser Ile His Thr Glu Val Gly Asn His Thr Thr Gly Ala
        420                 425                 430

Lys Val Asn Gly Lys Ile Val Pro Leu Asp Tyr Gln Ile Lys Asn Gly
    435                 440                 445

Asp Ile Val Asp Ile Leu Thr Ser Thr Ser Thr Gly Pro Ser Arg
450                 455                 460

Asp Trp Gln Lys Leu Val Tyr Thr Arg Arg Ala Arg Asn Lys Ile Lys
465                 470                 475                 480

Gln Phe Phe Arg Asn Ala Asp Arg Glu Glu Asn Ile Ile Thr Gly Arg
            485                 490                 495

Asp Leu Leu Glu Lys Gln Leu Arg Asp Leu Glu Phe Asn Pro Lys Glu
        500                 505                 510

Ile Met Thr Lys Asp Lys Val Thr Ala Val Ala Gln Lys Met His Tyr
    515                 520                 525

Gly Ser Glu Asp Asp Leu Phe Ala Ala Leu Gly Phe Gly Asp Val Gln
530                 535                 540

Pro Val Gly Ile Ala Asn Arg Leu Thr Ser Asp Val Arg Lys Gln Arg
545                 550                 555                 560

Glu Ala Asn Arg Gln Arg Glu Arg Glu Ala Ile Leu Ala Asp Ser
            565                 570                 575

Thr Glu Ala Pro Ala Lys Lys Lys Ser Lys Asp His His Asn Glu Asp
        580                 585                 590

Gln Glu Lys Gln Asp Arg Lys Arg Gln Lys Val Ser Ser Ser Gly Gly
    595                 600                 605

Val Ile Ile Gln Gly Val Asp Asn Leu Leu Val Arg Leu Ser His Cys
610                 615                 620

Cys Ser Pro Ile Pro Gly Asp Glu Ile Val Gly Tyr Ile Thr Lys Gly
625                 630                 635                 640

Arg Gly Val Ser Val His Arg Val Asp Cys Pro Asn Val Lys Ser Ala
```

```
                    645                 650                 655
Glu Ala Asn Gly Glu Arg Leu Ile Asp Val Gln Trp Glu Asn Pro Glu
            660                 665                 670

Gly Asp Arg Thr Asn Tyr Asn Ser Asp Leu Glu Ile Gln Gly Tyr Asn
        675                 680                 685

Arg Asn Gly Met Leu Asn Asp Val Leu Lys Val Ile Asn Asn His Thr
    690                 695                 700

Lys Phe Leu Thr Asn Val Asn Gly Lys Val Asp His Asn Lys Met Val
705                 710                 715                 720

Ile Ile Ser Val Ser Leu Gly Val Arg Asn Leu Glu His Leu Gln Arg
                725                 730                 735

Ile Ile Asp Ser Leu Lys Asn Val Gln Asp Leu Tyr Val Val Glu Arg
            740                 745                 750

Lys Met Phe
        755

<210> SEQ ID NO 45
<211> LENGTH: 2202
<212> TYPE: DNA
<213> ORGANISM: Bacillus licheniformis

<400> SEQUENCE: 45
atggcgaacg aacaagtatt aaccgctgag caagtcattg agaaggcgaa aagttacctt     60
tccgatgaac atgttgcttt tataaaaaag gcttatcagt acgcggaaga cgcacatcgc    120
gaacaatacc gcaaatcggg cgagccgtat attatccatc cgatccaggt cgcgggaatc    180
ctcgtcgatt tagaaatgga ccccgccaca atagcgggag gatttctcca tgatgtggtg    240
gaagatacga gcgtaacgct tgaagattta aggaagcat tcaacgaaga gttgcgatg     300 cttgtcgacg gcgtcacgaa gcttgggaaa attaaatata atcacagga gaacagcag     360 gcagaaaatc atcggaaaat gttttgtggct atggctcagg acatccgcgt cattttgatc    420
aagctggcgg accgccttca caacatgaga accctgaagc atctgccgca ggaaaagcag    480
cgcagaattt caaatgagac gcttgaaata tttgctccgc tggctcatcg ccttgggatt    540
tcaaaaataa agtgggagct tgaggatacc gctttacggt atttaaatcc gcagcaatat    600
taccggatcg tcaatttgat gaagaaaaag cgggccgaaa gggaattgta cgtcgaagag    660
gtcgtaaacg aagtgaaaag ccgcgtcgaa gaggtcaata ttaaagcgga cttttccggc    720
cggccgaagc atatttacag catctacaga aaaatggcga tgcaaaacaa gcaattcaac    780
gaaatttacg acttgctcgc agtccggatc ctcgtcaaca gcatcaagga ctgctacgcg    840
gttttaggca tcattcatac gtgctggaag ccgatgccgg gcagatttaa agactatatc    900
gcaatgccga agccgaacat gtaccaatcg ctccacacca cggtcatcgg tccgaagggc    960
gatccgctgg aagtccagat caggacgttt gaaatgcatg aaattgcgga gtacggaatc   1020
gctgcccact gggcttacaa agaaggcaaa aatgccaatg aagattcaag ctttgataaa   1080
aagctttcct ggttccgcga aattttggaa tttcagaatg agtcgagcga tgccgaagaa   1140
tttatggaat ctcttaaaat cgatttgttt tcggacatgg tattcgtttt tacgccgaaa   1200
ggggacgtca tcgaattgcc gtcaggatcc gtgccgatcg acttttcgta ccgaatccat   1260
tcagaaatag gcaataaaac gatcgggcc aaagtaaacg gcaaaatggt cacccttgat   1320
tacaagctgc gcacagggga tatcgtagaa attctgacgt ccaagcattc gtacggtccg   1380
agtcaggact ggatcaacct tgcgcagaca tctcaagcga agcataaaat ccgtcagttc   1440
tttaaaaagc agcgcagaga ggaaaatgtc gaaaaaggca gagaactggt tgaaaaagaa   1500
```

-continued

```
attaaaaacc tggactttga agtgaaggac gtcttaacag ccgagaatct gcagaaggtc    1560
gccgacaaat tcaactttgc caatgaagaa gacatgtatg ccgctgtcgg ctataacggc    1620
attacagccg ctcaagttgc aaaccgcctt acggaaaaag aacggaagat cagagatcag    1680
gaagaacagg tgaaaagcgt tcaggacgta acgcctgaag tgaaacctta ccaagggaag    1740
aaacgcgaag cgggtgttcg cgtcaaaggc gttgacaacc ttttgatcag gctgtcaaaa    1800
tgctgcaacc ctgttccggg agatccgatc gtcggattca ttacaaaagg cagggcgta    1860 tccgtccatc gcgaggactg cccgaatgtt ttaacaaatg aagcgctcga ccggctcatt    1920
caagtagaat gggagcatga accgcagacc cagcggagaa agaatataa cgtcgaaatt    1980 gagattctcg ctatgaccg ccgcggtctt cttaatgaag ttctacaggc agttaatgag    2040
acaaaaacaa atatttcatc tgtttcaggt aaatcggacc gcaataaagt ggcgacgatc    2100
catatggcga tcttcattca aaatattaac catttgcata agtagttga acggattaag    2160 cagatcaaag atatttactc cgtgcgcagg gtgatgaatt ag                       2202
```

<210> SEQ ID NO 46
<211> LENGTH: 733
<212> TYPE: PRT
<213> ORGANISM: Bacillus licheniformis

<400> SEQUENCE: 46

```
Met Ala Asn Glu Gln Val Leu Thr Ala Glu Gln Val Ile Glu Lys Ala
1               5                   10                  15

Lys Ser Tyr Leu Ser Asp Glu His Val Ala Phe Ile Lys Lys Ala Tyr
            20                  25                  30

Gln Tyr Ala Glu Asp Ala His Arg Glu Gln Tyr Arg Lys Ser Gly Glu
        35                  40                  45

Pro Tyr Ile Ile His Pro Ile Gln Val Ala Gly Ile Leu Val Asp Leu
    50                  55                  60

Glu Met Asp Pro Ala Thr Ile Ala Gly Gly Phe Leu His Asp Val Val
65                  70                  75                  80

Glu Asp Thr Ser Val Thr Leu Glu Asp Leu Lys Glu Ala Phe Asn Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Glu Val Val Asn Glu
    210                 215                 220

Val Lys Ser Arg Val Glu Glu Val Asn Ile Lys Ala Asp Phe Ser Gly
225                 230                 235                 240

Arg Pro Lys His Ile Tyr Ser Ile Tyr Arg Lys Met Ala Met Gln Asn
                245                 250                 255
```

```
Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Gly
305                 310                 315                 320

Asp Pro Leu Glu Val Gln Ile Arg Thr Phe Glu Met His Glu Ile Ala
                325                 330                 335

Glu Tyr Gly Ile Ala Ala His Trp Ala Tyr Lys Glu Gly Lys Asn Ala
            340                 345                 350

Asn Glu Asp Ser Ser Phe Asp Lys Lys Leu Ser Trp Phe Arg Glu Ile
        355                 360                 365

Leu Glu Phe Gln Asn Glu Ser Ser Asp Ala Glu Glu Phe Met Glu Ser
    370                 375                 380

Leu Lys Ile Asp Leu Phe Ser Asp Met Val Phe Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
            420                 425                 430

Asn Gly Lys Met Val Thr Leu Asp Tyr Lys Leu Arg Thr Gly Asp Ile
        435                 440                 445

Val Glu Ile Leu Thr Ser Lys His Ser Tyr Gly Pro Ser Gln Asp Trp
    450                 455                 460

Ile Asn Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Val Lys Asp Val Leu
            500                 505                 510

Thr Ala Glu Asn Leu Gln Lys Val Ala Asp Lys Phe Asn Phe Ala Asn
        515                 520                 525

Glu Glu Asp Met Tyr Ala Ala Val Gly Tyr Asn Gly Ile Thr Ala Ala
530                 535                 540

Gln Val Ala Asn Arg Leu Thr Glu Lys Glu Arg Lys Ile Arg Asp Gln
545                 550                 555                 560

Glu Glu Gln Val Lys Ser Val Gln Asp Val Thr Pro Glu Val Lys Pro
                565                 570                 575

Tyr Gln Gly Lys Lys Arg Glu Ala Gly Val Arg Val Lys Gly Val Asp
            580                 585                 590

Asn Leu Leu Ile Arg Leu Ser Lys Cys Cys Asn Pro Val Pro Gly Asp
        595                 600                 605

Pro Ile Val Gly Phe Ile Thr Lys Gly Arg Gly Val Ser Val His Arg
    610                 615                 620

Glu Asp Cys Pro Asn Val Leu Thr Asn Glu Ala Leu Asp Arg Leu Ile
625                 630                 635                 640

Gln Val Glu Trp Glu His Glu Pro Gln Thr Gln Arg Arg Lys Glu Tyr
                645                 650                 655

Asn Val Glu Ile Glu Ile Leu Gly Tyr Asp Arg Arg Gly Leu Leu Asn
            660                 665                 670

Glu Val Leu Gln Ala Val Asn Glu Thr Lys Thr Asn Ile Ser Ser Val
```

```
            675                 680                 685
Ser Gly Lys Ser Asp Arg Asn Lys Val Ala Thr Ile His Met Ala Ile
            690                 695                 700

Phe Ile Gln Asn Ile Asn His Leu His Lys Val Val Glu Arg Ile Lys
705                 710                 715                 720

Gln Ile Lys Asp Ile Tyr Ser Val Arg Arg Val Met Asn
                725                 730

<210> SEQ ID NO 47
<211> LENGTH: 2205
<212> TYPE: DNA
<213> ORGANISM: Bacillus subtilis

<400> SEQUENCE: 47
atggcgaacg aacaagtatt gactgccgag caagttatag ataaagcacg cagctatcta      60
tctgatgagc atatcgcatt tgtcgaaaaa gcatatctgt acgctgaaga tgctcatcgc     120
gagcaatacc gcaaatcggg cgagccatat attattcatc cgattcaggt tgcgggggata    180 ctcgttgatc ttgaaatgga cccttccaca atcgcgggcg attttttgca cgatgtcgtg    240
gaagatacag atgtgacgct cgatgacctg aaagaagcat tttccgaaga gtggcaatg     300 cttgtagacg gcgtaacgaa actcggcaaa attaaatata atctcaaga ggaacagcag     360 gcggaaaatc atcgcaaaat gtttgtcgct atggctcaag atatcagggt catattgatc    420
aagctggcgg atcgtcttca caatatgcgg acactgaaac atctgcctca ggaaaaacag    480
cggagaatct ccaatgaaac gctggaaatt tttgctcctt tggcgcatcg tctcgggatt    540
tcaaaaatta gtgggaatt ggaagatacg gcgctccgtt atttgaaccc tcagcaatat    600
tacagaattg tcaacctcat gaagaagaaa cgtgcagaac gagagcttta tgtcgatgag    660
gttgtcaatg aagtgaagaa acgtgtcgaa gaagtaaata tcaaggctga cttctcggga    720
cgcccgaaac atatttacag catttatcga aaaatggtgc tgcaaaataa gcaattcaat    780
gaaatttacg atttgttggc tgtccgtatt cttgtgaata gcataaagga ctgctacgcg    840
gtgcttggca tcattcacac atgctggaaa ccgatgccag gcagattcaa agattatatc    900
gcaatgccga agccgaatat gtatcaatcg cttcatacaa cggttattgg gcctaaagcg    960
gatccgcttg aagtgcagat ccgcaccttt gaaatgcatg aaatagcgga atacggggtt   1020
gcggctcact gggcttataa agaagggaaa gcagccaatg aaggtgcaac ctttgagaaa   1080
aagctttctt ggttccgtga aatttttagaa tttcaaaatg aatcgacaga tgcagaagaa   1140
tttatggaat cgctcaaaat tgatttgttc tctgacatgg tgtatgtctt tacgccaaaa   1200
ggagatgtaa tcgagcttcc gtccggttct gttccgattg acttttctta ccggattcac   1260
tctgaaatcg gcaataaaac aatcggtgcc aaagtaaacg gaaaaatggt tacgcttgac   1320
cataagcttc ggacaggtga tatcgttgaa attctcacct ctaagcattc ctacggtccg   1380
agccaggatt gggtgaagct tgcccaaaca tcccaagcga agcataaaat ccgtcaattc   1440
tttaagaaac agcggcgtga agaaaatgtc gaaaaaggcc gtgagctggt cgaaaaagaa   1500
attaaaaact tggattttga attgaaggat gttttaacgc cggagaatat tcaaaaggtt   1560
gctgacaaat ttaatttctc aaatgaagag gatatgtacg cggcggtcgg ttacaacggc   1620
atcacagctc tgcaggtggc gaaccgccta acagaaaaag agaaagca gcgcgaccag     1680 gaagaacagg aaaagatcgt tcaggaagtc actggggaac taagccata cccgcaagga   1740 agaaaacggg aagctggcgt tcgtgtcaag ggcattgaca acctcctgt ccgtttatca   1800 aaatgctgca atcctgtgcc aggtgatgat attgtcggct ttatcacaaa aggcagaggg   1860
```

-continued

```
gtttcggtcc atcgcgaaga ctgtccgaat gtcaaaacga atgaagccca agagcggctg   1920
atcccggtag agtgggaaca tgagtcacaa gttcaaaagc gcaaggaata caatgttgag   1980
atagagattc ttgggtatga ccgccgcgga ttgctgaacg aggtactcca ggcagtgaat   2040
gaaacgaaaa ccaatatttc atctgtctct ggcaaatcgg atcgcaataa agtggcaacc   2100
atccatatgg cgatttttat ccagaatatc aatcacttgc ataaagtcgt cgagcgtatt   2160
aaacagatta gagatatcta ttctgtgcgc cgcgtcatga actaa                   2205
```

<210> SEQ ID NO 48
<211> LENGTH: 734
<212> TYPE: PRT
<213> ORGANISM: Bacillus subtilis

<400> SEQUENCE: 48

```
Met Ala Asn Glu Gln Val Leu Thr Ala Glu Gln Val Ile Asp Lys Ala
1               5                   10                  15

Arg Ser Tyr Leu Ser Asp Glu His Ile Ala Phe Val Glu Lys Ala Tyr
                20                  25                  30

Leu Tyr Ala Glu Asp Ala His Arg Glu Gln Tyr Arg Lys Ser Gly Glu
            35                  40                  45

Pro Tyr Ile Ile His Pro Ile Gln Val Ala Gly Ile Leu Val Asp Leu
        50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Asp Glu Val Val Asn Glu
    210                 215                 220

Val Lys Lys Arg Val Glu Glu Val Asn Ile Lys Ala Asp Phe Ser Gly
225                 230                 235                 240

Arg Pro Lys His Ile Tyr Ser Ile Tyr Arg Lys Met Val Leu Gln Asn
                245                 250                 255

Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Ala
305                 310                 315                 320
```

```
Asp Pro Leu Glu Val Gln Ile Arg Thr Phe Glu Met His Glu Ile Ala
            325                 330                 335

Glu Tyr Gly Val Ala Ala His Trp Ala Tyr Lys Glu Gly Lys Ala Ala
            340                 345                 350

Asn Glu Gly Ala Thr Phe Glu Lys Lys Leu Ser Trp Phe Arg Glu Ile
            355                 360                 365

Leu Glu Phe Gln Asn Glu Ser Thr Asp Ala Glu Glu Phe Met Glu Ser
370                 375                 380

Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
                420                 425                 430

Asn Gly Lys Met Val Thr Leu Asp His Lys Leu Arg Thr Gly Asp Ile
            435                 440                 445

Val Glu Ile Leu Thr Ser Lys His Ser Tyr Gly Pro Ser Gln Asp Trp
450                 455                 460

Val Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Leu Lys Asp Val Leu
            500                 505                 510

Thr Pro Glu Asn Ile Gln Lys Val Ala Asp Lys Phe Asn Phe Ser Asn
            515                 520                 525

Glu Glu Asp Met Tyr Ala Ala Val Gly Tyr Asn Gly Ile Thr Ala Leu
530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Glu Val Thr Gly Glu Pro Lys Pro
                565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
            595                 600                 605

Asp Asp Ile Val Gly Phe Ile Thr Lys Gly Arg Gly Val Ser Val His
610                 615                 620

Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
                645                 650                 655

Tyr Asn Val Glu Ile Glu Ile Leu Gly Tyr Asp Arg Arg Gly Leu Leu
            660                 665                 670

Asn Glu Val Leu Gln Ala Val Asn Glu Thr Lys Thr Asn Ile Ser Ser
            675                 680                 685

Val Ser Gly Lys Ser Asp Arg Asn Lys Val Ala Thr Ile His Met Ala
690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730
```

<210> SEQ ID NO 49
<211> LENGTH: 2241
<212> TYPE: DNA
<213> ORGANISM: Pseudomonas putida

<400> SEQUENCE: 49

```
atggtacagg tgagagtgca ccagccggtc aacactgacg gcagtatcaa tctcgaagca      60
tggttggacc atgtggtaag cgtcgattcg gcactggatc gcgcagcgct gaaagaagcc     120
tgcgagtttg ctcttgaggt agagaaaaag gcaacccgg ccaagcattc ctgggcggat      180
ggtacgtcca gcttccaggc aggcctggaa atcgccgaaa ttctggctga cctcaagctc     240
gaccaggact ccctggtggc tgcggtcatc taccgctcgg tgcgcgaggg caaggtcacc     300
ctcgccgagg tcagccagcg gtttggcccg gtggtgtcca agctgatcga cggtgtgctg     360
cgcatggccg ccatcagtgc cagcctcagc ccacgacagt cgctggtgct gggctcgcag     420
gcgcaggtag agaacctgcg caagatgctg gtggccatgg tcgacgacgt gcgcgtggcg     480
ctgatcaagc tggccgaacg cacgtgcgca atccgggcgg tcaagtccgc cgatgacgag     540
aaacgcctgc gtgtcgcgcg tgaagtgttc gacatctacg cgccgctcgc gcaccgcctg     600
ggtatcggtc acatcaagtg ggagctggaa gacctgtcct tccgctacct ggagcccgac     660
cagtacaagc agatcgccaa gctgttgcat gagcggcggc tggaccgcga gcgcttcatc     720
agcgacgtga tgaaccagct gcagaacgag ttgctcgcca ctggcgtgaa ggccgacatc     780
agcggccggg cgaaacatat ctattcgatc tggcgcaaga tgcagcgcaa aggcctggag     840
ttcagccaga tctacgacgt gcgtgcggtg cgcgtgctgg tgccggaaat ccgcgactgc     900
tacaccgcgc tgggcatcgt gcacaccttg tggcggcata ttcccaagga gttcgacgac     960
tacatcgcca cccccaagga gaacggctac cgctcgttgc acactgcggt aatcggcccc    1020
gagggcaagg tgctggaggt gcagatccgt acccacggca tgcacgaaga ggccgaactt    1080
ggcgtatgcg cccactggcg ctacaagggc accgacgtca agcccagctc caaccactac    1140
gaagaaaaga tttcctggtt gcgtcaggtg ctggagtggc acgaagagct gggcgacatc    1200
ggtggcctgg ccgagcagtt gcgggtcgac atcgagcctg accgggttta tgtgttcacc    1260
cccgacggcc acgccatcga cctgcccaaa ggcgccacgc cattggactt cgcctaccgc    1320
gtgcacaccg agatcggcca caactgccgc ggcgcgaaga tcaacggccg tatcgtgccg    1380
ctgaactaca gcctgcagac tggcgagcag gtggagatca tcaccagcaa gcacggcaac    1440
cccagccgtg actggttgaa ctccaacctg ggctacgtca ccacctcgcg ggcgcgggcc    1500
aagatcgtcc actggttcaa attgcaggcc cgcgaccaga acgttgctgc cggcaagacc    1560
ttgcttgagc gcgagctcag tcgtctgggc ctgccgcagg ttgatttcga gcgcctggcc    1620
gagaagacca acgtcaagac cgccgaggac atgtttgcct cgctcggtgc tggcgacctg    1680
cgcctggctc atctggtcaa cgctgcccag cagttgctgg agcctgagcg tatcgagcag    1740
atcgagctgg tgccgcgcaa gcctaccggg ccgcgtaccg gcaagcgtgg cgacattcag    1800
atccagggtg tcggcaacct gctgacacag atggccggct gctgccagcc gctaccgggc    1860
gatgccattg tcggttacat caccccaggc cggggcgtga gcattcatcg ccaggactgc    1920
gcctcggtac tgcagctggc gggcaaagag ccagagcgca tgatccaggt gagctggggg    1980
ccgatcccgg tgcagaccta cccggtcgac atcgtcatcc gcgcctacga ccgcccgggc    2040
ctgctgcgcg atgtgtcgca ggtgctgctg aacgagaaga tcaacgtgct ggcggtgaac    2100
acccgttcga acaaggaaga caacaccgcg ctgatgtcgc tgaccatcga gattccaggc    2160
ctggacgcgc tggggcgcct gctggggcgg atctcgcagt tgccgaacat catcgagacg    2220
```
cggcgtaatc gtacccctg a                                              2241

<210> SEQ ID NO 50
<211> LENGTH: 746
<212> TYPE: PRT
<213> ORGANISM: Pseudomonas putida

<400> SEQUENCE: 50

Met Val Gln Val Arg Val His Gln Pro Val Asn Thr Asp Gly Ser Ile
1               5                   10                  15

Asn Leu Glu Ala Trp Leu Asp His Val Ser Val Asp Ser Ala Leu
            20                  25                  30

Asp Arg Ala Ala Leu Lys Glu Ala Cys Glu Phe Ala Leu Glu Val Glu
        35                  40                  45

Lys Lys Gly Asn Pro Ala Lys His Ser Trp Ala Asp Gly Thr Ser Ser
    50                  55                  60

Phe Gln Ala Gly Leu Glu Ile Ala Glu Ile Leu Ala Asp Leu Lys Leu
65                  70                  75                  80

Asp Gln Asp Ser Leu Val Ala Ala Val Ile Tyr Arg Ser Val Arg Glu
                85                  90                  95

Gly Lys Val Thr Leu Ala Glu Val Ser Gln Arg Phe Gly Pro Val Val
            100                 105                 110

Ser Lys Leu Ile Asp Gly Val Leu Arg Met Ala Ala Ile Ser Ala Ser
        115                 120                 125

Leu Ser Pro Arg Gln Ser Leu Val Leu Gly Ser Gln Ala Gln Val Glu
    130                 135                 140

Asn Leu Arg Lys Met Leu Val Ala Met Val Asp Val Arg Val Ala
145                 150                 155                 160

Leu Ile Lys Leu Ala Glu Arg Thr Cys Ala Ile Arg Ala Val Lys Ser
                165                 170                 175

Ala Asp Asp Glu Lys Arg Leu Arg Val Ala Arg Glu Val Phe Asp Ile
            180                 185                 190

Tyr Ala Pro Leu Ala His Arg Leu Gly Ile Gly His Ile Lys Trp Glu
        195                 200                 205

Leu Glu Asp Leu Ser Phe Arg Tyr Leu Glu Pro Asp Gln Tyr Lys Gln
    210                 215                 220

Ile Ala Lys Leu Leu His Glu Arg Arg Leu Asp Arg Glu Arg Phe Ile
225                 230                 235                 240

Ser Asp Val Met Asn Gln Leu Gln Asn Glu Leu Leu Ala Thr Gly Val
                245                 250                 255

Lys Ala Asp Ile Ser Gly Arg Ala Lys His Ile Tyr Ser Ile Trp Arg
            260                 265                 270

Lys Met Gln Arg Lys Gly Leu Glu Phe Ser Gln Ile Tyr Asp Val Arg
        275                 280                 285

Ala Val Arg Val Leu Val Pro Glu Ile Arg Asp Cys Tyr Thr Ala Leu
    290                 295                 300

Gly Ile Val His Thr Leu Trp Arg His Ile Pro Lys Glu Phe Asp Asp
305                 310                 315                 320

Tyr Ile Ala Asn Pro Lys Glu Asn Gly Tyr Arg Ser Leu His Thr Ala
                325                 330                 335

Val Ile Gly Pro Glu Gly Lys Val Leu Glu Val Gln Ile Arg Thr His
            340                 345                 350

Gly Met His Glu Glu Ala Glu Leu Gly Val Cys Ala His Trp Arg Tyr
        355                 360                 365

```
Lys Gly Thr Asp Val Lys Pro Ser Ser Asn His Tyr Glu Glu Lys Ile
            370                 375                 380

Ser Trp Leu Arg Gln Val Leu Glu Trp His Glu Leu Gly Asp Ile
385                 390                 395                 400

Gly Gly Leu Ala Glu Gln Leu Arg Val Asp Ile Glu Pro Asp Arg Val
                405                 410                 415

Tyr Val Phe Thr Pro Asp Gly His Ala Ile Asp Leu Pro Lys Gly Ala
            420                 425                 430

Thr Pro Leu Asp Phe Ala Tyr Arg Val His Thr Glu Ile Gly His Asn
                435                 440                 445

Cys Arg Gly Ala Lys Ile Asn Gly Arg Ile Val Pro Leu Asn Tyr Ser
450                 455                 460

Leu Gln Thr Gly Glu Gln Val Glu Ile Ile Thr Ser Lys His Gly Asn
465                 470                 475                 480

Pro Ser Arg Asp Trp Leu Asn Ser Asn Leu Gly Tyr Val Thr Thr Ser
                485                 490                 495

Arg Ala Arg Ala Lys Ile Val His Trp Phe Lys Leu Gln Ala Arg Asp
                500                 505                 510

Gln Asn Val Ala Ala Gly Lys Thr Leu Leu Glu Arg Glu Leu Ser Arg
            515                 520                 525

Leu Gly Leu Pro Gln Val Asp Phe Glu Arg Leu Ala Glu Lys Thr Asn
530                 535                 540

Val Lys Thr Ala Glu Asp Met Phe Ala Ser Leu Gly Ala Gly Asp Leu
545                 550                 555                 560

Arg Leu Ala His Leu Val Asn Ala Ala Gln Gln Leu Leu Glu Pro Glu
                565                 570                 575

Arg Ile Glu Gln Ile Glu Leu Val Pro Arg Lys Pro Thr Gly Pro Arg
            580                 585                 590

Thr Gly Lys Arg Gly Asp Ile Gln Ile Gln Gly Val Gly Asn Leu Leu
        595                 600                 605

Thr Gln Met Ala Gly Cys Cys Gln Pro Leu Pro Gly Asp Ala Ile Val
        610                 615                 620

Gly Tyr Ile Thr Gln Gly Arg Gly Val Ser Ile His Arg Gln Asp Cys
625                 630                 635                 640

Ala Ser Val Leu Gln Leu Ala Gly Lys Glu Pro Glu Arg Met Ile Gln
                645                 650                 655

Val Ser Trp Gly Pro Ile Pro Val Gln Thr Tyr Pro Val Asp Ile Val
                660                 665                 670

Ile Arg Ala Tyr Asp Arg Pro Gly Leu Leu Arg Asp Val Ser Gln Val
                675                 680                 685

Leu Leu Asn Glu Lys Ile Asn Val Leu Ala Val Asn Thr Arg Ser Asn
690                 695                 700

Lys Glu Asp Asn Thr Ala Leu Met Ser Leu Thr Ile Glu Ile Pro Gly
705                 710                 715                 720

Leu Asp Ala Leu Gly Arg Leu Leu Gly Arg Ile Ser Gln Leu Pro Asn
                725                 730                 735

Ile Ile Glu Thr Arg Arg Asn Arg Thr Pro
            740                 745

<210> SEQ ID NO 51
<211> LENGTH: 2109
<212> TYPE: DNA
<213> ORGANISM: Pseudomonas putida

<400> SEQUENCE: 51
```

```
atgccgggta tagaagcctt ggccgaacgg ctttcgacct atcttggccc cgaacaggtc    60
aacctggttc ggcgtgccta tttctacgcc gaacaggccc acgatgggca acgccgccgc   120
agtggcgagc cctacgtgac ccacccgctg gccgtggcca gcatcctcgc cgacatgcac   180
atggaccatc agagcctgat ggcggccatg ctgcacgatg tgatcgaaga caccggcatc   240
gccaaggaag ccctcagcca gcagtttggc gagaccgtgg ccgaattggt cgatggggtc   300
agcaagctga cccagatgaa tttcgagacc aaggccgagg cgcaggcgga aaacttccag   360
aagatggcca tggccatggc ccgcgatatc cgcgtgatcc tggtcaagct ggccgaccgc   420
ctgcacaaca tgcgcaccct ggaagtgctg tctggcgaaa agcgccggcg cattgccaag   480
gaaaccctcg agatctacgc ccccatcgca aaccgcctgg ggatgcacac cgtgcgcgta   540
gagttcgaag accttggctt caaggccatg cacccgatgc gctcgtcgct gattcatcgt   600
gcagtgaaga gcgcgcgcgg caaccgcaaa gagatcgtcg ccaagatcga gcactcgctg   660
gccaactgcc tggccgccga cggcatcgag ggcgaagtca gcggtcggca gaaacacctc   720
tatggcatct acaagaagat gcgcggcaag cgccgtgcct tcaacgagat catggacgtg   780
tatgccttcc gcatcatcgt cgacaaggtt gacacctgtt accgcgtgct cggcgccgta   840
cacaacctgt acagccgct gcccggacgc ttcaaggatt acatcgcgat ccccaaggcc   900
aacggctacc agtcgttgca caccaccctg ttcggcatgc acggcgtgcc catcgaaatc   960
cagattcgca cccgcgaaat ggaagagatg gccaacaacg gcatcgccgc gcactggctg  1020
tacaagtcaa cgacgacga gcagcccaag ggcagccacg cgcgcgcccg ccagtgggtc  1080
aagggtatcc ttgaactgca gcaacgtgcc ggcaactccc tggaattcat cgagagcgtg  1140
aagatcgacc tgttcccgga cgaggtctac gtgttcacgc ccaaaggccg gatcatggag  1200
ttgcccaaag gctccacggc cgtcgacttc gcctacgcgg tccacaccga cgtcggcaac  1260
agttgcatcg cttgccgcat caaccgccgc ctggcgccgc tgtccgaacc gctacaaagc  1320
ggctcgacag tggaaatcgt cagcgccccg ggcgctcggc aaacccggc atggctcaac  1380
tttgtggtct cgggcaaggc acgcacgaat atccgccacg cgctcaagca acagcgccgc  1440
tcggagtcca tcagcctggg cgagcgcctg ctgaacaagg tactcactgg cttcgacagc  1500
agcctggaga aaatccccca ggaacgcatc cagtctattc tcgccgagta ccgcctggag  1560
ctcatagaag acctgctcga agacatcggc ctgggcaacc gcatggccta cgtggtcgcg  1620
cgccgcctgc tgtcggccga aggcgaacag ctgccggcgc cagaaggccc actggcgatc  1680
cgcggcaccg aaggcctggt gctcagctac gccaagtgct gcacgccgat cccgggtgac  1740
ccgattgtcg gccacctgtc ggccggcaag ggcatggtcg tgcacctgga aactgccgc  1800
aacatcagtg aaatccgcca caaccccgaa agtgcgtgc aactctcctg gccaaggac  1860
atcactggcg agttcaatgt cgaactgcgt gtcgaactgg aacaccagcg cgggctgatc  1920
gccctgctgg ccagcagcgt caacgccgcc gacggcaaca ttgagaagat cagcatggac  1980
gaacgcgacg gccgtatcag cgtggtccaa ctggtggtca gcgtgcacga ccgcgtgcac  2040
ctggcgcgtg tgatcaagaa gctgcgtacc ctgaccggtg tggtccgcat cacccgcatg  2100
cgtacgtag                                                          2109
```

<210> SEQ ID NO 52
<211> LENGTH: 702
<212> TYPE: PRT
<213> ORGANISM: Pseudomonas putida

<400> SEQUENCE: 52

```
Met Pro Gly Ile Glu Ala Leu Ala Glu Arg Leu Ser Thr Tyr Leu Gly
1               5                   10                  15

Pro Glu Gln Val Asn Leu Val Arg Arg Ala Tyr Phe Tyr Ala Glu Gln
            20                  25                  30

Ala His Asp Gly Gln Arg Arg Ser Gly Pro Tyr Val Thr His
        35                  40                  45

Pro Leu Ala Val Ala Ser Ile Leu Ala Asp Met His Met Asp His Gln
50                  55                  60

Ser Leu Met Ala Ala Met Leu His Asp Val Ile Glu Asp Thr Gly Ile
65                  70                  75                  80

Ala Lys Glu Ala Leu Ser Gln Gln Phe Gly Thr Val Ala Glu Leu
                85                  90                  95

Val Asp Gly Val Ser Lys Leu Thr Gln Met Asn Phe Glu Thr Lys Ala
            100                 105                 110

Glu Ala Gln Ala Glu Asn Phe Gln Lys Met Ala Met Ala Met Ala Arg
            115                 120                 125

Asp Ile Arg Val Ile Leu Val Lys Leu Ala Asp Arg Leu His Asn Met
        130                 135                 140

Arg Thr Leu Glu Val Leu Ser Gly Glu Lys Arg Arg Ile Ala Lys
145                 150                 155                 160

Glu Thr Leu Glu Ile Tyr Ala Pro Ile Ala Asn Arg Leu Gly Met His
                165                 170                 175

Thr Val Arg Val Glu Phe Glu Asp Leu Gly Phe Lys Ala Met His Pro
            180                 185                 190

Met Arg Ser Ser Leu Ile His Arg Ala Val Lys Ser Ala Arg Gly Asn
        195                 200                 205

Arg Lys Glu Ile Val Ala Lys Ile Glu His Ser Leu Ala Asn Cys Leu
210                 215                 220

Ala Ala Asp Gly Ile Glu Gly Glu Val Ser Gly Arg Gln Lys His Leu
225                 230                 235                 240

Tyr Gly Ile Tyr Lys Lys Met Arg Gly Lys Arg Ala Phe Asn Glu
                245                 250                 255

Ile Met Asp Val Tyr Ala Phe Arg Ile Ile Val Asp Lys Val Asp Thr
            260                 265                 270

Cys Tyr Arg Val Leu Gly Ala Val His Asn Leu Tyr Lys Pro Leu Pro
        275                 280                 285

Gly Arg Phe Lys Asp Tyr Ile Ala Ile Pro Lys Ala Asn Gly Tyr Gln
290                 295                 300

Ser Leu His Thr Thr Leu Phe Gly Met His Gly Val Pro Ile Glu Ile
305                 310                 315                 320

Gln Ile Arg Thr Arg Glu Met Glu Glu Met Ala Asn Asn Gly Ile Ala
                325                 330                 335

Ala His Trp Leu Tyr Lys Ser Asn Asp Asp Glu Gln Pro Lys Gly Ser
            340                 345                 350

His Ala Arg Ala Arg Gln Trp Val Lys Gly Ile Leu Glu Leu Gln Gln
        355                 360                 365

Arg Ala Gly Asn Ser Leu Glu Phe Ile Glu Ser Val Lys Ile Asp Leu
370                 375                 380

Phe Pro Asp Glu Val Tyr Val Phe Thr Pro Lys Gly Arg Ile Met Glu
385                 390                 395                 400

Leu Pro Lys Gly Ser Thr Ala Val Asp Phe Ala Tyr Ala Val His Thr
                405                 410                 415

Asp Val Gly Asn Ser Cys Ile Ala Cys Arg Ile Asn Arg Arg Leu Ala
            420                 425                 430
```

```
Pro Leu Ser Glu Pro Leu Gln Ser Gly Ser Thr Val Glu Ile Val Ser
        435                 440                 445

Ala Pro Gly Ala Arg Pro Asn Pro Ala Trp Leu Asn Phe Val Val Ser
    450                 455                 460

Gly Lys Ala Arg Thr Asn Ile Arg His Ala Leu Lys Gln Gln Arg Arg
465                 470                 475                 480

Ser Glu Ser Ile Ser Leu Gly Glu Arg Leu Leu Asn Lys Val Leu Thr
                485                 490                 495

Gly Phe Asp Ser Ser Leu Glu Lys Ile Pro Gln Glu Arg Ile Gln Ser
            500                 505                 510

Ile Leu Ala Glu Tyr Arg Leu Glu Leu Ile Glu Asp Leu Leu Glu Asp
        515                 520                 525

Ile Gly Leu Gly Asn Arg Met Ala Tyr Val Val Ala Arg Arg Leu Leu
    530                 535                 540

Ser Ala Glu Gly Glu Gln Leu Pro Ala Pro Glu Gly Pro Leu Ala Ile
545                 550                 555                 560

Arg Gly Thr Glu Gly Leu Val Leu Ser Tyr Ala Lys Cys Cys Thr Pro
                565                 570                 575

Ile Pro Gly Asp Pro Ile Val Gly His Leu Ser Ala Gly Lys Gly Met
            580                 585                 590

Val Val His Leu Glu Asn Cys Arg Asn Ile Ser Glu Ile Arg His Asn
        595                 600                 605

Pro Glu Lys Cys Val Gln Leu Ser Trp Ala Lys Asp Ile Thr Gly Glu
    610                 615                 620

Phe Asn Val Glu Leu Arg Val Glu Leu Glu His Gln Arg Gly Leu Ile
625                 630                 635                 640

Ala Leu Leu Ala Ser Ser Val Asn Ala Ala Asp Gly Asn Ile Glu Lys
                645                 650                 655

Ile Ser Met Asp Glu Arg Asp Gly Arg Ile Ser Val Val Gln Leu Val
            660                 665                 670

Val Ser Val His Asp Arg Val His Leu Ala Arg Val Ile Lys Lys Leu
        675                 680                 685

Arg Thr Leu Thr Gly Val Val Arg Ile Thr Arg Met Arg Thr
    690                 695                 700

<210> SEQ ID NO 53
<211> LENGTH: 2157
<212> TYPE: DNA
<213> ORGANISM: Enterococcus faecium

<400> SEQUENCE: 53
atgggtcccg aacatgtagc atttgttgag aaagcatgcg aatacgcgac tgctgcacat      60
gacggacagt ttagaaaatc aggcgaaccc tacattattc atcctatcca agtcgcaggt     120
atattagcag atttaaaaat ggatccccat acagtggcta caggcttctt acatgatgtt     180
gttgaagata cagaaatcac tttagaagat ctgagagaag aatttggcga tgacgttgct     240
atgttagtgg acggcgtaac caaattaggg aaaataaaat ataaatccca cgaagagcag     300
ctagcagaaa accaccgaaa gatgctgcta gcaatggctc aagatttacg agttatcatg     360
gtcaaattag ctgatagact acataacatg cgtacgttga agcacctgcg agaagataag     420
caaagaagga tcgctcagga aactttagaa atctatgcgc ctcttgcaca tcgtctaggg     480
atcagccgga tcaatgggaa attagaagat acagcacttc gttatctaaa tccaaaacag     540
tattaccgta tcgtccactt gatgcagacg aagagagaag aacgtgaaaa atacgtaagt     600
```

```
ggtactgttg aagatattcg aatagcgaca gaagagctgg ggattttttgc agaaatctat    660
ggacggccaa aacacattta ttcaatctat cgtaaaatga aagatcagaa aaagcagttc    720
aacgaaattt atgacttgct agctattcga gtgatcgtag attcaatcaa ggattgttat    780
gctgtattag gagcaatcca cacaaaatgg aaaccaatgc ccggcagatt taaggattat    840
attgccatgc caaaagctaa tatgtaccaa tctttgcata ctaccgtgat cggtccggca    900
ggaaatccgg tagaaattca aatccgaaca caggaaatgc atgaaatcgc tgaattcggg    960
gttgctgcac actgggccta taagaaggaa aaaatgaaa aagtagaacc agatggtatg   1020
acgaaacaat taagctggtt ccatgagata ctcgaacttc aagacgaaag ctatgatgct   1080
tctgaattta tggaaggcgt aaaaggagat atctttagtg ataaagtcta cgtcttcaca   1140
ccaaaaggag acgttactga gttaccaaaa ggatccggac cattggactt tgcatacagt   1200
atccatacag atatcggtaa caaaaccact ggtgcaaaag taaatggcaa aatggtgcag   1260
cttgattaca aattgaaaaa cggagatatc attgagatca tgacttctcc aaattcattt   1320
ggcccaagtc gcgactggtt gaaattagtt gctactagca aagcaagaaa taagatcaaa   1380
cgtttcttca aagcccaaga tcgagaagaa aatgtgatca aaggccacga atccgtggtc   1440
aaatgtatta cagatctagg atttacgcct aaagatattt tgacgaagaa caaactgcaa   1500
gaagcactcg atcgttttaa ttatcaaaca gaagatgatc tctatgcagc tgtagggtat   1560
ggagaagtta gccccttgac gatggccaat cgtctgactg aaaaagaacg taaagaacaa   1620
aaaatcgagc agcaaaagca agaagcagaa gaaatcatga atcagccgaa aaaagaacct   1680
gacaaaatga agtacgtca tgaaggtggc gttgtcattc aaggggtaga aaacttacta   1740
attcgtatca gtcgctgctg taatccgatt cctggtgatg atatcgttgg ttatatcact   1800
aaaggcagag ggatatccat tcatcgtcga gattgtccga atgttcagcc tgacaaacca   1860
aatgtagcag aacgtttgat tgaagtcgaa tgggaagata catcgaatac acgaaaagag   1920
tatgatgcag atttggaaat ttacggctat aatcgttcag gcttattgaa tgatgtactt   1980
caaacagtca atgcgctaac gaaaaatctc aacagcgttg aagcacggac gaataaagat   2040
aaaatggcga cgatccattt gacggttggt atccagaatt tatcccacct aaagagtatc   2100
gtggataaaa tcaaagcagt acctgatgtc tacagtgtac gccggacgaa tggatag     2157
```

<210> SEQ ID NO 54
<211> LENGTH: 718
<212> TYPE: PRT
<213> ORGANISM: Enterococcus faecium

<400> SEQUENCE: 54

```
Met Gly Pro Glu His Val Ala Phe Val Glu Lys Ala Cys Glu Tyr Ala
1               5                   10                  15

Thr Ala His Asp Gly Gln Phe Arg Lys Ser Gly Glu Pro Tyr Ile
            20                  25                  30

Ile His Pro Ile Gln Val Ala Gly Ile Leu Ala Asp Leu Lys Met Asp
        35                  40                  45

Pro His Thr Val Ala Thr Gly Phe Leu His Asp Val Val Glu Asp Thr
    50                  55                  60

Glu Ile Thr Leu Glu Asp Leu Arg Glu Glu Phe Gly Asp Asp Val Ala
65                  70                  75                  80

Met Leu Val Asp Gly Val Thr Lys Leu Gly Lys Ile Lys Tyr Lys Ser
                85                  90                  95

His Glu Glu Gln Leu Ala Glu Asn His Arg Lys Met Leu Leu Ala Met
            100                 105                 110
```

```
Ala Gln Asp Leu Arg Val Ile Met Val Lys Leu Ala Asp Arg Leu His
        115                 120                 125

Asn Met Arg Thr Leu Lys His Leu Arg Glu Asp Lys Gln Arg Arg Ile
130                 135                 140

Ala Gln Glu Thr Leu Glu Ile Tyr Ala Pro Leu Ala His Arg Leu Gly
145                 150                 155                 160

Ile Ser Arg Ile Lys Trp Glu Leu Glu Asp Thr Ala Leu Arg Tyr Leu
                165                 170                 175

Asn Pro Lys Gln Tyr Tyr Arg Ile Val His Leu Met Gln Thr Lys Arg
            180                 185                 190

Glu Glu Arg Glu Lys Tyr Val Ser Gly Thr Val Glu Asp Ile Arg Ile
        195                 200                 205

Ala Thr Glu Glu Leu Gly Ile Phe Ala Glu Ile Tyr Gly Arg Pro Lys
210                 215                 220

His Ile Tyr Ser Ile Tyr Arg Lys Met Lys Asp Gln Lys Lys Gln Phe
225                 230                 235                 240

Asn Glu Ile Tyr Asp Leu Leu Ala Ile Arg Val Ile Val Asp Ser Ile
                245                 250                 255

Lys Asp Cys Tyr Ala Val Leu Gly Ala Ile His Thr Lys Trp Lys Pro
            260                 265                 270

Met Pro Gly Arg Phe Lys Asp Tyr Ile Ala Met Pro Lys Ala Asn Met
        275                 280                 285

Tyr Gln Ser Leu His Thr Thr Val Ile Gly Pro Ala Gly Asn Pro Val
290                 295                 300

Glu Ile Gln Ile Arg Thr Gln Glu Met His Glu Ile Ala Glu Phe Gly
305                 310                 315                 320

Val Ala Ala His Trp Ala Tyr Lys Glu Gly Lys Asn Glu Lys Val Glu
                325                 330                 335

Pro Asp Gly Met Thr Lys Gln Leu Ser Trp Phe His Glu Ile Leu Glu
            340                 345                 350

Leu Gln Asp Glu Ser Tyr Asp Ala Ser Glu Phe Met Glu Gly Val Lys
        355                 360                 365

Gly Asp Ile Phe Ser Asp Lys Val Tyr Val Phe Thr Pro Lys Gly Asp
370                 375                 380

Val Thr Glu Leu Pro Lys Gly Ser Gly Pro Leu Asp Phe Ala Tyr Ser
385                 390                 395                 400

Ile His Thr Asp Ile Gly Asn Lys Thr Gly Ala Lys Val Asn Gly
                405                 410                 415

Lys Met Val Gln Leu Asp Tyr Lys Leu Lys Asn Gly Asp Ile Ile Glu
            420                 425                 430

Ile Met Thr Ser Pro Asn Ser Phe Gly Pro Ser Arg Asp Trp Leu Lys
        435                 440                 445

Leu Val Ala Thr Ser Lys Ala Arg Asn Lys Ile Lys Arg Phe Phe Lys
450                 455                 460

Ala Gln Asp Arg Glu Glu Asn Val Ile Lys Gly His Glu Ser Val Val
465                 470                 475                 480

Lys Cys Ile Thr Asp Leu Gly Phe Thr Pro Lys Asp Ile Leu Thr Lys
                485                 490                 495

Asn Lys Leu Gln Glu Ala Leu Asp Arg Phe Asn Tyr Gln Thr Glu Asp
            500                 505                 510

Asp Leu Tyr Ala Ala Val Gly Tyr Gly Glu Val Ser Pro Leu Thr Met
        515                 520                 525

Ala Asn Arg Leu Thr Glu Lys Glu Arg Lys Glu Gln Lys Ile Glu Gln
```

```
                530             535             540
Gln Lys Gln Glu Ala Glu Glu Ile Met Asn Gln Pro Lys Lys Glu Pro
545                 550                 555                 560

Asp Lys Met Lys Val Arg His Glu Gly Gly Val Val Ile Gln Gly Val
                565                 570                 575

Glu Asn Leu Leu Ile Arg Ile Ser Arg Cys Cys Asn Pro Ile Pro Gly
            580                 585                 590

Asp Asp Ile Val Gly Tyr Ile Thr Lys Gly Arg Gly Ile Ser Ile His
        595                 600                 605

Arg Arg Asp Cys Pro Asn Val Gln Pro Asp Lys Pro Asn Val Ala Glu
    610                 615                 620

Arg Leu Ile Glu Val Glu Trp Glu Asp Thr Ser Asn Thr Arg Lys Glu
625                 630                 635                 640

Tyr Asp Ala Asp Leu Glu Ile Tyr Gly Tyr Asn Arg Ser Gly Leu Leu
                645                 650                 655

Asn Asp Val Leu Gln Thr Val Asn Ala Leu Thr Lys Asn Leu Asn Ser
            660                 665                 670

Val Glu Ala Arg Thr Asn Lys Asp Lys Met Ala Thr Ile His Leu Thr
        675                 680                 685

Val Gly Ile Gln Asn Leu Ser His Leu Lys Ser Ile Val Asp Lys Ile
    690                 695                 700

Lys Ala Val Pro Asp Val Tyr Ser Val Arg Arg Thr Asn Gly
705                 710                 715

<210> SEQ ID NO 55
<211> LENGTH: 2205
<212> TYPE: DNA
<213> ORGANISM: Enterococcus faecium

<400> SEQUENCE: 55
atggcgaacg aacaagtatt gactgccgag caagttatag ataaagcacg cagctatcta      60
tctgatgagc atatcgcatt tgtcgaaaaa gcatatctgt acgctgaaga tgctcatcgc     120
gagcaatacc gcaaatcggg cgagccatat attattcatc cgattcaggt tgcggggata     180
ctcgttgatc ttgaaatgga cccttccaca atcgcgggcg atttttgca cgatgtcgtg      240 gaagatacag atgtgacgct cgatgacctg aaagaagcat tttccgaaga gtggcaatg      300 cttgtagacg gcgtaacgaa actcggcaaa attaaatata atctcaaga ggaacagcag      360 gcggaaaatc atcgcaaaat gtttgtcgct atggctcaag atatcagggt catattgatc     420
aagctggcgg atcgtcttca caatatgcgg acactgaaac atctgcctca ggaaaaacag     480
cggagaatct ccaatgaaac gctggaaatt tttgctccct tggcgcatcg tctcgggatt     540
tcaaaaatta gtgggaatt ggaagatacg gcgctccgtt atttgaaccc tcagcaatat     600
tacagaattg tcaacctcat gaagaagaaa cgtgcagaac gagagcttta tgtcgatgag     660
gttgtcaatg aagtgaagaa acgtgtcgaa gaagtaaata tcaaggctga cttctcggga     720
cgcccgaaac atatttacag catttatcga aaaatggtgc tgcaaaataa gcaattcaat     780
gaaatttacg atttgttggc tgtccgtatt cttgtgaata gcataaagga ctgctacgcg     840
gtgcttggca tcattcacac atgctggaaa ccgatgccag gcagattcaa agattatatc     900
gcaatgccga agccgaatat gtatcaatcg cttcatacaa cggttattgg gcctaaagcg     960
gatccgcttg aagtgcagat ccgcaccttt gaaatgcatg aaatagcgga atacgggggt    1020
gcggctcact gggcttataa agaagggaaa gcagccaatg aaggtgcaac ctttgagaaa    1080
aagctttctt ggttccgtga aattttagaa tttcaaaatg aatcgacaga tgcagaagaa    1140
```

-continued

```
tttatggaat cgctcaaaat tgatttgttc tctgacatgg tgtatgtctt tacgccaaaa    1200
ggagatgtaa tcgagcttcc gtccggttct gttccgattg acttttctta ccggattcac    1260
tctgaaatcg gcaataaaac aatcggtgcc aaagtaaacg aaaaatggt tacgcttgac     1320 cataagcttc ggacaggtga tatcgttgaa attctcacct ctaagcattc ctacggtccg    1380
agccaggatt gggtgaagct tgcccaaaca tcccaagcga agcataaaat ccgtcaattc    1440
tttaagaaac agcggcgtga agaaaatgtc gaaaaaggcc gtgagctggt cgaaaaagaa    1500
attaaaaact tggattttga attgaaggat gttttaacgc cggagaatat tcaaaaggtt    1560
gctgacaaat ttaatttctc aaatgaagag gatatgtacg cggcggtcgg ttacaacggc    1620
atcacagctc tgcaggtggc gaaccgccta acagaaaaag agagaaagca gcgcgaccag    1680
gaagaacagg aaaagatcgt tcaggaagtc actggggaac ctaagccata cccgcaagga    1740
agaaaacggg aagctggcgt tcgtgtcaag ggcattgaca acctccttgt ccgtttatca    1800
aaatgctgca atcctgtgcc aggtgatgat attgtcggct ttatcacaaa aggcagaggg    1860
gtttcggtcc atcgcgaaga ctgtccgaat gtcaaaacga atgaagccca agagcggctg    1920
atcccggtag agtgggaaca tgagtcacaa gttcaaaagc gcaaggaata caatgttgag    1980
atagagattc ttgggtatga ccgccgcgga ttgctgaacg aggtactcca ggcagtgaat    2040
gaaacgaaaa ccaatatttc atctgtctct ggcaaatcgg atcgcaataa agtggcaacc    2100
atccatatgg cgattttat ccagaatatc aatcacttgc ataaagtcgt cgagcgtatt    2160
aaacagatta gagatatcta ttctgtgcgc cgcgtcatga actaa                    2205
```

<210> SEQ ID NO 56
<211> LENGTH: 734
<212> TYPE: PRT
<213> ORGANISM: Enterococcus faecium

<400> SEQUENCE: 56

```
Met Ala Asn Glu Gln Val Leu Thr Ala Glu Gln Val Ile Asp Lys Ala
1               5                   10                  15

Arg Ser Tyr Leu Ser Asp Glu His Ile Ala Phe Val Glu Lys Ala Tyr
            20                  25                  30

Leu Tyr Ala Glu Asp Ala His Arg Glu Gln Tyr Arg Lys Ser Gly Glu
        35                  40                  45

Pro Tyr Ile Ile His Pro Ile Gln Val Ala Gly Ile Leu Val Asp Leu
    50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190
```

```
Arg Tyr Leu Asn Pro Gln Gln Tyr Arg Ile Val Asn Leu Met Lys
        195                 200                 205

Lys Lys Arg Ala Glu Arg Glu Leu Tyr Val Asp Glu Val Val Asn Glu
    210                 215                 220

Val Lys Lys Arg Val Glu Val Asn Ile Lys Ala Asp Phe Ser Gly
225                 230                 235                 240

Arg Pro Lys His Ile Tyr Ser Ile Tyr Arg Lys Met Val Leu Gln Asn
                245                 250                 255

Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
        290                 295                 300

Pro Asn Met Tyr Gln Ser Leu His Thr Thr Val Ile Gly Pro Lys Ala
305                 310                 315                 320

Asp Pro Leu Glu Val Gln Ile Arg Thr Phe Glu Met His Glu Ile Ala
                325                 330                 335

Glu Tyr Gly Val Ala Ala His Trp Ala Tyr Lys Glu Gly Lys Ala Ala
            340                 345                 350

Asn Glu Gly Ala Thr Phe Glu Lys Lys Leu Ser Trp Phe Arg Glu Ile
        355                 360                 365

Leu Glu Phe Gln Asn Glu Ser Thr Asp Ala Glu Glu Phe Met Glu Ser
    370                 375                 380

Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
            420                 425                 430

Asn Gly Lys Met Val Thr Leu Asp His Lys Leu Arg Thr Gly Asp Ile
        435                 440                 445

Val Glu Ile Leu Thr Ser Lys His Ser Tyr Gly Pro Ser Gln Asp Trp
    450                 455                 460

Val Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Leu Lys Asp Val Leu
            500                 505                 510

Thr Pro Glu Asn Ile Gln Lys Val Ala Asp Lys Phe Asn Phe Ser Asn
        515                 520                 525

Glu Glu Asp Met Tyr Ala Ala Val Gly Tyr Asn Gly Ile Thr Ala Leu
    530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Glu Val Thr Gly Glu Pro Lys Pro
                565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
        595                 600                 605

Asp Asp Ile Val Gly Phe Ile Thr Lys Gly Arg Gly Val Ser Val His
```

```
                610             615             620
Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
                645                 650                 655

Tyr Asn Val Glu Ile Glu Ile Leu Gly Tyr Asp Arg Arg Gly Leu Leu
                    660                 665                 670

Asn Glu Val Leu Gln Ala Val Asn Glu Thr Lys Thr Asn Ile Ser Ser
                675                 680                 685

Val Ser Gly Lys Ser Asp Arg Asn Lys Val Ala Thr Ile His Met Ala
            690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730
```

<210> SEQ ID NO 57
<211> LENGTH: 2205
<212> TYPE: DNA
<213> ORGANISM: Enterococcus faecalis

<400> SEQUENCE: 57

```
atggcgaacg aacaagtatt gactgccgag caagttatag ataaagcacg cagctatcta      60
tctgatgagc atatcgcatt tgtcgaaaaa gcatatctgt acgctgaaga tgctcatcgc     120
gagcaatacc gcaaatcggg cgagccatat attattcatc cgattcaggt tgcgggaata     180
ctcgttgatc ttgaaatgga cccttccaca atcgcgggcg attttttgca cgatgtcgtg     240
gaagatacag atgtgacgct cgatgacctg aaagaagcat ttccgaagaa gtggcaatg      300
cttgtagacg gcgtaacgaa actcggcaaa attaaatata atctcaaga ggaacagcag      360
gcggaaaatc atcgcaaaat gtttgtcgct atggctcaag atatcagggt catattgatc     420
aagctggcgg atcgtcttca caatatgcgg acactgaaac atctgcctca ggaaaaacag     480
cggagaatct ccaatgaaac gctggaaatt tttgctcctt tggcgcatcg tctcgggatt     540
tcaaaaatta gtgggaatt ggaagatacg gcgctccgtt atttgaaccc tcagcaatat     600
tacagaattg tcaacctcat gaagaagaaa cgtgcagaac gagagcttta tgtcgatgag     660
gttgtcaatg aagtgaagaa acgtgtcgaa gaagtaaata tcaaggctga cttctcggga     720
cgcccgaaac atatttacag catttatcga aaaatggtgc tgcaaaataa gcaattcaat     780
gaaatttacg atttgttggc tgtccgtatt cttgtgaata gcataaagga ctgctacgcg     840
gtgcttggca tcattcacac atgctggaaa ccgatgccag gcagattcaa agattatatc     900
gcaatgccga agccgaatat gtatcaatcg cttcatacaa cggttattgg gcctaaagcg     960
gatccgcttg aagtgcagat ccgcaccttt gaaatgcatg aaatagcgga atacggggtt    1020
gcggctcact gggcttataa agaagggaaa gcagccaatg aaggtgcaac ctttgagaaa    1080
aagctttctt ggttccgtga aattttagaa tttcaaaatg aatcgacaga tgcagaagaa    1140
tttatggaat cgctcaaaat tgatttgttc tctgacatgg tgtatgtctt tacgccaaaa    1200
ggagatgtaa tcgagcttcc gtccggttct gttccgattg acttttctta ccggattcac    1260
tctgaaatcg gcaataaaac aatcggtgcc aagtaaacg gaaaaatggt tacgcttgac    1320
cataagcttc ggacaggtga tatcgttgaa attctcacct ctaagcattc ctacggtccg    1380
agccaggatt gggtgaagct tgcccaaaca tcccaagcga agcataaaat ccgtcaattc    1440
tttaagaaac agcggcgtga agaaaatgtc gaaaaaggcc gtgagctggt cgaaaaagaa    1500
```

```
attaaaaact tggattttga attgaaggat gttttaacgc cggagaatat tcaaaaggtt    1560
gctgacaaat ttaatttctc aaatgaagag gatatgtacg cggcggtcgg ttacaacggc    1620
atcacagctc tgcaggtggc gaaccgccta acagaaaaag agagaaagca gcgcgaccag    1680
gaagaacagg aaaagatcgt tcaggaagtc actggggaac taagccata cccgcaagga     1740 agaaaacggg aagctggcgt tcgtgtcaag ggcattgaca acctccttgt ccgtttatca    1800
aaatgctgca atcctgtgcc aggtgatgat attgtcggct ttatcacaaa aggcagaggg    1860
gtttcggtcc atcgcgaaga ctgtccgaat gtcaaaacga atgaagccca agagcggctg    1920
atcccggtag agtgggaaca tgagtcacaa gttcaaaagc gcaaggaata caatgttgag    1980
atagagattc ttgggtatga ccgccgcgga ttgctgaacg aggtactcca ggcagtgaat    2040
gaaacgaaaa ccaatatttc atctgtctct ggcaaatcgg atcgcaataa agtggcaacc    2100
atccatatgg cgattttat ccagaatatc aatcacttgc ataaagtcgt cgagcgtatt     2160
aaacagatta gagatatcta ttctgtgcgc cgcgtcatga actaa                    2205
```

<210> SEQ ID NO 58
<211> LENGTH: 734
<212> TYPE: PRT
<213> ORGANISM: Enterococcus faecalis

<400> SEQUENCE: 58

```
Met Ala Asn Glu Gln Val Leu Thr Ala Glu Gln Val Ile Asp Lys Ala
1               5                   10                  15

Arg Ser Tyr Leu Ser Asp Glu His Ile Ala Phe Val Glu Lys Ala Tyr
            20                  25                  30

Leu Tyr Ala Glu Asp Ala His Arg Glu Gln Tyr Arg Lys Ser Gly Glu
        35                  40                  45

Pro Tyr Ile Ile His Pro Ile Gln Val Ala Gly Ile Leu Val Asp Leu
    50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Asp Glu Val Val Asn Glu
    210                 215                 220

Val Lys Lys Arg Val Glu Glu Val Asn Ile Lys Ala Asp Phe Ser Gly
225                 230                 235                 240

Arg Pro Lys His Ile Tyr Ser Ile Tyr Arg Lys Met Val Leu Gln Asn
                245                 250                 255
```

-continued

Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
290                 295                 300

Pro Asn Met Tyr Gln Ser Leu His Thr Thr Val Ile Gly Pro Lys Ala
305                 310                 315                 320

Asp Pro Leu Glu Val Gln Ile Arg Thr Phe Glu Met His Glu Ile Ala
            325                 330                 335

Glu Tyr Gly Val Ala Ala His Trp Ala Tyr Lys Glu Gly Lys Ala Ala
            340                 345                 350

Asn Glu Gly Ala Thr Phe Glu Lys Lys Leu Ser Trp Phe Arg Glu Ile
        355                 360                 365

Leu Glu Phe Gln Asn Glu Ser Thr Asp Ala Glu Glu Phe Met Glu Ser
    370                 375                 380

Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
            405                 410                 415

Tyr Arg Ile His Ser Glu Ile Gly Asn Lys Thr Ile Gly Ala Lys Val
            420                 425                 430

Asn Gly Lys Met Val Thr Leu Asp His Lys Leu Arg Thr Gly Asp Ile
        435                 440                 445

Val Glu Ile Leu Thr Ser Lys His Ser Tyr Gly Pro Ser Gln Asp Trp
    450                 455                 460

Val Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
            485                 490                 495

Val Glu Lys Glu Ile Lys Asn Leu Asp Phe Glu Leu Lys Asp Val Leu
            500                 505                 510

Thr Pro Glu Asn Ile Gln Lys Val Ala Asp Lys Phe Asn Phe Ser Asn
        515                 520                 525

Glu Glu Asp Met Tyr Ala Ala Val Gly Tyr Asn Gly Ile Thr Ala Leu
    530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Glu Val Thr Gly Glu Pro Lys Pro
            565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
        595                 600                 605

Asp Asp Ile Val Gly Phe Ile Thr Lys Gly Arg Gly Val Ser Val His
    610                 615                 620

Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
            645                 650                 655

Tyr Asn Val Glu Ile Glu Ile Leu Gly Tyr Asp Arg Arg Gly Leu Leu
            660                 665                 670

Asn Glu Val Leu Gln Ala Val Asn Glu Thr Lys Thr Asn Ile Ser Ser

-continued

```
               675                 680                 685
Val Ser Gly Lys Ser Asp Arg Asn Lys Val Ala Thr Ile His Met Ala
        690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730
```

<210> SEQ ID NO 59
<211> LENGTH: 2205
<212> TYPE: DNA
<213> ORGANISM: Rhodococcus erythropolis

<400> SEQUENCE: 59

| | | | | |
|---|---|---|---|---|
| atggcgaacg | aacaagtatt | gactgccgag | caagttatag | ataaagcacg cagctatcta | 60 |
| tctgatgagc | atatcgcatt | tgtcgaaaaa | gcatatctgt | acgctgaaga tgctcatcgc | 120 |
| gagcaatacc | gcaaatcggg | cgagccatat | attattcatc | cgattcaggt tgcgggdata | 180 |
| ctcgttgatc | ttgaaatgga | cccttccaca | atcgcgggcg | attttttgca cgatgtcgtg | 240 |
| gaagatacag | atgtgacgct | cgatgacctg | aaagaagcat | tttccgaaga gtggcaatg | 300 |
| cttgtagacg | gcgtaacgaa | actcggcaaa | attaaatata | atctcaaga ggaacagcag | 360 |
| gcggaaaatc | atcgcaaaat | gtttgtcgct | atggctcaag | atatcaggdt catattgatc | 420 |
| aagctggcgg | atcgtcttca | caatatgcgg | acactgaaac | atctgcctca ggaaaaacag | 480 |
| cggagaatct | ccaatgaaac | gctggaaatt | tttgctcctt | tggcgcatcg tctcgggatt | 540 |
| tcaaaaatta | agtgggaatt | ggaagatacg | gcgctccgtt | atttgaaccc tcagcaatat | 600 |
| tacagaattg | tcaacctcat | gaagaagaaa | cgtgcagaac | gagagcttta tgtcgatgag | 660 |
| gttgtcaatg | aagtgaagaa | acgtgtcgaa | gaagtaaata | tcaaggctga cttctcggga | 720 |
| cgcccgaaac | atatttacag | catttatcga | aaaatggtgc | tgcaaaataa gcaattcaat | 780 |
| gaaatttacg | atttgttggc | tgtccgtatt | cttgtgaata | gcataaagga ctgctacgcg | 840 |
| gtgcttggca | tcattcacac | atgctggaaa | ccgatgccag | gcagattcaa agattatatc | 900 |
| gcaatgccga | agccgaatat | gtatcaatcg | cttcatacaa | cggttattgg gcctaaagcg | 960 |
| gatccgcttg | aagtgcagat | ccgcaccttt | gaaatgcatg | aaatagcgga atacggggtt | 1020 |
| gcggctcact | gggcttataa | agaagggaaa | gcagccaatg | aaggtgcaac ctttgagaaa | 1080 |
| aagctttctt | ggttccgtga | aatttttagaa | tttcaaaatg | aatcgacaga tgcagaagaa | 1140 |
| tttatggaat | cgctcaaaat | tgatttgttc | tctgacatgg | tgtatgtctt tacgccaaaa | 1200 |
| ggagatgtaa | tcgagcttcc | gtccggttct | gttccgattg | actttttctta ccggattcac | 1260 |
| tctgaaatcg | gcaataaaac | aatcggtgcc | aaagtaaacg | gaaaaatggt tacgcttgac | 1320 |
| cataagcttc | ggacaggtga | tatcgttgaa | attctcacct | ctaagcattc ctacggtccg | 1380 |
| agccaggatt | gggtgaagct | tgcccaaaca | tcccaagcga | agcataaaat ccgtcaattc | 1440 |
| tttaagaaac | agcggcgtga | agaaaatgtc | gaaaaaggcc | gtgagctggt cgaaaaagaa | 1500 |
| attaaaaact | tggattttga | attgaaggat | gttttaacgc | cggagaatat tcaaaaggtt | 1560 |
| gctgacaaat | taattttctc | aaatgaagag | gatatgtacg | cggcggtcgg ttacaacggc | 1620 |
| atcacagctc | tgcaggtggc | gaaccgccta | acagaaaaag | agaaagca gcgcgaccag | 1680 |
| gaagaacagg | aaaagatcgt | tcaggaagtc | actggggaac | ctaagccata cccgcaagga | 1740 |
| agaaaacggg | aagctggcgt | tcgtgtcaag | ggcattgaca | acctccttgt ccgtttatca | 1800 |
| aaatgctgca | atcctgtgcc | aggtgatgat | attgtcggct | ttatcacaaa aggcagaggg | 1860 |

-continued

```
gtttcggtcc atcgcgaaga ctgtccgaat gtcaaaacga atgaagccca agagcggctg    1920
atcccggtag agtgggaaca tgagtcacaa gttcaaaagc gcaaggaata caatgttgag    1980
atagagattc ttgggtatga ccgccgcgga ttgctgaacg aggtactcca ggcagtgaat    2040
gaaacgaaaa ccaatatttc atctgtctct ggcaaatcgg atcgcaataa agtggcaacc    2100
atccatatgg cgatttttat ccagaatatc aatcacttgc ataaagtcgt cgagcgtatt    2160
aaacagatta gagatatcta ttctgtgcgc cgcgtcatga actaa                    2205
```

<210> SEQ ID NO 60
<211> LENGTH: 734
<212> TYPE: PRT
<213> ORGANISM: Rhodococcus erythropolis

<400> SEQUENCE: 60

```
Met Ala Asn Glu Gln Val Leu Thr Ala Glu Gln Val Ile Asp Lys Ala
1               5                   10                  15

Arg Ser Tyr Leu Ser Asp Glu His Ile Ala Phe Val Glu Lys Ala Tyr
            20                  25                  30

Leu Tyr Ala Glu Asp Ala His Arg Glu Gln Tyr Arg Lys Ser Gly Glu
        35                  40                  45

Pro Tyr Ile Ile His Pro Ile Gln Val Ala Gly Ile Leu Val Asp Leu
    50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Asp Glu Val Val Asn Glu
    210                 215                 220

Val Lys Lys Arg Val Glu Glu Val Asn Ile Lys Ala Asp Phe Ser Gly
225                 230                 235                 240

Arg Pro Lys His Ile Tyr Ser Ile Tyr Arg Lys Met Val Leu Gln Asn
                245                 250                 255

Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Ala
305                 310                 315                 320
```

```
Asp Pro Leu Glu Val Gln Ile Arg Thr Phe Glu Met His Glu Ile Ala
            325                 330                 335

Glu Tyr Gly Val Ala Ala His Trp Ala Tyr Lys Glu Gly Lys Ala Ala
            340                 345                 350

Asn Glu Gly Ala Thr Phe Glu Lys Lys Leu Ser Trp Phe Arg Glu Ile
            355                 360                 365

Leu Glu Phe Gln Asn Glu Ser Thr Asp Ala Glu Glu Phe Met Glu Ser
370                 375                 380

Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
                420                 425                 430

Asn Gly Lys Met Val Thr Leu Asp His Lys Leu Arg Thr Gly Asp Ile
            435                 440                 445

Val Glu Ile Leu Thr Ser Lys His Ser Tyr Gly Pro Ser Gln Asp Trp
450                 455                 460

Val Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Leu Lys Asp Val Leu
            500                 505                 510

Thr Pro Glu Asn Ile Gln Lys Val Ala Asp Lys Phe Asn Phe Ser Asn
            515                 520                 525

Glu Glu Asp Met Tyr Ala Ala Val Gly Tyr Asn Gly Ile Thr Ala Leu
530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Glu Val Thr Gly Glu Pro Lys Pro
                565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
            595                 600                 605

Asp Asp Ile Val Gly Phe Ile Thr Lys Gly Arg Gly Val Ser Val His
            610                 615                 620

Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
                645                 650                 655

Tyr Asn Val Glu Ile Glu Ile Leu Gly Tyr Asp Arg Arg Gly Leu Leu
            660                 665                 670

Asn Glu Val Leu Gln Ala Val Asn Glu Thr Lys Thr Asn Ile Ser Ser
            675                 680                 685

Val Ser Gly Lys Ser Asp Arg Asn Lys Val Ala Thr Ile His Met Ala
            690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730
```

<210> SEQ ID NO 61
<211> LENGTH: 1170
<212> TYPE: DNA
<213> ORGANISM: Lactobacillus plantarum

<400> SEQUENCE: 61

| | | |
|---|---|---|
| atgctagaca aaatcattta taaaaactta tttagtaaag cgttcgatat tactattgaa | 60 |
| gtcacttatt gggatgggca aattgaacgg tatggtaccg gcatgccagc tgttaaagtt | 120 |
| cgattaaata aagaaatccc aattaagcta ttaactaatc agccaacatt ggttttaggt | 180 |
| gaagcataca tgaatgggga tattgaagta gacgggagca ttcaggaatt aattgcctct | 240 |
| gcttaccgcc aaaaagacag ttttttgaca cataattcat ttttgaaaca cttgccaaaa | 300 |
| atatcacatt ccgaaaaaag cagtacaaaa gatattcaaa gtcattatga tatcggcaat | 360 |
| gatttttata actatggtt agatgatacc atgacctact cttgtgcgta ctttgaacat | 420 |
| gacgatgata cttaaaaaca ggcacaactc aataaagtga gacatatttt aaataagctg | 480 |
| gcaacccagc ctggtaaaag attattggat gttgggagtg gttggggaac attattattt | 540 |
| atggccgcgg atgagtttgg gttagatgca acgggtatta ctttaagtca agaacagtat | 600 |
| gattatacac aagcgcaaat caagcaacgt catttggagg aaaaagtgca tgtgcagtta | 660 |
| aaggactatc gagaagtcac tggccaattt gattatgtca cctcggtagg tatgtttgaa | 720 |
| catgttggta agaaaatct agggttgtac tttaataaaa ttcaagcgtt cttagttcca | 780 |
| ggaggtcgag ctttaattca tggcattaca ggtcaacatg aaggtgccgg cgttgatcca | 840 |
| tttattaacc aatatatttt cccagggggc tatatcccaa atgttgctga gaatctcaaa | 900 |
| catattatgg ctgctaagtt acaattttca gacattgaac ccttgcggcg ccattaccaa | 960 |
| aagacgttag aaatctggta tcacaattat cagcaggtcg aacaacaggt cgtcaagaat | 1020 |
| tatggggaac gatttgaccg catgtggcaa ttatatttac aggcatgtgc agctgctttt | 1080 |
| gaggccggaa atatcgatgt tattcaatat ctattagtga aagcgccgag tggaactggc | 1140 |
| cttccgatga ctcgccatta tatttatgat | 1170 |

<210> SEQ ID NO 62
<211> LENGTH: 390
<212> TYPE: PRT
<213> ORGANISM: Lactobacillus plantarum

<400> SEQUENCE: 62

Met Leu Asp Lys Ile Ile Tyr Lys Asn Leu Phe Ser Lys Ala Phe Asp
1               5                   10                  15

Ile Thr Ile Glu Val Thr Tyr Trp Asp Gly Gln Ile Glu Arg Tyr Gly
            20                  25                  30

Thr Gly Met Pro Ala Val Lys Val Arg Leu Asn Lys Glu Ile Pro Ile
        35                  40                  45

Lys Leu Leu Thr Asn Gln Pro Thr Leu Val Leu Gly Glu Ala Tyr Met
    50                  55                  60

Asn Gly Asp Ile Glu Val Asp Gly Ser Ile Gln Glu Leu Ile Ala Ser
65                  70                  75                  80

Ala Tyr Arg Gln Lys Asp Ser Phe Leu Thr His Asn Ser Phe Leu Lys
                85                  90                  95

His Leu Pro Lys Ile Ser His Ser Glu Lys Ser Ser Thr Lys Asp Ile
            100                 105                 110

Gln Ser His Tyr Asp Ile Gly Asn Asp Phe Tyr Lys Leu Trp Leu Asp
        115                 120                 125

Asp Thr Met Thr Tyr Ser Cys Ala Tyr Phe Glu His Asp Asp Asp Thr

```
                130             135             140
Leu Lys Gln Ala Gln Leu Asn Lys Val Arg His Ile Leu Asn Lys Leu
145                 150                 155                 160

Ala Thr Gln Pro Gly Lys Arg Leu Leu Asp Val Gly Ser Gly Trp Gly
                165                 170                 175

Thr Leu Leu Phe Met Ala Ala Asp Glu Phe Gly Leu Asp Ala Thr Gly
                180                 185                 190

Ile Thr Leu Ser Gln Glu Gln Tyr Asp Tyr Thr Gln Ala Gln Ile Lys
                195                 200                 205

Gln Arg His Leu Glu Glu Lys Val His Val Gln Leu Lys Asp Tyr Arg
                210                 215                 220

Glu Val Thr Gly Gln Phe Asp Tyr Val Thr Ser Val Gly Met Phe Glu
225                 230                 235                 240

His Val Gly Lys Glu Asn Leu Gly Leu Tyr Phe Asn Lys Ile Gln Ala
                245                 250                 255

Phe Leu Val Pro Gly Gly Arg Ala Leu Ile His Gly Ile Thr Gly Gln
                260                 265                 270

His Glu Gly Ala Gly Val Asp Pro Phe Ile Asn Gln Tyr Ile Phe Pro
                275                 280                 285

Gly Gly Tyr Ile Pro Asn Val Ala Glu Asn Leu Lys His Ile Met Ala
                290                 295                 300

Ala Lys Leu Gln Phe Ser Asp Ile Glu Pro Leu Arg Arg His Tyr Gln
305                 310                 315                 320

Lys Thr Leu Glu Ile Trp Tyr His Asn Tyr Gln Gln Val Glu Gln Gln
                325                 330                 335

Val Val Lys Asn Tyr Gly Glu Arg Phe Asp Arg Met Trp Gln Leu Tyr
                340                 345                 350

Leu Gln Ala Cys Ala Ala Ala Phe Glu Ala Gly Asn Ile Asp Val Ile
                355                 360                 365

Gln Tyr Leu Leu Val Lys Ala Pro Ser Gly Thr Gly Leu Pro Met Thr
                370                 375                 380

Arg His Tyr Ile Tyr Asp
385                 390

<210> SEQ ID NO 63
<211> LENGTH: 1191
<212> TYPE: DNA
<213> ORGANISM: Lactobacillus plantarum

<400> SEQUENCE: 63
atgctagaaa aaaccttta ccacaccctt ctaagccact cattcaatat gcccgtcaca      60
gtcaactact gggatggaag tagtgaaact tatggtgaag cacaccaga agtcacggtg     120 acttttaaag aagccattcc aatgcgtgaa attaccaaga acgcttcaat tgcccttggt     180
gaagcttata tggatggcaa gattgaaatt gatggcagta ttcaaaaatt aattgaatcg     240
gcctatgaat cggcagaaag tttcttcaac aattctaagt tcaagaagtt catgcctaaa     300
caatctcact ctgaaaagaa gagtcaacaa gacatccaaa gccattacga tgtgggtaac     360
gacttctaca gatgtggct tgatccaacc atgacctatt cttgtgctta cttcaaacat     420
gacactgata cattagaaga agcccagatt cataaggttc atcacatcat tcaaaagctc     480
aacccacaac ctggcaagac cttactagac attggttgcg gttggggtac gttgatgttg     540
actgccgcta agaatacgg cttaaaagtc gtcggggtca cgttatcaca gaacaatat     600 aacctagttg ctcaacgcat caaggatgaa ggcctcagtg atgttgctga agtccggtta     660
```

```
caagattacc gtgaacttgg cgacgaaact ttcgactaca ttaccagtgt tgggatgttc    720
gaacacgtcg gtaaggacaa cttagcaatg tactttgaac gcgttaacca ctatcttaaa    780
gctgacggcg ttgccttatt gcacggcatc acccggcaac aaggtggcgc cactaacggt    840
tggttagata agtacatttt cccaggtggc tacgttcctg ggatgaccga aaacttacaa    900
cacattgttg acgccggctt acaagtcgct gacgttgaaa ccctccgtcg ccattaccaa    960
cggacgactg aaatctggga taaaaacttt aacgctaagc gcgctgccat cgaagaaaag   1020
atgggcgtgc gcttcactcg catgtgggat ctctacctac aagcctgtgc cgcttccttc   1080
cagtctggta acattgacgt catgcagtac ctcgtaacta aaggtgcttc atcacgaacc   1140
ttaccaatga cccggaaata catgtatgcg gataaccgaa tcaataaagc t            1191
```

<210> SEQ ID NO 64
<211> LENGTH: 397
<212> TYPE: PRT
<213> ORGANISM: Lactobacillus plantarum

<400> SEQUENCE: 64

```
Met Leu Glu Lys Thr Phe Tyr His Thr Leu Leu Ser His Ser Phe Asn
1               5                   10                  15

Met Pro Val Thr Val Asn Tyr Trp Asp Gly Ser Ser Glu Thr Tyr Gly
            20                  25                  30

Glu Gly Thr Pro Glu Val Thr Val Thr Phe Lys Glu Ala Ile Pro Met
        35                  40                  45

Arg Glu Ile Thr Lys Asn Ala Ser Ile Ala Leu Gly Glu Ala Tyr Met
    50                  55                  60

Asp Gly Lys Ile Glu Ile Asp Gly Ser Ile Gln Lys Leu Ile Glu Ser
65                  70                  75                  80

Ala Tyr Glu Ser Ala Glu Ser Phe Phe Asn Asn Ser Lys Phe Lys Lys
                85                  90                  95

Phe Met Pro Lys Gln Ser His Ser Glu Lys Lys Ser Gln Asp Ile
            100                 105                 110

Gln Ser His Tyr Asp Val Gly Asn Asp Phe Tyr Lys Met Trp Leu Asp
        115                 120                 125

Pro Thr Met Thr Tyr Ser Cys Ala Tyr Phe Lys His Asp Thr Asp Thr
    130                 135                 140

Leu Glu Glu Ala Gln Ile His Lys Val His Ile Ile Gln Lys Leu
145                 150                 155                 160

Asn Pro Gln Pro Gly Lys Thr Leu Leu Asp Ile Gly Cys Gly Trp Gly
                165                 170                 175

Thr Leu Met Leu Thr Ala Ala Lys Glu Tyr Gly Leu Lys Val Val Gly
            180                 185                 190

Val Thr Leu Ser Gln Glu Gln Tyr Asn Leu Val Ala Gln Arg Ile Lys
        195                 200                 205

Asp Glu Gly Leu Ser Asp Val Ala Glu Val Arg Leu Gln Asp Tyr Arg
    210                 215                 220

Glu Leu Gly Asp Glu Thr Phe Asp Tyr Ile Thr Ser Val Gly Met Phe
225                 230                 235                 240

Glu His Val Gly Lys Asp Asn Leu Ala Met Tyr Phe Glu Arg Val Asn
                245                 250                 255

His Tyr Leu Lys Ala Asp Gly Val Ala Leu Leu His Gly Ile Thr Arg
            260                 265                 270

Gln Gln Gly Gly Ala Thr Asn Gly Trp Leu Asp Lys Tyr Ile Phe Pro
        275                 280                 285
```

Gly Gly Tyr Val Pro Gly Met Thr Glu Asn Leu Gln His Ile Val Asp
        290                 295                 300

Ala Gly Leu Gln Val Ala Asp Val Glu Thr Leu Arg Arg His Tyr Gln
305                 310                 315                 320

Arg Thr Thr Glu Ile Trp Asp Lys Asn Phe Asn Ala Lys Arg Ala Ala
                325                 330                 335

Ile Glu Glu Lys Met Gly Val Arg Phe Thr Arg Met Trp Asp Leu Tyr
            340                 345                 350

Leu Gln Ala Cys Ala Ala Ser Phe Gln Ser Gly Asn Ile Asp Val Met
        355                 360                 365

Gln Tyr Leu Val Thr Lys Gly Ala Ser Ser Arg Thr Leu Pro Met Thr
370                 375                 380

Arg Lys Tyr Met Tyr Ala Asp Asn Arg Ile Asn Lys Ala
385                 390                 395

<210> SEQ ID NO 65
<211> LENGTH: 1149
<212> TYPE: DNA
<213> ORGANISM: Escherichia coli

<400> SEQUENCE: 65
atgagttcat cgtgtataga agaagtcagt gtaccggatg acaactggta ccgtatcgcc      60
aacgaattac ttagccgtgc cggtatagcc attaacggtt ctgccccggc ggatattcgt     120
gtgaaaaacc ccgatttttt taaacgcgtt ctgcaagaag ctctttgggg ttaggcgaa      180
agttatatgg atggctggtg gaatgtgac cgactggata tgttttttag caaagtctta     240
cgcgcaggtc tcgagaacca actcccccat catttcaaag acacgctgcg tattgccggc     300
gctcgtctct tcaatctgca gagtaaaaaa cgtgcctgga tagtcggcaa agagcattac     360
gatttgggta tgacttgtt cagccgcatg cttgatccct tcatgcaata ttcctgcgct     420
tactggaaag atgccgataa tctggaatct gcccagcagg cgaagctcaa atgatttgt     480
gaaaaattgc agttaaaacc agggatgcgc gtactggata ttggctgcgg ctggggcgga     540
ctggcacact acatggcatc taattatgac gtaagcgtgg tgggcgtcac catttctgcc     600
gaacagcaaa aaatggctca ggaacgctgt gaaggcctgg atgtcaccat tttgctgcaa     660
gattatcgtg acctgaacga ccagtttgat cgtattgttt ctgtggggat gttcgagcac     720
gtcggaccga aaaattacga tacctatttt gcggtggtgg atcgtaattt gaaaccggaa     780
ggcatattcc tgctccatac tatcggttcg aaaaaaaccg atctgaatgt tgatccctgg     840
attaataaat atattttttcc gaacggttgc ctgccctctg tacgccagat tgctcagtcc     900
agcgaacccc actttgtgat ggaagactgg cataacttcg gtgctgatta cgatactacg     960
ttgatggcgt ggtatgaacg attcctcgcc gcatggccag aaattgcgga taactatagt    1020
gaacgcttta acgaatgtt tacctattat ctgaatgcct gtgcaggtgc tttccgcgcc    1080
cgtgatattc agctctggca ggtcgtgttc tcacgcggtg ttgaaaacgg ccttcgagtg    1140
gctcgctaa                                                             1149

<210> SEQ ID NO 66
<211> LENGTH: 382
<212> TYPE: PRT
<213> ORGANISM: Escherichia coli

<400> SEQUENCE: 66

Met Ser Ser Ser Cys Ile Glu Glu Val Ser Val Pro Asp Asp Asn Trp
1               5                   10                  15

Tyr Arg Ile Ala Asn Glu Leu Leu Ser Arg Ala Gly Ile Ala Ile Asn
           20                  25                  30

Gly Ser Ala Pro Ala Asp Ile Arg Val Lys Asn Pro Asp Phe Phe Lys
        35                  40                  45

Arg Val Leu Gln Glu Gly Ser Leu Gly Leu Gly Glu Ser Tyr Met Asp
 50                  55                  60

Gly Trp Trp Glu Cys Asp Arg Leu Asp Met Phe Phe Ser Lys Val Leu
 65                  70                  75                  80

Arg Ala Gly Leu Glu Asn Gln Leu Pro His His Phe Lys Asp Thr Leu
                 85                  90                  95

Arg Ile Ala Gly Ala Arg Leu Phe Asn Leu Gln Ser Lys Lys Arg Ala
            100                 105                 110

Trp Ile Val Gly Lys Glu His Tyr Asp Leu Gly Asn Asp Leu Phe Ser
        115                 120                 125

Arg Met Leu Asp Pro Phe Met Gln Tyr Ser Cys Ala Tyr Trp Lys Asp
130                 135                 140

Ala Asp Asn Leu Glu Ser Ala Gln Gln Ala Lys Leu Lys Met Ile Cys
145                 150                 155                 160

Glu Lys Leu Gln Leu Lys Pro Gly Met Arg Val Leu Asp Ile Gly Cys
                165                 170                 175

Gly Trp Gly Gly Leu Ala His Tyr Met Ala Ser Asn Tyr Asp Val Ser
            180                 185                 190

Val Val Gly Val Thr Ile Ser Ala Glu Gln Gln Lys Met Ala Gln Glu
        195                 200                 205

Arg Cys Glu Gly Leu Asp Val Thr Ile Leu Leu Gln Asp Tyr Arg Asp
210                 215                 220

Leu Asn Asp Gln Phe Asp Arg Ile Val Ser Val Gly Met Phe Glu His
225                 230                 235                 240

Val Gly Pro Lys Asn Tyr Asp Thr Tyr Phe Ala Val Val Asp Arg Asn
                245                 250                 255

Leu Lys Pro Glu Gly Ile Phe Leu Leu His Thr Ile Gly Ser Lys Lys
            260                 265                 270

Thr Asp Leu Asn Val Asp Pro Trp Ile Asn Lys Tyr Ile Phe Pro Asn
        275                 280                 285

Gly Cys Leu Pro Ser Val Arg Gln Ile Ala Gln Ser Ser Glu Pro His
290                 295                 300

Phe Val Met Glu Asp Trp His Asn Phe Gly Ala Asp Tyr Asp Thr Thr
305                 310                 315                 320

Leu Met Ala Trp Tyr Glu Arg Phe Leu Ala Ala Trp Pro Glu Ile Ala
                325                 330                 335

Asp Asn Tyr Ser Glu Arg Phe Lys Arg Met Phe Thr Tyr Tyr Leu Asn
            340                 345                 350

Ala Cys Ala Gly Ala Phe Arg Ala Arg Asp Ile Gln Leu Trp Gln Val
        355                 360                 365

Val Phe Ser Arg Gly Val Glu Asn Gly Leu Arg Val Ala Arg
370                 375                 380

<210> SEQ ID NO 67
<211> LENGTH: 1188
<212> TYPE: DNA
<213> ORGANISM: Pseucomonas putida

<400> SEQUENCE: 67
gtgctcgccc agttgagcaa gctgcgtcac ggccacctgc gcctgctcag ccacgggcag     60
cagtggagtt tcggtgatgc cgacagcccg ttgcaggccg aggtggagat cctcgatgac    120

```
gccacctgga gcctgatcgc cggcaatggc tcgatcggag ctggcgaagc ctacattcac    180
ggctattggc gcagccccga cctggcgctg gtgacccgcc tgttcgtcgc caaccttgaa    240
gtgctcgacg cgctcgaggg tggcctggcc cgcctgggcc gccctgccct gcgcctgctg    300
caccggctca accgcaacga caagcgcggc gcccggcgca acattctggc ccactacgac    360
ctgggcaatg ccctgttcga gcggctgctg accccacca tgatgtattc ggctgcgcaa    420
ttcgaacacc cggggcaaac actggagcag gcccagttgc acaagctgga gcgcatctgc    480
cagaagctcg aactgagccc tgacgatcac ctgctggaaa ttggcagcgg ctggggcagc    540
ctcgctatcc acgcagccac ccgttacggc tgcagggtca ccaccacgac gctctccgag    600
gcgcagtaca gccatacccct ggagcgcgtc aaggccttgg ggctggggca gcgtgtgcaa    660
gtgctccgcg aagactaccg cgaccttcaa ggcacgttcg acaaactggt ttcgatcgag    720
atgatcgaag cggtcggtca tcgctacctg ccggtgtatt ccgccagtg tgcttcgctg    780
ctcaagcctg aaggcctgat gctattgcag gcgatcacca tccgcgacca gcgctatgcc    840
caggcgcagc gctcggtcga ctttatccag cgctacatct tccccggtgg cgccctgcct    900
tcgctgagcg tgttgctcga caccgccagc cggcacactg gcctgaacct tgtgcacatg    960
gaagattttg gcctggacta cgcccacacc ctgcgacact ggcgtgaaaa cctgcgtcag   1020
gcacgcactg cgctgacgga ccttggctac gacgacatgt ccagcgcct gtgggagttt   1080
tacctctgct actgccaggg cggtttcgag gagcgcgcga tcggtgttgc gcacctgctc   1140
tgggcagcac cccaggcacg ccgtgcgccc ttgcctggcg gtgcctga               1188
```

<210> SEQ ID NO 68
<211> LENGTH: 395
<212> TYPE: PRT
<213> ORGANISM: Pseudomonas putida

<400> SEQUENCE: 68

```
Met Leu Ala Gln Leu Ser Lys Leu Arg His Gly His Leu Arg Leu Leu
1               5                   10                  15

Ser His Gly Gln Gln Trp Ser Phe Gly Asp Ala Asp Ser Pro Leu Gln
            20                  25                  30

Ala Glu Val Glu Ile Leu Asp Asp Ala Thr Trp Ser Leu Ile Ala Gly
        35                  40                  45

Asn Gly Ser Ile Gly Ala Gly Glu Ala Tyr Ile His Gly Tyr Trp Arg
    50                  55                  60

Ser Pro Asp Leu Ala Leu Val Thr Arg Leu Phe Val Ala Asn Leu Glu
65                  70                  75                  80

Val Leu Asp Ala Leu Glu Gly Gly Leu Ala Arg Leu Gly Arg Pro Ala
                85                  90                  95

Leu Arg Leu Leu His Arg Leu Asn Arg Asn Asp Lys Arg Gly Ala Arg
            100                 105                 110

Arg Asn Ile Leu Ala His Tyr Asp Leu Gly Asn Ala Leu Phe Glu Arg
        115                 120                 125

Leu Leu Asp Pro Thr Met Met Tyr Ser Ala Ala Gln Phe Glu His Pro
    130                 135                 140

Gly Gln Thr Leu Glu Gln Ala Gln Leu His Lys Leu Glu Arg Ile Cys
145                 150                 155                 160

Gln Lys Leu Glu Leu Ser Pro Asp Asp His Leu Leu Glu Ile Gly Ser
                165                 170                 175

Gly Trp Gly Ser Leu Ala Ile His Ala Ala Thr Arg Tyr Gly Cys Arg
            180                 185                 190
```

Val Thr Thr Thr Thr Leu Ser Glu Ala Gln Tyr Ser His Thr Leu Glu
        195                 200                 205

Arg Val Lys Ala Leu Gly Leu Gly Gln Arg Val Gln Val Leu Arg Glu
        210                 215                 220

Asp Tyr Arg Asp Leu Gln Gly Thr Phe Asp Lys Leu Val Ser Ile Glu
225                 230                 235                 240

Met Ile Glu Ala Val Gly His Arg Tyr Leu Pro Val Tyr Phe Arg Gln
                245                 250                 255

Cys Ala Ser Leu Leu Lys Pro Glu Gly Leu Met Leu Leu Gln Ala Ile
                260                 265                 270

Thr Ile Arg Asp Gln Arg Tyr Ala Gln Ala Gln Arg Ser Val Asp Phe
        275                 280                 285

Ile Gln Arg Tyr Ile Phe Pro Gly Gly Ala Leu Pro Ser Leu Ser Val
        290                 295                 300

Leu Leu Asp Thr Ala Ser Arg His Thr Gly Leu Asn Leu Val His Met
305                 310                 315                 320

Glu Asp Phe Gly Leu Asp Tyr Ala His Thr Leu Arg His Trp Arg Glu
                325                 330                 335

Asn Leu Arg Gln Ala Arg Thr Ala Leu Thr Asp Leu Gly Tyr Asp Asp
                340                 345                 350

Met Phe Gln Arg Leu Trp Glu Phe Tyr Leu Cys Tyr Cys Gln Gly Gly
        355                 360                 365

Phe Glu Glu Arg Ala Ile Gly Val Ala His Leu Leu Trp Ala Ala Pro
370                 375                 380

Gln Ala Arg Arg Ala Pro Leu Pro Gly Gly Ala
385                 390                 395

<210> SEQ ID NO 69
<211> LENGTH: 1167
<212> TYPE: DNA
<213> ORGANISM: Enterococcus faecalis

<400> SEQUENCE: 69
atgttagaaa aagaaacgta cagtcaactg tttaaatggt cttttttcaaa aaagacacaa        60 gtcacatact gggatggtac cgtcaaagag tatgggcaag ggtcggggga tccggttttt       120
aaaattgtat tcaatgaaaa aattcctgtg aaggatttac tgaataacgc ttcgttaact       180
ttaggggaag cctacatgga tcgcaaaatt gaaatcgaag gcgatatcca agcgctgatt       240
tatgatgtgt ataaccaaaa ggatagcttt ttacacaatg ctaaatttat taaatggctt       300
cctaaagaaa gtcattcaaa aaacgttcg caagaggata ttcacagcca ttacgatcta       360
ggaaatgatt tttacaaaaa atggcttgac caaacaatga cgtattcatg tgcttatttt       420
aaaacgcctg aagatacatt agaacaagcg caagtgaata agttcatca tattttagat       480 aaattgttta tcaaagaggg cgacacttta ctggatattg ctgcggctg gggcacgtta       540 attttaactg cggtgaaaga atatggagcc aaagcaactg ggattacatt aagtgaagag       600
caatttcatc atattcgcca tattatgaaa aagaagatc tacaagatcg aatgactgtc       660
aaattgatgg attatcgtga tttaaaagga gagtcttttg accatattac gagtgttggg       720
atgtttgaac atgtcggtgc ggaaaatcta catgaatatt tgatgtcgt tcagcggaat       780 ttagcgccta aaggtacggc gttgattcat gggatcagtc gccaacaagg tggggctaaa       840
aatgcttgga ttaatcgtta tattttccct ggtggctata ttcctggtgt cactgagcta       900
gtcggccata tgacagaaaa cgacttgcaa gtgattgact tggaaagttt gcgcagagat       960

-continued

```
tatcaattga cgttggaaca ttggacaaaa aacttccata atatagaagc agaaattgtt      1020
gacgaaaaag gcgagcgctt ctatcgaatg tgggacttat atttgcaagc atgtgcagcc      1080
tcattccaag caagcaatat tgatgttatt caatatttat tggttcatcc agataacaat      1140
gatattccaa tgcgccggat tggttaa                                          1167
```

<210> SEQ ID NO 70
<211> LENGTH: 388
<212> TYPE: PRT
<213> ORGANISM: Enterococcus faecalis

<400> SEQUENCE: 70

```
Met Leu Glu Lys Glu Thr Tyr Ser Gln Leu Phe Lys Trp Ser Phe Ser
1               5                   10                  15

Lys Lys Thr Gln Val Thr Tyr Trp Asp Gly Thr Val Lys Glu Tyr Gly
            20                  25                  30

Gln Gly Ser Gly Asp Pro Val Phe Lys Ile Val Phe Asn Glu Lys Ile
        35                  40                  45

Pro Val Lys Asp Leu Asn Asn Ala Ser Leu Thr Leu Gly Glu Ala
    50                  55                  60

Tyr Met Asp Arg Lys Ile Glu Ile Glu Gly Asp Ile Gln Ala Leu Ile
65                  70                  75                  80

Tyr Asp Val Tyr Asn Gln Lys Asp Ser Phe Leu His Asn Ala Lys Phe
                85                  90                  95

Ile Lys Trp Leu Pro Lys Glu Ser His Ser Lys Lys Arg Ser Gln Glu
            100                 105                 110

Asp Ile His Ser His Tyr Asp Leu Gly Asn Asp Phe Tyr Lys Lys Trp
        115                 120                 125

Leu Asp Gln Thr Met Thr Tyr Ser Cys Ala Tyr Phe Lys Thr Pro Glu
    130                 135                 140

Asp Thr Leu Glu Gln Ala Gln Val Asn Lys Val His His Ile Leu Asp
145                 150                 155                 160

Lys Leu Phe Ile Lys Glu Gly Asp Thr Leu Leu Asp Ile Gly Cys Gly
                165                 170                 175

Trp Gly Thr Leu Ile Leu Thr Ala Val Lys Glu Tyr Gly Ala Lys Ala
            180                 185                 190

Thr Gly Ile Thr Leu Ser Glu Glu Gln Phe His His Ile Arg His Ile
        195                 200                 205

Ile Glu Lys Glu Asp Leu Gln Asp Arg Met Thr Val Lys Leu Met Asp
    210                 215                 220

Tyr Arg Asp Leu Lys Gly Glu Ser Phe Asp His Ile Thr Ser Val Gly
225                 230                 235                 240

Met Phe Glu His Val Gly Ala Glu Asn Leu His Glu Tyr Phe Asp Val
                245                 250                 255

Val Gln Arg Asn Leu Ala Pro Lys Gly Thr Ala Leu Ile His Gly Ile
            260                 265                 270

Ser Arg Gln Gln Gly Gly Ala Lys Asn Ala Trp Ile Asn Arg Tyr Ile
        275                 280                 285

Phe Pro Gly Gly Tyr Ile Pro Gly Val Thr Glu Leu Val Gly His Met
    290                 295                 300

Thr Glu Asn Asp Leu Gln Val Ile Asp Leu Glu Ser Leu Arg Arg Asp
305                 310                 315                 320

Tyr Gln Leu Thr Leu Glu His Trp Thr Lys Asn Phe His Asn Ile Glu
                325                 330                 335

Ala Glu Ile Val Asp Glu Lys Gly Glu Arg Phe Tyr Arg Met Trp Asp
```

```
                         340                 345                 350
Leu Tyr Leu Gln Ala Cys Ala Ala Ser Phe Gln Ala Ser Asn Ile Asp
            355                 360                 365

Val Ile Gln Tyr Leu Leu Val His Pro Asp Asn Asn Asp Ile Pro Met
370                 375                 380

Arg Arg Ile Gly
385

<210> SEQ ID NO 71
<211> LENGTH: 5323
<212> TYPE: DNA
<213> ORGANISM: artificial sequence
<220> FEATURE:
<223> OTHER INFORMATION: a constructed shuttle vector for gram-positive
      bacteria

<400> SEQUENCE: 71
gaattcagat ctctcgagcc cgggatcgat ggtacctcgc gaaagcttgg atgttgtaca      60
ggataatgtc cagaaggtcg atagaaagcg tgagaaacag cgtacagacg atttagagat    120
gtagaggtac ttttatgccg agaaaacttt ttgcgtgtga cagtccttaa aatatactta    180
gagcgtaagc gaaagtagta gcgacagcta ttaactttcg gttgcaaagc tctaggattt    240
ttaatggacg cagcgcatca cacgcaaaaa ggaaattgga ataaatgcga aatttgagat    300
gttaattaaa gaccttttg aggtcttttt ttcttagatt tttggggtta tttaggggag    360
aaaacatagg ggggtactac gacctccccc ctaggtgtcc attgtccatt gtccaaacaa    420
ataaataaat attgggtttt taatgttaaa aggttgtttt ttatgttaaa gtgaaaaaaa    480
cagatgttgg gaggtacagt gatagttgta gatagaaaag aagagaaaaa agttgctgtt    540
actttaagac ttacaacaga agaaaatgag atattaaata gaatcaaaga aaatataat     600 attagcaaat cagatgcaac cggtattcta ataaaaaaat atgcaaagga ggaatacggt    660 gcatttttaaa caaaaaaaga tagacagcac tggcatgctg cctatctatg actaaatttt    720
gttaagtgta ttagcaccgt tattatatca tgagcgaaaa tgtaataaaa gaaactgaaa    780
acaagaaaaa ttcaagagga cgtaattgga catttgtttt atatccagaa tcagcaaaag    840
ccgagtggtt agagtatttta aaagagttac acattcaatt tgtagtgtct ccattacatg    900
atagggatac tgatacagaa ggtaggatga aaaagagca ttatcatatt ctagtgatgt     960
atgagggtaa taaatcttat gaacagataa aaataattaa cagaagaatt gaatgcgact    1020
attccgcaga ttgcaggaag tgtgaaaggt cttgtgagat atatgcttca catgacgat    1080 cctaataaat ttaaatatca aaaagaagat atgatagttt atggcggtgt agatgttgat    1140
gaattattaa agaaacaac aacagataga tataaattaa ttaaagaaat gattgagttt    1200
attgatgaac aaggaatcgt agaatttaag agtttaatgg attatgcaat gaagtttaaa    1260
tttgatgatt ggttcccgct tttatgtgat aactcggcgt atgttattca agaatatata    1320
aaatcaaatc ggtataaatc tgaccgatag atttgaatt taggtgtcac aagacactct    1380
tttttcgcac cagcgaaaac tggtttaagc cgactgcgca aaagacataa tcgattcaca    1440
aaaaataggc acacgaaaaa caagttaagg gatgcagttt atgcatccct taacttactt    1500
attaaataat ttatagctat tgaaaagaga taagaattgt tcaaagctaa tattgtttaa    1560
atcgtcaatt cctgcatgtt ttaaggaatt gttaaattga tttttttgtaa atattttctt    1620 gtattctttg ttaacccatt tcataacgaa ataattatac ttttgtttat ctttgtgtga    1680
tattcttgat tttttttctac ttaatctgat aagtgagcta ttcactttag gtttaggatg    1740
```

```
aaaatattct cttggaacca tacttaatat agaaatatca acttctgcca ttaaaagtaa    1800
tgccaatgag cgttttgtat ttaataatct tttagcaaac ccgtattcca cgattaaata    1860
aatctcatta gctatactat caaaaacaat tttgcgtatt atatccgtac ttatgttata    1920
aggtatatta ccatatattt tataggattg gttttttagga aatttaaact gcaatatatc   1980
cttgtttaaa acttggaaat tatcgtgatc aacaagttta ttttctgtag ttttgcataa    2040
tttatggtct atttcaatgg cagttacgaa attacacctc tttactaatt caagggtaaa    2100
atggcctttt cctgagccga tttcaaagat attatcatgt tcatttaatc ttatatttgt    2160
cattatttta tctatattat gttttgaagt aataaagttt tgactgtgtt ttatattttt    2220
ctcgttcatt ataaccctct ttaatttggt tatatgaatt ttgcttatta acgattcatt    2280
ataaccactt atttttgtt tggttgataa tgaactgtgc tgattacaaa aatactaaaa     2340
atgcccatat ttttcctcc ttataaaatt agtataatta tagcacgagc tctgataaat     2400
atgaacatga tgagtgatcg ttaaatttat actgcaatcg gatgcgatta ttgaataaaa    2460
gatatgagag atttatctaa tttcttttt cttgtaaaaa agaaagttc ttaaaggttt      2520 tatagttttg gtcgtagagc acacggttta acgacttaat tacgaagtaa ataagtctag    2580
tgtgttagac tttatgaaat ctatatacgt ttatatatat ttattatccg gatctgcatc    2640
gcaggatgct gctggctacc ctgtggaaca cctacatctg tattaacgaa gcgctggcat    2700
tgaccctgag tgatttttct ctggtcccgc cgcatccata ccgccagttg tttaccctca    2760
caacgttcca gtaaccgggc atgttcatca tcagtaaccc gtatcgtgag catcctctct    2820
cgtttcatcg gtatcattac ccccatgaac agaaattccc ccttacacgg aggcatcaag    2880
tgaccaaaca ggaaaaaacc gcccttaaca tggcccgctt tatcagaagc cagacattaa    2940
cgcttctgga gaaactcaac gagctggacg cggatgaaca ggcagacatc tgtgaatcgc    3000
ttcacgacca cgctgatgag ctttaccgca gctgcctcgc gcgtttcggt gatgacggtg    3060
aaaacctctg acacatgcag ctcccggaga cggtcacagc ttgtctgtaa gcggatgccg    3120
ggagcagaca gcccgtcag ggcgcgtcag cgggtgttgg cgggtgtcgg ggcgcagcca     3180
tgacccagtc acgtagcgat agcggagtgt atactggctt aactatgcgg catcagagca    3240
gattgtactg agagtgcacc atatgcggtg tgaaataccg cacagatgcg taaggagaaa    3300
ataccgcatc aggcgctctt ccgcttcctc gctcactgac tcgctgcgct cggtcgttcg    3360
gctgcggcga gcggtatcag ctcactcaaa ggcggtaata cggttatcca cagaatcagg    3420
ggataacgca ggaaagaaca tgtgagcaaa aggccagcaa aaggccagga accgtaaaaa    3480
ggccgcgttg ctggcgtttt tccataggct ccgcccccct gacgagcatc acaaaaatcg    3540
acgctcaagt cagaggtggc gaaacccgac aggactataa agataccagg cgtttccccc    3600
tggaagctcc ctcgtgcgct ctcctgttcc gaccctgccg cttaccggat acctgtccgc    3660
ctttctccct tcgggaagcg tggcgctttc tcaatgctca cgctgtaggt atctcagttc    3720
ggtgtaggtc gttcgctcca agctgggctg tgtgcacgaa ccccccgttc agcccgaccg    3780
ctgcgcctta tccggtaact atcgtcttga gtccaacccg gtaagacacg acttatcgcc    3840
actggcagca gccactggta acaggattag cagagcgagg tatgtaggcg gtgctacaga    3900
gttcttgaag tggtggccta actacggcta cactagaagg acagtatttg gtatctgcgc    3960
tctgctgaag ccagttacct tcggaaaaag agttggtagc tcttgatccg gcaaacaaac    4020
caccgctggt agcggtggtt ttttgtttg caagcagcag attacgcgca gaaaaaaagg     4080
atctcaagaa gatcctttga tcttttctac ggggtctgac gctcagtgga acgaaaactc    4140
```

```
acgttaaggg attttggtca tgagattatc aaaaaggatc ttcacctaga tccttttaaa    4200
ttaaaaatga agttttaaat caatctaaag tatatatgag taaacttggt ctgacagtta    4260
ccaatgctta atcagtgagg cacctatctc agcgatctgt ctatttcgtt catccatagt    4320
tgcctgactc cccgtcgtgt agataactac gatacgggga ggcttaccat ctggcccccag   4380 tgctgcaatg ataccgcgag acccacgctc accggctcca gatttatcag caataaacca    4440
gccagccgga agggccgagc gcagaagtgg tcctgcaact ttatccgcct ccatccagtc    4500
tattaattgt tgccgggaag ctagagtaag tagttcgcca gttaatagtt tgcgcaacgt    4560
tgttgccatt gctgcaggca tcgtggtgtc acgctcgtcg tttggtatgg cttcattcag    4620
ctccggttcc caacgatcaa ggcgagttac atgatccccc atgttgtgca aaaaagcggt    4680
tagctccttc ggtcctccga tcgttgtcag aagtaagttg gccgcagtgt tatcactcat    4740
ggttatggca gcactgcata attctcttac tgtcatgcca tccgtaagat gcttttctgt    4800
gactggtgag tactcaacca agtcattctg agaatagtgt atgcggcgac cgagttgctc    4860
ttgcccggcg tcaacacggg ataataccgc gccacatagc agaactttaa aagtgctcat    4920
cattggaaaa cgttcttcgg ggcgaaaact ctcaaggatc ttaccgctgt tgagatccag    4980
ttcgatgtaa cccactcgtg cacccaactg atcttcagca tctttactt tcaccagcgt     5040 ttctgggtga gcaaaaacag gaaggcaaaa tgccgcaaaa aagggaataa gggcgacacg    5100
gaaatgttga atactcatac tcttcctttt tcaatattat tgaagcattt atcagggtta    5160
ttgtctcatg agcggataca tatttgaatg tatttagaaa aataaacaaa tagggggttcc    5220 gcgcacattt ccccgaaaag tgccacctga cgtctaagaa accattatta tcatgacatt    5280
aacctataaa aataggcgta tcacgaggcc ctttcgtctt caa                      5323

<210> SEQ ID NO 72
<211> LENGTH: 60
<212> TYPE: DNA
<213> ORGANISM: artificial sequence
<220> FEATURE:
<223> OTHER INFORMATION: primer

<400> SEQUENCE: 72
agctcgagga attcaggcct acgcgtctta agtctagatc aacttgtttc ttatttcaca    60

<210> SEQ ID NO 73
<211> LENGTH: 57
<212> TYPE: DNA
<213> ORGANISM: artificial sequence
<220> FEATURE:
<223> OTHER INFORMATION: primer

<400> SEQUENCE: 73
gactcgaggc ggccgcgttt aaacagatct actagtaggt taattaagag atacgat       57

<210> SEQ ID NO 74
<211> LENGTH: 282
<212> TYPE: DNA
<213> ORGANISM: Lactobacillus plantarum

<400> SEQUENCE: 74
gtaaatgaga agtaggccgt cattgcgcgt gccaagaatg aaaataaagt caaaataatg    60
aaaatccaac gatttgaaag cttaatgaaa gcttgatatt gttggatttt tattgattga   120
cgaaatgttg aaattatttt caatttttc gacggtggtg gtattattac ctttgtattt    180
tgattagggg tgtctctaat ctaccatttc aggttacgat aaaattgacg ttgactagct    240
```

```
caaaggttaa ggttatcgta gcaccgaaat taaaggaaag ag                  282
```

<210> SEQ ID NO 75
<211> LENGTH: 51
<212> TYPE: DNA
<213> ORGANISM: artificial sequence
<220> FEATURE:
<223> OTHER INFORMATION: primer

<400> SEQUENCE: 75

```
tactcgagct taagacgcgt gtaaatgaga agtaggccgt cattgcgcgt g        51
```

<210> SEQ ID NO 76
<211> LENGTH: 42
<212> TYPE: DNA
<213> ORGANISM: artificial sequence
<220> FEATURE:
<223> OTHER INFORMATION: primer

<400> SEQUENCE: 76

```
taggatccac tagtctcttt cctttaattt cggtgctacg at                  42
```

<210> SEQ ID NO 77
<211> LENGTH: 78
<212> TYPE: DNA
<213> ORGANISM: artificial sequence
<220> FEATURE:
<223> OTHER INFORMATION: primer

<400> SEQUENCE: 77

```
atcaattgag gcctagatct gactagtata tataggagga attttttgtaa tggttgattt  60 cgaatattca ataccaac                                             78
```

<210> SEQ ID NO 78
<211> LENGTH: 67
<212> TYPE: DNA
<213> ORGANISM: artificial sequence
<220> FEATURE:
<223> OTHER INFORMATION: primer

<400> SEQUENCE: 78

```
atgcggccgc gctagcggat ccagatctgt ttaaacctta agttacacag attttttgaa   60
tatttgt                                                         67
```

<210> SEQ ID NO 79
<211> LENGTH: 1222
<212> TYPE: DNA
<213> ORGANISM: artificial sequence
<220> FEATURE:
<223> OTHER INFORMATION: synthetic fragment with bdhB coding region and
     5' Shine-Delgarno sequence

<400> SEQUENCE: 79

```
actagtatat ataggaggaa tttttgtaat ggttgatttc gaatattcaa taccaactag   60 aattttttc ggtaaagata agataaatgt acttggaaga gagcttaaaa aatatggttc   120
taaagtgctt atagtttatg gtggaggaag tataaagaga aatggaatat atgataaagc   180
tgtaagtata cttgaaaaaa acagtattaa attttatgaa cttgcaggag tagagccaaa   240
tccaagagta actacagttg aaaaggagt taaaatatgt agagaaatg gagttgaagt   300 agtactagct ataggtggag gaagtgcaat agattgcgca aaggttatag cagcagcatg   360
tgaatatgat ggaaatccat gggatattgt gttagatggc tcaaaaataa aagggtgct   420 tcctatagct agtatattaa ccattgctgc aacaggatca gaaatggata cgtgggcagt   480
```

```
aataaataat atggatacaa acgaaaaact aattgcggca catccagata tggctcctaa    540
gttttctata ttagatccaa cgtatacgta taccgtacct accaatcaaa cagcagcagg    600
aacagctgat attatgagtc atatatttga ggtgtatttt agtaatacaa aaacagcata    660
tttgcaggat agaatggcag aagcgttatt aagaacttgt attaaatatg gaggaatagc    720
tcttgagaag ccggatgatt atgaggcaag agccaatcta atgtgggctt caagtcttgc    780
gataaatgga cttttaacat atggtaaaga cactaattgg agtgtacact taatggaaca    840
tgaattaagt gcttattacg acataacaca cggcgtaggg cttgcaattt taacacctaa    900
ttggatggag tatattttaa ataatgatac agtgtacaag tttgttgaat atggtgtaaa    960
tgtttgggga atagacaaag aaaaaaatca ctatgacata gcacatcaag caatacaaaa   1020
aacaagagat tactttgtaa atgtactagg tttaccatct agactgagag atgttggaat   1080
tgaagaagaa aaattggaca taatggcaaa ggaatcagta aagcttacag gaggaaccat   1140
aggaaaccta agaccagtaa acgcctccga agtcctacaa atattcaaaa aatctgtgta   1200
acttaaggtt taaacagatc tg                                            1222

<210> SEQ ID NO 80
<211> LENGTH: 60
<212> TYPE: DNA
<213> ORGANISM: artificial sequence
<220> FEATURE:
<223> OTHER INFORMATION: primer

<400> SEQUENCE: 80
ctgaactagt ggcggccgca agaggagaaa ttaactatgt tagacaaaat catttataaa    60

<210> SEQ ID NO 81
<211> LENGTH: 33
<212> TYPE: DNA
<213> ORGANISM: artificial sequence
<220> FEATURE:
<223> OTHER INFORMATION: primer

<400> SEQUENCE: 81
tcagagatct tcaatcataa atataatggc gag                                 33

<210> SEQ ID NO 82
<211> LENGTH: 60
<212> TYPE: DNA
<213> ORGANISM: artificial sequence
<220> FEATURE:
<223> OTHER INFORMATION: primer

<400> SEQUENCE: 82
ctgaactagt ggcggccgca agaggagaaa ttaactatgc tagaaaaaac cttttaccac    60

<210> SEQ ID NO 83
<211> LENGTH: 33
<212> TYPE: DNA
<213> ORGANISM: artificial sequence
<220> FEATURE:
<223> OTHER INFORMATION: primer

<400> SEQUENCE: 83
tcagagatct ttaagcttta ttgattcggt tat                                 33

<210> SEQ ID NO 84
<211> LENGTH: 36
<212> TYPE: DNA
<213> ORGANISM: artificial sequence
```

-continued

```
<220> FEATURE:
<223> OTHER INFORMATION: primer

<400> SEQUENCE: 84
acaggagaat gaattcatga gttcatcgtg tataga                                    36

<210> SEQ ID NO 85
<211> LENGTH: 20
<212> TYPE: DNA
<213> ORGANISM: artificial sequence
<220> FEATURE:
<223> OTHER INFORMATION: primer

<400> SEQUENCE: 85
ttagcgagcc actcgaaggc                                                      20

<210> SEQ ID NO 86
<211> LENGTH: 25
<212> TYPE: DNA
<213> ORGANISM: artificial sequence
<220> FEATURE:
<223> OTHER INFORMATION: primer

<400> SEQUENCE: 86
gttgtggaag atactggtgt tactt                                                25

<210> SEQ ID NO 87
<211> LENGTH: 20
<212> TYPE: DNA
<213> ORGANISM: artificial sequence
<220> FEATURE:
<223> OTHER INFORMATION: primer

<400> SEQUENCE: 87
agtccttgat tgaatccacg                                                      20

<210> SEQ ID NO 88
<211> LENGTH: 38
<212> TYPE: DNA
<213> ORGANISM: artificial sequence
<220> FEATURE:
<223> OTHER INFORMATION: primer

<400> SEQUENCE: 88
aaaaaagcgg ccgctcttta ttcttcaact aaagcacc                                  38

<210> SEQ ID NO 89
<211> LENGTH: 42
<212> TYPE: DNA
<213> ORGANISM: artificial sequence
<220> FEATURE:
<223> OTHER INFORMATION: primer

<400> SEQUENCE: 89
aaaaaagcgg ccgcaatgta tttagaaaaa taaacaaata gg                             42

<210> SEQ ID NO 90
<211> LENGTH: 20
<212> TYPE: DNA
<213> ORGANISM: artificial sequence
<220> FEATURE:
<223> OTHER INFORMATION: primer

<400> SEQUENCE: 90
tgtaattttg cggtcggtgg                                                      20
```

```
<210> SEQ ID NO 91
<211> LENGTH: 22
<212> TYPE: DNA
<213> ORGANISM: artificial sequence
<220> FEATURE:
<223> OTHER INFORMATION: primer

<400> SEQUENCE: 91
gcggataaca atttcacaca gg                                              22

<210> SEQ ID NO 92
<211> LENGTH: 20
<212> TYPE: DNA
<213> ORGANISM: artificial sequence
<220> FEATURE:
<223> OTHER INFORMATION: primer

<400> SEQUENCE: 92
tgtaattttg cggtcggtgg                                                 20

<210> SEQ ID NO 93
<211> LENGTH: 22
<212> TYPE: DNA
<213> ORGANISM: artificial sequence
<220> FEATURE:
<223> OTHER INFORMATION: primer

<400> SEQUENCE: 93
gcggataaca atttcacaca gg                                              22

<210> SEQ ID NO 94
<211> LENGTH: 29
<212> TYPE: DNA
<213> ORGANISM: Artificial Sequence
<220> FEATURE:
<223> OTHER INFORMATION: Primer LDH EcoRV F

<400> SEQUENCE: 94
gacgtcatga ccacccgccg atcccttttt                                      29

<210> SEQ ID NO 95
<211> LENGTH: 30
<212> TYPE: DNA
<213> ORGANISM: Artificial Sequence
<220> FEATURE:
<223> OTHER INFORMATION: Primer LDH AatIIR

<400> SEQUENCE: 95
gatatccaac accagcgacc gacgtattac                                      30

<210> SEQ ID NO 96
<211> LENGTH: 6509
<212> TYPE: DNA
<213> ORGANISM: Artificial Sequence
<220> FEATURE:
<223> OTHER INFORMATION: Vector pFP988

<400> SEQUENCE: 96
tcgaggcccc gcacatacga aaagactggc tgaaaacatt gagcctttga tgactgatga     60
tttggctgaa gaagtggatc gattgtttga gaaagaaga agaccataaa ataccttgt      120 ctgtcatcag acagggtatt ttttatgctg tccagactgt ccgctgtgta aaaatagga    180 ataaaggggg gttgttatta ttttactgat atgtaaaata taatttgtat aaggaattgt    240
gagcggataa caattcctac gaaaatgaga gggagaggaa acatgattca aaaacgaaag    300
cggacagttt cgttcagact tgtgcttatg tgcacgctgt tatttgtcag tttgccgatt    360
```

```
acaaaaacat cagccggatc ccaccatcac catcaccatt aagaattcct agaaactcca    420
agctatcttt aaaaaatcta gtaaatgcac gagcaacatc ttttgttgct cagtgcattt    480
tttattttgt acactagata tttcttctcc gcttaaatca tcaaagaaat ctttatcact    540
tgtaaccagt ccgtccacat gtcgaattgc atctgaccga attttacgtt tccctgaata    600
attctcatca atcgtttcat caatttatc tttatactt atattttgtg cgttaatcaa    660
atcataattt ttatatgttt cctcatgatt tatgtcttta ttattatagt ttttattctc    720
tctttgatta tgtctttgta tcccgtttgt attacttgat cctttaactc tggcaaccct    780
caaaattgaa tgagacatgc tacacctccg gataataaat atatataaac gtatatagat    840
ttcataaagt ctaacacact agacttattt acttcgtaat taagtcgtta aaccgtgtgc    900
tctacgacca aaactataaa acctttaaga actttctttt tttacaagaa aaagaaatt    960 agataaatct ctcatatctt ttattcaata atcgcatccg attgcagtat aaatttaacg    1020
atcactcatc atgttcatat ttatcagagc tcgtgctata attatactaa ttttataagg    1080
aggaaaaaat atgggcattt ttagtatttt tgtaatcagc acagttcatt atcaaccaaa    1140
caaaaaataa gtggttataa tgaatcgtta ataagcaaaa ttcatataac caaattaaag    1200
agggttataa tgaacgagaa aaatataaaa cacagtcaaa actttattac ttcaaaacat    1260
aatatagata aaataatgac aaatataaga ttaaatgaac atgataatat ctttgaaatc    1320
ggctcaggaa aaggccattt tacccttgaa ttagtaaaga ggtgtaattt cgtaactgcc    1380
attgaaatag accataaatt atgcaaaact acagaaaata aacttgttga tcacgataat    1440
ttccaagttt taaacaagga tatattgcag tttaaatttc ctaaaaacca atcctataaa    1500
atatatggta atataccta taacataagt acggatataa tacgcaaaat tgttttttgat    1560 agtatagcta atgagattta tttaatcgtg gaatacgggt ttgctaaaag attattaaat    1620
acaaaacgct cattggcatt acttttaatg gcagaagttg atatttctat attaagtatg    1680
gttccaagag aatattttca tcctaaacct aaagtgaata gctcacttat cagattaagt    1740
agaaaaaaat caagaatatc acacaaagat aaacaaagt ataattattt cgttatgaaa    1800
tgggttaaca aagaatacaa gaaatatttt acaaaaatc aatttaacaa ttccttaaaa    1860
catgcaggaa ttgacgattt aaacaatatt agctttgaac aattcttatc tcttttcaat    1920
agctataaat tatttaataa gtaagttaag ggatgcagtt catcgatgaa ggcaactaca    1980
gctcaggcga caaccatacg ctgagagatc ctcactacgt agaagataaa ggccacaaat    2040
acttagtatt tgaagcaaac actggaactg aagatggcta ccaaggcgaa gaatctttat    2100
ttaacaaagc atactatggc aaaagcacat cattcttccg tcaagaaagt caaaaacttc    2160
tgcaaagcga taaaaaacgc acggctgagt tagcaaacgg cgctctcggt atgattgagc    2220
taaacgatga ttcacactg aaaaaagtga tgaaaccgct gattgcatct aacacagtaa    2280
cagatgaaat tgaacgcgcg aacgtctttta aaatgaacgg caaatggtac ctgttcactg    2340
actcccgcgg atcaaaatg acgattgacg gcattacgtc taacgatatt tacatgcttg    2400 gttatgttc taattcttta actggcccat acaagccgct gaacaaaact ggccttgtgt    2460 taaaatgga tcttgatcct aacgatgtaa cctttactta ctcacacttc gctgtacctc    2520
aagcgaaagg aaacaatgtc gtgattacaa gctatatgac aaacagagga ttctacgcag    2580
acaaacaatc aacgtttgcg ccaagcttgc atgcgagagt agggaactgc caggcatcaa    2640
ataaaacgaa aggctcagtc gaaagactgg gcctttcgtt ttatctgttg tttgtcggtg    2700
aacgctctcc tgagtaggac aaatccgccg ggagcggatt tgaacgttgc gaagcaacgg    2760
```

```
cccggagggt ggcgggcagg acgcccgcca taaactgcca ggcatcaaat taagcagaag    2820
gccatcctga cggatggcct ttttgcgttt ctacaaactc tttttgttta tttttctaaa    2880
tacattcaaa tatgtatccg ctcatgctcc ggatctgcat cgcaggatgc tgctggctac    2940
cctgtggaac acctacatct gtattaacga agcgctggca ttgaccctga gtgatttttc    3000
tctggtcccg ccgcatccat accgccagtt gtttaccctc acaacgttcc agtaaccggg    3060
catgttcatc atcagtaacc cgtatcgtga gcatcctctc tcgtttcatc ggtatcatta    3120
cccccatgaa cagaaattcc cccttacacg gaggcatcaa gtgaccaaac aggaaaaaac    3180
cgcccttaac atgcccgct ttatcagaag ccagacatta acgcttctgg agaaactcaa    3240
cgagctggac gcggatgaac aggcagacat ctgtgaatcg cttcacgacc acgctgatga    3300
gctttaccgc agctgcctcg cgcgtttcgg tgatgacggt gaaaacctct gacacatgca    3360
gctcccggag acgtcacag cttgtctgta agcggatgcc gggagcagac aagcccgtca    3420
gggcgcgtca gcgggtgttg gcgggtgtcg ggcgcagcc atgacccagt cacgtagcga    3480
tagcggagtg tatactggct taactatgcg gcatcagagc agattgtact gagagtgcac    3540
catatgcggt gtgaaatacc gcacagatgc gtaaggagaa ataccgcat caggcgctct    3600 tccgcttcct cgctcactga ctcgctgcgc tcggtcgttc ggctgcggcg agcggtatca    3660
gctcactcaa aggcggtaat acggttatcc acagaatcag gggataacgc aggaaagaac    3720
atgtgagcaa aaggccagca aaaggccagg aaccgtaaaa aggccgcgtt gctggcgttt    3780
ttccataggc tccgcccccc tgacgagcat cacaaaaatc gacgctcaag tcagaggtgg    3840
cgaaacccga caggactata aagataccag gcgtttcccc ctggaagctc cctcgtgcgc    3900
tctcctgttc cgaccctgcc gcttaccgga tacctgtccg cctttctccc ttcgggaagc    3960
gtggcgcttt ctcaatgctc acgctgtagg tatctcagtt cggtgtaggt cgttcgctcc    4020
aagctgggct gtgtgcacga accccccgtt cagcccgacc gctgcgcctt atccggtaac    4080
tatcgtcttg agtccaaccc ggtaagacac gacttatcgc cactggcagc agccactggt    4140
aacaggatta gcagagcgag gtatgtaggc ggtgctacag agttcttgaa gtggtggcct    4200
aactacggct acactagaag gacagtattt ggtatctgcg ctctgctgaa gccagttacc    4260
ttcggaaaaa gagttggtag ctcttgatcc ggcaaacaaa ccaccgctgg tagcggtggt    4320
ttttttgttt gcaagcagca gattacgcgc agaaaaaaag gatctcaaga agatcctttg    4380
atcttttcta cggggtctga cgctcagtgg aacgaaaact cacgttaagg attttggtc     4440 atgagattat caaaaaggat cttcacctag atccttttaa attaaaaatg aagttttaaa    4500
tcaatctaaa gtatatatga gtaaacttgg tctgacagtt accaatgctt aatcagtgag    4560
gcacctatct cagcgatctg tctatttcgt tcatccatag ttgcctgact ccccgtcgtg    4620
tagataacta cgatacggga gggcttacca tctggcccca gtgctgcaat gataccgcga    4680
gacccacgct caccggctcc agatttatca gcaataaacc agccagccgg aagggccgag    4740
cgcagaagtg gtcctgcaac tttatccgcc tccatccagt ctattaattg ttgccgggaa    4800
gctagagtaa gtagttcgcc agttaatagt ttgcgcaacg ttgttgccat tgctgcaggc    4860
atcgtggtgt cacgctcgtc gtttggtatg gcttcattca gctccggttc caacgatca    4920 aggcgagtta catgatcccc catgttgtgc aaaaaagcgg ttagctcctt cggtcctccg    4980
atcgttgtca gaagtaagtt ggccgcagtg ttatcactca tggttatggc agcactgcat    5040
aattctctta ctgtcatgcc atccgtaaga tgcttttctg tgactggtga gtactcaacc    5100
aagtcattct gagaatagtg tatgcggcga ccgagttgct cttgcccggc gtcaatacgg    5160
```

```
gataataccg cgccacatag cagaacttta aaagtgctca tcattggaaa acgttcttcg    5220
gggcgaaaac tctcaaggat cttaccgctg ttgagatcca gttcgatgta acccactcgt    5280
gcacccaact gatcttcagc atctttact  ttcaccagcg tttctgggtg agcaaaaaca    5340
ggaaggcaaa atgccgcaaa aagggaata  agggcgacac ggaaatgttg aatactcata    5400
ctcttccttt ttcaatatta ttgaagcatt tatcagggtt attgtctcat gagcggatac    5460
atatttgaat gtatttagaa aaataaacaa ataggggttc cgcgcacatt tccccgaaaa    5520
gtgccacctg acgtctaaga aaccattatt atcatgacat taacctataa aaataggcgt    5580
atcacgaggc cctttcgtct cgcgcgtttc ggtgatgacg gtgaaaacct ctgacacatg    5640
cagctcccgg agacggtcac agcttgtctg taagcggatg ccgggagcag acaagcccgt    5700
cagggcgcgt cagcgggtgt tcatgtgcgt aactaacttg ccatcttcaa acaggagggc    5760
tggaagaagc agaccgctaa cacagtacat aaaaaggag  acatgaacga tgaacatcaa    5820
aaagtttgca aaacaagcaa cagtattaac ctttactacc gcactgctgg caggaggcgc    5880
aactcaagcg tttgcgaaag aaacgaacca aaagccatat aaggaaacat acggcatttc    5940
ccatattaca cgccatgata tgctgcaaat ccctgaacag caaaaaaatg aaaaatatca    6000
agttcctgaa ttcgattcgt ccacaattaa aaatatctct tctgcaaaag gcctggacgt    6060
ttgggacagc tggccattac aaaacgctga cggcactgtc gcaaactatc acggctacca    6120
catcgtcttt gcattagccg gagatcctaa aaatgcggat gacacatcga tttacatgtt    6180
ctatcaaaaa gtcggcgaaa cttctattga cagctggaaa aacgctggcc gcgtctttaa    6240
agacagcgac aaattcgatg caaatgattc tatcctaaaa gaccaaacac aagaatggtc    6300
aggttcagcc acatttacat ctgacggaaa aatccgttta ttctacactg atttctccgg    6360
taaacattac ggcaaacaaa cactgacaac tgcacaagtt aacgtatcag catcagacag    6420
ctctttgaac atcaacggtg tagaggatta taaatcaatc tttgacggtg acggaaaaac    6480
gtatcaaaat gtacagcatg ccacgcgtc                                     6509
```

<210> SEQ ID NO 97
<211> LENGTH: 47
<212> TYPE: DNA
<213> ORGANISM: Artificial Sequence
<220> FEATURE:
<223> OTHER INFORMATION: Primer Cm F

<400> SEQUENCE: 97
atttaaatct cgagtagagg atcccaacaa acgaaaattg gataaag    47

<210> SEQ ID NO 98
<211> LENGTH: 29
<212> TYPE: DNA
<213> ORGANISM: Artificial Sequence
<220> FEATURE:
<223> OTHER INFORMATION: Primer Cm R

<400> SEQUENCE: 98
acgcgttatt ataaaagcca gtcattagg    29

<210> SEQ ID NO 99
<211> LENGTH: 58
<212> TYPE: DNA
<213> ORGANISM: Artificial Sequence
<220> FEATURE:
<223> OTHER INFORMATION: Primer P11 F-StuI

<400> SEQUENCE: 99

```
cctagcgcta tagttgttga cagaatggac atactatgat atattgttgc tatagcga        58
```

<210> SEQ ID NO 100
<211> LENGTH: 62
<212> TYPE: DNA
<213> ORGANISM: Artificial Sequence
<220> FEATURE:
<223> OTHER INFORMATION: Primer P11 R-SpeI

<400> SEQUENCE: 100

```
ctagtcgcta tagcaacaat atatcatagt atgtccattc tgtcaacaac tatagcgcta      60
gg                                                                    62
```

<210> SEQ ID NO 101
<211> LENGTH: 38
<212> TYPE: DNA
<213> ORGANISM: Artificial Sequence
<220> FEATURE:
<223> OTHER INFORMATION: Primer PldhL F-HindIII

<400> SEQUENCE: 101

```
aagcttgtcg acaaaccaac attatgacgt gtctgggc                              38
```

<210> SEQ ID NO 102
<211> LENGTH: 28
<212> TYPE: DNA
<213> ORGANISM: Artificial Sequence
<220> FEATURE:
<223> OTHER INFORMATION: Primer PldhL R-BamHI

<400> SEQUENCE: 102

```
ggatcctcat cctctcgtag tgaaaatt                                         28
```

<210> SEQ ID NO 103
<211> LENGTH: 26
<212> TYPE: DNA
<213> ORGANISM: artificial sequence
<220> FEATURE:
<223> OTHER INFORMATION: primer

<400> SEQUENCE: 103

```
gcatgcatgc tagacaaaat cattta                                           26
```

<210> SEQ ID NO 104
<211> LENGTH: 26
<212> TYPE: DNA
<213> ORGANISM: artificial sequence
<220> FEATURE:
<223> OTHER INFORMATION: primer

<400> SEQUENCE: 104

```
gcatgcatca taaatataat ggcgag                                           26
```

<210> SEQ ID NO 105
<211> LENGTH: 1476
<212> TYPE: DNA
<213> ORGANISM: Bacillus subtilis

<400> SEQUENCE: 105

```
atggctaact acttcaatac actgaatctg cgccagcagc tggcacagct gggcaaatgt      60
cgctttatgg gccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
```

```
aaagcgaccg aaaatggttt taaagtgggt acttacgaag aactgatccc acaggcggat    300
ctggtgatta acctgacgcc ggacaagcag cactctgatg tagtgcgcac cgtacagcca    360
ctgatgaaag acggcgcggc gctgggctac tcgcacggtt tcaacatcgt cgaagtgggc    420
gagcagatcc gtaaagatat caccgtagtg atggttgcgc cgaaatgccc aggcaccgaa    480
gtgcgtgaag agtacaaacg tgggttcggc gtaccgacgc tgattgccgt tcacccggaa    540
aacgatccga aaggcgaagg catggcgatt gccaaagcct gggcggctgc aaccggtggt    600
caccgtgcgg gtgtgctgga atcgtccttc gttgcggaag tgaaatctga cctgatgggc    660
gagcaaacca tcctgtgcgg tatgttgcag gctggctctc tgctgtgctt cgacaagctg    720
gtggaagaag gtaccgatcc agcatacgca gaaaaactga ttcagttcgg ttgggaaacc    780
atcaccgaag cactgaaaca gggcggcatc accctgatga tggaccgtct ctctaaccca    840
gcgaaactgc gtgcttatgc gctttctgaa cagctgaaag agatcatggc acccctgttc    900
cagaaacata tggacgacat catctccggc gaattctctt ccggtatgat ggcggactgg    960
gccaacgatg ataagaaact gctgacctgg cgtgaagaga ccggcaaaac cgcgtttgaa   1020
accgcgccgc agtatgaagg caaaatcggc gagcaggagt acttcgataa aggcgtactg   1080
atgattgcga tggtgaaagc gggcgttgaa ctggcgttcg aaaccatggt cgattccggc   1140
atcattgaag agtctgcata ttatgaatca ctgcacgagc tgccgctgat tgccaacacc   1200
atcgcccgta agcgtctgta cgaaatgaac gtggttatct ctgataccgc tgagtacggt   1260
aactatctgt tctcttacgc ttgtgtgccg ttgctgaaac cgtttatggc agagctgcaa   1320
ccgggcgacc tgggtaaagc tattccggaa ggcgcggtag ataacgggca actgcgtgat   1380
gtgaacgaag cgattcgcag ccatgcgatt gagcaggtag gtaagaaact gcgcggctat   1440
atgacagata tgaaacgtat tgctgttgcg ggttaa                             1476

<210> SEQ ID NO 106
<211> LENGTH: 62
<212> TYPE: DNA
<213> ORGANISM: Artificial Sequence
<220> FEATURE:
<223> OTHER INFORMATION: Primer P11 F

<400> SEQUENCE: 106
tcgagagcgc tatagttgtt gacagaatgg acatactatg atatattgtt gctatagcgc    60
cc                                                                   62

<210> SEQ ID NO 107
<211> LENGTH: 58
<212> TYPE: DNA
<213> ORGANISM: Artificial Sequence
<220> FEATURE:
<223> OTHER INFORMATION: Primer P11 R

<400> SEQUENCE: 107
gggcgctata gcaacaatat atcatagtat gtccattctg tcaacaacta tagcgctc      58

<210> SEQ ID NO 108
<211> LENGTH: 38
<212> TYPE: DNA
<213> ORGANISM: Artificial Sequence
<220> FEATURE:
<223> OTHER INFORMATION: Primer PldhL F

<400> SEQUENCE: 108
gagctcgtcg acaaaccaac attatgacgt gtctgggc                            38
```

<210> SEQ ID NO 109
<211> LENGTH: 30
<212> TYPE: DNA
<213> ORGANISM: Artificial Sequence
<220> FEATURE:
<223> OTHER INFORMATION: Primer PldhL R

<400> SEQUENCE: 109
ggatcctacc atgtttgtgc aaaataagtg                                    30

<210> SEQ ID NO 110
<211> LENGTH: 1224
<212> TYPE: DNA
<213> ORGANISM: Artificial Sequence
<220> FEATURE:
<223> OTHER INFORMATION: Condon optimized EgTER

<400> SEQUENCE: 110
atggcgatgt ttacgaccac cgcaaaagtt attcagccga aaattcgtgg tttatttgc      60 accaccaccc acccgattgg ttgcgaaaaa cgtgttcagg aagaaatcgc atacgcacgc    120
gcgcacccgc cgaccagccc gggtccgaaa cgtgtgctgg ttattggctg cagtacgggc    180
tatggcctga gcacccgtat caccgcggcc tttggttatc aggccgcaac cctgggcgtg    240
tttctggcag gcccgccgac caaaggccgt ccggccgcgg cgggttggta taatacggtt    300
gcgttcgaaa aagccgccct ggaagcaggt ctgtatgcac gttctctgaa tggtgatgcg    360
ttcgattcta ccacgaaagc ccgcaccgtg aagcaattaa acgtgatctg ggtaccgtt     420 gatctggtgg tgtatagcat tgcagcgccg aaacgtaccg atccggccac cggcgtgctg    480
cataaagcgt gcctgaaacc gattggtgca acctacacca tcgtacggt gaacaccgat     540 aaagcagaag ttaccgatgt gagtattgaa ccggccagtc cggaagaaat cgcagatacc    600
gtgaaagtta tgggtggcga agattgggaa ctgtggattc aggcactgag cgaagccggc    660
gtgctggccg aaggcgcaaa aaccgttgcg tattcttata ttggcccgga aatgacgtgg    720
ccggtgtatt ggagtggcac cattggcgaa gccaaaaaag atgttgaaaa agcggcgaaa    780
cgcatcaccc agcagtacgg ctgtccggcg tatccggttg ttgccaaagc gctggtgacc    840
caggccagta gcgccattcc ggtggtgccg ctgtatattt gcctgctgta tcgtgttatg    900
aaagaaaaag gcacccatga aggctgcatt gaacagatgg tgcgtctgct gacgacgaaa    960
ctgtatccgg aaaatggtgc gccgatcgtg atgaagcgg gccgtgtgcg tgttgatgat   1020
tgggaaatgg cagaagatgt tcagcaggca gttaaagatc tgtggagcca ggtgagtacg   1080
gccaatctga agatattag cgattttgca ggttatcaga ccgaatttct gcgtctgttt    1140
ggctttggta ttgatggtgt ggattacgat cagccggttg atgttgaagc ggatctgccg   1200
agcgccgccc agcagtaagt cgac                                         1224

<210> SEQ ID NO 111
<211> LENGTH: 29
<212> TYPE: DNA
<213> ORGANISM: artificial sequence
<220> FEATURE:
<223> OTHER INFORMATION: primer

<400> SEQUENCE: 111
tcgcgagtaa atgagaagta ggccgtcat                                     29

<210> SEQ ID NO 112
<211> LENGTH: 26

```
<212> TYPE: DNA
<213> ORGANISM: artificial sequence
<220> FEATURE:
<223> OTHER INFORMATION: primer

<400> SEQUENCE: 112
ctcgagatca taaatataat ggcgag                                         26

<210> SEQ ID NO 113
<211> LENGTH: 342
<212> TYPE: PRT
<213> ORGANISM: Bacillus subtilis

<400> SEQUENCE: 113
```

| Met | Val | Lys | Val | Tyr | Tyr | Asn | Gly | Asp | Ile | Lys | Glu | Asn | Val | Leu | Ala |
|---|---|---|---|---|---|---|---|---|---|---|---|---|---|---|---|
| 1 | | | | 5 | | | | | 10 | | | | | 15 | |

Gly Lys Thr Val Ala Val Ile Gly Tyr Gly Ser Gln Gly His Ala His
                20                  25                  30

Ala Leu Asn Leu Lys Glu Ser Gly Val Asp Val Ile Gly Val Arg
            35                  40                  45

Gln Gly Lys Ser Phe Thr Gln Ala Gln Glu Asp Gly His Lys Val Phe
 50                  55                  60

Ser Val Lys Glu Ala Ala Ala Gln Ala Glu Ile Ile Met Val Leu Leu
65                  70                  75                  80

Pro Asp Glu Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
        115                 120                 125

Pro Lys Gly Pro Gly His Leu Val Arg Arg Thr Tyr Glu Gln Gly Ala
    130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Glu Thr Glu Thr Asp Leu Phe
            180                 185                 190

Gly Glu Gln Ala Val Leu Cys Gly Gly Leu Ser Ala Leu Val Lys Ala
        195                 200                 205

Gly Phe Glu Thr Leu Thr Glu Ala Gly Tyr Gln Pro Glu Leu Ala Tyr
    210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
        275                 280                 285

Glu Trp Ile Val Glu Asn Gln Val Asn Arg Pro Arg Phe Asn Ala Ile
    290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Glu Ala Val
                325                 330                 335

Val Ser Val Ala Gln Asn
            340

<210> SEQ ID NO 114
<211> LENGTH: 405
<212> TYPE: PRT
<213> ORGANISM: Euglena gracilis

<400> SEQUENCE: 114

Met Ala Met Phe Thr Thr Thr Ala Lys Val Ile Gln Pro Lys Ile Arg
1               5                   10                  15

Gly Phe Ile Cys Thr Thr Thr His Pro Ile Gly Cys Glu Lys Arg Val
                20                  25                  30

Gln Glu Glu Ile Ala Tyr Ala Arg Ala His Pro Pro Thr Ser Pro Gly
            35                  40                  45

Pro Lys Arg Val Leu Val Ile Gly Cys Ser Thr Gly Tyr Gly Leu Ser
    50                  55                  60

Thr Arg Ile Thr Ala Ala Phe Gly Tyr Gln Ala Ala Thr Leu Gly Val
65                  70                  75                  80

Phe Leu Ala Gly Pro Pro Thr Lys Gly Arg Pro Ala Ala Ala Gly Trp
                85                  90                  95

Tyr Asn Thr Val Ala Phe Glu Lys Ala Ala Leu Glu Ala Gly Leu Tyr
                100                 105                 110

Ala Arg Ser Leu Asn Gly Asp Ala Phe Asp Ser Thr Thr Lys Ala Arg
            115                 120                 125

Thr Val Glu Ala Ile Lys Arg Asp Leu Gly Thr Val Asp Leu Val Val
        130                 135                 140

Tyr Ser Ile Ala Ala Pro Lys Arg Thr Asp Pro Ala Thr Gly Val Leu
145                 150                 155                 160

His Lys Ala Cys Leu Lys Pro Ile Gly Ala Thr Tyr Thr Asn Arg Thr
                165                 170                 175

Val Asn Thr Asp Lys Ala Glu Val Thr Asp Val Ser Ile Glu Pro Ala
                180                 185                 190

Ser Pro Glu Glu Ile Ala Asp Thr Val Lys Val Met Gly Gly Glu Asp
            195                 200                 205

Trp Glu Leu Trp Ile Gln Ala Leu Ser Glu Ala Gly Val Leu Ala Glu
210                 215                 220

Gly Ala Lys Thr Val Ala Tyr Ser Tyr Ile Gly Pro Glu Met Thr Trp
225                 230                 235                 240

Pro Val Tyr Trp Ser Gly Thr Ile Gly Glu Ala Lys Lys Asp Val Glu
                245                 250                 255

Lys Ala Ala Lys Arg Ile Thr Gln Gln Tyr Gly Cys Pro Ala Tyr Pro
            260                 265                 270

Val Val Ala Lys Ala Leu Val Thr Gln Ala Ser Ser Ala Ile Pro Val
        275                 280                 285

Val Pro Leu Tyr Ile Cys Leu Leu Tyr Arg Val Met Lys Glu Lys Gly
    290                 295                 300

Thr His Glu Gly Cys Ile Glu Gln Met Val Arg Leu Leu Thr Thr Lys
305                 310                 315                 320

Leu Tyr Pro Glu Asn Gly Ala Pro Ile Val Asp Glu Ala Gly Arg Val
                325                 330                 335

Arg Val Asp Asp Trp Glu Met Ala Glu Asp Val Gln Ala Val Lys
            340                 345                 350

Asp Leu Trp Ser Gln Val Ser Thr Ala Asn Leu Lys Asp Ile Ser Asp
            355                 360                 365

-continued

```
Phe Ala Gly Tyr Gln Thr Glu Phe Leu Arg Leu Phe Gly Phe Gly Ile
        370                 375                 380

Asp Gly Val Asp Tyr Asp Gln Pro Val Asp Val Glu Ala Asp Leu Pro
385                 390                 395                 400

Ser Ala Ala Gln Gln
            405
```